US012617843B2

(12) United States Patent
Zwick et al.

(10) Patent No.: US 12,617,843 B2
(45) Date of Patent: May 5, 2026

(54) HUMAN BROADLY NEUTRALIZING ANTIBODIES AGAINST THE MEMBRANE-PROXIMAL EXTERNAL REGION OF HIV ENV FOR VACCINE DESIGN AND INTERVENTION

(71) Applicant: The Scripps Research Institute, La Jolla, CA (US)

(72) Inventors: Michael Zwick, La Jolla, CA (US); Lei Zhang, La Jolla, CA (US); Adriana Irimia, La Jolla, CA (US); Jiang Zhu, La Jolla, CA (US); Ian Wilson, La Jolla, CA (US)

(73) Assignee: THE SCRIPPS RESEARCH INSTITUTE, La Jolla, CA (US)

( * ) Notice: Subject to any disclaimer, the term of this patent is extended or adjusted under 35 U.S.C. 154(b) by 517 days.

(21) Appl. No.: 17/768,701

(22) PCT Filed: Oct. 14, 2020

(86) PCT No.: PCT/US2020/055486
§ 371 (c)(1),
(2) Date: Apr. 13, 2022

(87) PCT Pub. No.: WO2021/076559
PCT Pub. Date: Apr. 22, 2021

(65) Prior Publication Data
US 2024/0124560 A1 Apr. 18, 2024

Related U.S. Application Data

(60) Provisional application No. 62/914,640, filed on Oct. 14, 2019.

(51) Int. Cl.
A61P 31/18 (2006.01)
C07K 16/10 (2006.01)
G01N 33/569 (2006.01)

(52) U.S. Cl.
CPC .......... C07K 16/1063 (2013.01); A61P 31/18 (2018.01); G01N 33/56988 (2013.01); C07K 2317/31 (2013.01); *G01N 2469/10* (2013.01)

(58) Field of Classification Search
CPC ............... C07K 16/1063; A61P 31/18; G01N 33/56988
USPC ....................................................... 424/136.1
See application file for complete search history.

(56) References Cited

U.S. PATENT DOCUMENTS

| | | | |
|---|---|---|---|
| 12,281,142 B2 * | 4/2025 | Steichen | A61K 39/21 |
| 2011/0110936 A1 | 5/2011 | Nam et al. | |
| 2012/0269821 A1 | 10/2012 | Haynes et al. | |
| 2018/0002406 A1 | 1/2018 | Connors et al. | |

| | | | |
|---|---|---|---|
| 2021/0363195 A1 * | 11/2021 | Steichen | C12N 7/00 |
| 2023/0174629 A1 * | 6/2023 | McIlwain | G01N 33/56983 |
| | | | 424/133.1 |
| 2025/0059238 A1 * | 2/2025 | Burton | A61K 39/12 |

FOREIGN PATENT DOCUMENTS

| | | |
|---|---|---|
| WO | 2013070776 A1 | 5/2013 |
| WO | 2016149710 A2 | 9/2016 |

OTHER PUBLICATIONS

Almagro & Franssen, Frontiers in Bioscience, 13:1619-33 (2008).*
Edwards et al., J Mol Biol 334:103-118 (2003).*
Marchalonis et al., Dev & Comp Immunol. 30:223-247 (2006).*
Lippow et al., (Nature Biotechnology, 25(10):1171-1176 (2007).*
Sulea et al., (Scientific Reports, 8(260):1-11 (2018)).*
Hasegawa et al. (MABS, vol. 9, No. 5, pp. 854-873 (2017)).*
Altshuler et al., (Biochemistry (Moscow), 75(13):1584-1605 (2010)).*
Vajda et al., (Current Opinion in Structural Biology, 67 pp. 226-231 (2021)).*
Marks et al., (J. Biol. Chem. 295(29) 9823-9837 (2020)).*
Akbar et al., (Cell Reports 34, 108856, Mar. 16, 2021).*
Lo et al., (BMC Genomics vol. 22, Article No. 116 (2021)).*
Zhang et al (Nat Commun. Nov. 26, 2019;10(1):5389; published on-line Nov. 26, 2019).*
Scheepers et al (PLoS Pathog Sep. 2, 2022;18(9):e1010450.*
Caillat et al (Viruses. Oct. 23, 2020;12(11):1210).*
Maillie et al (Elife. Apr. 7, 2025:12:RP90139).*
U.S. Appl. No. 19/178,333, Steichen; Jon M.*
International Search Report for PCT/US2020/055486, mailed Mar. 3, 2021.
Written Opinion of the International Searching Authority for PCT/US2020/055486, mailed Mar. 3, 2021.
Third Party Observation submitted in PCT/US2020/055486 on Feb. 14, 2022.
Mccoy, L.E., et al., "Identification and Specificity of Broadly Neutralizing Antibodies Against HIV," Immunological Reviews, vol. 275, Issue 1, pp. 11-20, Jan. 2017.
Krebs, S.J., et al., "Longitudinal Analysis Reveals Early Development of Three MPER-Directed Neutralizing Antibody Lineages from an HIV-1-Infected Individual," Immunity, vol. 50, pp. 677-391, Mar. 19, 2019.
Kunert, R., et al., "Characterization of Molecular Features, Antigen-Binding, and in Vitro Properties of IgG and IgM Variants of 4E10, an Anti-HIV Type 1 Neutralizing Monoclonal Antibody," Aids Research and Human Retroviruses, vol. 20, No. 7, pp. 755-762, Jul. 2004.
Liu, H., et al., "The Development of HIV Vaccines Targeting gp41 Membrane-Proximal External Region (MPER): Challenges and Prospects," Protein Cell, vol. 9, Issue 7, pp. 596-615, Jul. 2018.

(Continued)

*Primary Examiner* — Lynn A Bristol

(74) *Attorney, Agent, or Firm* — Nixon & Vanderhye, PC

(57) ABSTRACT

The present disclosure relates to anti-HIV antibodies and their use in the treatment or prevention of HIV/AIDS and in the development of HIV vaccines.

17 Claims, 13 Drawing Sheets

Specification includes a Sequence Listing.

(56) References Cited

OTHER PUBLICATIONS

Binley, J.M., et al., "Comprehensive Cross-Clade Neutralization Analysis of a Panel of Anti-Human Immunodeficiency Virus Type I Monoclonal Antibodies," Journal of Virology, vol. 78, Issue 23, pp. 13232-13252, Dec. 2004.
Latonya D. Williams, et al., "Potent and broad HIV-neutralizing antibodies in memory B cells and plasma", Sci Immunol., 2(7), 34 pages, Jan. 27, 2017.

* cited by examiner

FIGURE 6
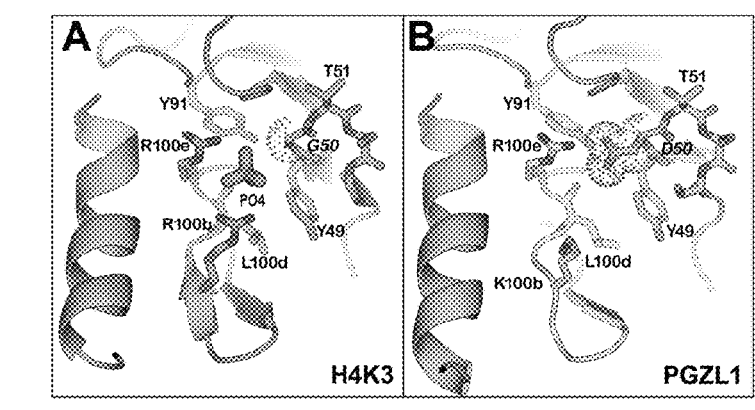
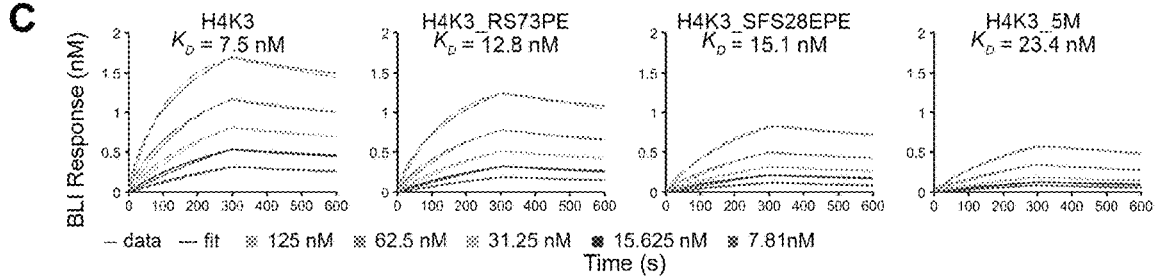
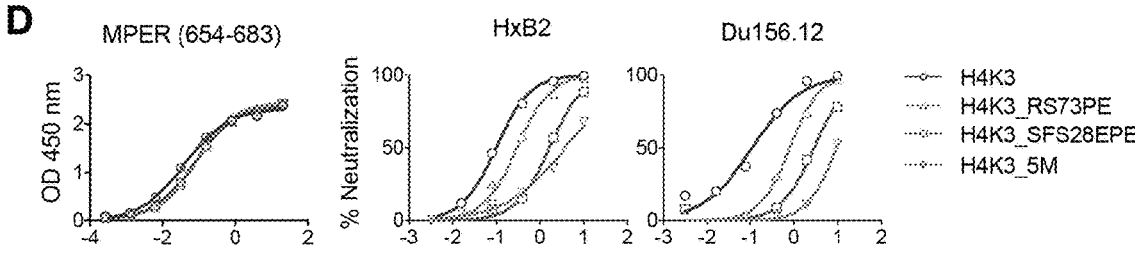
| Antibody | BLI | | | ELISA | | Neutralization | | | |
|---|---|---|---|---|---|---|---|---|---|
| | PDT-081 | | | PDT-081 | | HxB2 | | Du156.12 | |
| | $K_D$ (nM) | $k_{on}$ ($10^4$ $M^{-1}s^{-1}$) | $k_{off}$ ($10^{-4}$ $s^{-1}$) | $EC_{50}$ (µg/ml) | Fold Increase | $IC_{50}$ (µg/ml) | Fold Increase | $IC_{50}$ (µg/ml) | Fold Increase |
| H4K3 | 7.5 | 6.8 | 5.1 | 0.039 | | 0.099 | | 0.110 | |
| H4K3_RS73PE | 12.8 | 3.9 | 5.1 | 0.090 | 2.3 | 0.299 | 3.0 | 0.814 | 7.4 |
| H4K3_SFS28EPE | 15.1 | 3.6 | 5.4 | 0.076 | 2.0 | 1.62 | 16.4 | 2.89 | 26.3 |
| H4K3_5M | 23.4 | 2.9 | 6.7 | 0.083 | 2.1 | 3.72 | 37.7 | 9.31 | 84.5 |
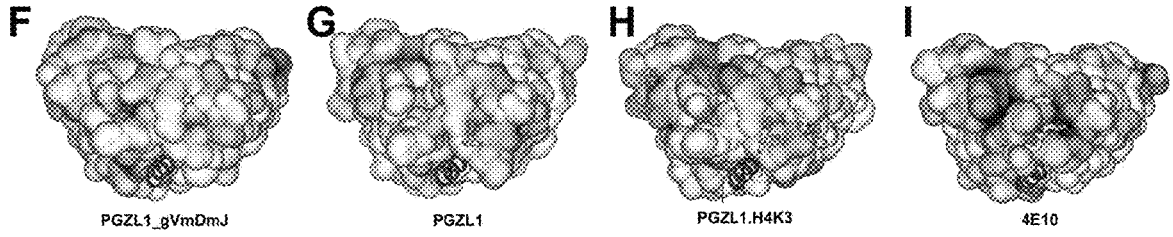

FIGURE 7
a
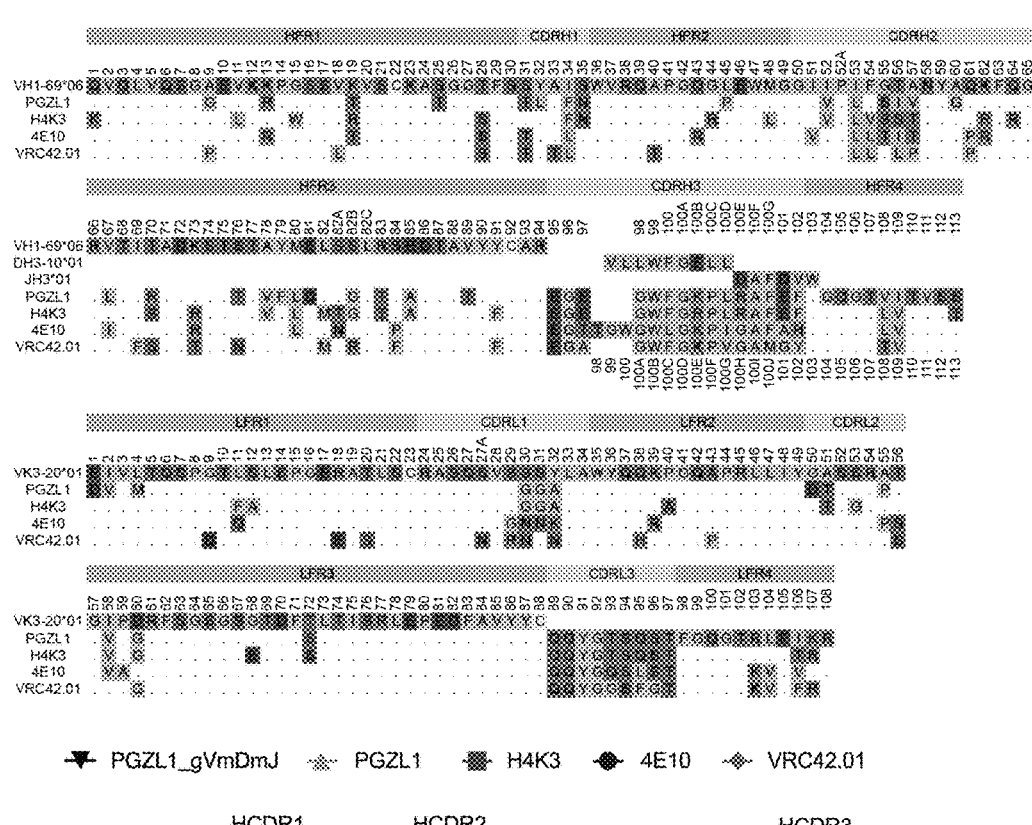
b
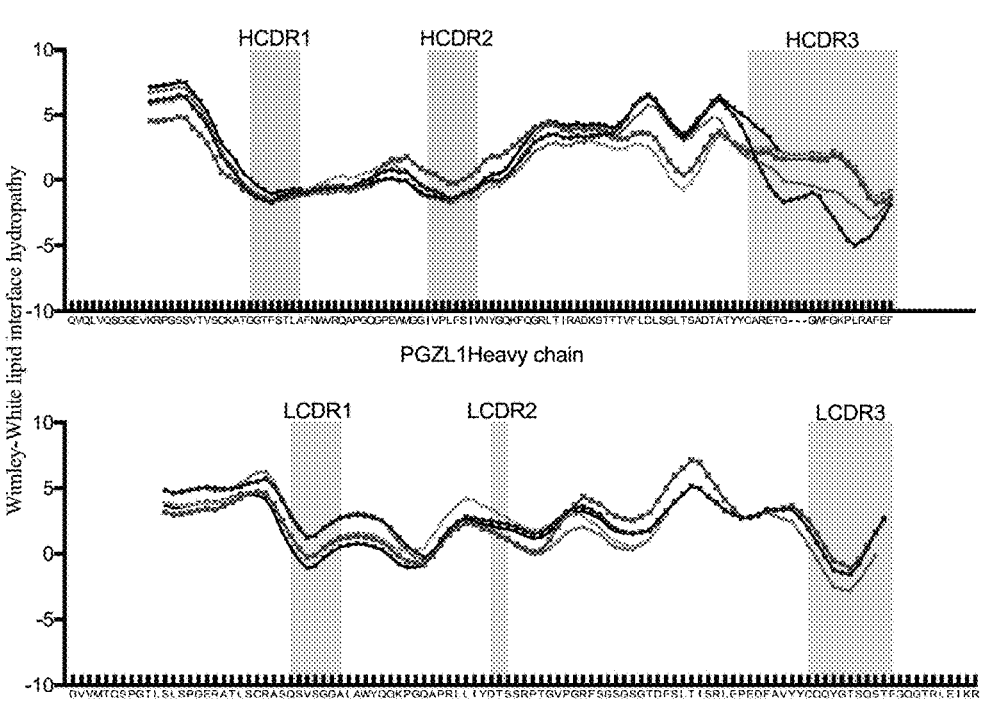

FIGURE 8
a    Germline gene distribution (Donor PG13)
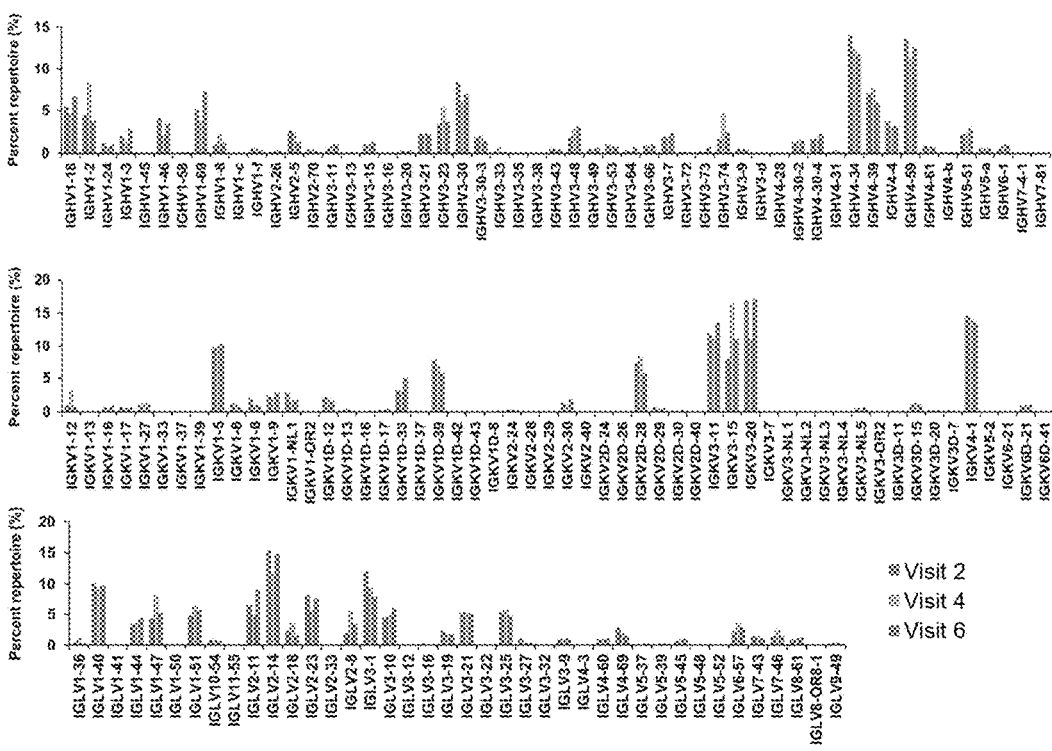
b    Somatic hypermutation distribution (Donor PG13)
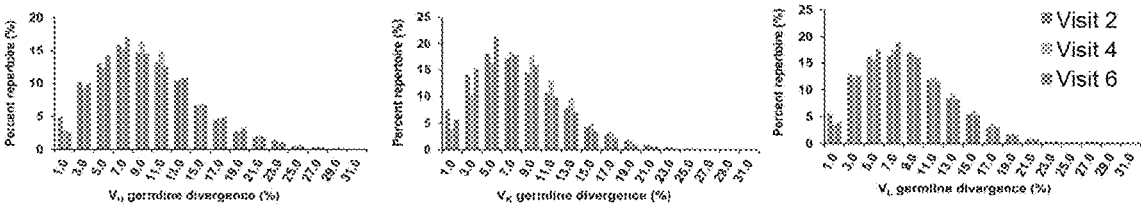
c    CDR3 length distribution (Donor PG13)
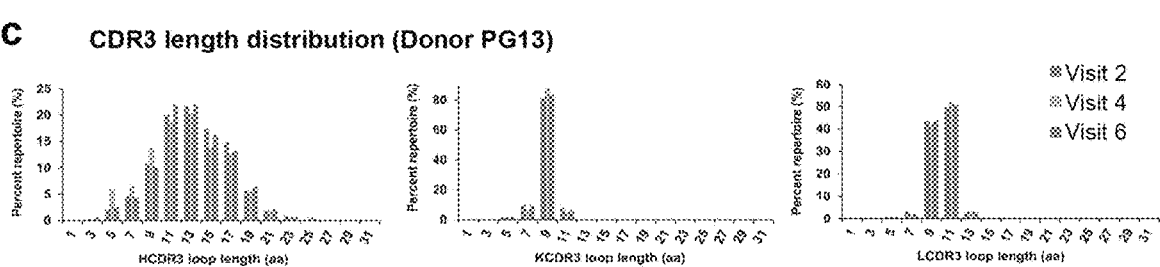

FIGURE 9 a

| Visit | CDR3 identity >80% (HC), >85% (KC) | Translatable to amino acid sequences | Non-redundant sequences | Clustering based on a SeqID of 90% | SeqID-based selection of representative sequences |
|---|---|---|---|---|---|
| #2 | 727 HCs | 555 HCs | 366 HCs | 65 HC clusters | 10 HC representatives |
| | 93 KCs | 23 KCs | 22 KCs | 10 KC clusters | 4 KC representatives |
| #4 | 759 HCs | 597 HCs | 377 HCs | 48 HC clusters | 8 HC representatives |
| | 112 KCs | 28 KCs | 28 KCs | 12 KC clusters | 3 KC representatives |
| #6 | 853 HCs | 644 HCs | 460 HCs | 79 HC clusters | 9 HC representatives |
| | 141 KCs | 14 KCs | 14 KCs | 8 KC clusters | 3 KC representatives |

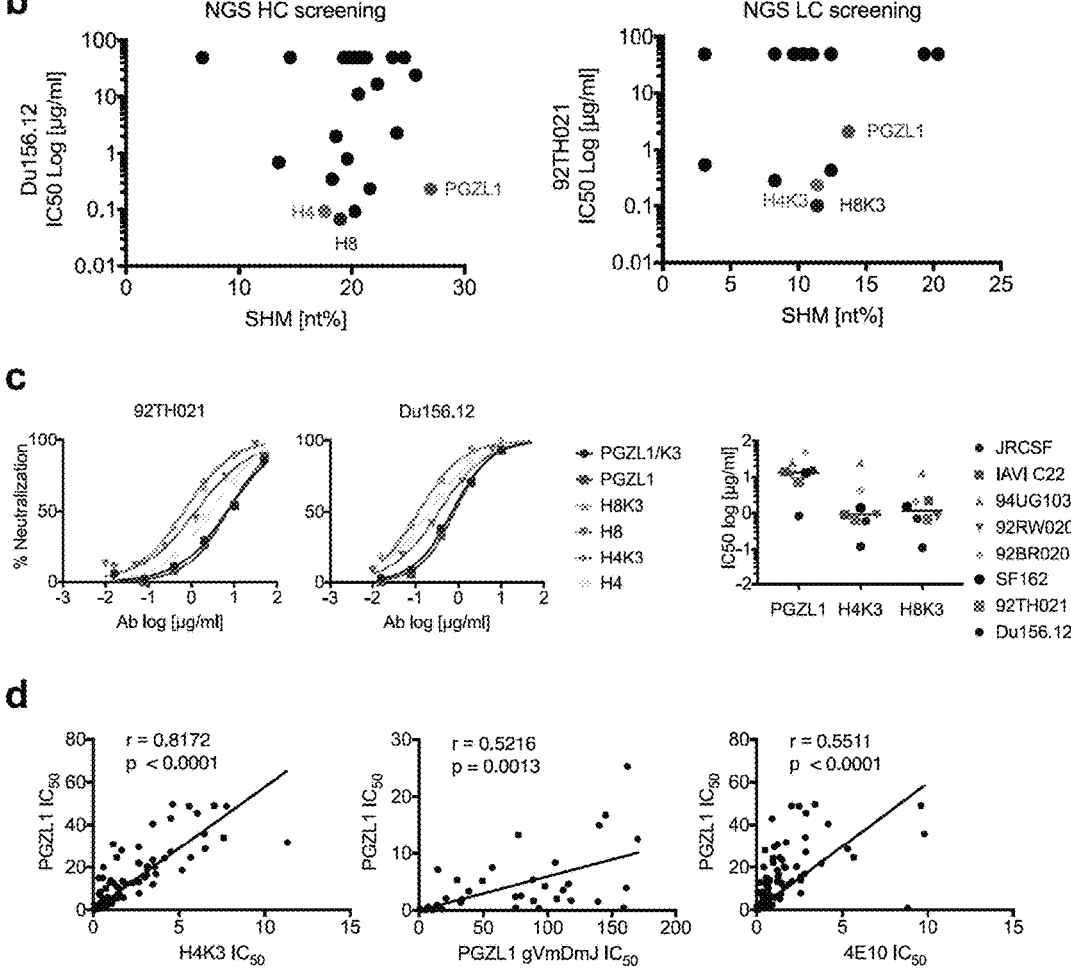

1

HUMAN BROADLY NEUTRALIZING ANTIBODIES AGAINST THE MEMBRANE-PROXIMAL EXTERNAL REGION OF HIV ENV FOR VACCINE DESIGN AND INTERVENTION

CROSS-REFERENCE TO RELATED APPLICATIONS

This application is the U.S. national phase of International Application No. PCT/US2020/055486, filed Oct. 14, 2020, which designated the U.S. and claims the benefit of U.S. Provisional Application No. 62/914,640, filed Oct. 14, 2019, each of which is incorporated herein by reference in its entirety.

GOVERNMENT INTEREST

This invention was made with government support under Grant Nos. AI011244, AI114401, AI143563, AI100663 and AI144462 awarded by the NIH. The government has certain rights in the invention.

FIELD OF THE INVENTION

The field of the invention generally relates to anti-HIV antibodies and their use in the treatment or prevention of HIV/AIDS, and in the development of HIV vaccines.

REFERENCE TO SEQUENCE LISTING SUBMITTED ELECTRONICALLY

The content of the electronically submitted sequence listing (Name: 6761_0310_Sequence_Listing.txt; Size: 129 kilobytes; and Date of Creation: Apr. 12, 2022) filed with the application is incorporated herein by reference in its entirety.

BACKGROUND

A key goal in HIV vaccine design is to elicit broadly neutralizing antibodies (bnAbs). Burton & Hangartner, Annu Rev Immunol 34, 635-659 (2016). Most bnAbs to HIV-1 have been cloned from elite donors whose plasma shows broad neutralizing activity. These bnAbs target six distinct sites on the HIV-1 envelope glycoprotein (Env) spike, including the CD4-binding site (CD4bs), V2 apex, N332/V3 base supersite, silent face, gp120-gp41 interface including the fusion peptide, and membrane-proximal external region (MPER). As bnAbs arise from complex affinity maturation pathways, efforts are underway to dissect the structural and genetic bases of bnAb function to uncover common elements that can simplify vaccine design. Kwong & Mascola, Immunity 48, 855-871 (2018).

MPER bnAbs show outstanding breadth, neutralizing up to >98% primary isolates, but have uncommon features. Molinos-Albert et al., Front. Immunol. 8, 1154 (2017). MPER bnAbs are often from the IgG3 subtype, which has caused speculation that eliciting these bnAbs involves certain B cell subsets, class-switching, or a specific hinge region. Haynes B F et al., Hum. Antibodies 14, 59-67 (2005); Krebs S J, et al., Immunity 50, 677-691 e613 (2019). While 2F5, 4E10, 10E8, DH511, DH517, VRC46 and VRC43.01 are IgG3s, the MPER bnAb VRC42 was isolated as an IgG1 from the same subject as the latter two bnAbs. Krebs S J, et al., Immunity 50, 677-691 e613 (2019). Notably, long heavy complementarity-determining region (CDR) H3 loops with aromatic residues at the tip facilitate bnAb binding to the hydrophobic MPER and nearby membrane. Irimia A, et al., Immunity 44, 21-31 (2016). However, B cell receptors (BCRs) with long and hydrophobic CDRH3s tend to be down-regulated during B cell ontogeny, and some MPER bnAbs, e.g. 4E10, are mildly polyreactive. Ivanov I I, et al., J Immunol 174, 7773-7780 (2005); Haynes B F, et al., Science 308, 1906-1908 (2005). Further, 4E10 knock-in mice exhibit B cell tolerance via clonal deletion and anergy. Doyle-Cooper C, et al., J Immunol 191, 3186-3191(2013). BnAbs 10E8 and DH511 were recently shown to recognize a similar epitope as 4E10 with less polyreactivity and higher potency, but key information is missing on the precise antigens and mechanisms that drove their evolution. Huang J, et al., Nature 491, 406-412 (2012); Williams L D, et al., Sci Immunol 2, eaa12200 (2017).

The hydrophobic MPER is often truncated from Env constructs to render soluble gp140 trimers; thus, the MPER has been commonly studied in isolation. Sanders R W, et al., PLoS Pathog 9, e1003618 (2013). MPER peptide, $N^{671}WFDITNWLWYIK^{683}$ (residues 1-13 of SEQ ID NO: 146), adopts a mainly α-helical conformation with W672-D674 in a $3_{10}$ helix when bound to 4E10 and is fully helical when bound to 10E8 and DH511. Williams L D, et al., Sci Immunol 2, eaa12200 (2017); Cardoso R M, et al., Immunity 22, 163-173 (2005). However, MPER peptides constrained as an α-helix have not elicited nAbs. Molinos-Albert L M, et al., Front. Immunol. 8, 1154 (2017). One issue is that the membrane can hinder antibody access to the MPER on the virus. Irimia A, et al., Immunity 44, 21-31 (2016). Further, cryo-EM reconstructions have revealed interaction of 10E8 with N-linked glycans on membrane extracted Env at positions 88 and 625. Lee J H, et al., Science 351, 1043-1048 (2016). Thus, elicited antibodies should accommodate membrane and adjacent glycans on the Env trimer. MPER accessibility increases transiently when Env binds to CD4 receptor, just prior to co-receptor binding and virus entry into host cells, but structural details of this transient state are lacking.

Recently, vaccine design has focused on targeting common elements among certain bnAb precursors. For example, VRC01-class CD4bs antibodies typically use germline gene VH1-2, for which specific immunogens have been designed. Jardine J G, et al., Science 351, 1458-1463 (2016). Germline-encoded residues important for Env recognition by different V2 apex bnAbs have also been identified, whereas other bnAb precursors recognize a transmitted-founder (T/F) Env. Andrabi R, et al., Immunity 43, 959-973 (2015); Liao H X, et al., Nature 496, 469-476 (2013). Germline revertants of many bnAbs do not bind to Env, although some somatic hypermutations (SHM) are dispensable with 4E10 and 10E8. Klein F, et al., Cell 153, 126-138 (2013); Soto C, et al., PLoS One 11, e0157409 (2016). Interestingly, a recently described 4E10-like bnAb, VRC42, plus two other MPER bnAb lineages with limited SHM were elicited by a single T/F Env. Krebs S J, et al., Immunity 50, 677-691 e613 (2019).

Thus, there remains a need for the development of broadly neutralizing antibodies that can be used in the treatment or prevention of HIV/AIDS, and in the development of an HIV vaccines.

BRIEF SUMMARY

In one aspect, provided herein are monoclonal antibodies and antigen-binding fragments thereof that specifically bind to MPER of HIV gp41. In some embodiments, an antibody described herein is a monoclonal antibody. In some embodiments, an antibody described herein is a human antibody. In some embodiments, an antibody described herein is a broadly neutralizing antibody. In some embodiments, an antibody described herein is a bispecific antibody. In some embodiments, an antibody described herein is a trispecific antibody. In some embodiments, an antibody described herein specifically binds to MPER of HIV gp41 of at least one HIV isolate in the 130-member indicator virus panel disclosed herein. In some embodiments, an antibody described herein specifically binds the Env of at least two, at least three, at least four, or at least five HIV isolates in the 130-member indicator virus panel.

In one aspect, provided herein are pharmaceutical compositions comprising a monoclonal antibody or antigen-binding fragments thereof described herein that specifically binds to MPER of HIV gp41.

In one aspect, provided herein are isolated polynucleotides encoding a monoclonal antibody or antigen-binding fragments thereof described herein that specifically binds to MPER of HIV gp41.

In one aspect, provided herein are methods of producing a monoclonal antibody or antigen-binding fragments thereof described herein that specifically binds to MPER of HIV gp41.

In one aspect, provided herein are methods of neutralizing an HIV virus, comprising contacting the virus with a monoclonal antibody or antigen-binding fragments thereof described herein that specifically binds to MPER of HIV gp41.

In one aspect, provided herein are methods of reducing the likelihood of HIV infection in a subject exposed to HIV comprising administering to the subject a monoclonal antibody or antigen-binding fragments thereof described herein that specifically binds to MPER of HIV gp41.

In one aspect, provided herein are methods of treating HIV/AIDS comprising administering to a subject in need thereof a monoclonal antibody or antigen-binding fragments thereof described herein that specifically binds to MPER of HIV gp41.

In one aspect, provided herein are methods of reducing viral load comprising administering to a subject in need thereof a monoclonal antibody or antigen-binding fragments thereof described herein that specifically binds to MPER of HIV gp41.

In one aspect, provided herein are methods of producing an engineered variant of a monoclonal antibody or antigen-binding fragments thereof described herein that specifically binds to MPER of HIV gp41.

In one aspect, provided herein are methods of identifying an agent as an HIV vaccine candidate comprising vaccine candidate, comprising contacting the protein with an antibody or antigen-binding fragment thereof described herein under conditions sufficient to form an immune complex and detecting the presence of the immune complex.

In some embodiments, the disclosure provides:

[1.] An isolated monoclonal antibody or antigen-binding fragment thereof that is capable of binding HIV Env MPER and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of any of the VH regions shown in Table 1;

[2.] an isolated monoclonal antibody or antigen-binding fragment thereof or antigen-binding fragment thereof that is capable of binding HIV Env MPER and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of PGZL1 VH, PGZL1.H4K3 VH, or PGZL1_gVmDmJ VH;

[3.] an isolated monoclonal antibody or antigen-binding fragment thereof that is capable of binding HIV Env MPER and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to a VH CDR3 shown in Table 2;

[4.] an isolated monoclonal antibody or antigen-binding fragment thereof that is capable of binding HIV Env MPER and comprises a VH CDR1, VH CDR2, VH CDR3, VL CDR1, VL CDR2, and VL CDR3, wherein the VH CDR3 comprises the VH CDR3 of any of the VH regions shown in Table 1 comprising 0, 1, 2, 3, 4, or 5 substitutions, insertions, or deletions;

[5.] an isolated monoclonal antibody or antigen-binding fragment thereof that is capable of binding HIV Env MPER and comprises a VH CDR1, VH CDR2, VH CDR3, VL CDR1, VL CDR2, and VL CDR3, wherein the VH CDR3 comprises the VH CDR3 of PGZL1 VH, PGZL1.H4K3 VH, or PGZL1_gVmDmJ VH comprising 0, 1, 2, 3, 4, or 5 substitutions, insertions, or deletions;

[6.] an isolated monoclonal antibody or antigen-binding fragment thereof that is capable of binding HIV Env MPER and comprises a VH CDR1, VH CDR2, VH CDR3, VL CDR1, VL CDR2, and VL CDR3, wherein the VH CDR3 comprises a VH CDR3 shown in Table 2 comprising 0, 1, 2, 3, 4, or 5 substitutions, insertions, or deletions;

[7.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises an amino acid sequence that is at least about 90%, 95%, 97%, 98%, 99% or 100% identical to the VH CDR1 of any of the VH regions shown in Table 1;
(b) the VH CDR2 comprises an amino acid sequence that is at least about 90%, 95%, 97%, 98%, 99% or 100% identical to the VH CDR2 of any of the VH regions shown in Table 1; and
(c) the VH CDR3 comprises an amino acid sequence that is at least about 90%, 95%, 97%, 98%, 99% or 100% identical to the VH CDR3 of any of the VH regions shown in Table 1;

[8.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein
(a) the VH CDR1 comprises an amino acid sequence that is at least about 90%, 95%, 97%, 98%, 99% or 100% identical to the VH CDR1 of PGZL1 VH, PGZL1.H4K3 VH, or PGZL1_gVmDmJ VH;
(b) the VH CDR2 comprises an amino acid sequence that is at least about 90%, 95%, 97%, 98%, 99% or 100% identical to the VH CDR2 of PGZL1 VH, PGZL1.H4K3 VH, or PGZL1_gVmDmJ VH; and (c) the VH CDR3 comprises an amino acid sequence that is at least about 90%, 95%, 97%, 98%, 99% or 100% identical to the VH CDR3 of PGZL1 VH, PGZL1.H4K3 VH, or PGZL1_gVmDmJ VH;

[9.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein
  (a) the VH CDR1 comprises an amino acid sequence that is at least about 90%, 95%, 97%, 98%, 99% or 100% identical to a VH CDR1 shown in Table 2;
  (b) the VH CDR2 comprises an amino acid sequence that is at least about 90%, 95%, 97%, 98%, 99% or 100% identical to a VH CDR2 shown in Table 2; and
  (c) the VH CDR3 comprises an amino acid sequence that is at least about 90%, 95%, 97%, 98%, 99% or 100% identical to a VH CDR3 shown in Table 2;

[10.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein
  (a) the VH CDR1 comprises the VH CDR1 of any of the VH regions shown in Table 1 comprising 0, 1, 2, 3, 4, or 5 substitutions, insertions, or deletions;
  (b) the VH CDR2 comprises the VH CDR2 of any of the VH regions shown in Table 1 comprising 0, 1, 2, 3, 4, or 5 substitutions, insertions, or deletions; and
  (c) the VH CDR3 comprises the VH CDR3 of any of the VH regions shown in Table 1 comprising 0, 1, 2, 3, 4, or 5 substitutions, insertions, or deletions;

[11.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein
  (a) the VH CDR1 comprises the VH CDR1 of PGZL1 VH, PGZL1.H4K3 VH, or PGZL1_gVmDmJ VH comprising 0, 1, 2, 3, 4, or 5 substitutions, insertions, or deletions;
  (b) the VH CDR2 comprises the VH CDR2 of PGZL1 VH, PGZL1.H4K3 VH, or PGZL1_gVmDmJ VH comprising 0, 1, 2, 3, 4, or 5 substitutions, insertions, or deletions; and
  (c) the VH CDR3 comprises the VH CDR3 of PGZL1 VH, PGZL1.H4K3 VH, or PGZL1_gVmDmJ VH comprising 0, 1, 2, 3, 4, or 5 substitutions, insertions, or deletions;

[12.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein
  (a) the VH CDR1 comprises a VH CDR1 shown in Table 2 comprising 0, 1, 2, 3, 4, or 5 substitutions, insertions, or deletions;
  (b) the VH CDR2 comprises a VH CDR2 shown in Table 2 comprising 0, 1, 2, 3, 4, or 5 substitutions, insertions, or deletions; and
  (c) the VH CDR3 comprises a VH CDR3 shown in Table 2 comprising 0, 1, 2, 3, 4, or 5 substitutions, insertions, or deletions;

[13.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein
  (a) the VH CDR1 comprises the VH CDR1 of any of the VH regions shown in Table 1;
  (b) the VH CDR2 comprises the VH CDR2 of any of the VH regions shown in Table 1; and
  (c) the VH CDR3 comprises the VH CDR3 of any of the VH regions shown in Table 1;

[14.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein
  (a) the VH CDR1 comprises the VH CDR1 of PGZL1 VH, PGZL1.H4K3 VH, or PGZL1_gVmDmJ VH;
  (b) the VH CDR2 comprises the VH CDR2 of PGZL1 VH, PGZL1.H4K3 VH, or PGZL1_gVmDmJ VH; and
  (c) the VH CDR3 comprises the VH CDR3 of PGZL1 VH, PGZL1.H4K3 VH, or PGZL1_gVmDmJ VH;

[15.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein
  (a) the VH CDR1 comprises a VH CDR1 shown in Table 2;
  (b) the VH CDR2 comprises a VH CDR2 shown in Table 2; and
  (c) the VH CDR3 comprises a VH CDR3 shown in Table 2;

[16.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, and VH CDR3 comprises the VH CDR1, VH CDR2, and VH CDR3 of any of the VH regions shown in Table 1;

[17.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, and VH CDR3 comprises the VH CDR1, VH CDR2, and VH CDR3 of PGZL1 VH, PGZL1.H4K3 VH, or PGZL1_gVmDmJ VH;

[18.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, and VH CDR3 comprises a set of VH CDR1, VH CDR2, and VH CDR3 shown in Table 2;

[19.] The isolated monoclonal antibody or antigen-binding fragment thereof of any one of [1] to [18], wherein (a) the VL CDR1 comprises an amino acid sequence that is at least about 90%, 95%, 97%, 98%, 99% or 100% identical to the VL CDR1 of any of the VL regions shown in Table 1;

(b) the VL CDR2 comprises an amino acid sequence that is at least about 90%, 95%, 97%, 98%, 99% or 100% identical to the VL CDR2 of any of the VL regions shown in Table 1; and (c) the VL CDR3 comprises an amino acid sequence that is at least about 90%, 95%, 97%, 98%, 99% or 100% identical to the VL CDR3 of any of the VL regions shown in Table 1;

[20.] the isolated monoclonal antibody or antigen-binding fragment thereof of any one of [1] to [18], wherein (a) the VL CDR1 comprises an amino acid sequence that is at least about 90%, 95%, 97%, 98%, 99% or 100% identical to the VL CDR1 of PGZL1 VL, PGZL1.H4K3 VL, or PGZL1_gVmDmJ VL;

(b) the VL CDR2 comprises an amino acid sequence that is at least about 90%, 95%, 97%, 98%, 99% or 100% identical to the VL CDR2 of PGZL1 VL, PGZL1.H4K3 VL, or PGZL1_gVmDmJ VL; and (c) the VL CDR3 comprises an amino acid sequence that is at least about 90%, 95%, 97%, 98%, 99% or 100% identical to the VL CDR3 of PGZL1 VL, PGZL1.H4K3 VL, or PGZL1_gVmDmJ VL;

[21.] the isolated monoclonal antibody or antigen-binding fragment thereof of any one of [1] to [18], wherein (a) the VL CDR1 comprises an amino acid sequence that is at least about 90%, 95%, 97%, 98%, 99% or 100% identical to a VL CDR1 shown in Table 2;

(b) the VL CDR2 comprises an amino acid sequence that is at least about 90%, 95%, 97%, 98%, 99% or 100% identical to a VL CDR2 shown in Table 2; and (c) the VL CDR3 comprises an amino acid sequence that is at least about 90%, 95%, 97%, 98%, 99% or 100% identical to a VL CDR3 shown in Table 2;

[22.] the isolated monoclonal antibody or antigen-binding fragment thereof of any one of [1] to [18], wherein (a) the VL CDR1 comprises the VL CDR1 of any of the VL regions shown in Table 1 comprising 0, 1, 2, 3, 4, or 5 substitutions, insertions, or deletions;

(b) the VL CDR2 comprises the VL CDR2 of any of the VL regions shown in Table 1 comprising 0, 1, 2, 3, 4, or 5 substitutions, insertions, or deletions; and (c) the VL CDR3 comprises the VL CDR3 of Any of the VL regions shown in Table 1 comprising 0, 1, 2, 3, 4, or 5 substitutions, insertions, or deletions;

[23.] the isolated monoclonal antibody or antigen-binding fragment thereof of any one of [1] to [18], wherein (a) the VL CDR1 comprises the VL CDR1 of PGZL1 VL, PGZL1.H4K3 VL, or PGZL1_gVmDmJ VL comprising 0, 1, 2, 3, 4, or 5 substitutions, insertions, or deletions;

(b) the VL CDR2 comprises the VL CDR2 of PGZL1 VL, PGZL1.H4K3 VL, or PGZL1_gVmDmJ VL comprising 0, 1, 2, 3, 4, or 5 substitutions, insertions, or deletions; and (c) the VL CDR3 comprises the VL CDR3 of PGZL1 VL, PGZL1.H4K3 VL, or PGZL1_gVmDmJ VL comprising 0, 1, 2, 3, 4, or 5 substitutions, insertions, or deletions;

[24.] the isolated monoclonal antibody or antigen-binding fragment thereof of any one of [1] to [18], wherein (a) the VL CDR1 comprises a VL CDR1 shown in Table 2 comprising 0, 1, 2, 3, 4, or 5 substitutions, insertions, or deletions;

(b) the VL CDR2 comprises a VL CDR2 shown in Table 2 comprising 0, 1, 2, 3, 4, or 5 substitutions, insertions, or deletions; and (c) the VL CDR3 comprises a VL CDR3 shown in Table 2 comprising 0, 1, 2, 3, 4, or 5 substitutions, insertions, or deletions;

[25.] the isolated monoclonal antibody or antigen-binding fragment thereof of any one of [1] to [18], wherein (a) the VL CDR1 comprises the VL CDR1 of any of the VL regions shown in Table 1;

(b) the VL CDR2 comprises the VL CDR2 of any of the VL regions shown in Table 1; and (c) the VL CDR3 comprises the VL CDR3 of any of the VL regions shown in Table 1;

[26.] the isolated monoclonal antibody or antigen-binding fragment thereof of any one of [1] to [18], wherein (a) the VL CDR1 comprises the VL CDR1 of PGZL1 VL, PGZL1.H4K3 VL, or PGZL1_gVmDmJ VL;

(b) the VL CDR2 comprises the VL CDR2 of PGZL1 VL, PGZL1.H4K3 VL, or PGZL1_gVmDmJ VL; and (c) the VL CDR3 comprises the VL CDR3 of PGZL1 VL, PGZL1.H4K3 VL, or PGZL1_gVmDmJ VL;

[27.] the isolated monoclonal antibody or antigen-binding fragment thereof of any one of [1] to [18], wherein (a) the VL CDR1 comprises a VL CDR1 shown in Table 2;

(b) the VL CDR2 comprises a VL CDR2 shown in Table 2; and (c) the VL CDR3 comprises a VL CDR3 shown in Table 2;

[28.] the isolated monoclonal antibody or antigen-binding fragment thereof of any one of [1] to [18], wherein the VL CDR1, VL CDR2, and VL CDR3 comprises the VL CDR1, VL CDR2, and VL CDR3 of any of the VL regions shown in Table 1;

[29.] the isolated monoclonal antibody or antigen-binding fragment thereof of any one of [1] to [18], wherein the VL CDR1, VL CDR2, and VL CDR3 comprises the VL CDR1, VL CDR2, and VL CDR3 of PGZL1 VL, PGZL1.H4K3 VL, or PGZL1_gVmDmJ VL;

[30.] the isolated monoclonal antibody or antigen-binding fragment thereof of any one of [1] to [18], wherein the VL CDR1, VL CDR2, and VL CDR3 comprises a set of VL CDR1, VL CDR2, and VL CDR3 shown in Table 2;

[31.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PGZL1, PGZL1.H4K3, or PGZL1_gVmDmJ VH CDR1, VH CDR2, VH CDR3, VL CDR1, VL CDR2, and VL CDR3, respectively;

[32.] an isolated monoclonal antibody or antigen-binding fragment thereof that is capable of binding HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PGZL1, PGZL1.H4K3, or PGZL1_gVmDmJ VH CDR1, VH CDR2, VH CDR3, VL CDR1, VL CDR2, and VL CDR3, respectively, as shown in Table 2;

[33.] the isolated monoclonal antibody or antigen-binding fragment thereof of any one of [1] to [32], wherein the VH comprises the VH FR1, VH FR2, VH FR3, and VH FR4 of any of the VH regions shown in Table 1;

[34.] the isolated monoclonal antibody or antigen-binding fragment thereof of any one of [1] to [32], wherein the VH comprises the VH FR1, VH FR2, VH FR3, and VH FR4 of PGZL1 VH, PGZL1.H4K3 VH, or PGZL1_gVmDmJ VH;

[35.] the isolated monoclonal antibody or antigen-binding fragment thereof of any one of [1] to [32], wherein the VH comprises a set of VH FR1, VH FR2, VH FR3, and VH FR4 shown in Table 3;

[36.] the isolated monoclonal antibody or antigen-binding fragment thereof of any one of [1] to [35], wherein the VL comprises the VL FR1, VL FR2, VL FR3, and VL FR4 of any of the VL regions shown in Table 1;

[37.] the isolated monoclonal antibody or antigen-binding fragment thereof of any one of [1] to [35], wherein the VL comprises the VL FR1, VL FR2, VL FR3, and VL FR4 GZL1 VL, PGZL1.H4K3 VL, or PGZL1_gVmDmJ VL;

[38.] the isolated monoclonal antibody or antigen-binding fragment thereof of any one of [1] to [35], wherein the VL comprises a set of VL FR1, VL FR2, VL FR3, and VL FR4 shown in Table 3;

[39.] the isolated monoclonal antibody or antigen-binding fragment thereof of any one of [1] to [38], wherein the VH comprises any of the VH regions shown in Table 1;

[40.] the isolated monoclonal antibody or antigen-binding fragment thereof of any one of [1] to [38], wherein the VH comprises PGZL1 VH, PGZL1.H4K3 VH, or PGZL1_gVmDmJ VH;

[41.] the isolated monoclonal antibody or antigen-binding fragment thereof of any one of [1] to [40], wherein the VL comprises any of the VL regions shown in Table 1;

[42.] the isolated monoclonal antibody or antigen-binding fragment thereof of any one of [1] to [40], wherein the VL comprises PGZL1 VL, PGZL1.H4K3 VL, or PGZL1_gVmDmJ VL;

[43.] an isolated monoclonal antibody or antigen-binding fragment thereof that is capable of binding HIV Env MPER and comprises a heavy chain variable region (VH) and a light chain variable region (VL), wherein the VH comprises an amino acid sequence that is at least about 90%, 95%, 97%, 98%, 99% or 100% identical to any of the VH regions shown in Table 1;

[44.] an isolated monoclonal antibody or antigen-binding fragment thereof that is capable of binding HIV Env MPER and comprises a heavy chain variable region (VH) and a light chain variable region (VL), wherein the VH comprises an amino acid sequence that is at least about 90%, 95%, 97%, 98%, 99% or 100% identical to the PGZL1 VH, PGZL1.H4K3 VH, or PGZL1_gVmDmJ VH;

[45.] the isolated monoclonal antibody or antigen-binding fragment thereof of any one of [43] to [44], wherein the VH CDR1, VH CDR2, and VH CDR3 comprise the VH CDR1, VH CDR2, and VH CDR3, respectively, of any of the VH regions shown in Table 1;

[46.] the isolated monoclonal antibody or antigen-binding fragment thereof of any one of [43] to [44], wherein the VH CDR1, VH CDR2, and VH CDR3 comprise the VH CDR1, VH CDR2, and VH CDR3, respectively, of PGZL1 VH, PGZL1.H4K3 VH, or PGZL1_gVmDmJ VH;

[47.] the isolated monoclonal antibody or antigen-binding fragment thereof of any one of [43] to [44], wherein the VH CDR1, VH CDR2, and VH CDR3 comprise a set of VH CDR1, VH CDR2, and VH CDR3 shown in Table 2;

[48.] the isolated monoclonal antibody or antigen-binding fragment thereof of any one of [43] to [47], wherein the VL comprises an amino acid sequence that is at least about 90%, 95%, 97%, 98%, 99% or 100% identical to any of the VL regions shown in Table 1;

[49.] the isolated monoclonal antibody or antigen-binding fragment thereof of any one of [43] to [47], wherein the VL comprises an amino acid sequence that is at least about 90%, 95%, 97%, 98%, 99% or 100% identical to the VL of PGZL1 VL, PGZL1.H4K3 VL, or PGZL1_gVmDmJ VL;

[50.] the isolated monoclonal antibody or antigen-binding fragment thereof of any one of [43] to [49], wherein the VL CDR1, VL CDR2, and VL CDR3 comprise the VL CDR1, VL CDR2, and VL CDR3, respectively, of any of the VL regions shown in Table 1;

[51.] the isolated monoclonal antibody or antigen-binding fragment thereof of any one of [44] to [49], wherein the VL CDR1, VL CDR2, and VL CDR3 comprise the VL CDR1, VL CDR2, and VL CDR3, respectively, of PGZL1 VL, PGZL1.H4K3 VL, or PGZL1_gVmDmJ VL;

[52.] the isolated monoclonal antibody or antigen-binding fragment thereof of any one of [43] to [49], wherein the VL CDR1, VL CDR2, and VL CDR3 comprise a set of VL CDR1, VL CDR2, and VL CDR3, respectively, shown in Table 2;

[53.] an isolated monoclonal antibody or antigen-binding fragment thereof that is capable of binding HIV Env MPER and comprises a heavy chain variable region (VH) and a light chain variable region (VL), wherein the VH comprises an amino acid sequence that is at least about 90%, 95%, 97%, 98%, 99% or 100% identical to any of the VH regions shown in Table 1 and the VL comprises an amino acid sequence that is at least about 90%, 95%, 97%, 98%, 99% or 100% identical to any of the VH regions shown in Table 1;

[54.] an isolated monoclonal antibody or antigen-binding fragment thereof that is capable of binding HIV Env MPER and comprises a heavy chain variable region (VH) and a light chain variable region (VL), wherein the VH comprises an amino acid sequence that is at least about 90%, 95%, 97%, 98%, 99% or 100% identical to PGZL1 VH, PGZL1.H4K3 VH, or PGZL1_gVmDmJ VH and the VL comprises an amino acid sequence that is at least about 90%, 95%, 97%, 98%, 99% or 100% identical to PGZL1 VL, PGZL1.H4K3 VL, or PGZL1_gVmDmJ VL;

[55.] an isolated monoclonal antibody or antigen-binding fragment thereof that is capable of binding HIV Env MPER and comprises a heavy chain variable region (VH) and a light chain variable region (VL), wherein the VH and VL comprise an amino acid sequence that is at least about 90%, 95%, 97%, 98%, 99% or 100% identical to PGZL1 VH and VL, PGZL1.H4K3 VH and VL, or PGZL1_gVmDmJ VH and VL, respectively;

[56.] the isolated monoclonal antibody or antigen-binding fragment thereof of any one of [53] to [55], wherein the VH CDR1, VH CDR2, VH CDR3, VL CDR1, VL CDR2, and VL CDR3 comprise the VH CDR1, VH CDR2, VH CDR3, VL CDR1, VL CDR2, and VL CDR3, respectively, of any of the VH and VL regions shown in Table 1;

[57.] the isolated monoclonal antibody or antigen-binding fragment thereof of any one of [53] to [55], wherein the VH CDR1, VH CDR2, VH CDR3, VL CDR1, VL CDR2, and VL CDR3 comprise the VH CDR1, VH CDR2, VH CDR3, VL CDR1, VL CDR2, and VL CDR3, respectively, of PGZL1, PGZL1.H4K3, or PGZL1_gVmDmJ;

[58.] the isolated monoclonal antibody or antigen-binding fragment thereof of any one of [53] to [55], wherein the VH CDR1, VH CDR2, VH CDR3, VL CDR1, VL CDR2, and VL CDR3 comprise a set of VH CDR1, VH CDR2, VH CDR3, VL CDR1, VL CDR2, and VL CDR3, respectively, shown in Table 2;

[59.] an isolated monoclonal antibody or antigen-binding fragment thereof that is capable of binding HIV Env MPER and comprises a heavy chain variable region (VH) and a light chain variable region (VL), wherein the VH comprises any of the VH regions shown in Table 1 and the VL comprises any of the VH regions shown in Table 1;

[60.] an isolated monoclonal antibody or antigen-binding fragment thereof that is capable of binding HIV Env MPER and comprises a heavy chain variable region (VH) and a light chain variable region (VL), wherein the VH comprises PGZL1 VH, PGZL1.H4K3 VH, or PGZL1_gVmDmJ VH and the VL comprises PGZL1 VL, PGZL1.H4K3 VL, or PGZL1_gVmDmJ VL;

[61.] an isolated monoclonal antibody or antigen-binding fragment thereof that is capable of binding HIV Env MPER and comprises a heavy chain variable region (VH) and a light chain variable region (VL), wherein the VH and VL comprise PGZL1 VH and VL, PGZL1.H4K3 VH and VL, or PGZL1_gVmDmJ VH and VL;

[62.] the isolated antibody of any one of [1] to [61], wherein the antibody is not PGZL1, or PGZL1.H4K3;

[63.] the monoclonal antibody or antigen-binding fragment thereof of any one of [1] to [62], further comprising a heavy and/or light chain constant region;

[64.] the monoclonal antibody or antigen-binding fragment thereof of any one of [1] to [62], further comprising a human heavy and/or light chain constant region;

[65.] the monoclonal antibody or antigen-binding fragment thereof of [63] or [64], wherein the heavy chain constant region is selected from the group consisting of a human immunoglobulin IgG1, IgG2, IgG3, IgG4, IgA1, and IgA2 constant region;

[66.] the monoclonal antibody or antigen-binding fragment thereof of any one of [63] to [65], wherein the heavy chain constant region comprises a native amino acid sequence;

[67.] the antibody of any one of [63] to [65], wherein the heavy chain constant region comprises a non-native variant amino acid sequence;

[68.] the isolated monoclonal antibody or antigen-binding fragment thereof of any one of [1] to [67], wherein the antibody is a recombinant antibody, a chimeric antibody, a human antibody, an antibody fragment, a bispecific antibody, or a trispecific antibody;

[69.] the isolated monoclonal antibody or antigen-binding fragment thereof of [68], wherein the antibody fragment comprises a single-chain Fv (scFv), Fab fragment, F(ab')2 fragment, or an isolated VH domain;

[70.] the antibody or antigen-binding fragment thereof of any one of [1] to [67], wherein the antibody is a bispecific antibody;

[71.] the antibody or antigen-binding fragment thereof of any one of [1] to [67], wherein the antibody is a trispecific antibody;

[72.] the antibody or antigen-binding fragment thereof of any one of [1] to [71], which is capable of competing with PGZL1, PGZL1.H4K3 VH, or PGZL1_gVmDmJ for binding to the HIV Env MPER;

[73.] the antibody or antigen-binding fragment thereof of any one of [1] to [71], which binds to the same epitope(s) of the HIV Env MPER as PGZL1, PGZL1.H4K3 VH, or PGZL1_gVmDmJ;

[74.] the antibody or antigen-binding fragment thereof of any one of [1] to [73], wherein the HIV Env MPER comprises the amino acid sequence of DLLA-LDRWQNLWNWFDITNWLWYIK (SEQ ID NO: 2);

[75.] the antibody or antigen-binding fragment thereof of any one of [1] to [73] that is capable of binding
  (a) cells that express well-ordered HIV-1 membrane Env trimers;
  (b) cells that display MPER-TM peptide;
  (c) MPER peptide; and/or
  (d) Env trimers from detergent-solubilized HIV-1 virions;
  optionally wherein the MPER comprises the amino acid sequence of DLLA-LDRWQNLWNWFDITNWLWYIK (SEQ ID NO: 2);

[76.] the antibody or antigen-binding fragment thereof of any one of [1] to [73], wherein the antibody is capable of neutralizing at least two cross-clade isolates of HIV;

[77.] the antibody or antigen-binding fragment thereof of any one of [1] to [73], wherein the antibody is capable of neutralizing at least one clade A HIV isolate, at least one clade B HIV isolate, and at least one clade C HIV isolate;

[78.] the antibody or antigen-binding fragment thereof of [77], wherein the antibody is capable of neutralizing at least about 40%, 50%, 60%, 70%, 80%, 90%, or 100% of cross-clade HIV isolates in the 130-member indicator virus panel;

[79.] the antibody or antigen-binding fragment thereof of [78], wherein the antibody is capable of neutralizing the cross-clade HIV isolates with a median IC50 equal to or less than about 2 µg/ml, about 1.5 µg/ml, about 1 µg/ml, about 0.8 µg/ml, 0.5 µg/ml, or 0.3 µg/ml;

[80.] a pharmaceutical composition comprising the antibody or antigen-binding fragment thereof of any one of [1] to [79] and a pharmaceutically acceptable excipient;

[81.] an isolated polynucleotide encoding the antibody or antigen-binding fragment thereof of any one of [1] to [79];

[82.] the isolated polynucleotide of [81], which is a DNA;

[83.] the isolated polynucleotide of [81], which is an mRNA;

[84.] the isolated polynucleotide of [83], wherein the mRNA comprises a modified nucleotide;

[85.] an isolated vector comprising the polynucleotide of [81];

[86.] the isolated vector of [81], wherein the vector is a viral vector;

[87.] a recombinant virus comprising the polynucleotide of [81];

[88.] the recombinant virus of [87], which is a recombinant adeno-associated virus (AAV);

[89.] a host cell comprising the polynucleotide of [81] or the vector of [86];

[90.] the host cell of [89], which is *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, or human cell in tissue culture;

[91.] a method of producing the antibody or antigen-binding fragment thereof of any one of [1] to [79] comprising culturing the host cell of [89] or [90] so that the antibody or antigen-binding fragment thereof is expressed and the antibody or antigen-binding fragment thereof is produced;

[92.] a method of neutralizing an HIV virus comprising contacting the virus with a sufficient amount of the antibody or antigen-binding fragment thereof of any one of [1] to [79];

[93.] a method of reducing the likelihood of HIV infection in a subject exposed to HIV comprising administering to the subject a therapeutically sufficient amount of the antibody or antigen-binding fragment thereof of any one of [1] to [79];

[94.] a method of treating HIV/AIDS comprising administering to a subject in need thereof a therapeutically sufficient amount of the antibody or antigen-binding fragment thereof of any one of [1] to [79];

[95.] a method of reducing viral load comprising administering to a subject in need thereof a therapeutically sufficient amount of the antibody or antigen-binding fragment thereof of any one of [1] to [79];

[96.] the method of [93] to [95], wherein the administering to the subject is by at least one mode selected from oral, parenteral, subcutaneous, intramuscular, intravenous, vaginal, rectal, buccal, sublingual, and transdermal;

[97.] the method of any one of [93] to [96], further comprising administering at least one additional therapeutic agent;

[98.] the method of [97], wherein the additional therapeutic agent is an antiretroviral agent, a reservoir activator, or a second antibody;

[99.] the method of [97], wherein the additional therapeutic agent comprises a broadly neutralizing antibody;

[100.] the method of [97], wherein the additional therapeutic agent comprises two broadly neutralizing antibodies;

[101.] the method of [97], wherein the additional therapeutic agent comprises three broadly neutralizing antibodies;

[102]. a method for detecting HIV in a sample comprising contacting the sample with the antibody of any one of [1] to [79];

[103.] a method of purifying HIV from a sample comprising contacting the sample with the antibody of any one of [1] to [79];

[104.] A kit comprising the antibody of any one of [1] to [79], or the pharmaceutical composition of [80 and a) a detection reagent, b) an HIV antigen, c) a notice that reflects approval for use or sale for human administration, or d) any combination thereof;

[105.] a method of producing an engineered variant of an antibody of any one of [1] to [79] comprising (a) substituting one or more amino acid residues of the VH; and/or substituting one or more amino acid residues of the VL to create an engineered variant antibody, and (b) producing the engineered variant antibody;

[106.] the method of [105] wherein the antibody is PGZL1 or PGZL.H4K3;

[107.] a method of identifying an agent as an HIV vaccine candidate comprising:

(a) contacting the agent with an antibody or antigen-binding fragment thereof of any one of [1] to [79] under conditions sufficient to form an immune complex, and (b) detecting the presence of the immune complex, wherein the presence of the immune complex indicates that the agent is a vaccine candidate;

[108.] the method of [107] wherein the antibody is PGZL1_gVmDmJ;

[109.] the method of [107] wherein the antibody is PGZL1_gVgDgJ.

BRIEF DESCRIPTION OF THE DRAWINGS

FIG. 6. MPER-induced PO4 Binding Site of H4K3, Lipid Site Mutants Characterization and Distribution of Charge on the PGZL1 Variants Surface. (A, B) Stick rendering of the PO4 binding site in (A) H4K3, and (B) PGZL1. The side chain at LC position 50 in each antibody is surrounded by dots. Select HC residues of the two antibodies are shown in blue (A) and green (B) and the LC in brown. The MPER is shown as a pink ribbon. (C) BLI binding kinetics of H4K3 lipid binding site mutants to immobilized MPER peptide. (D) ELISA binding of H4K3 lipid binding site mutants to MPER peptide and neutralization (log $IC_{50}$) of HxB2 and Du156.12. (E) BLI, ELISA and neutralization statistics. (F-I) Surface rendering, along the MPER helical axis (red ribbon), of the solvent accessible electrostatic potential contoured at ±5 kT/e for (F) PGZL1 gVmDmJ, (G) PGZL1, (H) H4K3 and (I) 4E10. Observed lipid fragments and anions are shown as sticks.

FIG. 7. Amino-acid sequence and calculated lipid inser-tion propensity of MPER bnAbs. (A) Amino-acid alignment of PGZL1 gVmDmJ, PGZL1, H4K3, 4E10 and VRC42.01. Amino acid residues are colored by their physico-chemical properties: pink, aliphatic; orange, aromatic; magenta, Gly and Pro; yellow, Cys; green, hydrophilic; red, acidic; blue, basic. The CDRs are indicated according to Kabat. Sequences shown are QVQLVQS-GAEVKKPGSSVKVSCK-ASGGTFSSYAISWVRQAPGQGLEWMGGIIPIFGTAN YAQKFQGRVTITADKSTSTAYMELSSLRSEDTAVYY-CAR (SEQ ID NO: 159), VLLWFGELL (SEQ ID NO: 160), DAFDVW (SEQ ID NO: 161), EIVLTQSPGTLSLSPGER-ATLSCRASQSVSSSYLAWYQQKPGQAPRLLIY-GASSRATGIPD RFSGSGSGTDFTLTISRLEPED-FAVYYC (SEQ ID NO: 162), GWFGKPLRAFEF (SEQ ID NO: 163), GQGTVITVSS (SEQ ID NO: 164), GWFGR-PLRAFEF (SEQ ID NO: 165), EGTTGWGWLGKPIGA-FAH (SEQ ID NO: 166), GWFGKPVGAMGY (SEQ ID NO: 167), LVSST (SEQ ID NO: 168), LLTIT (SEQ ID NO: 169), QQYGTSQSTFGQGTRLEIKR (SEQ ID NO: 170), QQYGTSQST (SEQ ID NO: 171), QQYGQSLST (SEQ ID NO: 172), QQYGGSFGT (SEQ ID NO: 173), and GNNK (SEQ ID NO: 174). (B) Lipid insertion propensity plots of the four antibodies for the heavy chains (top panel) and light chains (bottom panel). Lipid insertion property was calcu-lated using the Wimley-White lipid interface hydropathy scale as computed with MPEx software; curve smoothing utilized the default window size of 19 amino acids.

FIG. 8. Unbiased B cell repertoire profiles of donor PG13 at three time points. Distributions are plotted. (A) Germline V gene usage for heavy and light (κ and λ) chains. (B) Germline gene divergence, or degree of SHM. (C) CDR3 loop length (H, heavy chain; K, κ chain; L, λ chain). Color coding denotes the time point analyzed, with sample visits V2 shown in blue, V4 in green, and V6 in orange.

FIG. 9. Neutralization of HIV-1 by PGZL1 recombinant antibodies selected from NGS lineage analysis of the Donor PG13 antibody repertoire. (A) Details of bioinformatics procedure used for selecting PGZL1-like sequences. (B) Scatter plots showing neutralization ($IC_{50}$) of HIV-1 isolate Du156.12 vs SHM (nucleotide level, nt %) with heavy chains (HC) that were initially paired with the wild-type PGZL1 light chain (left panel). From this screen, the heavy chains that yielded the highest neutralization potency, H4 and H8, were subsequently paired with a panel of light chains (LC) and subsequently assayed for neutralization of HIV-1 isolate 92TH021 (right panel). (C) Neutralization curves of 92TH021 and Du156.12 by PGZL1 and NGS recombinant variants are shown on the left and middle panels, respectively. On the right panel, log $IC_{50}$s are plotted for each antibody against the 6-isolate cross-clade panel. (D) Correlation of neutralization ($IC_{50}$ s) against a 130-member panel of HIV isolates comparing PGZL1 and H4K3 (left panel), PGZL1 and PGZL1 gVmDmJ (middle panel), as well as PGZL1 and 4E10 (right panel).

DETAILED DESCRIPTION

Figure 1:
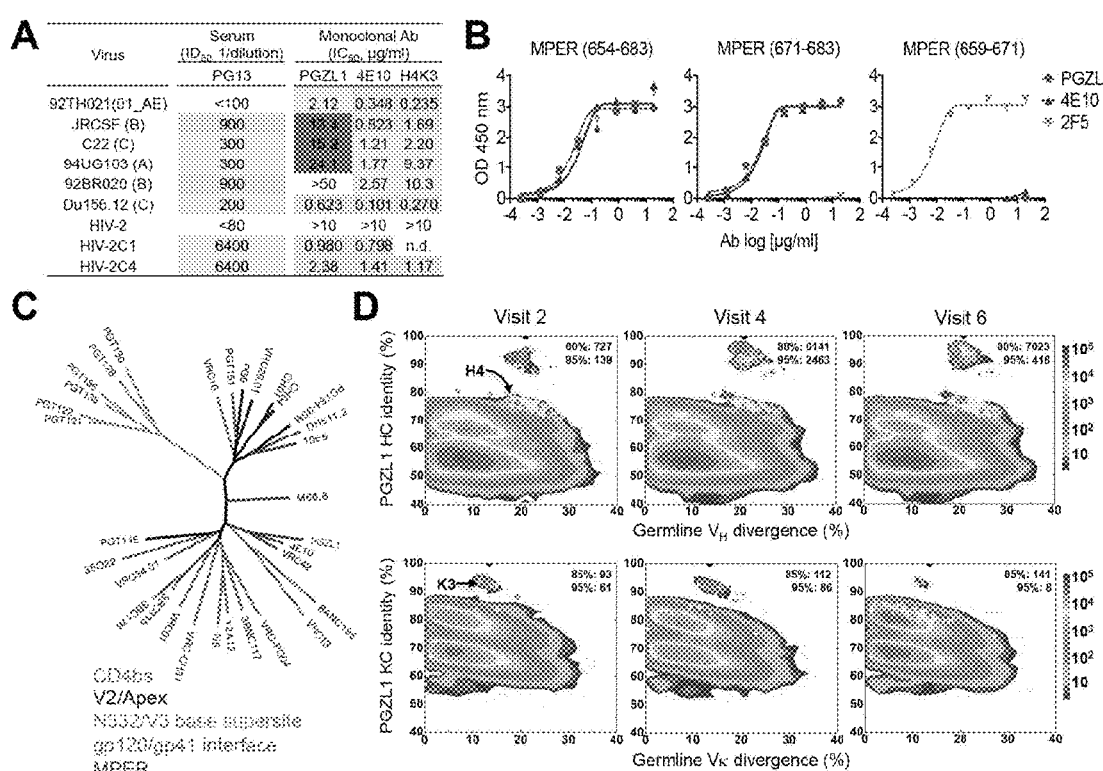
FIG. 1. Properties of an MPER-targeted bnAb. (A) Neutralization of HIV-1 6-virus panel and HIV-2 (HIV-1 MPER) chimeras by PG13 plasma as well as monoclonal antibodies PGZL1, 4E10 and H4K3. (B) ELISA binding of PGZL1 to MPER peptides, using 4E10 and 2F5 as controls. (C) Maximum likelihood (ML) tree of HC variable regions of described bnAbs, colored by Env specificity. (D) Divergence/identity analysis of donor PG13 antibody repertoire over 3 visits in 9 months. NGS-derived antibody chains are plotted as a function of sequence identity to PGZL1 and divergence from their putative germline genes. Colors indicate sequence density. Sequences with a CDR3 identity of ≥80/85% (HC/KC) and with a CDR3 identity of ≥95% are shown as yellow and orange dots on the 2D plots, with the number of sequences highlighted in yellow and orange shades, respectively. Sequences bioinformatically selected for synthesis are shown as magenta stars on the 2D plots, with the number of sequences ("Syn") highlighted in magenta shade. (E-F) Neutralization breadth and potency of PGZL1 and H4K3 against a 130-virus panel (E), and the same data as in panel E but subdivided by HIV subtype (F). Sequences shown are EGEGWFGKPLRAFEF (SEQ ID NO: 63), EGEGWFGRPLRAFEF (SEQ ID NO: 66), EGTTGWGWLGKPIGAFAH (SEQ ID NO: 125); GKNC-DYNWDFEH (SEQ ID NO: 147).

The membrane-proximal external region (MPER) of HIV-1 envelope glycoprotein can be targeted by neutralizing antibodies of exceptional breadth. Such antibodies usually have long, hydrophobic CDRH3s, lack activity as inferred germline precursors, are often from the minor IgG3 subclass, and some, like 4E10, are polyreactive. Described herein are MPER broadly neutralizing antibodies from the major IgG1 subclass, PGZL1, which share germline V/D-region genes with 4E10, have a shorter CDRH3, and are less polyreactive. A recombinant sub-lineage variant pan-neutralized a 130-isolate panel at 1.4 μg/ml ($IC_{50}$). Notably, a germline revertant with mature CDR3s neutralized 12% of viruses, and still bound to MPER after DJ reversion. Crystal structures of lipid-bound PGZL1 variants and cryo-EM reconstruction of an Env-PGZL1 complex reveal how these antibodies recognize the MPER and viral membrane. Discovery of common genetic and structural elements among MPER antibodies from different patients suggests they may be elicited using carefully designed immunogens.

Provided herein are anti-HIV antibodies that bind to the membrane-proximal external region (MPER) of gp41. An antibody provided herein is capable of neutralizing all 130 members of a cross-clade panel of isolates at 1.4 μg/ml ($IC_{50}$). A germline revertant antibody disclosed herein with mature CDR3s is capable of neutralizing neutralized 12% of viruses in the 130-member panel, and binding to MPER after DJ reversion. Due to their unique properties, antibodies disclosed herein can be used to identify vaccine candidate agents (e.g., peptide antigens) capable of eliciting broadly neutralizing anti-HIV responses in human subjects.

One aspect of the present disclosure relates to anti-HIV antibodies, and to nucleotide sequences encoding, compositions comprising, and kits comprising thereof. In another aspect, it relates to methods of treatment and prevention of HIV using an antibody disclosed herein. In another aspect, it relates to methods of diagnosing and monitoring of HIV infection using an antibody disclosed herein. In another aspect, it relates to methods of identifying an agent as an HIV vaccine candidate.

I. Definitions

To facilitate an understanding of the present invention, a number of terms and phrases are defined below.

The terms "human immunodeficiency virus" or "HIV," as used herein, refer generally to a retrovirus that is the causative agent for acquired immunodeficiency syndrome (AIDS), variants thereof (e.g., simian acquired immunodeficiency syndrome, SAIDS), and diseases, conditions, or opportunistic infections associated with AIDS or its variants, and includes HIV-Type 1 (HIV-1) and HIV-Type 2 (HIV-2) of any clade or strain therein, related retroviruses (e.g., simian immunodeficiency virus (SIV)), and variants thereof (e.g., engineered retroviruses, e.g., chimeric HIV viruses, e.g., simian-human immunodeficiency viruses (SHIVs)). In one embodiment, an HIV virus is an HIV-Type-1 virus. Previous names for HIV include human T-lymphotropic virus-III (HTLV-III), lymphadenopathy-associated virus (LAV), and AIDS-associated retrovirus (ARV).

As used herein, the term "clade" refers to related human immunodeficiency viruses (HIVs) classified according to their degree of genetic similarity. There are currently four known groups of HIV-1 isolates: M, N, O, and P. Group M (major strains) viruses are responsible for the majority of the global HIV epidemic. The other three groups, i.e., N, O and P are quite uncommon and only occur in Cameroon, Gabon and Equatorial Guinea. In one embodiment, an HIV virus is a Group M HIV virus. Within group M, there are known to be at least nine genetically distinct subtypes or clades of HIV-1: subtypes or clades A, B, C, D, F, G, H, J and K. Additionally, different subtypes can combine genetic material to form a hybrid virus, known as a 'circulating recombinant form' (CRFs). Subtype/clade B is the dominant HIV subtype in the Americas, Western Europe and Australasia. Subtype/clade C is very common in the high AIDS prevalence countries of Southern Africa, as well as in the horn of Africa and India. Just under half of all people living with HIV have subtype C. In certain exemplary embodiments, methods described herein can be used to treat a subject (e.g., a human) infected with HIV (e.g., HIV-1) or to block or prevent HIV (e.g., HIV-1) infection in subject (e.g., a human) at risk of HIV transmission. The HIV may be of two, three, four, five, six, seven, eight, nine, ten, or more clades and/or two or more groups of HIV.

Acquired immune deficiency syndrome ("AIDS") is a disease caused by the human immunodeficiency virus, or HIV.

As used herein, the term "envelope glycoprotein" or "Env" refers to the glycoprotein that is expressed on the surface of the envelope of HIV virions and the surface of the plasma membrane of HIV infected cells. "Envelope glycoprotein" or "Env" encompass, but are not limited to, native Env, an isoform of Env, or a variant of Env (e.g., SOSIP) derived from an HIV isolate, for example, Du156.12. Env is the sole virally encoded gene product on the surface of the virus and, as such, is the only target of neutralizing antibodies. Env is a trimer of heterodimers composed of two non-covalently associated subunits: the receptor-binding gp120 and the gp41 containing the fusion machinery. Each subunit is derived from a gp160 precursor glycoprotein following cleavage by cellular furins. HIV-1 gp120 binds the CD4 molecule on the surface of human target T cells to initiate the viral entry process, and following co-receptor engagement, fusion is mediated by gp41. The gp41 domain comprises the fusion peptide, fusion peptide proximal region, heptad repeats 1 and 2 (HR1, HR2), the membrane proximal external region (MPER), the transmembrane domain (TM) and the cytoplasmic tail (CT). gp140 env is the uncleaved ectodomain of gp160. In some embodiments, gp140 comprises MPER. In one embodiment, Env is a Du156.12 Env polypeptide. GenBank™ accession number DQ411852.1 provide Du156.12 env polypeptide sequence. In one embodiment, Du156.12 Env comprises the amino acid sequence of MRVRGIPRNWPQWWTWGILGFW- MIIMCKVAGNSWVTVYYGVPVWTEAKTTLFCASD AKAYEKEVHNVWATHACVPTDPNPQEI-FLKNVTENFNMWKNDMVDQMHEDIISLWDQ SLKPCVKLTPLCVTLNCVTYNNSMNS-SATYNNSMNGEIKNCSFNTTTELRDKKQKVYAL FYRTDVVPLNNNNNNSEYILINCNT-STITQACPKVSFDPIPIHYCAPAGYAILKCTDKKFN GTGSCNNVSTVQCTHGIKPVVSTQLLLNGSLAEEE-IIIKSENLTDNIKTIIVQLNQSIGINCT RPNNN-TRKSVRIGPGQTFYATGDIIGDIRQAHCNIS-RNQWNETLEQVKKKLGEHFHNQTK IKFEPPSGGDLEITTHSFNCRGEFFYCNTADLFT-NATKLVNDTENKAVITIPCRIKQIINMW QGV-GRAMYAPPIEGNITCNSNITGLLLTRDGGG-NVTEINRTEIFRPGGGNMKDNWRNEL YKYKVVEIKPLGVAPTGAKRKVVKREKRAVGL-GAVLFGFLGAAGSTMGAASITLTAQA RQLLS-GIVQQQSNLLRAIEAQQHMLQLTVWGIKQLQARV-LAIERYLKDQQLLGLWGCSG KLICTTNVPWNSSWSNKSQTDIWNNTTWMQWERE-ISNYTDTIYRLLEDSQNQQEENEKD LLA-LDRWQNLWNWFDITNWLWYIKIFIMIVGGLIGL-RIIFGVLSIVKRVREGYSPLSFQTL TPTPRGLDRLGRIEEEGGEQDKDRSIRLVNGFLA-LAWDDLRSLCLFSYHQLRDFILIAARA VELL-GRSSLRGLQKGWEALKYLGNLIQYWGLELKR-RAINLLDISAIAVAEGTDRIIDIVLR TGRAIRNIPRRIRQGFGATLL (SEQ ID NO: 1). In one embodiment, the MPER comprises the amino acid sequence of DLLALDRWQNLWNWFDITNWLWYIK (SEQ ID NO: 2). In one embodiment, the MPER comprises the amino acid sequence of ELLALDKWASLWNWFDITKWLWYIK (SEQ ID NO: 3). In one embodiment, the MPER comprises the amino acid sequence of ELQKLN-SWDVFGNWFDITKWLWYIK (SEQ ID NO: 4).

The term "well-ordered Env trimer" or "well-ordered trimer" as used herein refers to an envelope glycoprotein trimer comprising three cleaved gp140 polypeptides that closely mimic the quaternary structure of the Env ectodomain on the surface of the envelope of HIV or SIV virions and the surface of the plasma membrane of HIV or SIV infected cells. In one embodiment, the gp140 polypeptides comprise MPER. In one embodiment, the well-ordered trimer comprises three MPERs. In one embodiment, the gp120 and gp41 ectodomain is linked by a covalent linkage, for example, a disulfide bond. In one embodiment, the gp140 polypeptide comprises one or more mutations to promote trimer formation. In one embodiment, the gp140 polypeptide comprises one or more Cys substitutions to promote disulfide formation. In one embodiment, the well-ordered trimer is a SOSIP gp140 trimer. Well-ordered SOSIP trimers have been disclosed in US Patent Appl. Pub. No. 2014/0212458, and Sanders, R. W. et al., PLoS Pathog. 9, e1003618 (2013), each of which is incorporated by reference herein in its entirety. In one embodiment, a well-ordered trimer is formed from a clade A Env. In one embodiment, a well-ordered trimer is formed from a clade B Env. In one embodiment, a well-ordered trimer is formed from a clade C Env. In one embodiment, a well-ordered trimer is formed from a circulating recombinant form Env, wherein 'circulating recombinant form' (CRF) refers to a hybrid virus comprising a combination of genetic material from different subtypes. In one embodiment, a well-ordered trimer is Du156.12 SOSIP comprising MPER. In one embodiment, a well-ordered Env trimer is a native flexibly linked (NFL) trimer as described in Shama, et al., Cell Reports, 11(4):539-50 (2015). In one embodiment, a well-ordered Env trimer is a DS-SOSIP as described in Chuang G Y, et al., J. Virology, 91(10). pii: e02268-16 (2017). In one embodiment, a well-ordered trimer is formed from an SIV Env. In one embodiment, a well-ordered trimer is an SIV Env SOSIP. In one embodiment, a well-ordered trimer is formed from an Env comprising a mutation (e.g., substitution or deletion) in the CD4 binding site. In one embodiment, a well-ordered trimer is formed from an Env comprising a mutation (e.g., substitution or deletion) in the CD4 binding site wherein the mutation reduces or disrupts the binding between Env and CD4. In one embodiment, a well-ordered trimer is a CRF or C108 SOSIP. See, e.g., Andrabi R., et al, Immunity 43(5): 959-973 (2015). In some embodiments, the gp120 and gp41 ectodomain is linked by a peptide linker, for example, a Gly-Ser linker, as described in Georgiev I S, et al., J. Virology 89(10): 5318-5329 (2015). In some embodiments, the well-ordered Env trimer is stable.

The term "antibody" means an immunoglobulin molecule (or a group of immunoglobulin molecules) that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the terms "antibody" and "antibodies" are terms of art and can be used interchangeably herein and refer to a molecule with an antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), affybodies, Fab fragments, F(ab')$_2$ fragments, disulfide-linked Fvs (sdFv), anti-idiotypic (anti-Id) antibodies (including, e.g., anti-anti-Id antibodies), bispecific antibodies, and multi-specific antibodies. In certain embodiments, antibodies described herein refer to polyclonal antibody populations. Antibodies can be of any type (e.g., IgG, IgE, IgM, IgD, IgA, or IgY), any class (e.g., IgG$_1$, IgG$_2$, IgG$_3$, IgG$_4$, IgA$_1$, or IgA$_2$), or any subclasses (isotypes) thereof (e.g. IgG1, IgG2, IgG3, IgG4, IgA1 and IgA2), of immunoglobulin molecule, based on the identity of their heavy-chain constant domains referred to as alpha, delta, epsilon, gamma, and mu, respectively. The different classes of immunoglobulins have different and well-known subunit structures and three-dimensional configurations. Antibodies can be naked or conjugated or fused to other molecules such as toxins, radioisotopes, other polypeptides etc.

As used herein, the terms "antigen-binding domain," "antigen-binding region," "antigen-binding site," and similar terms refer to the portion of antibody molecules, which comprises the amino acid residues that confer on the antibody molecule its specificity for the antigen (e.g., HIV Env MPER). The antigen-binding region can be derived from any animal species, such as mouse and humans.

As used herein, the terms "variable region" or "variable domain" are used interchangeably and are common in the art. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen (e.g., HIV Env MPER). In certain embodiments, the variable region comprises 3 CDRs (CDR1, CDR2, and CDR3) and 4 framework regions (FR1, FR2, FR3, and FR4) in the order of FR1-CDR1-FR2-CDR2-FR3-CDR3-FR4 from the N terminus to the C terminus. In certain embodiments, the variable region is a human variable region. In certain embodiments, the variable region comprises human CDRs and human framework regions (FRs). In certain embodiments, the variable region comprises CDRs and framework regions (FRs) wherein one or more of the CDRs were modified by a substitution, deletion, or insertion relative to the CDRs of a parental antibody. In certain embodiments, the variable region comprises CDRs and framework regions (FRs) wherein one or more of the FRs were modified by a substitution, deletion, or insertion relative to the FRs of a parental antibody. In certain embodiments, the variable region comprises CDRs and framework regions (FRs) wherein one or more of the CDRs and one or more of the FRs were modified by a substitution, deletion, or insertion relative to the CDRs and FRs of a parental antibody. In certain embodiments, the parental antibody is PGZL1. In certain embodiments, the variable region comprises human CDRs and primate (e.g., non-human primate) framework regions (FRs).

A skilled artisan understands that there are several methods for determining CDRs. One approach is based on cross-species sequence variability (i.e., Kabat E A, et al., Sequences of Proteins of Immunological Interest, (5th ed., 1991, National Institutes of Health, Bethesda Md.) ("Kabat"). Another approach is based on crystallographic studies of antigen-antibody complexes (Al-lazikani B., et al, J. Mol. Biol. 273:927-948 (1997)) ("Chothia"). In addition, combinations of these two approaches are sometimes used in the art to determine CDRs. In some embodiments, the CDR sequences are identified according to Kabat. In some embodiments, the CDR sequences are identified according to Chothia. It is understood that the identification of CDRs in a variable region also identifies the FRs as the sequences flanking the CDRs.

The Kabat numbering system is generally used when referring to a residue in the variable domain (approximately residues 1-107 of the light chain and residues 1-113 of the heavy chain) (e.g., Kabat E A, et al., Sequences of Immunological Interest. (5th Ed., 1991, National Institutes of Health, Bethesda, Md.) ("Kabat").

The amino acid position numbering as in Kabat, refers to the numbering system used for heavy chain variable domains or light chain variable domains of the compilation of antibodies in Kabat E A, et al. (Sequences of Immunological Interest. (5th Ed., 1991, National Institutes of Health, Bethesda, Md.), "Kabat"). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software, available, for example, at bioinforg.uk/abs/ software. In some embodiments, the CDR sequences are identified according to Kabat. In some embodiments, the CDR sequences are identified according to Chothia. In some embodiments, the CDR sequences are identified according to AbM. In some embodiments, the VH CDR3 sequence is identified according to Kabat. In some embodiments, the VH CDR3 sequence is identified according to Chothia. In some embodiments, the VH CDR3 sequence is identified according to AbM.

| Loop | Kabat | AbM | Chothia |
|---|---|---|---|
| L1 | L24-L34 | L24-L34 | L24-134 |
| L2 | L50-L56 | L50-156 | L50-156 |
| L3 | L89-L97 | L89-197 | L89-L97 |
| H1 | H31-H35B | H26-H35B | H26-H32 . . . 34 |
|  |  |  | (Kabat Numbering) |
| H1 | H31-H35 | H26-H35 | H26-H32 |
|  |  |  | (Chothia Numbering) |
| H2 | H50-H65 | H50-H58 | H52-H56 |
| H3 | H95-H102 | H95-H102 | H95-H102 |

The terms "VL" and "VL domain" are used interchangeably to refer to the light chain variable region of an antibody.

The terms "VH" and "VH domain" are used interchangeably to refer to the heavy chain variable region of an antibody.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')$_2$, and Fv fragments, linear antibodies, and single chain antibodies.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "polyclonal antibody" describes a composition of different (diverse) antibody molecules, which are capable of binding to or reacting with several different specific antigenic determinants on the same or on different antigens. Usually, the variability of a polyclonal antibody is primarily located in the so-called variable regions of the polyclonal antibody, in particular in the CDR regions. In the present disclosure, a mixture of two or more polyclonal antibodies (a polycomposition) is produced in one mixture from a polyclonal polycomposition cell line, which is produced from two or more parental polyclonal cell lines each expressing antibody molecules, which are capable of binding to a distinct target, but it may also be a mixture of two or more polyclonal antibodies produced separately. A mixture of monoclonal antibodies providing the same antigen/ epitope coverage as a polyclonal antibody described herein will be considered as an equivalent of a polyclonal antibody.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g., mouse) with the desired specificity, affinity, and capability, while the constant regions are homologous to the sequences in antibodies or antigen-binding fragments thereof derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following. In certain embodiments, an anti-HIV antibody disclosed herein binds to HIV Env MPER with a $K_D$ of at least about 0.1 μM or less, at least about 0.01 μM or less, at least about 1 nM or less, or at least about 0.1 nM or less. In certain embodiments, an anti-HIV antibody disclosed herein binds to HIV Env MPER with a $K_D$ of at least about 0.01 μM or less. In some embodiments, the HIV Env is Du156.12 Env. In one embodiment, the MPER comprises the amino acid sequence of DLLALDRWQNLWNWFDITNWLWYIK (SEQ ID NO: 2). In one embodiment, the MPER comprises the amino acid sequence of ELLALDKWASLWNWFDITKWLWYIK (SEQ ID NO: 3). In one embodiment, the MPER comprises the amino acid sequence of ELQKLN- SWDVFGNWFDITKWLWYIK (SEQ ID NO: 4). In one embodiment, an anti-HIV antibody disclosed herein is capable of binding to cells that express functional, well-ordered HIV-1 membrane Env trimers. In one embodiment, an anti-HIV antibody disclosed herein is capable of binding to cells that display MPER-TM peptide in a flow cytometry assay. In one embodiment, an anti-HIV antibody disclosed herein is capable of binding to MPER peptide in biolayer interferometry (BLI) assay. In one embodiment, an anti-HIV antibody disclosed herein is capable of binding to MPER peptide in ELISA. In one embodiment, an anti-HIV antibody disclosed herein is capable of binding Env trimers from detergent-solubilized HIV-1 virions in an ELISA assay. In one embodiment, an anti-HIV antibody disclosed herein is capable of binding Env trimers from detergent-solubilized HIV-1 virions in a BN-PAGE gel mobility-shift assay. In one embodiment, the MPER comprises the amino acid sequence of DLLALDRWQNLWNWFDITNWLWYIK (SEQ ID NO: 2). In one embodiment, the MPER comprises the amino acid sequence of ELLALDKWASLWNWFDITKWLWYIK (SEQ ID NO: 3). In one embodiment, the MPER comprises the amino acid sequence of ELQKLN-SWDVFGNWFDITKWLWYIK (SEQ ID NO: 4).

"Or better" when used herein to refer to binding affinity refers to a stronger binding between a molecule and its binding partner. "Or better" when used herein refers to a stronger binding, represented by a smaller numerical $K_D$ value. For example, an antibody, which has an affinity for an antigen of "0.6 nM or better", the antibody's affinity for the antigen is <0.6 nM, i.e. 0.59 nM, 0.58 nM, 0.57 nM etc. or any value less than 0.6 nM.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), ELISA, biolayer interferometry (BLI), flow cytometry or other assays known in the art. In a specific embodiment, molecules that immunospecifically bind to an antigen bind to the antigen with a $K_D$ that is at least 2 logs, 2.5 logs, 3 logs, or 4 logs lower than the $K_D$ when the molecules bind non-specifically to another antigen. In one example, the antibody may specifically bind to cells that express functional, well-ordered HIV-1 membrane Env trimers. In one example, the antibody may specifically bind to cells that display MPER-TM peptide. In one example, the antibody may specifically bind to the MPER peptide. In one example, the antibody may specifically bind to the MPER peptide in biolayer interferometry (BLI) assay. In one example, the antibody may specifically bind to the MPER peptide in ELISA assay. In one example, the antibody may specifically bind to Env trimers from detergent-solubilized HIV-1 virions. In one example, the antibody may specifically bind to Env trimers from detergent-solubilized HIV-1 virions in an ELISA assay. In one example, the antibody may specifically bind to Env trimers from detergent-solubilized HIV-1 virions in a BN-PAGE gel mobility-shift assay. The antibody may bind to HIV Env MPER with a $K_D$ at least 2 logs, 2.5 logs, 3 logs, or 4 logs lower than $K_D$ of binding to other viral or non-viral polypeptides. An antibody that specifically binds to Env encompass, but are not limited to, antibodies that specifically bind to native Env, an isoform of Env, or a variant of Env (e.g., SOSIP) derived from an HIV isolate, for example, Du156.12. In one embodiment, the antibody specifically binds to Du156.12 Env. In one embodiment, the antibody specifically binds to Du156.12 MPER peptide.

By "preferentially binds," it is meant that the antibody specifically binds to an epitope more readily than it would bind to a related, similar, homologous, or analogous epitope. Thus, an antibody, which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term "broadly neutralizing antibody" or "bnAb," as used herein, with respect to HIV (e.g., HIV-1), refers to an antibody that recognizes HIV Env of more than one isolate or strain of HIV and inhibits or prevents receptor binding of target cells as evaluated in an in vitro neutralization assay. In one embodiment, a broadly neutralizing antibody inhibits infection of a susceptible target cell by HIV. In one embodiment, a broadly neutralizing antibody specifically binds an HIV Env and inhibits infection of a susceptible target cell (e.g., TZM-b1) by an HIV pseudovirus comprising an Env polypeptide. HIV pseudovirus neutralization assays have been disclosed in the art, for example, in Walker L. M., et al., Nature 477, 466-470 (2011), Li M., et al., J. Virol. 79:10108-10125 (2005), each of which is incorporated herein by reference in its entirety for all purposes. In one embodiment, a broadly neutralizing antibody neutralizes 2, 3, 4, 5, 6, 7, 8, 9, or more HIV strains or pseudoviruses. In one embodiment, a broadly neutralizing antibody neutralizes 2, 3, 4, 5, 6, 7, 8, 9, or more HIV strains or pseudoviruses that belong to the same or different clades. In one embodiment, a broadly neutralizing antibody is capable of neutralizing HIV strains or pseudoviruses from at least two different clades. In one embodiment, a broadly neutralizing antibody is capable of neutralizing at least one clade B strain or pseudovirus and one clade C strain or pseudovirus. In one embodiment, a broadly neutralizing antibody is capable of neutralizing more than one clade B strain or pseudovirus and more than one clade C strain or pseudovirus. In one embodiment, a broadly neutralizing antibody is capable of neutralizing an HIV strain or pseudovirus from at least one, at least two, at least three, at least four, at least five, at least six, at least seven, at least eight, at least nine, at least ten, or at least eleven clades represented in the 130-member indicator virus panel. In one embodiment, a broadly neutralizing antibody is capable of neutralizing an HIV strain or pseudovirus from at least one, at least two, at least three, at least four, at least five, at least six, at least seven, at least eight, at least nine, at least ten, at least eleven, at least twelve, at least thirteen, at least fourteen, or all fifteen clades selected from the group consisting of clades A, A (T/F), AC, ACD, B, B (T/F), BC, C, C (T/F), CD, CRF01_AE, CRF01_AE (T/F), CRF02_AG, D, and G. In one embodiment, a broadly neutralizing antibody is capable of neutralizing an HIV strain or pseudovirus from at least one, at least two, at least three, at least four, at least five, at least six, at least seven, at least eight, at least nine, at least ten, or all eleven clades selected from the group consisting of clades A, AC, ACD, AE, AG, B, BC, C, CD, D, G.

In one embodiment, the breadth of neutralization is tested on an indicator virus panel comprising cross-clade HIV isolates. In one embodiment, the virus panel comprises the 9 cross-clade isolates of 92TH021, JRCSF, C22, 94UG103, 92BR020, Du156.12, HIV-2, HIV-2C1, and HIV-2C4. In one embodiment, the virus panel comprises the 130 cross-clade isolates of NIH-065_191955 All, NIH-063_0330.v4.c3, NIH-066_191084 B7.19, NAC_BG505, NIH-057_MS208.A1, NIH-064_0260.v5.c1, NAC_KNH1144, NAC_94UG103, NAC_92RW020, NIH-060_Q769ENVd22, NIH-058_Q23ENV17, NIH-056_Q168ENVa2, NIH-061_Q259ENVd2.17, NIH-059_Q461ENVe2, NIH-117_T278.5, NIH-100_6041.v3.c23, NIH-099_3301.v1.c24, NIH-102_6545.v4.c1, NIH-101_6540.v4.c1, NIH-103_0815.v3.c3, NIH-104_3103.v3.c10, NIH-073_C3347.c11, NIH-080_BJOX025000.01.1, NIH-075_CNE8, NAC 92TH021, NIH-081 BJOX028000.10.3, NIH-078 BJOX015000.11.5, NIH-079_BJOX010000.06.2, NIH-074_C4118.c09, NIH-069_C1080.c03, NIH-077_BJOX009000.02.4, NIH-068_620345.c01, NIH-076_CNE5, NIH-070_R2184.c04, NIH-072_R3265.c06, NIH-071_R1166.c01, NIH-115_928.28, NIH-118_T255.34, NIH-116_T263.8, NIH-108 T235.47, NIH-114 T257.31, NIH-107 T251.18, NIH-106 T250.4, NIH-119 T211.9, NAC_MN, NAC_HxB2, NIH-012_1012.11.TC21.3257, NAC_ADA, NAC_WITO.33, NIH-006_AC10.0.29, NIH-003_SC422661.8, NAC_89.6, NAC_BaL.26, NAC_RHPA4.7, NIH-014_6244.13.B5.4567, NAC_TRJO.58, NAC_92BR020, NIH-008_WEAU.d15.410.787, NAC_REJO.67, NIH-009_1006.11.C3.1601, NAC_SS1196.1, NAC_YU2, NAC JRCSF, NAC_JRFL, NIH-004_PVO.4, NAC_DH12, NIH-005_TRO.11, NAC_SF162, NIH-011_1056.10.TA11.1826, NIH-016_SC05.8C11.2344, NIH-013_6240.08.TA5.4622, NIH-007_CAAN5342.A2, NIH-010_1054.07.TC4.1499, NIH-001_6535.3, NIH-015_62357.14.D3.4589, NIH-002_QH0692.42, NIH-050_CNE21, NIH-054_CNE53, NIH-055_CNE58, NIH-048_CNE19, NIH-053_CNE52, NIH-051_CNE17, NIH-052_CNE30, NIH-049_CNE20, NIH-030_HIV-0013095.2.11, NIH-026_ZM135M.PL10a, NIH-017_Du156.12, NIH-019_Du422.1, NIH-018_Du172.17, NIH-032_HIV-16845.2.22, NIH-039_Ce2060 G9, NAC 931N905, NIH-029 HIV-001428.2.42, NIH-041 BF1266.431a, NIH-023 ZM249M.PL1, NIH-031_HIV-16055.2.3, NIH-043_ZM249M.B10, NIH-025_ZM109F.PB4, NIH-040_Ce703010054 2A2, NIH-036_Ce2010 F5, NIH-020_ZM197M.PB7, NIH-044_ZM247F.F7, NIH-046_1394C9G1(Rev.), NIH-047_Ce704809221 1B3, NAC_IAVIC22, NIH-034_Ce0393 C3, NIH-045_7030102001E5(Rev.), NIH-021_ZM214M.PL15, NIH-024_ZM53M.PB12, NIH-035_Ce1176 A3, NIH-022_ZM233M.PB6, NIH-027_CAP45.G3, NIH-042_ZM246F.D5, NHI-028_CAP210.E8, NIH-038_Ce1172 H1, NIH-095_6480.v4.c25, NIH-096_6952.v1.c20, NIH-097_6811.v7.c18, NIH-094_3817.v2.c59, NIH-098_89.F1 2 25, NIH-089_3016.v5.c45, NIH-090_A07412M1.vrc12, NIH-091_231965.c01, NIH-086 X2131 C1 B5, NIH-082 X1193 c1, NIH-084_X1254 c3, NIH-083_P0402 c2 11, NIH-087_P1981 C5 3, NIH-088_X1632 S2 B10, and NIH-085_X2088 c9. In one embodiment, a broadly neutralizing antibody is capable of neutralizing at least 4, 5, 6, 7, 8 or 9 of the cross-clade HIV isolates in the 9-member indicator virus panel. In one embodiment, a broadly neutralizing antibody is capable of neutralizing at least 6 of the cross-clade HIV isolates in the 9-member indicator virus panel. In one embodiment, a broadly neutralizing antibody is capable of neutralizing at least about 50%, 60%, 70%, 80%, 90%, 95%, or 100% of cross-clade HIV isolates in the 130-member indicator virus panel. In one embodiment, a broadly neutralizing antibody is capable of neutralizing at least about 60% of cross-clade HIV isolates in the 130-member indicator virus panel. In one embodiment, a broadly neutralizing antibody is capable of neutralizing at least about 70% of cross-clade HIV isolates in the 130-member indicator virus panel. In one embodiment, a broadly neutralizing antibody is capable of neutralizing at least about 75% of cross-clade HIV isolates in the 130-member indicator virus panel. In one embodiment, a broadly neutralizing antibody is capable of neutralizing at least about 80% of cross-clade HIV isolates in the 130-member indicator virus panel. In one embodiment, a broadly neutralizing antibody is capable of neutralizing at least about 90% of cross-clade HIV isolates in the 130-member indicator virus panel. In one embodiment, a broadly neutralizing antibody is capable of neutralizing at least about 95% of cross-clade HIV isolates in the 130-member indicator virus panel. In one embodiment, a broadly neutralizing antibody is capable of neutralizing at least about 98% of cross-clade HIV isolates in the 130-member indicator virus panel. In one embodiment, a broadly neutralizing antibody is capable of neutralizing at least about 100% of cross-clade HIV isolates in the 130-member indicator virus panel.

In one embodiment, the potency of neutralization by a broadly neutralizing antibody is expressed as the median $IC_{50}$ neutralization activity against a virus panel, for example the 9-virus panel, or 130-virus panel disclosed herein. In one embodiment, a broadly neutralizing antibody is capable of neutralizing at least about 4, 5, 6, 7, 8, or 9 of the cross-clade HIV isolates in the 9-member indicator virus panel with a median $IC_{50}$ equal to or less than about 0.1 μg/ml, 0.07 μg/ml, 0.06 μg/ml, 0.05 μg/ml, 0.025 μg/ml, 0.01 μg/ml or 0.005 μg/ml. In one embodiment, a broadly neutralizing antibody is capable of neutralizing at least 6 of the cross-clade HIV isolates in the 9-member indicator virus panel with a median $IC_{50}$ equal to or less than 0.05 μg/ml. In one embodiment, a broadly neutralizing antibody is capable of neutralizing at least about 50%, 60%, 70%, 80%, 90%, 95%, or 100% of cross-clade HIV isolates in the 130-member indicator virus panel with a median $IC_{50}$ equal to or less than about 2 μg/ml, about 1.5 μg/ml, about 1 μg/ml, about 0.5 μg/ml, about 0.1 μg/ml, 0.07 μg/ml, 0.06 μg/ml, 0.05 μg/ml, 0.025 μg/ml, 0.01 μg/ml or 0.005 μg/ml. In one embodiment, a broadly neutralizing antibody is capable of neutralizing at least about 70% of cross-clade HIV isolates in the 130-member indicator virus panel with a median $IC_{50}$ equal to or less than 0.5 μg/ml. In one embodiment, a broadly neutralizing antibody is capable of neutralizing at least about 75% of cross-clade HIV isolates in the 130-member indicator virus panel with a median $IC_{50}$ equal to or less than 0.5 μg/ml. In one embodiment, a broadly neutralizing antibody is capable of neutralizing at least about 80% of cross-clade HIV isolates in the 130-member indicator virus panel with a median $IC_{50}$ equal to or less than 0.5 μg/ml. In one embodiment, a broadly neutralizing antibody is capable of neutralizing at least about 90% of cross-clade HIV isolates in the 130-member indicator virus panel with a median $IC_{50}$ equal to or less than 1 μg/ml. In one embodiment, a broadly neutralizing antibody is capable of neutralizing at least about 95% of cross-clade HIV isolates in the 130-member indicator virus panel with a median $IC_{50}$ equal to or less than 1.5 µg/ml. In one embodiment, a broadly neutralizing antibody is capable of neutralizing at least about 98% of cross-clade HIV isolates in the 130-member indicator virus panel with a median $IC_{50}$ equal to or less than 2 µg/ml. In one embodiment, a broadly neutralizing antibody is capable of neutralizing at least about 100% of cross-clade HIV isolates in the 130-member indicator virus panel with a median $IC_{50}$ equal to or less than 2 µg/ml.

The term "$IC_{50}$" refers to the half maximal inhibitory concentration of an inhibitor, e.g., a broadly neutralizing antibody. For example, $IC_{50}$ is the concentration of an inhibitor, e.g., a broadly neutralizing antibody, where the response, e.g., infection by pseudovirus, is reduced by half.

The phrase "substantially similar," or "substantially the same", as used herein, denotes a sufficiently high degree of similarity between two numeric values (generally one associated with an antibody described herein and the other associated with a reference/comparator antibody) such that one of skill in the art would consider the difference between the two values to be of little or no biological and/or statistical significance within the context of the biological characteristic measured by said values (e.g., $K_D$ values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition, which is "isolated" is a polypeptide, antibody, polynucleotide, vector, cell, or composition, which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition, which is isolated is substantially pure.

As used herein, "substantially pure" refers to material, which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides described herein are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin S., et al, Proc. Natl. Acad. Sci., 87:2264-2268 (1990), as modified in Karlin S., et al., Proc. Natl. Acad. Sci., 90:5873-5877 (1993), and incorporated into the NBLAST and XBLAST programs (Altschul S F, et al., Nucleic Acids Res., 25:3389-3402 (1991)). In certain embodiments, Gapped BLAST can be used as described in Altschul S F, et al., Nucleic Acids Res. 25:3389-3402 (1997). BLAST-2, WU-BLAST-2 (Altschul S F, et al., Methods in Enzymology, 266:460-480 (1996)), ALIGN, ALIGN-2 (Genentech, South San Francisco, California) or Megalign (DNASTAR™) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as $100 \times (Y/Z)$, where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman (Advances in Applied Mathematics 2: 482 489 (1981)) to find the best segment of homology between two sequences. When using Bestfit or any other sequence alignment program to determine whether a particular sequence is, for instance, 95% identical to a reference sequence described herein, the parameters are set such that the percentage of identity is calculated over the full length of the reference nucleotide sequence and that gaps in identity of up to 5% of the total number of nucleotides in the reference sequence are allowed.

In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies described herein do not abrogate the binding of the polypeptide or antibody containing the amino acid sequence, to the antigen(s). Methods of identifying nucleotide and amino acid conservative substitutions, which do not eliminate antigen binding are well-known in the art (see, e.g., Brummell D A, et al., Biochem. 32: 1180-1 187 (1993); Kobayashi et al., Protein Eng. 12(10): 879-884 (1999); and Burks E A, et al., Proc. Natl. Acad. Sci. USA 94:.412-417 (1997)).

As used herein, the terms "treatment" or "therapy" (as well as different forms thereof, including curative or palliative) refer to treatment of an infected person. As used herein, the term "treating" includes alleviating or reducing at least one adverse or negative effect or symptom of a condition, disease or disorder. This condition, disease or disorder can be HIV infection.

Terms such as "treating" or "treatment" or "to treat" or "alleviating" or "to alleviate" refer to therapeutic measures that cure, slow down, lessen symptoms of, and/or halt progression of a diagnosed pathologic condition or disorder, such as HIV or AIDS. Thus, those in need of treatment include those already diagnosed with or suspected of having the disorder. In certain embodiments, a subject is successfully "treated" for the disorder according to the methods described herein if the patient shows one or more of the following: a reduction in the number of or complete absence of viral load; a reduction in the viral burden; inhibition of or an absence of the virus into peripheral organs; relief of one or more symptoms associated with the disorder; reduced morbidity and mortality; improvement in quality of life; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

As used herein, the terms "prevention" or "prophylaxis" refer to preventing a subject from becoming infected with, or reducing the risk of a subject from becoming infected with, or halting transmission of, or the reducing the risk of transmission of a virus. Prophylactic or preventative measures refer to measures that prevent and/or slow the development of a targeted pathological condition or disorder. Thus, those in need of prophylactic or preventative measures include those prone to have the disorder and those in whom the disorder is to be prevented. In one embodiment, prevention encompasses passive immunization of a subject in need thereof comprising administering an effective amount of an antibody disclosed herein.

As employed above and throughout the disclosure the term "effective amount" refers to an amount effective, at dosages, and for periods of time necessary, to achieve the desired result with respect to the treatment of the relevant disorder, condition, or side effect. An "effective amount" can be determined empirically and in a routine manner, in relation to the stated purpose. It will be appreciated that the effective amount of components of the present invention will vary from patient to patient not only with the particular vaccine, component or composition selected, the route of administration, and the ability of the components to elicit a desired result in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors, which those skilled in the art will recognize, with the appropriate dosage being at the discretion of the attending physician. Dosage regimes may be adjusted to provide the improved therapeutic response. An effective amount is also one in which any toxic or detrimental effects of the components are outweighed by the therapeutically beneficial effects.

The term "therapeutically effective amount" refers to an amount of an antibody, recombinant virus, immunoconjugate, or other drug effective to "treat" a disease or disorder in a subject or mammal. To the extent an antibody can prevent growth and/or kill existing cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "subject," "individual," and "patient" are used interchangeably herein, and refer to an animal, for example a human, to whom treatment, including prophylactic treatment, with the antibody or pharmaceutical composition according to the present disclosure, is provided. In one embodiment, the subject, individual, or patient has been infected with HIV. In one embodiment, the subject, individual, or patient suffers from AIDS. In one embodiment, the subject, individual, or patient has been exposed to HIV. In one embodiment, the subject, individual, or patient is at risk of being exposed to HIV.

Administration "in combination with" one or more further therapeutic agents includes simultaneous (concurrent) or consecutive administration in any order.

The terms "pharmaceutically composition," "pharmaceutical formulation," "pharmaceutically acceptable formulation," or "pharmaceutically acceptable composition" all of which are used interchangeably, refer to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. "Pharmaceutically acceptable" or "pharmaceutical formulation" refers to a preparation, which is in such form as to permit the biological activity of the active ingredient to be effective, and which contains no additional components, which are unacceptably toxic to a subject to which the formulation would be administered. The formulation can be sterile.

The term "antiretroviral therapy" or "ART," as used herein, refers to any of the therapies used to manage progression of a retrovirus (e.g., HIV) infection in a subject (e.g., a human), including, for example, nucleoside reverse transcriptase inhibitors (NRTIs), non-nucleoside reverse transcriptase inhibitors (NNRTIs), protease inhibitors (PIs), fusion inhibitors, entry inhibitors, maturation inhibitors, cellular inhibitors, integrase strand transfer inhibitors, and multi-class combinations. Such drugs include, but are not limited to, lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddI), stavudine (d4T), abacavir sulfate (ABC), etravirine (ETR), delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir (RTV), darunavir (DRV), atazanavir sulfate (ATV), nelfinavir mesylate (NFV), enfuvirtide (T-20), maraviroc and raltegravir. ART drugs can also include antibodies that target HIV proteins or cellular proteins associated with disease progression. Also included are immune-based therapies, such as IL-2, IL-12, and alpha-epibromide. Each of these drugs can be administered alone or in combination with any other ART drug or any HIV-specific neutralizing antibody, such as a broadly neutralizing antibody, which is incorporated by reference herein in its entirety for all purposes.

The term "reservoir activator," as used herein, refers to an agent capable of activating a viral reservoir (e.g., an HIV reservoir). In one embodiment, a reservoir activator comprises a histone deacytelase (HDAC) inhibitor (e.g., romidepsin, vorinostat, and panobinostat), immunologic activator (e.g., cytokines and TLR agonists), or a dedicated small molecule drug.

The term "immunomodulator," as used herein, refers to an agent, such as an antibody or peptide, which is capable of increasing, inducing, or extending an immune response (e.g., a cell-mediated immune response and/or a humoral immune response) when administered to a subject (e.g., a human, e.g., a human infected with HIV or at risk of an HIV infection or transmission). Immunomodulators include, but are not limited to immune checkpoint inhibitors, for example, a PD-1, PD-L1, LAG-3, or TIGIT antagonist. In one embodiment, an immunomodulator used in the methods described herein comprises an anti-PD-1 antibody, anti-PD-L1 antibody, anti-LAG3 antibody, or an anti-TIGIT antibody. An immunomodulator can be administered in conjunction with (e.g., prior to, concurrently with, or subsequent to, or within the context of a treatment regimen that includes the administration of a broadly neutralizing antibody described herein.

As used in this specification and the appended claims, the singular forms "a," "an," and "the" include plural referents unless the content clearly dictates otherwise. Thus, for example, reference to "a cell" includes a combination of two or more cells, and the like.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" as used herein when referring to a measurable value such as an amount, a temporal duration, and the like, is meant to encompass variations of up to ±20% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope described herein are approximations, the numerical values set forth in the specific examples are reported as precisely as possible. Any numerical value, however, inherently contain certain errors necessarily resulting from the standard deviation found in their respective testing measurements.

It is understood that wherever embodiments are described herein with the language "comprising," otherwise analogous embodiments described in terms of "consisting of" and/or "consisting essentially of" are also provided.

II. Anti-HIV Antibodies

In one aspect, provided herein are anti-HIV antibodies and antigen-binding fragments thereof that bind to Env MPER. In some embodiments, an antibody described herein is a monoclonal antibody. In some embodiments, an antibody described herein is a human antibody. In some embodiments, an antibody described herein is a broadly neutralizing antibody. In some embodiments, an antibody described herein specifically binds the Env of at least one HIV isolate in the 130-member indicator virus panels of Table 10. In some embodiments, an antibody described herein specifically binds the Env of at least two, at least three, at least four, or at least five HIV isolates in the 130-member indicator virus panel of Table 10. In some embodiments, an antibody described herein binds Env at the MPER epitope region. In some embodiments, an antibody described herein binds to cells that express well-ordered HIV-1 membrane Env trimers. In some embodiments, an antibody described herein binds to cells that display MPER-TM peptide. In some embodiments, an antibody described herein binds to MPER peptide. In some embodiments, an antibody described herein binds to Env trimers from detergent-solubilized HIV-1 virions. In some embodiments, MPER comprises the amino acid sequence of DLLALDRWQNLWNWFDITNWLWYIK (SEQ ID NO: 2). In some embodiments, an antibody described herein binds to wild-type Env, but does not bind a mutant variant of Env comprising a substitution or deletion in the MPER. In some embodiments, the Env is a clade A Env. In some embodiments, the Env is a clade B Env. In some embodiments, the Env is a clade C Env. In some embodiments, the Env is Du156.12 Env.

In one aspect, provided herein is an antibody and an antigen-binding fragment thereof that is capable of neutralizing the Du156.12 HIV isolate.

In one aspect, provided herein is antibody and an antigen-binding fragment thereof that is capable of neutralizing at least two cross-clade isolates of HIV. In one embodiment, the antibody is capable of neutralizing at least one clade B isolate and at least one clade C isolate.

In one embodiment, an antibody or antigen-binding fragment thereof disclosed herein is a broadly neutralizing antibody.

In one embodiment, an antibody or antigen-binding fragment thereof disclosed herein neutralizes 2, 3, 4, 5, 6, 7, 8, 9, or more HIV strains or pseudoviruses that belong to the same or different clades. In one embodiment, an antibody disclosed herein is capable of neutralizing HIV strains or pseudoviruses from at least two different clades. In one embodiment, an antibody disclosed herein is capable of neutralizing at least one clade B strain or pseudovirus and one clade C strain or pseudovirus. In one embodiment, an antibody disclosed herein is capable of neutralizing more than one clade B strain or pseudovirus and more than one clade C strain or pseudovirus. In one embodiment, an antibody disclosed herein is capable of neutralizing an HIV strain or pseudovirus from at least one, at least two, at least three, at least four, at least five, at least six, at least seven, at least eight, at least nine, at least ten, or eleven clades represented in the 130-member indicator virus panel. In one embodiment, an antibody disclosed herein is capable of neutralizing an HIV strain or pseudovirus from at least one, at least two, at least three, at least four, at least five, at least six, at least seven, at least eight, at least nine, at least ten, or eleven clades selected from the group consisting of clades A, AC, ACD, AE, AG, B, BC, C, CD, D, and G.

In one embodiment, an antibody or antigen-binding fragment thereof disclosed herein is a broadly neutralizing anti-HIV Env antibody. In one embodiment, an antibody or antigen-binding fragment thereof disclosed herein specifically binds to HIV Env MPER. In one embodiment, an antibody disclosed herein specifically binds to a well-ordered HIV Env trimer. In one embodiment, an antibody disclosed herein is a monoclonal antibody. In one embodiment, an antibody disclosed herein is an F(ab) or F(ab')₂. In one embodiment, an antibody disclosed herein is a recombinant antibody, a chimeric antibody, an antibody fragment, a bispecific antibody, or a trispecific antibody.

In one embodiment, an antibody or antigen-binding fragment thereof disclosed herein is a not polyreactive. In one embodiment, an antibody or antigen-binding fragment thereof disclosed herein is less polyreactive than 4E10. In one embodiment, an antibody or antigen-binding fragment thereof disclosed herein is less reactive towards one or more of ssDNA, dsDNA, ovalbumin (Ova), lipids, cholesterol, DOPC, DOPE, and DOPS than 4E10.

TABLE 1

| Variable heavy chain (VH) and light chain (VL) domains. | |
| --- | --- |
| PGZL1 VH | EVQLVQSGGEVKRPGSSVTVSCKATGGTFSTLAFNWVRQAPGQGP EWMGGIVPLFSIVNYGQKFQGRLTIRADKSTTTVFLDLSGLTSADTA TYYCAREGEGWFGKPLRAFEFWGQGTVITVSS (SEQ ID NO: 5) |
| PGZL1.H4K3 VH | KVQLVQSGAELKKPWSSVRVSCKASGGSFSSYAFNWVRQAPGQRL EWLGGIVPLVSSTNYAQRFRGRVTISADRSTSTVYLEMTGLTSADT AVYFCAREGEGWFGRPLRAFEFWGQGTLVTVST (SEQ ID NO: 6) |
| PGZL1_gVmDmJ VH | QVQLVQSGAEVKKPGSSVKVSCKASGGTFSSYAISWVRQAPGQGL EWMGGIIPIFGTANYAQKFQGRVTITADKSTSTAYMELSSLRSEDTA VYYCAREGEGWFGKPLRAFEFWGQGTVITVSS (SEQ ID NO: 7) |
| PGZL1 VL | DVVMTQSPGTLSLSPGERATLSCRASQSVSGGALAWYQQKPGQAP RLLIYDTSSRPTGVPGRFSGSGSGTDFSLTISRLEPEDFAVYYCQQYG TSQSTFGQGTRLEIK (SEQ ID NO: 8) |
| PGZL1.H4K3 VL | EIVLTQSPGTFALSPGERATLSCRASQSVSGGALAWYQQKAGQAPR LLIYGTSGRATGVPGRFSGSGSETDFSLTISRLEPEDFAVYYCQQYGT SQSTFGQGTRLETR (SEQ ID NO: 9) |
| PGZL1_gVmDmJ VL | EIVLTQSPGTLSLSPGERATLSCRASQSVSSSYLAWYQQKPGQAPRL LIYGASSRATGIPDRESGSGSGTDFTLTISRLEPEDFAVYYCQQYGTS QSTFGQGTRLETR (SEQ ID NO: 10) |
| PGZL1_V2H1 VH | QVQLVQSGAEVKKPGSSVKVSCKASGGTFSNDVISWVRQAPGQGL EWMGRVIPILDITNYAQKFQGRVTITADKSTSTVYMDLSSLRSEDTA VYFCAREGEGWFGKPLRAFEVWGQGTQITVSS (SEQ ID NO: 11) |
| PGZL1_V2H2 VH | QVQLVQSGAEVKKPGSSVKVSCKASGSTFSSYAISWVRQAPGQGLE WVGGIVPLVSSTNYAQRFRGRVTISADRSTSTVYLEMTGLTSADTA VYFCAREGEGWFGRPLRAFEFWGQGTLVTVST (SEQ ID NO: 12) |
| PGZL1_V2H3 VH | KVQLVQSGAELKKPWSSVRVSCKASGGSFSSYAFNWVRQAPGQKL EWLGGIASLLVSRPSYAQRFRGRITISADRSATTVYLEMTGLTSADT AVYFCAREGEGWFGKPLRAFEFWGQGTLVTVST (SEQ ID NO: 13) |
| PGZL1_V2H4 VH | KVQLVQSGAELKKPWSSVRVSCKASGGSFSSYAFNWVRQAPGQRL EWLGGIVPLVSSTNYAQRFRGRVTISADRSTSTVYLEMTGLTSADT AVYFCAREGEGWFGRPLRAFEFWGQGTLVTVST (SEQ ID NO: 14) |
| PGZL1_V2H5 | GVQLVQSGAEVKKPGSSMTVSCKATGGTFSSLAFNWVRQAPGQGP |

TABLE 1-continued

| Variable heavy chain (VH) and light chain (VL) domains. |

| VH | EWMGGICPVFSALVNYGQRFQGRLTIRADKSTTTVYLDLIRLTSDD<br>TATYYCAREGEGRFGKPLRAFEVWGQGTQITVSS (SEQ ID NO: 15) |
| PGZL1_V2H6<br>VH | KVQLVQSGAEVKRPGSSVTISCKDRGGSFSSYAFNWVRQAPGQGLE<br>WMGGIIPLISIANYASRRFRGRVTITADRSTSSIFLDLTRLTSVDTALY<br>FCAREGEGWFGKPLGAFEFWGQGTAVTVTS (SEQ ID NO: 16) |
| PGZL1_V2H7<br>VH | GVQLVQSGAEVKRPGSSVTVSCKATGGTFSTLAFSWVRQAPGQGP<br>EWMGGIVPLFTIVNYGQRFQGRLTIRADKSTTTVFLDLSGLTSADTA<br>TYYCAREGEGWFGKPLRALEIWGQGTVITVSS (SEQ ID NO: 17) |
| PGZL1_V2H8<br>VH | RVQLVQSGAELKKPWSSVRVSCKASGGSFSSYAFSWVRQAPGQGL<br>EWLGGIVPLVSSTNYAPKFRGRITISADRSANTVYLEMTRLTSADTA<br>VYFCAREGEGWFGRPLRAFEFWGQGTLVTVST (SEQ ID NO: 18) |
| PGZL1_V2H9<br>VH | KVQLVQSGAEVMRPGSSGYLSCKASGGSFSSYAFNWVRQAPGQGL<br>EWMGGIIPLISIANYAEEFRGRVTITADRSTSSIFLDLTRLTSVDTALY<br>FCAREGEGWFGKPLGAFEFWGQGTAVTVTS (SEQ ID NO: 19) |
| PGZL1_V2H10<br>VH | RVQLVQSGAEVKRPGSSVTIACKASGGSCSSYALHWERQARGQGL<br>EWMGGIMPPYRVANYAEELRGRVTMTGDRSTSSIFLDLTRLTSVDT<br>ALYFCAREGEGWFGKPLGAFEFWGQGTAVTVTS (SEQ ID NO: 20) |
| PGZL1_V4H1<br>VH | QVQLAQSGTEVKKPGSSVKVSCKSSGGTSSNYAITWVRQAPGQGLE<br>WMGGIVPLVSSTNYAQRFKGRVTISADRSTSTVFMEVIRLTSEDTGV<br>YFCAREGEGWFGKPLRAFEFWGHGTAVTVSS (SEQ ID NO: 21) |
| PGZL1_V4H2<br>VH | GVQLVQSGAEVNEGPGSSVEVSCKATGGTFSTLAFNWVRQAPGQG<br>PEWMGGIVPLFSIVNYGQRFQGRVTIRADKSTTTVFLDLSRLTSADT<br>ATYYCAREGEGWFGKPLRALEIWGQGTVITVSS (SEQ ID NO: 22) |
| PGZL1_V4H3<br>VH | GVQLVQSGAEVKRPGSSMTVSCRATGGTFSSLAFNWVRQAPGQGP<br>EWMGREIVPLFRIANYGQKFQGRLTIRADKSTTTIYLDLSSLTSADT<br>ATYYCAREGEGWFGKPLRAFEFWGQGTVITVSS (SEQ ID NO: 23) |
| PGZL1_V4H4<br>VH | KVQLVQSGAELKKPWSSVNEVSCKVSGGSFSSYAFNWVRQAPGQR<br>LEWLGGIVPLVSSTNYAQRFRGRITISADRSTSTVYLEMTGLTSADT<br>AVYFCAREGEGWFGKPLRAFEFWGQGTLVTVST (SEQ ID NO: 24) |
| PGZL1_V4H5<br>VH | KVQLVQSGAEVKRPGSSVTISCKGTRGGSFSSYAFNWVRQAPGLGL<br>EWMGGIIPLISIANYAERFRGRVTITADRSTSSIFLDLTRLTSVDTALY<br>FCAREGEGWFGKPLGAFEFWGQGTAVTVTS (SEQ ID NO: 25) |
| PGZL1_V4H6<br>VH | RVQLVQSGAEVKRPGSSVTVSCKATGGTFSTLAFSWVRQAPGQGPE<br>WMGGIVPLFTIVNYGQRFQGRLTIRADKSTTTVFLDLSGLTSADTAT<br>YYCAREGEGWFGKPLRAPEIWGQGTVITVSS (SEQ ID NO: 26) |
| PGZL1_V4H7<br>VH | GVQLVASGAEVKKPGSSVEVSCKATGGTFNSLAFNWVRQAPGQGP<br>EYMGGIVPLFSIVNYGQRFQGRLTIRADKSTTTVYMDLNRLTSDDT<br>ATYYCAREGEGWFGKPLRAFQLWGQGTVITVSS (SEQ ID NO: 27) |
| PGZL1_V4H8<br>VH | KVQLVQSGAEVKRPGSSVTISCKDSGGSFSSYAFNWVRQAPGQGLE<br>WMGGIIPLISSTNYAEKFRGRVTITADRSTSSIFLDLTRLTSADTALYF<br>CAREGEGWFGKPLGAFEFWGQGTAVTVTS (SEQ ID NO: 28) |
| PGZL1_V6H1<br>VH | KVQLVQSGDVKLKTPWSSVRVSCKASGGSFSSYAFNWVRQAPGQR<br>LEWLGGIVPLVSSTNYAQRFRGRVTISADRSANTVYLEMTGLTSAD<br>TAIYFCAREGEGWFGKPLRAFEFWGQGTLVSVST (SEQ ID NO: 29) |
| PGZL1_V6H2<br>VH | KVQLVQSGAELKKPWSSVRVSCKASGGSFSSYAFNWVRQAPGQRL<br>ECMGGIVPLVSSTNYAQRFRGRITISADRSASTVYLEMTGLTSADTA<br>VYFCAREGEGWFGKPLRAFEFWGQGTLVAVST (SEQ ID NO: 30) |
| PGZL1_V6H3<br>VH | KVQLVQSGAELKKPWSSVRVSCKATGGSFSSYAFNWVRPAPGQRL<br>EWLGGIVPLVSSTNYAQRFRGRITISADRSASTVYLEMTGLTSADTA<br>VYFCAREGEGWFGRPLRAFEFWGQGTLVTVST (SEQ ID NO: 31) |
| PGZL1_V6H4<br>VH | KVQLVQSGAEVKRPGSSVTISCKASGGSFSSYAFNWVRQAPGLGLE<br>WMGGIIPLISIANYAQRRFRGRVTITADRSTSSIFLDLTRLTSVDTAL<br>YFCAREGEGWFGKPLGAFEFWGQGTAVTVTS (SEQ ID NO: 32) |
| PGZL1_V6H5<br>VH | KVQLVQSGAELKKPWSSMRVSCKASGGSFSSYAFNWVRQAPGQRL<br>EWLGGIVPLVSSTNYAQRFRGRITISADRSASTVYLEMTGLTSADTA<br>VYFCAREGEGWFGKPLRAFEFWGQGTLVTVSA (SEQ ID NO: 33) |
| PGZL1_V6H6<br>VH | GVQLVQSGAEVKKPGSSVTVSCKATGGTFSSLAFNWVRPMAPGQG<br>PEWMGGIVPLFSIVNYGQRFQGRLTIRADKSTTTVYLDLIRLTSDDT<br>ATYYCAREGEGWFGKPLRAFEFWGQGTLITVSS (SEQ ID NO: 34) |

TABLE 1-continued

Variable heavy chain (VH) and light chain (VL) domains.

PGZL1_V6H7      GVQLVQSGAEVKKPGVSVTVSCKATGGTFSSLAFNWVRQAPGQGP
VH             EYMGGIVPLFSIVNYAQRFQGRLTIRADKSTTTVYMDLNRLTSDDT
               ATYYCAREGEGWFGKPLRAFQLWGQGTVITVSS (SEQ ID NO: 35)

PGZL1_V6H8      GVQLVQSGAEVKRPGSSVEVSCKATGGTFSTLAFSWVRQAPGQGP
VH             EWMGGIVPLFTIVNYGQRFQGRLTIRADKSTTTVFLDLSGLTSADTA
               TYYCAREGEGWFGKPLRALEIWGQGTVITVSS (SEQ ID NO: 36)

PGZL1_V6H9      KVQLVQSGAEMKRPGSSVHAACKDRGGSFSSYAIIWVRQARELGFE
VH             WMGGIIPLLSRANYAQRWFRGRVTITAHESTSSIFLDLTRLTSVDTA
               LYFCAREGEGWFGKPLGAFEFWGQGTAVTVTS (SEQ ID NO: 37)

PGZL1_V2K1 VL   EIVLTQSPGTLSLSPGERATLSCRASQSVNSNYLAWYQQKPGQAPRL
               LIYRALGRATGIPDRFSGSGSGTDFTLTISRLEPEDFAVYYCQQYGTS
               ESTFGQGTRLEIR (SEQ ID NO: 38)

PGZL1_V2K2 VL   EIVLTQSPGTLSLSPGERATLSCRASQSVSGGALAWYQQKAGQAPR
               LLIYDTSGRATGVPGRESGSGSETDFSLTISRLEPEDFAVYYCQQYGT
               SQSTFGQGTRLETR (SEQ ID NO: 39)

PGZL1_V2K3 VL   EIVLTQSPGTFALSPGERATLSCRASQSVSGGALAWYQQKAGQAPR
               LLIYGTSGRATGVPGRFSGSGSETDFSLTISRLEPEDFAVYYCQQYGT
               SQSTFGQGTRLETR (SEQ ID NO: 40)

PGZL1_V2K4 VL   RIVLTQSPGTLSLSPGARATLSCRASQSVSGGSLAWYQQKAGRAPR
               SVIYDAVRRATAIPGRESGSGSETDFSLTISRLEPEDLAVYYCQQYGT
               SQSTFGQGTRLEIR (SEQ ID NO: 41)

PGZL1_V4K1 VL   EIVLTQPPGNFWSLSPGQRATLSCRAGQSVSGGSLAWYQQKAGQAP
               RLLIYDTSSRATGVRDRFSGSGSETDFSLTISRLEPEDFAVYYCQQYG
               TSQSTFGQGTRLEMR (SEQ ID NO: 42)

PGZL1_V4K2 VL   EIVLTQSPVTLSLSPGRKGTLSCRASQSVSGGSLAWYQQKPGQAPRL
               LIYDSSRATGVPGRFSGSGSETDFSLTISRLEAEDFAVYYCQQYGTS
               QSTFGQGTRLEIR (SEQ ID NO: 43)

PGZL1_V4K3 VL   DIVLTQSPGRFSLSPEERATLSCRASQSVSGGYVAWYQQKAGQAPR
               LPIYDYVSRATGVPGRFSGSGSETDFSLTISRLEPEDFAVYYCQQYG
               TSQSTFGQGTRLEIR (SEQ ID NO: 44)

PGZL1_V6K1 VL   EMVLTQSPGTLSLSPGEGATLSCRASQSVVYNSLAWYQQRPGQAPR
               LAILAASRRATGIPDRESGSGSGTDFTLTISRLEPEDFAVYYCQQYGT
               SQGTFGQGTKVEIK (SEQ ID NO: 45)

PGZL1_V6K2 VL   EIVLTQSPGTLSLSPGERATLSCRASQSVSSSYLAWYQQKPGQAPRL
               LIYGAYIRATGIPDRESGSGSGTDFTLTISRLEPEDFAVYYCQQYGTS
               QGTFGQGTKVEIK (SEQ ID NO: 46)

PGZL1_V6K3 VL   RMVLTQSPGTLSLSPGEGATLSCGASQSVVYNSLAWYQQRPGQAP
               RLVILAASRRAAGIPDRESGSGSGTDFTLTISRLEPEDFAVYYCQQYG
               TSQGTFGQGTKVEIK (SEQ ID NO: 47)

PGZL1_gVgDgJ    QVQLVQSGAEVKKPGSSVKVSCKASGGTFSSYAISWVRQAPGQGL
VH             EWMGGIIPIFGTANYAQKFQGRVTITADKSTSTAYMELSSLRSEDTA
               VYYCAREGEGWFGEPLRAFDVWGQGTVITVSS (SEQ ID NO: 48)

PGZL1_gVgDgJ    EIVLTQSPGTLSLSPGERATLSCRASQSVSSSYLAWYQQKPGQAPRL
VL             LIYGASSRATGIPDRFSGSGSGTDFTLTISRLEPEDFAVYYCQQYGTS
               QSTFGQGTRLEIKR (SEQ ID NO: 49)

PGZL1_gVgDmJ    QVQLVQSGAEVKKPGSSVKVSCKASGGTFSSYAISWVRQAPGQGL
VH             EWMGGIIPIFGTANYAQKFQGRVTITADKSTSTAYMELSSLRSEDTA
               VYYCAREGEGWFGEPLRAFEFWGQGTVITVSS (SEQ ID NO: 50)

PGZL1_gVgDmJ    EIVLTQSPGTLSLSPGERATLSCRASQSVSSSYLAWYQQKPGQAPRL
VL             LIYGASSRATGIPDRFSGSGSGTDFTLTISRLEPEDFAVYYCQQYGTS
               QSTFGQGTRLEIKR (SEQ ID NO: 5])

PGZL1_W99A      QVQLVQSGGEVKRPGSSVTVSCKATGGTFSTLAFNWVRQAPGQGP
VH             EWMGGIVPLFSIVNYGQKFQGRLTIRADKSTTTVFLDLSGLTSADTA
               TYYCAREGEGAFGKPLRAFEFWGQGTVITVSS (SEQ ID NO: 52)

PGZL1_F100A     QVQLVQSGGEVKRPGSSVTVSCKATGGTFSTLAFNWVRQAPGQGP
VH             EWMGGIVPLFSIVNYGQKFQGRLTIRADKSTTTVFLDLSGLTSADTA
               TYYCAREGEGWAGKPLRAFEFWGQGTVITVSS (SEQ ID NO: 53)

TABLE 1-continued

| Variable heavy chain (VH) and light chain (VL) domains. |
|---|

| | |
|---|---|
| PGZL1_gVmDmJ_<br>W99A VH | QVQLVQSGAEVKKPGSSVKVSCKASGGTFSSYAISWVRQAPGQGL<br>EWMGGIIPIFGTANYAQKFQGRVTITADKSTSTAYMELSSLRSEDTA<br>VYYCAREGEGAFGKPLRAFEFWGQGTVITVSS (SEQ ID NO: 54) |
| PGZL1_gVmDmJ<br>F100A VH | QVQLVQSGAEVKKPGSSVKVSCKASGGTFSSYAISWVRQAPGQGL<br>EWMGGIIPIFGTANYAQKFQGRVTITADKSTSTAYMELSSLRSEDTA<br>VYYCAREGEGWAGKPLRAFEFWGQGTVITVSS (SEQ ID NO: 55) |
| PGZL1 VH<br>comprising<br>"TGW" insertion | QVQLVQSGGEVKRPGSSVTVSCKATGGTFSTLAFNWVRQAPGQGP<br>EWMGGIVPLFSIVNYGQKFQGRLTIRADKSTTTVFLDLSGLTSADTA<br>TYYCAREGETGWGWFGKPLRAFEFWGQGTVITVSS (SEQ ID NO:<br>56) |
| H4K3_RS73PE<br>VH | KVQLVQSGAELKKPWSSVRVSCKASGGSFSSYAFNWVRQAPGQRL<br>EWLGGIVPLVSSTNYAQRFRGRVTISADPETSTVYLEMTGLTSADTA<br>VYFCAREGEGWFGRPLRAFEFWGQGTLVTVST (SEQ ID NO: 57) |
| H4K3_SFS28EPE<br>VH | KVQLVQSGAELKKPWSSVRVSCKASGGEPSYAFNWVRQAPGQRL<br>EWLGGIVPLVSSTNYAQRFRGRVTISADRSTSTVYLEMTGLTSADT<br>AVYFCAREGEGWFGRPLRAFEFWGQGTLVTVST (SEQ ID NO: 58) |
| H4K3_5M VH | KVQLVQSGAELKKPWSSVRVSCKASGGEPSYAFNWVRQAPGQRL<br>EWLGGIVPLVSSTNYAQRFRGRVTISADPETSTVYLEMTGLTSADTA<br>VYFCAREGEGWFGRPLRAFEFWGQGTLVTVST (SEQ ID NO: 59) |
| PGZL1_V2K3_G<br>50D | EIVLTQSPGTFALSPGERATLSCRASQSVSGGALAWYQQKAGQAPR<br>LLIYDTSGRATGVPGRFSGSGSETDFSLTISRLEPEDFAVYYCQQYGT<br>SQSTFGQGTRLETR (SEQ ID NO: 60) |

TABLE 2

| Example VH and VL CDR sequences. The CDRs have been determined according to Kabat. | | | |
|---|---|---|---|
| | CDR1 | CDR2 | CDR3 |
| PGZL1 VH | GGTFSTLA<br>(SEQ ID NO: 61) | IVPLFSIV<br>(SEQ ID NO: 62) | EGEGWFGKPLRAFEF<br>(SEQ ID NO: 63) |
| PGZL1.H4K3<br>VH | GGSFSSYA<br>(SEQ ID NO: 64) | IVPLVSST<br>(SEQ ID NO: 65) | EGEGWFGRPLRAFEF<br>(SEQ ID NO: 66) |
| PGZL1_<br>gVmDmJ VH | GGTFSSYA<br>(SEQ ID NO: 67) | IIPIFGTA<br>(SEQ ID NO: 68) | EGEGWFGKPLRAFEF<br>(SEQ ID NO: 69) |
| PGZL1 VL | QSVSGGA<br>(SEQ ID NO: 70) | DTS<br>(SEQ ID NO: 71) | QQYGTSQSTF<br>(SEQ ID NO: 72) |
| PGZL1.H4K3<br>VL | QSVSGGA<br>(SEQ ID NO: 73) | GTS<br>(SEQ ID NO: 74) | QQYGTSQSTF<br>(SEQ ID NO: 75) |
| PGZL1_<br>gVmDmJ VL | QSVSSSY<br>(SEQ ID NO: 76) | GAS<br>(SEQ ID NO: 77) | QQYGTSQSTF<br>(SEQ ID NO: 78) |

TABLE 3

| Example VH and VL Framework (FR) sequences. The FRs have been determined according to Kabat. | | | |
|---|---|---|---|
| | FR1 | FR2 | FR3 | FR4 |
| PGZL1 VH | EVQLVQSGGE<br>VKRPGSSVTV<br>SCKAT (SEQ<br>ID NO: 79) | FNWVRQAPG<br>QGPEWMGG<br>(SEQ ID NO:<br>80) | NYGQKFQGRL<br>TIRADKSTTTV<br>FLDLSGLTSAD<br>TATYYCAR<br>(SEQ ID NO: 81) | WGQGTVITVSS<br>(SEQ ID NO: 82) |

TABLE 3-continued

Example VH and VL Framework (FR) sequences. The FRs have been determined according to Kabat.

| | FR1 | FR2 | FR3 | FR4 |
|---|---|---|---|---|
| PGZL1.H4K3 VH | KVQLVQSGA ELKKPWSSVR VSCKAS (SEQ ID NO: 83) | FNWVRQAPG QRLEWLGG (SEQ ID NO: 84) | NYAQRFRGRV TISADRSTSTV YLEMTGLTSA DTAVYFCAR (SEQ ID NO: 85) | WGQGTLVTVST (SEQ ID NO: 86) |
| PGZL1_ gVmDmJ VH | QVQLVQSGA EVKKPGSSVK VSCKAS (SEQ ID NO: 87) | ISWVRQAPGQ GLEWMGG (SEQ ID NO: 88) | NYAQKFQGRV TITADKSTSTA YMELSSLRSED TAVYYCAR (SEQ ID NO: 89) | WGQGTVITVSS (SEQ ID NO: 90) |
| PGZL1 VL | DVVMTQSPG TLSLSPGERA TLSCRAS (SEQ ID NO: 91) | LAWYQQKPG QAPRLLIY (SEQ ID NO: 92) | SRPTGVPGRFS GSGSGTDFSLT ISRLEPEDFAV YYC (SEQ ID NO: 93) | GQGTRLEIK (SEQ ID NO: 94) |
| PGZL1.H4K3 VL | EIVLTQSPGTF ALSPGERATL SCRAS (SEQ ID NO: 95) | LAWYQQKAG QAPRLLIY (SEQ ID NO: 96) | GRATGVPGRF SGSGSETDFSL TISRLEPEDFA VYYC (SEQ ID NO: 97) | GQGTRLETR (SEQ ID NO: 98) |
| PGZL1_ gVmDmJ VL | EIVLTQSPGTL SLSPGERATL SCRAS (SEQ ID NO: 99) | LAWYQQKPG QAPRLLIY (SEQ ID NO: 100) | SRATGIPDRES GSGSGTDFTLT ISRLEPEDFAV YYC (SEQ ID NO: 101) | GQGTRLETR (SEQ ID NO: 102) |

TABLE 4

Heavy chain (HC) and Light chain (LC) sequences.

| PGZL1 HC | MELGLRWVFLVAILEGVQCEVQLVQSGGEVKRPGSSVTVSCKATGGT FSTLAFNWVRQAPGQGPEWMGGIVPLFSIVNYGQKFQGRLTIRADKST TTVFLDLSGLTSADTATYYCAREGEGWFGKPLRAFEFWGQGTVITVSS ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKR VEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVL HQDWLNGKEYKCKVSNKALPAPIEKTISKAKGQPREPQVYTLPPSREE MTKNQVSLTCLVKGFYPSDIAVEWESNGQPENNYKTTPPVLDSDGSFF LYSKLTVDKSRWQQGNVFSCSVMHEALHNHYTQKSLSLSPGK (SEQ ID NO: 103) |
|---|---|
| PGZL1.H4 HC | MELGLRWVFLVAILEGVQCKVQLVQSGAELKKPWSSVRVSCKASGGS FSSYAFNWVRQAPGQRLEWLGGIVPLVSSTNYAQRFRGRVTISADRST STVYLEMTGLTSADTAVYFCAREGEGWFGRPLRAFEFWGQGTLVTVS TASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKR VEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVL HQDWLNGKEYKCKVSNKALPAPIEKTISKAKGQPREPQVYTLPPSREE MTKNQVSLTCLVKGFYPSDIAVEWESNGQPENNYKTTPPVLDSDGSFF LYSKLTVDKSRWQQGNVFSCSVMHEALHNHYTQKSLSLSPGK (SEQ ID NO: 104) |
| PGZL1_ gVmDmJ HC | MELGLRWVFLVAILEGVQCQVQLVQSGAEVKKPGSSVKVSCKASGGT FSSYAISWVRQAPGQGLEWMGGIIPIFGTANYAQKFQGRVTITADKSTS TAYMELSSLRSEDTAVYYCAREGEGWFGKPLRAFEFWGQGTVITVSS ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKR VEPKSCDKTHTCPPCPAPELLGGPSVFLFPPKPKDTLMISRTPEVTCVV VDVSHEDPEVKFNWYVDGVEVHNAKTKPREEQYNSTYRVVSVLTVL HQDWLNGKEYKCKVSNKALPAPIEKTISKAKGQPREPQVYTLPPSREE MTKNQVSLTCLVKGFYPSDIAVEWESNGQPENNYKTTPPVLDSDGSFF LYSKLTVDKSRWQQGNVFSCSVMHEALHNHYTQKSLSLSPGK (SEQ ID NO: 105) |

TABLE 4-continued

Heavy chain (HC) and Light chain (LC) sequences.

| | |
|---|---|
| PGZL1 LC | MGWSCIILFLVATATGVHDVVMTQSPGTLSLSPGERATLSCRASQSVS<br>GGALAWYQQKPGQAPRLLIYDTSSRPTGVPGRFSGSGSGTDFSLTISRL<br>EPEDFAVYYCQQYGTSQSTFGQGTRLEIKRTVAAPSVFIFPPSDEQLKS<br>GTASVVCLLNNFYPREAKVQWKVDNALQSGNSQESVTEQDSKDSTYS<br>LSSTLTLSKADYEKHKVYACEVTHQGLSSPVTKSFNRGEC (SEQ ID<br>NO: 106) |
| PGZL1.K3<br>LC | MGWSCIILFLVATATGVHEIVLTQSPGTFALSPGERATLSCRASQSVSG<br>GALAWYQQKAGQAPRLLIYGTSGRATGVPGRFSGSGSETDFSLTISRLE<br>PEDFAVYYCQQYGTSQSTFGQGTRLETRRTVAAPSVFIFPPSDEQLKSG<br>TASVVCLLNNFYPREAKVQWKVDNALQSGNSQESVTEQDSKDSTYSL<br>SSTLTLSKADYEKHKVYACEVTHQGLSSPVTKSFNRGEC (SEQ ID NO:<br>107) |
| PGZL1_<br>gVmDmJ LC | MGWSCIILFLVATATGVHEIVLTQSPGTLSLSPGERATLSCRASQSVSSS<br>YLAWYQQKPGQAPRLLIYGASSRATGIPDRFSGSGSGTDFTLTISRLEPE<br>DFAVYYCQQYGTSQSTFGQGTRLETRRTVAAPSVFIFPPSDEQLKSGTA<br>SVVCLLNNFYPREAKVQWKVDNALQSGNSQESVTEQDSKDSTYSLSS<br>TLTLSKADYEKHKVYACEVTHQGLSSPVTKSFNRGEC (SEQ ID NO:<br>108) |
| variant IgG Fc<br>region | ASTKGPSVFPLAPSSKSTSGGTAALGCLVKDYFPEPVTVSWNSGALTS<br>GVHTFPAVLQSSGLYSLSSVVTVPSSSLGTQTYICNVNHKPSNTKVDK<br>KVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTV<br>LHQDWLNGKEYKCKVSNKALPAPIEKTISKAKGQPREPQVYTLPPSRD<br>ELTKNQVSLTCLVKGFYPSDIAVEWESNGQPENNYKTTPPVLDSDGSF<br>FLYSKLTVDKSRWQQGNVFSCSVLHEALHSHYTQKSLSLSPGK (SEQ<br>ID NO: 109) |

In some embodiments, an isolated monoclonal antibody described herein comprises a VH, a VL, or a VH and VL as shown in Table 1.

In some embodiments, an isolated monoclonal antibody described herein comprises one, two, three, four, five or six of the VH CDR1, VH CDR2, VH CDR3, VL CDR1, VL CDR2, and VL CDR3 sequences of a VH or VL shown in Table 1. In some embodiments, the VH CDR1, VH CDR2, VH CDR3, VL CDR1, VL CDR2, and VL CDR3 is according to Kabat.

In some embodiments, an isolated monoclonal antibody described herein comprises one, two, three, four, five or six of the VH CDR1, VH CDR2, VH CDR3, VL CDR1, VL CDR2, and VL CDR3 sequences shown in Table 2.

In some embodiments, an isolated monoclonal antibody described herein comprises a VH CDR3 sequence of a VH shown in Table 1. In some embodiments, the VH CDR3 is according to Kabat.

In some embodiments, an isolated monoclonal antibody described herein comprises a VH CDR3 sequence shown in Table 2.

In some embodiments, an isolated monoclonal antibody described herein comprises a VH CDR1, VH CDR2, VH CDR3, VL CDR1, VL CDR2, and VL CDR3 sequence of a VH or VL shown in Table 1. In some embodiments, the VH CDR1, VH CDR2, VH CDR3, VL CDR1, VL CDR2, and VL CDR3 is according to Kabat.

Also provided herein are polypeptides that comprise an amino acid sequence having at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence, or is identical to the sequences shown in Tables 1-4.

In some embodiments, an isolated monoclonal antibody described herein specifically binds to HIV Env MPER and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of any of the VH regions shown in Table 1. In some embodiments, the antibody is a human antibody. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of any of the VH and VL regions shown in Table 1.

In some embodiments, an isolated monoclonal antibody described herein specifically binds to HIV Env MPER and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of PGZL1 VH, PGZL1.H4K3 VH, or PGZL1_gVmDmJ VH. In some embodiments, the antibody is a human antibody. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ.

In some embodiments, an isolated monoclonal antibody described herein specifically binds to HIV Env MPER and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to a VH CDR3 shown in Table 2. In some embodiments, the antibody is a human antibody. In some embodiments, the antibody comprises the VH CDR1, VH CDR2, VH CDR3, VL CDR1, VL CDR2, and VL CDR3 of an antibody described herein. In some embodiments, the antibody comprises a VH CDR1, VH CDR2, VH CDR3, VL CDR1, VL CDR2, and VL CDR3 shown in Table 2.

In some embodiments, an isolated monoclonal antibody described herein specifically binds to HIV Env MPER and comprises a VH CDR1, VH CDR2, VH CDR3, VL CDR1, VL CDR2, and VL CDR3, wherein the VH CDR3 comprises the VH CDR3 of any of the VH regions shown in Table 1 comprising 0, 1, 2, 3, 4, or 5 substitutions, insertions, or deletions. In some embodiments, the antibody is a human antibody. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2.

In some embodiments, an isolated monoclonal antibody described herein specifically binds to HIV Env MPER and comprises a VH CDR1, VH CDR2, VH CDR3, VL CDR1, VL CDR2, and VL CDR3, wherein the VH CDR3 comprises the VH CDR3 of PGZL1 VH, PGZL1.H4K3 VH, or PGZL1_gVmDmJ VH comprising 0, 1, 2, 3, 4, or 5 substitutions, insertions, or deletions. In some embodiments, the antibody is a human antibody. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2.

In some embodiments, an isolated monoclonal antibody described herein specifically binds to HIV Env MPER and comprises a VH CDR1, VH CDR2, VH CDR3, VL CDR1, VL CDR2, and VL CDR3, wherein the VH CDR3 comprises a VH CDR3 shown in Table 2 comprising 0, 1, 2, 3, 4, or 5 substitutions, insertions, or deletions. In some embodiments, the antibody is a human antibody. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to the VH CDR1 of any of the VH regions shown in Table 1; (b) the VH CDR2 comprises an amino acid sequence that is at least about 90%, 95%, 97%, 98%, 99% or 100% identical to the VH CDR2 of any of the VH regions shown in Table 1; and (c) the VH CDR3 comprises an amino acid sequence that is at least about 90%, 95%, 97%, 98%, 99% or 100% identical to the VH CDR3 of any of the VH regions shown in Table 1. In some embodiments, the antibody comprises the VL CDR1, VL CDR2, and VL CDR3 of an antibody described herein. In some embodiments, the antibody comprises the VL CDR1, VL CDR2, and VL CDR3 of PGZL1 VL, PGZL1.H4K3 VL, or PGZL1_gVmDmJ VL. In some embodiments, the antibody comprises a VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to the VH CDR1 of PGZL1 VH, PGZL1.H4K3 VH, or PGZL1_gVmDmJ VH; (b) the VH CDR2 comprises an amino acid sequence that is at least about 90%, 95%, 97%, 98%, 99% or 100% identical to the VH CDR2 of PGZL1 VH, PGZL1.H4K3 VH, or PGZL1_gVmDmJ VH; and (c) the VH CDR3 comprises an amino acid sequence that is at least about 90%, 95%, 97%, 98%, 99% or 100% identical to the VH CDR3 of PGZL1 VH, PGZL1.H4K3 VH, or PGZL1_gVmDmJ VH. In some embodiments, the antibody comprises the VL CDR1, VL CDR2, and VL CDR3 of an antibody described herein. In some embodiments, the antibody comprises the VL CDR1, VL CDR2, and VL CDR3 of PGZL1 VL, PGZL1.H4K3 VL, or PGZL1_gVmDmJ VL. In some embodiments, the antibody comprises a VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises an amino acid sequence that is at least about 90%, 95%, 97%, 98%, 99% or 100% identical to a VH CDR1 shown in Table 2; (b) the VH CDR2 comprises an amino acid sequence that is at least about 90%, 95%, 97%, 98%, 99% or 100% identical to a VH CDR2 shown in Table 2; and (c) the VH CDR3 comprises an amino acid sequence that is at least about 90%, 95%, 97%, 98%, 99% or 100% identical to a VH CDR3 shown in Table 2. In some embodiments, the antibody comprises the VL CDR1, VL CDR2, and VL CDR3 of an antibody described herein. In some embodiments, the antibody comprises the VL CDR1, VL CDR2, and VL CDR3 of PGZL1 VL, PGZL1.H4K3 VL, or PGZL1_gVmDmJ VL. In some embodiments, the antibody comprises a VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of any of the VH regions shown in Table 1 comprising 0, 1, 2, 3, 4, or 5 substitutions, insertions, or deletions; (b) the VH CDR2 comprises the VH CDR2 of any of the VH regions shown in Table 1 comprising 0, 1, 2, 3, 4, or 5 substitutions, insertions, or deletions; and (c) the VH CDR3 comprises the VH CDR3 of any of the VH regions shown in Table 1 comprising 0, 1, 2, 3, 4, or 5 substitutions, insertions, or deletions. In some embodiments, the antibody comprises the VL CDR1, VL CDR2, and VL CDR3 of an antibody described herein. In some embodiments, the antibody comprises the VL CDR1, VL CDR2, and VL CDR3 of PGZL1 VL, PGZL1.H4K3 VL, or PGZL1_gVmDmJ VL. In some embodiments, the antibody comprises a VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PGZL1 VH, PGZL1.H4K3 VH, or PGZL1_gVmDmJ VH comprising 0, 1, 2, 3, 4, or 5 substitutions, insertions, or deletions; (b) the VH CDR2 comprises the VH CDR2 of PGZL1 VH, PGZL1.H4K3 VH, or PGZL1_gVmDmJ VH comprising 0, 1, 2, 3, 4, or 5 substitutions, insertions, or deletions; and (c) the VH CDR3 comprises the VH CDR3 of PGZL1 VH, PGZL1.H4K3 VH, or PGZL1_gVmDmJ VH comprising 0, 1, 2, 3, 4, or 5 substitutions, insertions, or deletions. In some embodiments, the antibody comprises the VL CDR1, VL CDR2, and VL CDR3 of an antibody described herein. In some embodiments, the antibody comprises the VL CDR1, VL CDR2, and VL CDR3 of PGZL1 VL, PGZL1.H4K3 VL, or PGZL1_gVmDmJ VL. In some embodiments, the antibody comprises a VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises a VH CDR1 shown in Table 2 comprising 0, 1, 2, 3, 4, or 5 substitutions, insertions, or deletions; (b) a VH CDR2 comprises the VH CDR2 shown in Table 2 comprising 0, 1, 2, 3, 4, or 5 substitutions, insertions, or deletions; and (c) a VH CDR3 comprises the VH CDR3 shown in Table 2 comprising 0, 1, 2, 3, 4, or 5 substitutions, insertions, or deletions. In some embodiments, the antibody comprises the VL CDR1, VL CDR2, and VL CDR3 of an antibody described herein. In some embodiments, the antibody comprises the VL CDR1, VL CDR2, and VL CDR3 of PGZL1 VL, PGZL1.H4K3 VL, or PGZL1_gVmDmJ VL. In some embodiments, the antibody comprises a VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of any of the VH regions shown in Table 1; (b) the VH CDR2 comprises the VH CDR2 of any of the VH regions shown in Table 1; and (c) the VH CDR3 comprises the VH CDR3 of any of the VH regions shown in Table 1. In some embodiments, the antibody comprises the VL CDR1, VL CDR2, and VL CDR3 of an antibody described herein. In some embodiments, the antibody comprises the VL CDR1, VL CDR2, and VL CDR3 of PGZL1 VL, PGZL1.H4K3 VL, or PGZL1_gVmDmJ VL. In some embodiments, the antibody comprises a VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of PGZL1 VH, PGZL1.H4K3 VH, or PGZL1_gVmDmJ VH;

(b) the VH CDR2 comprises the VH CDR2 of PGZL1 VH, PGZL1.H4K3 VH, or PGZL1_gVmDmJ VH; and (c) the VH CDR3 comprises the VH CDR3 of PGZL1 VH, PGZL1.H4K3 VH, or PGZL1_gVmDmJ VH. In some embodiments, the antibody comprises the VL CDR1, VL CDR2, and VL CDR3 of an antibody described herein. In some embodiments, the antibody comprises the VL CDR1, VL CDR2, and VL CDR3 of PGZL1 VL, PGZL1.H4K3 VL, or PGZL1_gVmDmJ VL. In some embodiments, the antibody comprises a VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises a VH CDR1 shown in Table 2; (b) the VH CDR2 comprises a VH CDR2 shown in Table 2; and (c) the VH CDR3 comprises a VH CDR3 shown in Table 2. In some embodiments, the antibody comprises the VL CDR1, VL CDR2, and VL CDR3 of an antibody described herein. In some embodiments, the antibody comprises the VL CDR1, VL CDR2, and VL CDR3 of PGZL1 VL, PGZL1.H4K3 VL, or PGZL1_gVmDmJ VL. In some embodiments, the antibody comprises a VL CDR1, VL CDR2, and VL CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises an amino acid sequence that is at least about 90%, 95%, 97%, 98%, 99% or 100% identical to the VL CDR1 of any of the VL regions shown in Table 1; (b) the VL CDR2 comprises an amino acid sequence that is at least about 90%, 95%, 97%, 98%, 99% or 100% identical to the VL CDR2 of any of the VL regions shown in Table 1; and (c) the VL CDR3 comprises an amino acid sequence that is at least about 90%, 95%, 97%, 98%, 99% or 100% identical to the VL CDR3 of any of the VL regions shown in Table 1. In some embodiments, the antibody comprises the VH CDR1, VH CDR2, and VH CDR3 of an antibody described herein. In some embodiments, the antibody comprises the VH CDR1, VH CDR2, and VH CDR3 of PGZL1, PGZL1.H4K3, or PGZL1_gVmDmJ. In some embodiments, the antibody comprises a VH CDR1, VH CDR2, and VH CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises an amino acid sequence that is at least about 90%, 95%, 97%, 98%, 99% or 100% identical to the VL CDR1 of PGZL1 VL, PGZL1.H4K3 VL, or PGZL1_gVmDmJ VL; (b) the VL CDR2 comprises an amino acid sequence that is at least about 90%, 95%, 97%, 98%, 99% or 100% identical to the VL CDR2 of PGZL1 VL, PGZL1.H4K3 VL, or PGZL1_gVmDmJ VL; and (c) the VL CDR3 comprises an amino acid sequence that is at least about 90%, 95%, 97%, 98%, 99% or 100% identical to the VL CDR3 of PGZL1 VL, PGZL1.H4K3 VL, or PGZL1_gVmDmJ VL. In some embodiments, the antibody comprises the VH CDR1, VH CDR2, and VH CDR3 of an antibody described herein. In some embodiments, the antibody comprises the VH CDR1, VH CDR2, and VH CDR3 of PGZL1, PGZL1.H4K3, or PGZL1_gVmDmJ. In some embodiments, the antibody comprises a VH CDR1, VH CDR2, and VH CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises an amino acid sequence that is at least about 90%, 95%, 97%, 98%, 99% or 100% identical to a VL CDR1 shown in Table 2; (b) the VL CDR2 comprises an amino acid sequence that is at least about 90%, 95%, 97%, 98%, 99% or 100% identical to a VL CDR2 shown in Table 2; and (c) the VL CDR3 comprises an amino acid sequence that is at least about 90%, 95%, 97%, 98%, 99% or 100% identical to a VL CDR3 shown in Table 2. In some embodiments, the antibody comprises the VH CDR1, VH CDR2, and VH CDR3 of an antibody described herein. In some embodiments, the antibody comprises the VH CDR1, VH CDR2, and VH CDR3 of PGZL1, PGZL1.H4K3, or PGZL1_gVmDmJ. In some embodiments, the antibody comprises a VH CDR1, VH CDR2, and VH CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of any of the VL regions shown in Table 1 comprising 0, 1, 2, 3, 4, or 5 substitutions, insertions, or deletions; (b) the VL CDR2 comprises the VL CDR2 of any of the VL regions shown in Table 1 comprising 0, 1, 2, 3, 4, or 5 substitutions, insertions, or deletions; and (c) the VL CDR3 comprises the VL CDR3 of any of the VL regions shown in Table 1 comprising 0, 1, 2, 3, 4, or 5 substitutions, insertions, or deletions. In some embodiments, the antibody comprises the VH CDR1, VH CDR2, and VH CDR3 of an antibody described herein. In some embodiments, the antibody comprises the VH CDR1, VH CDR2, and VH CDR3 of PGZL1, PGZL1.H4K3, or PGZL1_gVmDmJ. In some embodiments, the antibody comprises a VH CDR1, VH CDR2, and VH CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of PGZL1 VL, PGZL1.H4K3 VL, or PGZL1_gVmDmJ VL comprising 0, 1, 2, 3, 4, or 5 substitutions, insertions, or deletions; (b) the VL CDR2 comprises the VL CDR2 of PGZL1 VL, PGZL1.H4K3 VL, or PGZL1_gVmDmJ VL comprising 0, 1, 2, 3, 4, or 5 substitutions, insertions, or deletions; and (c) the VL CDR3 comprises the VL CDR3 of PGZL1 VL, PGZL1.H4K3 VL, or PGZL1_gVmDmJ VL comprising 0, 1, 2, 3, 4, or 5 substitutions, insertions, or deletions. In some embodiments, the antibody comprises the VH CDR1, VH CDR2, and VH CDR3 of an antibody described herein. In some embodiments, the antibody comprises the VH CDR1, VH CDR2, and VH CDR3 of PGZL1, PGZL1.H4K3, or PGZL1_gVmDmJ. In some embodiments, the antibody comprises a VH CDR1, VH CDR2, and VH CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises a VL CDR1 shown in Table 2 comprising 0, 1, 2, 3, 4, or 5 substitutions, insertions, or deletions; (b) the VL CDR2 comprises a VL CDR2 shown in Table 2 comprising 0, 1, 2, 3, 4, or 5 substitutions, insertions, or deletions; and (c) the VL CDR3 comprises a VL CDR3 shown in Table 2 comprising 0, 1, 2, 3, 4, or 5 substitutions, insertions, or deletions. In some embodiments, the antibody comprises the VH CDR1, VH CDR2, and VH CDR3 of an antibody described herein. In some embodiments, the antibody comprises the VH CDR1, VH CDR2, and VH CDR3 of PGZL1, PGZL1.H4K3, or PGZL1_gVmDmJ. In some embodiments, the antibody comprises a VH CDR1, VH CDR2, and VH CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of any of the VL regions shown in Table 1; (b) the VL CDR2 comprises the VL CDR2 of any of the VL regions shown in Table 1; and (c) the VL CDR3 comprises the VL CDR3 of any of the VL regions shown in Table 1. In some embodiments, the antibody comprises the VH CDR1, VH CDR2, and VH CDR3 of an antibody described herein. In some embodiments, the antibody comprises the VH CDR1, VH CDR2, and VH CDR3 of PGZL1, PGZL1.H4K3 VH or PGZL1_gVmDmJ. In some embodiments, the antibody comprises a VH CDR1, VH CDR2, and VH CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises the VL CDR1 of PGZL1 VL, PGZL1.H4K3 VL, or PGZL1_gVmDmJ VL; (b) the VL CDR2 comprises the VL CDR2 of PGZL1 VL, PGZL1.H4K3 VL, or PGZL1_gVmDmJ VL; and (c) the VL CDR3 comprises the VL CDR3 of PGZL1 VL, PGZL1.H4K3 VL, or PGZL1_gVmDmJ VL. In some embodiments, the antibody comprises the VH CDR1, VH CDR2, and VH CDR3 of an antibody described herein. In some embodiments, the antibody comprises the VH CDR1, VH CDR2, and VH CDR3 of PGZL1, PGZL1.H4K3, or PGZL1_gVmDmJ. In some embodiments, the antibody comprises a VH CDR1, VH CDR2, and VH CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein (a) the VL CDR1 comprises a VL CDR1 shown in Table 2; (b) the VL CDR2 comprises a VL CDR2 shown in Table 2; and (c) the VL CDR3 comprises a VL CDR3 shown in Table 2. In some embodiments, the antibody comprises the VH CDR1, VH CDR2, and VH CDR3 of an antibody described herein. In some embodiments, the antibody comprises the VH CDR1, VH CDR2, and VH CDR3 of PGZL1, PGZL1.H4K3, or PGZL1_gVmDmJ. In some embodiments, the antibody comprises a VH CDR1, VH CDR2, and VH CDR3 shown in Table 2.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the VH CDR1, VH CDR2, VH CDR3, VL CDR1, VL CDR2, and VL CDR3, respectively, of any of the VH and VL regions shown in Table 1.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PGZL1, PGZL1.H4K3, or PGZL1_gVmDmJ VH CDR1, VH CDR2, VH CDR3, VL CDR1, VL CDR2, and VL CDR3, respectively.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PGZL1 VH CDR1, VH CDR2, VH CDR3, VL CDR1, VL CDR2, and VL CDR3, respectively.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PGZL1.H4K3 VH CDR1, VH CDR2, VH CDR3, VL CDR1, VL CDR2, and VL CDR3, respectively.

In some embodiments, an isolated monoclonal antibody described herein specifically binds to HIV Env MPER and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the PGZL1_gVmDmJ VH CDR1, VH CDR2, VH CDR3, VL CDR1, VL CDR2, and VL CDR3, respectively.

In some embodiments, an isolated monoclonal antibody described herein specifically binds to HIV Env MPER and comprises a heavy chain variable region (VH) and a light chain variable region (VL), wherein the VH comprises an amino acid sequence that is at least about 90%, 95%, 97%, 98%, 99% or 100% identical to the VH of any of the VH regions shown in Table 1. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2. In some embodiments, the antibody comprises the VL of an antibody described herein. In some embodiments, the antibody comprises the VL of PGZL1, PGZL1.H4K3, or PGZL1_gVmDmJ.

In some embodiments, an isolated monoclonal antibody described herein specifically binds to HIV Env MPER and comprises a heavy chain variable region (VH) and a light chain variable region (VL), wherein the VH comprises an amino acid sequence that is at least about 90%, 95%, 97%, 98%, 99% or 100% identical to the VH of PGZL1 VH, PGZL1.H4K3 VH, or PGZL1_gVmDmJ VH. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2. In some embodiments, the antibody comprises the VL of an antibody described herein. In some embodiments, the antibody comprises the VL of PGZL1, PGZL1.H4K3, or PGZL1_gVmDmJ.

In some embodiments, an isolated monoclonal antibody described herein specifically binds to HIV Env MPER and comprises a heavy chain variable region (VH) and a light chain variable region (VL), wherein the VL comprises an amino acid sequence that is at least about 90%, 95%, 97%, 98%, 99% or 100% identical to the VL of any of the VL regions shown in Table 1. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2. In some embodiments, the antibody comprises the VH of an antibody described herein. In some embodiments, the antibody comprises the VH of PGZL1 VH, PGZL1.H4K3 VH, or PGZL1_gVmDmJ VH.

In some embodiments, an isolated monoclonal antibody described herein specifically binds to HIV Env MPER and comprises a heavy chain variable region (VH) and a light chain variable region (VL), wherein the VL comprises an amino acid sequence that is at least about 90%, 95%, 97%, 98%, 99% or 100% identical to the VL of PGZL1 VL, PGZL1.H4K3 VL, or PGZL1_gVmDmJ VL. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2. In some embodiments, the antibody comprises the VH of an antibody described herein. In some embodiments, the antibody comprises the VH of PGZL1 VH, PGZL1.H4K3 VH, or PGZL1_gVmDmJ VH.

In some embodiments, an isolated monoclonal antibody described herein specifically binds to HIV Env MPER and comprises a heavy chain variable region (VH) and a light chain variable region (VL), wherein the VH and VL comprise an amino acid sequence that is at least about 90%, 95%, 97%, 98%, 99% or 100% identical to the any of the VH and VL regions shown in Table 1, respectively. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2.

In some embodiments, an isolated monoclonal antibody described herein specifically binds to HIV Env MPER and comprises a heavy chain variable region (VH) and a light chain variable region (VL), wherein the VH and VL comprise an amino acid sequence that is at least about 90%, 95%, 97%, 98%, 99% or 100% identical to the PGZL1, PGZL1.H4K3, or PGZL1_gVmDmJ VH and VL, respectively. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2.

In some embodiments, an isolated monoclonal antibody described herein specifically binds to HIV Env MPER and comprises a heavy chain variable region (VH) and a light chain variable region (VL), wherein the VH and VL comprise an amino acid sequence that is at least about 90%, 95%, 97%, 98%, 99% or 100% identical to the PGZL1_gVmDmJ VH and VL, respectively. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2.

In some embodiments, an isolated monoclonal antibody described herein specifically binds to HIV Env MPER and comprises a heavy chain variable region (VH) and a light chain variable region (VL), and the VH further comprises a VH FR1, VH FR2, VH FR3, and VH FR4, wherein the VH FR1, VH FR2, VH FR3, and VH FR4 comprises an amino acid sequence with at least about 80%, at least about 85%, at least about 90%, at least about 95%, at least about 97%, at least about 98%, at least about 99% or 100% identity to a VH FR1, VH FR2, VH FR3, and VH FR4, respectively, of any of the VH regions shown in Table 1. In some embodiments, an isolated monoclonal antibody described herein specifically binds to HIV Env MPER and comprises a heavy chain variable region (VH) and a light chain variable region (VL), and the VH further comprises a VH FR1, VH FR2, VH FR3, and VH FR4, wherein the VH FR1, VH FR2, VH FR3, and VH FR4 comprises an amino acid sequence with at least about 80%, at least about 85%, at least about 90%, at least about 95%, at least about 97%, at least about 98%, at least about 99% or 100% identity to the VH FR1, VH FR2, VH FR3, and VH FR4, respectively, of PGZL1 VH, PGZL1.H4K3 VH, or PGZL1_gVmDmJ VH. In some embodiments, an isolated monoclonal antibody described herein specifically binds to HIV Env MPER and comprises a heavy chain variable region (VH) and a light chain variable region (VL), and the VH further comprises a VH FR1, VH FR2, VH FR3, and VH FR4, wherein the VH FR1, VH FR2, VH FR3, and VH FR4 comprises an amino acid sequence with at least about 80%, at least about 85%, at least about 90%, at least about 95%, at least about 97%, at least about 98%, at least about 99% or 100% identity to a VH FR1, VH FR2, VH FR3, and VH FR4, respectively shown in Table 3.

In some embodiments, an isolated monoclonal antibody described herein specifically binds to HIV Env MPER and comprises a heavy chain variable region (VH) and a light chain variable region (VL), and the VL further comprises a VL FR1, VL FR2, VL FR3, and VL FR4, wherein the VL FR1, VL FR2, VL FR3, and VL FR4 comprises an amino acid sequence with at least about 80%, at least about 85%, at least about 90%, at least about 95%, at least about 97%, at least about 98%, at least about 99% or 100% identity to a VL FR1, VL FR2, VL FR3, and VL FR4, respectively, of any of the VL regions shown in Table 1. In some embodiments, an isolated monoclonal antibody described herein specifically binds to HIV Env MPER and comprises a heavy chain variable region (VH) and a light chain variable region (VL), and the VL further comprises a VL FR1, VL FR2, VL FR3, and VL FR4, wherein the VL FR1, VL FR2, VL FR3, and VL FR4 comprises an amino acid sequence with at least about 80%, at least about 85%, at least about 90%, at least about 95%, at least about 97%, at least about 98%, at least about 99% or 100% identity to the VL FR1, VL FR2, VL FR3, and VL FR4, respectively, of PGZL1 VL, PGZL1.H4K3 VL, or PGZL1_gVmDmJ VL. In some embodiments, an isolated monoclonal antibody described herein specifically binds to HIV Env MPER and comprises a heavy chain variable region (VH) and a light chain variable region (VL), and the VL further comprises a VL FR1, VL FR2, VL FR3, and VL FR4, wherein the VL FR1, VL FR2, VL FR3, and VL FR4 comprises an amino acid sequence with at least about 80%, at least about 85%, at least about 90%, at least about 95%, at least about 97%, at least about 98%, at least about 99% or 100% identity to a VL FR1, VL FR2, VL FR3, and VL FR4, respectively shown in Table 3.

In some embodiments, an isolated monoclonal antibody described herein specifically binds to HIV Env MPER and comprises a heavy chain variable region (VH) and a light chain variable region (VL), and further comprises a VH FR1, VH FR2, VH FR3, VH FR4, VL FR1, VL FR2, VL FR3, and VL FR4, wherein the VH FR1, VH FR2, VH FR3, VH FR4, VL FR1, VL FR2, VL FR3, and VL FR4 comprise an amino acid sequence with at least about 80%, at least about 85%, at least about 90%, at least about 95%, at least about 97%, at least about 98%, at least about 99% or 100% identity to a VH FR1, VH FR2, VH FR3, VH FR4, VL FR1, VL FR2, VL FR3, and VL FR4, respectively, of any of the VH and VL regions shown in Table 1. In some embodiments, an isolated monoclonal antibody described herein specifically binds to HIV Env MPER and comprises a heavy chain variable region (VH) and a light chain variable region (VL), and further comprises a VH FR1, VH FR2, VH FR3, VH FR4, VL FR1, VL FR2, VL FR3, and VL FR4, wherein the VH FR1, VH FR2, VH FR3, VH FR4, VL FR1, VL FR2, VL FR3, and VL FR4 comprise an amino acid sequence with at least about 80%, at least about 85%, at least about 90%, at least about 95%, at least about 97%, at least about 98%, at least about 99% or 100% identity to the VH FR1, VH FR2, VH FR3, VH FR4, VL FR1, VL FR2, VL FR3, and VL FR4, respectively, of PGZL1, PGZL1.H4K3, or PGZL1_gVmDmJ. In some embodiments, an isolated monoclonal antibody described herein specifically binds to HIV Env MPER and comprises a heavy chain variable region (VH) and a light chain variable region (VL), and further comprises a VH FR1, VH FR2, VH FR3, VH FR4, VL FR1, VL FR2, VL FR3, and VL FR4, wherein the VH FR1, VH FR2, VH FR3, VH FR4, VL FR1, VL FR2, VL FR3, and VL FR4 comprise an amino acid sequence with at least about 80%, at least about 85%, at least about 90%, at least about 95%, at least about 97%, at least about 98%, at least about 99% or 100% identity to a VH FR1, VH FR2, VH FR3, VH FR4, VL FR1, VL FR2, VL FR3, and VL FR4, respectively shown in Table 3.

In some embodiments, an isolated monoclonal antibody described herein specifically binds to HIV Env MPER and comprises a heavy chain variable region (VH) and a light chain variable region (VL), and the VH further comprises a VH FR1, VH FR2, VH FR3, and VH FR4, wherein the VH FR1, VH FR2, VH FR3, and VH FR4 comprises the amino acid sequence of a VH FR1, VH FR2, VH FR3, and VH FR4, respectively, of any of the VH regions shown in Table 1 comprising 0, 1, 2, 3, 4, or 5 substitutions, deletions, or insertions. In some embodiments, an isolated monoclonal antibody described herein specifically binds to HIV Env MPER and comprises a heavy chain variable region (VH) and a light chain variable region (VL), and the VH further comprises a VH FR1, VH FR2, VH FR3, and VH FR4, wherein the VH FR1, VH FR2, VH FR3, and VH FR4 comprises the amino acid sequence of a VH FR1, VH FR2, VH FR3, and VH FR4, respectively, of PGZL1 VH, PGZL1.H4K3 VH, or PGZL1_gVmDmJ VH comprising 0, 1, 2, 3, 4, or 5 substitutions, deletions, or insertions. In some embodiments, an isolated monoclonal antibody described herein specifically binds to HIV Env MPER and comprises a heavy chain variable region (VH) and a light chain variable region (VL), and the VH further comprises a VH FR1, VH FR2, VH FR3, and VH FR4, wherein the VH FR1, VH FR2, VH FR3, and VH FR4 comprises the amino acid sequence of a VH FR1, VH FR2, VH FR3, and VH FR4, respectively, shown in Table 3 comprising 0, 1, 2, 3, 4, or 5 substitutions, deletions, or insertions.

In some embodiments, an isolated monoclonal antibody described herein specifically binds to HIV Env MPER and comprises a heavy chain variable region (VH) and a light chain variable region (VL), and the VL further comprises a VL FR1, VL FR2, VL FR3, and VL FR4, wherein the VL FR1, VL FR2, VL FR3, and VL FR4 comprises the amino acid sequence of a VL FR1, VL FR2, VL FR3, and VL FR4, respectively, of any of the VL regions shown in Table 1 comprising 0, 1, 2, 3, 4, or 5 substitutions, deletions, or insertions. In some embodiments, an isolated monoclonal antibody described herein specifically binds to HIV Env MPER and comprises a heavy chain variable region (VH) and a light chain variable region (VL), and the VL further comprises a VL FR1, VL FR2, VL FR3, and VL FR4, wherein the VL FR1, VL FR2, VL FR3, and VL FR4 comprises the amino acid sequence of a VL FR1, VL FR2, VL FR3, and VL FR4, respectively, of PGZL1 VL, PGZL1.H4K3 VL, or PGZL1_gVmDmJ VL comprising 0, 1, 2, 3, 4, or 5 substitutions, deletions, or insertions. In some embodiments, an isolated monoclonal antibody described herein specifically binds to HIV Env MPER and comprises a heavy chain variable region (VH) and a light chain variable region (VL), and the VL further comprises a VL FR1, VL FR2, VL FR3, and VL FR4, wherein the VL FR1, VL FR2, VL FR3, and VL FR4 comprises the amino acid sequence of a VL FR1, VL FR2, VL FR3, and VL FR4, respectively shown in Table 3 comprising 0, 1, 2, 3, 4, or 5 substitutions, deletions, or insertions.

In some embodiments, an isolated monoclonal antibody described herein specifically binds to HIV Env MPER and comprises a heavy chain variable region (VH) and a light chain variable region (VL), and further comprises a VH FR1, VH FR2, VH FR3, VH FR4, VL FR1, VL FR2, VL FR3, and VL FR4, wherein the VH FR1, VH FR2, VH FR3, VH FR4, VL FR1, VL FR2, VL FR3, and VL FR4 comprise the amino acid sequence of a VH FR1, VH FR2, VH FR3, VH FR4, VL FR1, VL FR2, VL FR3, and VL FR4, respectively, of any of the VH and VL regions shown in Table 1 comprising 0, 1, 2, 3, 4, or 5 substitutions, deletions, or insertions. In some embodiments, an isolated monoclonal antibody described herein specifically binds to HIV Env MPER and comprises a heavy chain variable region (VH) and a light chain variable region (VL), and further comprises a VH FR1, VH FR2, VH FR3, VH FR4, VL FR1, VL FR2, VL FR3, and VL FR4, wherein the VH FR1, VH FR2, VH FR3, VH FR4, VL FR1, VL FR2, VL FR3, and VL FR4 comprise the amino acid sequence of a VH FR1, VH FR2, VH FR3, VH FR4, VL FR1, VL FR2, VL FR3, and VL FR4, respectively, of PGZL1, PGZL1.H4K3, or PGZL1_gVmDmJ comprising 0, 1, 2, 3, 4, or 5 substitutions, deletions, or insertions. In some embodiments, an isolated monoclonal antibody described herein specifically binds to HIV Env MPER and comprises a heavy chain variable region (VH) and alight chain variable region (VL), and further comprises a VH FR1, VH FR2, VH FR3, VH FR4, VL FR1, VL FR2, VL FR3, and VL FR4, wherein the VH FR1, VH FR2, VH FR3, VH FR4, VL FR1, VL FR2, VL FR3, and VL FR4 comprise the amino acid sequence of a VH FR1, VH FR2, VH FR3, VH FR4, VL FR1, VL FR2, VL FR3, and VL FR4, respectively shown in Table 3 comprising 0, 1, 2, 3, 4, or 5 substitutions, deletions, or insertions.

In some embodiments, an isolated monoclonal antibody described herein specifically binds to HIV Env MPER and comprises a heavy chain variable region (VH) and a light chain variable region (VL), wherein the VH comprises the VH FR1, VH FR2, VH FR3, and VH FR4 of any of the VH regions shown in Table 1. In some embodiments, an isolated monoclonal antibody described herein specifically binds to HIV Env MPER and comprises a heavy chain variable region (VH) and a light chain variable region (VL), wherein the VH comprises the VH FR1, VH FR2, VH FR3, and VH FR4 of PGZL1 VH, PGZL1.H4K3 VH, or PGZL1_gVmDmJ VH. In some embodiments, an isolated monoclonal antibody described herein specifically binds to HIV Env MPER and comprises a heavy chain variable region (VH) and a light chain variable region (VL), wherein the VH comprises a set of VH FR1, VH FR2, VH FR3, and VH FR4 shown in Table 3. In some embodiments, an isolated monoclonal antibody described herein specifically binds to HIV Env MPER and comprises a heavy chain variable region (VH) and a light chain variable region (VL), wherein the VL comprises the VL FR1, VL FR2, VL FR3, and VL FR4 of any of the VL regions shown in Table 1. In some embodiments, an isolated monoclonal antibody described herein specifically binds to HIV Env MPER and comprises a heavy chain variable region (VH) and a light chain variable region (VL), wherein the VL comprises the VL FR1, VL FR2, VL FR3, and VL FR4 GZL1 VL, PGZL1.H4K3 VL, or PGZL1_gVmDmJ VL. In some embodiments, an isolated monoclonal antibody described herein specifically binds to HIV Env MPER and comprises a heavy chain variable region (VH) and a light chain variable region (VL), wherein the VL comprises a set of VL FR1, VL FR2, VL FR3, and VL FR4 shown in Table 3. In some embodiments, the antibody comprises the VH CDR1, VH CDR2, VH CDR3, VL CDR1, VL CDR2, and VL CDR3 of an antibody described herein. In some embodiments, the antibody comprises the VH CDR1, VH CDR2, VH CDR3, VL CDR1, VL CDR2, and VL CDR3 of PGZL1, PGZL1.H4K3, or PGZL1_gVmDmJ. In some embodiments, the antibody comprises a VH CDR1, VH CDR2, VH CDR3, VL CDR1, VL CDR2, and VL CDR3 shown in Table 2. In some embodiments, the antibody comprises the VH or VL of an antibody described herein. In some embodiments, the antibody comprises the VH or VL of PGZL1, PGZL1.H4K3, or PGZL1_gVmDmJ.

In some embodiments, an isolated monoclonal antibody described herein specifically binds to HIV Env MPER and comprises a heavy chain variable region (VH) and a light chain variable region (VL), wherein the VH and VL comprise the VH FR1, VH FR2, VH FR3, VH FR4, VL FR1, VL FR2, VL FR3, and VL FR4 of any of the VH and VL regions shown in Table 1. In some embodiments, an isolated monoclonal antibody described herein specifically binds to HIV Env MPER and comprises a heavy chain variable region (VH) and a light chain variable region (VL), wherein the VH and VL comprise the VH FR1, VH FR2, VH FR3, VH FR4, VL FR1, VL FR2, VL FR3, and VL FR4 of PGZL1, PGZL1.H4K3, or PGZL1_gVmDmJ. In some embodiments, an isolated monoclonal antibody described herein specifically binds to HIV Env MPER and comprises a heavy chain variable region (VH) and a light chain variable region (VL), wherein the VH and VL comprise a set of VH FR1, VH FR2, VH FR3, VH FR4, VL FR1, VL FR2, VL FR3, and VL FR4 shown in Table 3.

In some embodiments, an isolated monoclonal antibody described herein comprises a heavy chain (HC) and a light chain (LC), wherein the HC and LC comprises the amino acid sequence of an HC and LC, respectively, shown in Table 4. In some embodiments, an isolated monoclonal antibody described herein comprises the PGZL1 HC and LC. In some embodiments, an isolated monoclonal antibody described herein comprises the PGZL1.H4K3 HC and LC. In some embodiments, an isolated monoclonal antibody described herein comprises the PGZL1_gVmDmJ HC and LC.

In some embodiments, an antibody described herein is PGZL1 comprising the PGZL1 VH and PGZL1 VL as shown in Table 1.

In some embodiments, an antibody described herein is PGZL1.H4K3 comprising the PGZL1.H4K3 VH and PGZL1.H4K3 VL as shown in Table 1.

In some embodiments, an antibody described herein is PGZL1_gVmDmJ comprising the PGZL1_gVmDmJ VH and PGZL1_gVmDmJ VL as shown in Table 1.

In some embodiments, an antibody described herein is not identical to PGZL1, PGZL1.H4K3, and PGZL1_gVmDmJ.

In some embodiments, an antibody described herein is markedly different from PGZL1, PGZL1.H4K3, and PGZL1_gVmDmJ.

In some embodiments, an antibody described herein comprises a VH that is not identical to any of the VH regions shown in Table 1.

In some embodiments, an antibody described herein comprises a VH that is markedly different from the VH regions shown in Table 1.

In some embodiments, an antibody described herein comprises a VL that is not identical to any of the VL regions shown in Table 1.

In some embodiments, an antibody described herein comprises a VL that is markedly different from the VL regions shown in Table 1.

In some embodiments, an antibody described herein comprises a VH CDR3 comprising a sequence that is not identical to the VHCDR3 of any of the VH regions shown in Table 1.

In some embodiments, an antibody described herein comprises a VH CDR1, VH CDR2, or VH CDR3 comprising an amino acid sequence that is not identical to the amino acid sequence of VH CDR1, VH CDR2, or VH CDR3 of any of the VH regions shown in Table 1.

In some embodiments, an antibody described herein comprises a VL CDR1, VL CDR2, or VL CDR3 comprising an amino acid sequence that is not identical to the amino acid sequence of VL CDR1, VL CDR2, or VL CDR3 of any of the VL regions shown in Table 1.

In some embodiments, an antibody described herein comprises a VH comprising an amino acid sequence that is not identical to the amino acid sequence of any of the VH regions shown in Table 1.

In some embodiments, an antibody described herein comprises a VL comprising an amino acid sequence that is not identical to the amino acid sequence of any of the VL regions shown in Table 1.

In some embodiments, an antibody described herein comprises at least one substitution, insertion, or deletion compared to the corresponding amino acid sequence of any of the VH and VL regions shown in Table 1.

In some embodiments, an isolated monoclonal antibody described herein further comprises heavy and/or light chain constant regions.

In some embodiments, an isolated monoclonal antibody described herein further comprises human heavy and/or light chain constant regions.

In some embodiments, the heavy chain constant region is selected from the group consisting of human immunoglobulins IgG1, IgG2, IgG3, IgG4, IgA1, and IgA2.

In some embodiments, the heavy chain constant region comprises a native amino acid sequence.

In some embodiments, the heavy chain constant region comprises a non-native variant amino acid sequence.

In one embodiment, an antibody described herein is a recombinant antibody, a chimeric antibody, a bispecific antibody, a trispecific antibody, or a multispecific antibody. In one embodiment, the antibody fragment comprises a single-chain Fv (scFv), F(ab) fragment, F(ab')$_2$ fragment, or an isolated VH domain.

In some embodiments, an antibody described herein is a multispecific antibody, e.g. a bispecific antibody. Multispecific antibodies are monoclonal antibodies that have binding specificities for at least two different sites. In some embodiments, one of the binding specificities is for HIV Env and the other is for any other antigen. In some embodiments, bispecific antibodies bind to two different epitopes of HIV Env. Bispecific antibodies can be prepared as full length antibodies or antibody fragments.

Techniques for making multispecific antibodies, e.g., bispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker A., et al., EMBO J. 10: 3655 (1991)), and "knob-in-hole" engineering (see, e.g., U.S. Pat. No. 5,731, 168). Multi-specific antibodies may also be made by engineering electrostatic steering effects for making antibody Fc-heterodimeric molecules (WO 2009/089004A1); crosslinking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991). Engineered antibodies with three or more functional antigen-binding sites, including "Octopus antibodies" and dual variable domain (DVD) immunoglobulins are also included herein (see, e.g. US 2006/0025576A1 and U.S. Pat. No. 10,093,733). The antibody or fragment disclosed herein also includes a "Dual Acting Fab" or "DAF" comprising an antigen-binding site that binds to different epitopes, e.g., two different HIV Env epitopes (see, US 2008/0069820, for example).

In some embodiments, an antibody described herein is a multispecific antibody, e.g. a bispecific antibody comprising a first antigen-binding domain comprising a VH domain or VH and VL domains disclosed herein, and a second antigen-binding region capable of binding an HIV Env epitope. In one embodiment, the second antigen-binding region binds to an HIV Env epitope region different from the HIV Env epitope region bound by an antibody disclosed herein. In one embodiment, the second agent is one or more anti-HIV Env antibody that binds to the CD4 binding site (CD4bs), V2 apex, N332/V3 base supersite, silent face, or gp120-gp41 interface. In one embodiment, the second antigen-binding region binds to the CD4 binding site (CD4bs) epitope region. In one embodiment, the second antigen-binding region binds to the V2 apex. In one embodiment, the second antigen-binding region binds to the N332/V3 base supersite. In one embodiment, the second antigen-binding region binds to the gp120-gp41 interface epitope region. In one embodiment, the second antigen-binding region binds to the silent face.

In one embodiment, an antibody described herein comprises a heavy and/or light chain constant region. In one embodiment, an antibody described herein comprises a human heavy and/or light chain constant region. In one embodiment, the heavy chain constant region is human immunoglobulin IgG1, IgG2, IgG3, IgG4, IgA1, or IgA2 constant region. In one embodiment, the heavy chain constant region is human immunoglobulin IgG1 constant region. In one embodiment, the heavy chain constant region comprises a native amino acid sequence. In one embodiment, the heavy chain constant region comprises a heavy chain constant region shown in Table 4. In one embodiment, the heavy chain constant region comprises he heavy chain constant region of a heavy chain shown in Table 4.

In one embodiment, an antibody disclosed herein is capable of neutralizing at least 5, at least 6, at least 7, at least 8, or 9 of the cross-clade HIV isolates in the 9-member indicator virus panel. In one embodiment, an antibody disclosed herein is capable of neutralizing at least 7 of the cross-clade HIV isolates in the 9-member indicator virus panel.

In one embodiment, an antibody disclosed herein is capable of neutralizing at least about 50%, at least about 60%, at least about 70%, at least about 80%, at least about 90%, or 100% of cross-clade HIV isolates in the 130-member indicator virus panel. In one embodiment, an antibody disclosed herein is capable of neutralizing at least about 50%, of cross-clade HIV isolates in the 130-member indicator virus panel. In one embodiment, an antibody disclosed herein is capable of neutralizing at least about 60%, of cross-clade HIV isolates in the 130-member indicator virus panel. In one embodiment, an antibody disclosed herein is capable of neutralizing at least about 70% of cross-clade HIV isolates in the 130-member indicator virus panel. In one embodiment, an antibody disclosed herein is capable of neutralizing at least about 80% of cross-clade HIV isolates in the 130-member indicator virus panel. In one embodiment, an antibody disclosed herein is capable of neutralizing at least about 90%, of cross-clade HIV isolates in the 130-member indicator virus panel. In one embodiment, an antibody disclosed herein is capable of neutralizing at least about 95%, of cross-clade HIV isolates in the 130-member indicator virus panel. In one embodiment, an antibody disclosed herein is capable of neutralizing at least about 98%, of cross-clade HIV isolates in the 130-member indicator virus panel. In one embodiment, an antibody disclosed herein is capable of neutralizing 100% of cross-clade HIV isolates in the 130-member indicator virus panel. In one embodiment, an antibody disclosed herein is capable of neutralizing the cross-clade HIV isolates of the 130-member indicator virus panel with a median $IC_{50}$ equal to or less than about 2 μg/ml, about 1.5 μg/ml, about 1 μg/ml, about 0.5 μg/ml, about 0.2 μg/ml, about 0.1 μg/ml, about 0.05 μg/ml, about 0.025 μg/ml, about 0.01 μg/ml, or about 0.005 μg/ml. In one embodiment, an antibody disclosed herein is capable of neutralizing the cross-clade HIV isolates of the 130-member indicator virus panel with a median $IC_{50}$ equal to or less than about 2 μg/ml. In one embodiment, an antibody disclosed herein is capable of neutralizing the cross-clade HIV isolates of the 130-member indicator virus panel with a median $IC_{50}$ equal to or less than about 1.5 μg/ml. In one embodiment, an antibody disclosed herein is capable of neutralizing the cross-clade HIV isolates of the 130-member indicator virus panel with a median $IC_{50}$ equal to or less than about 1 μg/ml. In one embodiment, an antibody disclosed herein is capable of neutralizing the cross-clade HIV isolates of the 130-member indicator virus panel with a median $IC_{50}$ equal to or less than about 2 μg/ml. In one embodiment, an antibody disclosed herein is capable of neutralizing the cross-clade HIV isolates of the 130-member indicator virus panel with a median $IC_{50}$ equal to or less than about 1.5 μg/ml. In one embodiment, an antibody disclosed herein is capable of neutralizing the cross-clade HIV isolates of the 130-member indicator virus panel with a median $IC_{50}$ equal to or less than about 1 μg/ml. In one embodiment, an antibody disclosed herein is capable of neutralizing at least about 95% cross-clade HIV isolates in the 130-member indicator virus panel with a median $IC_{50}$ equal to or less than about 1.5 μg/ml. In one embodiment, an antibody disclosed herein is capable of neutralizing at least about 98% cross-clade HIV isolates in the 130-member indicator virus panel with a median $IC_{50}$ equal to or less than about 1.5 μg/ml. In one embodiment, an antibody disclosed herein is capable of neutralizing at least about 95% cross-clade HIV isolates in the 130-member indicator virus panel with a median $IC_{50}$ equal to or less than about 2 μg/ml. In one embodiment, an antibody disclosed herein is capable of neutralizing at least about 98% cross-clade HIV isolates in the 130-member indicator virus panel with a median $IC_{50}$ equal to or less than about 2 μg/ml. In one embodiment, an antibody disclosed herein is capable of neutralizing the cross-clade HIV isolates of the 130-member indicator virus panel with a median $IC_{50}$ equal to or less than about 7 μg/ml, about 6 μg/ml, about 5 μg/ml, about 4 μg/ml, about 3 μg/ml, about 2 μg/ml, about 1 μg/ml, or about 0.5 μg/ml. In one embodiment, an antibody disclosed herein is capable of neutralizing the cross-clade HIV isolates of the 130-member indicator virus panel with a median $IC_{50}$ equal to or less than about 7 μg/ml. In one embodiment, an antibody disclosed herein is capable of neutralizing the cross-clade HIV isolates with a median $IC_{50}$ equal to or less than about 6 μg/ml. In one embodiment, an antibody disclosed herein is capable of neutralizing the cross-clade HIV isolates of the 130-member indicator virus panel with a median $IC_{80}$ equal to or less than about 5 μg/ml. In one embodiment, an antibody disclosed herein is capable of neutralizing the cross-clade HIV isolates of the 130-member indicator virus panel with a median $IC_{80}$ equal to or less than about 2 μg/ml. In one embodiment, an antibody disclosed herein is capable of neutralizing the cross-clade HIV isolates of the 130-member indicator virus panel with a median $IC_{80}$ equal to or less than about 1 μg/ml.

In another aspect, provided herein are antibodies that bind the same or an overlapping epitope of Env as an antibody described herein (e.g., PGZL1, PGZL1.H4K3, or PGZL1_gVmDmJ). In certain embodiments, the epitope of an antibody can be determined by, e.g., NMR spectroscopy, X-ray crystallography, negative-stain and cryo-EM (see, e.g., Lin M, et al., J Am Soc Mass Spectrom. 5: 961-971 (2018); Rantalainen et al., Cell Rep. 23(11); 3249-3261 (2018); Torrents de la Peña A et al., PLoS Pathog. 15; 15 (7):e1007920 (2019)), ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R, et al., (1994) Acta Crystallogr D Biol Crystallogr 50 (Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well-known X-ray diffraction techniques and may be refined using computer software such as Phenix (Adams et al., Acta Crystallogr Biol Crystallogr D66, 213-221 (2010)) and BUSTER (Bricogne G (1993) Acta Crystallogr D Biol Crystallogr 49 (Pt 1): 37-60; Bricogne G (1997) Meth. Enzymol. 276A: 361-423, ed Carter C W; Roversi P et al., (2000) Acta Crystallogr. D Biol. Crystallogr. 56 (Pt 10): 1316-1323). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. Usually, binding to the antigen is reduced or disrupted when a residue within the epitope is substituted to alanine. In one embodiment, the $K_D$ of binding to the antigen is increased by about 5-fold, 10-fold, 20-fold, 10-fold or more when a residue within the epitope is substituted for alanine. In one embodiment, binding affinity is determined by ELISA. In addition, antibodies that recognize and bind to the same or overlapping epitopes of Env (e.g., MPER of Du156.12 Env) can be identified using routine techniques such as an immunoassay, for example, by showing the ability of one antibody to block the binding of another antibody to a target antigen, i.e., a competitive binding assay.

In one embodiment, an antibody described herein immunospecifically binds to the same epitope as that bound by PGZL1, PGZL1.H4K3, or PGZL1_gVmDmJ antibody. PGZL1 and PGZL1.H4K3 antibodies bind to an epitope involving residues 671-683 of the MPER as well as lipids in the upper leaflet of the viral membrane. When bound by these PGZL1 antibodies, the MPER is helical and oriented upright with respect to the viral membrane such that PGZL1 and H4K3 makes hydrophobic and electrostatic interactions with the side of the MPER helix comprised by residues W672, F673, D674, T676, N677, L679, W680 and K683, similar to that observed with 4E10. Residues 671-674 of the MPER form a 310 helix when bound to PGZL1 variants similar to that bound by 4E10 and VRC42. Although, 10E8, 4E10 and PGZL1 variants bind to the same region 671-683 and the same helical side of MPER, the epitope (671-683) forms instead a continuous helix when bound to 10E8. Besides the MPER of HIV-1 Env, PGZL1 and H4K3 epitope also includes lipid head groups of the upper leaflet of the viral membrane, as do the epitopes of 4E10 and 10E8. PGZL1, H4K3 and 4E10 have a common lipid-binding site located in the heavy chain CDRH1 region S28-S30 that interacts with the $PO_4$ moiety of the lipid head group. Additional contacts of H4K3 with the viral membrane lipids are inferred from its interaction with a 06:0 PA lipid, $PO_4$ and $SO_4$ via the H4K3 FRH3 region (residues D72-S74), CDRH3 region (R100b-R100e of the heavy chain and Y91 of light chain), and FRL3 region (residues P59-R61), respectively. Thus, H4K3 binds to the viral membrane upper leaflet via CDRH1, FRH3, CDRH3 and FRL3 residues and the MPER region 671-683 via CDRH3, CDRL3, CDRH1 and CDRH2 residues.

In one embodiment, an antibody described herein immunospecifically binds to an epitope that overlaps the epitope bound by PGZL1, PGZL1.H4K3, or PGZL1_gVmDmJ.

In some embodiments, an antibody described herein is capable of competing with PGZL1, PGZL1.H4K3, or PGZL1_gVmDmJ for binding to HIV Env. In some embodiments, the HIV Env is Du156.12 Env.

In some embodiments, an antibody described herein is capable of competing with PGZL1, PGZL1.H4K3, or PGZL1_gVmDmJ for binding to MPER. In some embodiments, the MPER is Du156.12 MPER. In some embodiments, the MPER comprises the amino acid sequence of DLLALDRWQNLWNWFDITNWLWYIK (SEQ ID NO: 2).

In some embodiments, an antibody described herein does not neutralize one or more HIV isolates that are neutralized by 4E10. In some embodiments, an antibody described herein does not neutralize HIV-1 COT6 MPER Ala mutants $S_{671}A$ and $L_{679}A$. In some embodiments, an antibody described herein does not neutralize HIV-1 COT6 MPER Ala mutant $I_{675}A$.

In certain embodiments, the epitope of an antibody described herein is used as an immunogen to produce antibodies.

In one aspect, provided herein are methods for producing an engineered variant of an antibody described herein. In some embodiments, a method for producing an engineered variant comprises directed-evolution and yeast display. Methods for producing an engineered antibody are known to those skilled in the art, for example, as described in PCT/US2019/43578, filed on Jul. 26, 2019, which is incorporated herein by reference in its entirety for all purposes. In some embodiments, an engineered antibody possesses one or more improved properties, for example, higher binding affinity to target antigen, higher binding affinity to target antigen at low pH, increased median neutralization $IC_{50}$ potency, and increased breadth of neutralization compared to the parent antibody.

In some embodiments, a method of producing an engineered variant of a parent antibody comprises substituting one or more amino acid residues of the VH; and/or substituting one or more amino acid residues of the VL to create an engineered variant antibody, and producing the engineered variant antibody. In some embodiments, the parent antibody is an antibody described herein. In some embodiments, the parent antibody is PGZL1, PGZL1.H4K3, or PGZL1_gVmDmJ.

In some embodiments, the method further comprises determining that the engineered variant antibody has improved properties, for example, by determining the engineered variant antibody's binding affinity to target antigen, binding affinity to target antigen at low pH, median neutralization $IC_{50}$ potency, or breadth of neutralization compared to the parent antibody.

The affinity or avidity of an antibody for an antigen can be determined experimentally using any suitable method well-known in the art, e.g., flow cytometry, enzyme-linked immunoabsorbent assay (ELISA), biolayer interferometry (BLI) assay, radioimmunoassay (RIA), or kinetics (e.g., BIACORE™ analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., $K_D$ or Kd, $K_{on}$, $K_{off}$) are made with standardized solutions of antibody and antigen, and a standardized buffer, as known in the art and such as the buffer described herein.

In some embodiments, the broadly neutralizing anti-HIV Env antibody described herein is a monoclonal antibody. Monoclonal antibodies can be prepared using hybridoma methods, such as those described by Kohler and Milstein (1975) Nature 256:495. Using the hybridoma method, a host (e.g., mouse) is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid using any method known in the art.

In some embodiments, an antibody described herein is a monoclonal antibody. Monoclonal antibodies can be made using recombinant DNA methods, for example, as described in U.S. Pat. No. 4,816,567. The polynucleotides encoding a monoclonal antibody can be amplified from a suitable source or chemically synthetized. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells.

The polynucleotide(s) encoding a monoclonal antibody can be modified in a number of different manners using recombinant DNA technology to generate alternative antibodies. In some embodiments, the constant domains of the light and heavy chains can be substituted for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

Methods for engineering antibodies can also be used and are well-known in the art. An engineered antibody can have one or more amino acid residues substituted, deleted or inserted. These sequence modifications can be used to reduce immunogenicity or reduce, enhance or modify binding, affinity, on-rate, off-rate, avidity, specificity, half-life, or any other suitable characteristic, as known in the art. Antibodies can also be engineered to eliminate development liabilities by altering or eliminating sequence elements targeted for post-translational modification including glycosylation sites, oxidation sites, or deamination sites. In general, the CDR residues are directly and most substantially involved in influencing antibody binding. Accordingly, part or all of the CDR sequences are maintained while the variable framework and constant regions can be engineered by introducing substitutions, insertions, or deletions.

Antibodies disclosed herein can also optionally be engineered with retention of high affinity for the antigen and other favorable biological properties. To achieve this goal, engineered antibodies can be prepared by a process of analysis of the parental sequences and various conceptual engineered products using three-dimensional models of the parental and engineered sequences. Three-dimensional immunoglobulin models are commonly available and are familiar to those skilled in the art. Computer programs are available, which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In certain embodiments an antibody fragment is provided. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from antibody phage libraries. The antibody fragment can also be linear antibodies as described in U.S. Pat. No. 5,641,870, for example, and can be monospecific or bispecific. Other techniques for the production of antibody fragments will be apparent to the skilled practitioner.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs may be derived from an antibody of different class and in certain embodiments from an antibody from a different species. It may not be necessary to replace all of the CDRs with the complete CDRs from the donor variable region to transfer the antigen-binding capacity of one variable domain to another. Rather, it may only be necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies described herein will comprise antibodies (e.g., full-length antibodies or antigen-binding fragments thereof) in which at least a fraction of one or more of the constant region domains has been deleted or otherwise altered so as to provide desired biochemical characteristics such as increased serum half-life when compared with an antibody of approximately the same antigen-binding activity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies described herein can comprise alterations or modifications to one or more of the three heavy chain constant domains ($C_H1$, $C_H2$ or $C_H3$) and/or to the light chain constant domain ($C_L$). In some embodiments, modified constant regions wherein one or more domains are partially or entirely deleted are contemplated. In some embodiments, the modified antibodies will comprise domain deleted constructs or variants wherein the entire $C_H2$ domain has been removed ($\Delta CH2$ constructs). In some embodiments, the omitted constant region domain will be replaced by a short amino acid spacer (e.g., 10 residues) that provides some of the molecular flexibility typically imparted by the absent constant region.

It will be noted that in certain embodiments, the modified antibodies can be engineered to fuse the $C_H3$ domain directly to the hinge region of the respective modified antibodies. In other constructs it may be desirable to provide a peptide spacer between the hinge region and the modified $C_H2$ and/or $C_H3$ domains. For example, compatible constructs could be expressed wherein the $C_H2$ domain has been deleted and the remaining $C_H3$ domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies described herein can be provided by the partial deletion or substitution of a few or even a single amino acid. For example, it may be desirable to simply delete that part of one or more constant region domains that control the effector function (e.g., complement C1q binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments, it can be desirable to insert or replicate specific sequences derived from selected constant region domains. In further embodiments, an antibody disclosed herein comprises a variant IgG Fc region (e.g., variant IgG1 Fc region) comprising the M428L and N434S substitutions to improve the recycling of the antibody via the antibody salvage pathway. See, e.g., Grevys, et al., J. Immunology, 194:5497-508 (2015). In some embodiments, an antibody disclosed herein comprises the variant IgG Fc region shown in Table 4.

The half-life of an IgG is mediated by its pH-dependent binding to the neonatal receptor FcRn. In some embodiments, an antibody described herein comprises a variant Fc region that has been modified to enhance binding to FcRn (see, e.g., Petkova et al., Int. Immunol. 18: 1759-1769 (2006); Dall'Acqua et al., J. Immunol. 169: 5171-5180 (2002); Oganesyan et al., Mol. Immunol. 46: 1750-1755 (2009); Dall'Acqua et al., J. Biol. Chem. 281: 23514-23524 (2006), Hinton et al., J. Immunol. 176: 346-356 (2006); Datta-Mannan et al., Drug Metab. Dispos. 35: 86-94 (2007); Datta-Mannan et al., J. Biol. Chem. 282: 1709-1717 (2007); WO 06/130834; Strohl, Curr. Opin. Biotechnol. 20: 685-691 (2009); and Yeung et al., J. Immunol. 182: 7663-7671 (2009), the contents of each of which is herein incorporated by reference in its entirety).

In some embodiments, an antibody described herein comprises a variant Fc region that has been modified to have a selective affinity for FcRn at pH 6.0, but not pH 7.4. By way of example, the variant Fc region contains one or more of the following modifications that increase half-life: IgG1-M252Y, S254T, T256E; IgG1-T250Q, M428L; IgG1-M428L and N434S (the "LS" mutation); IgG1-H433K, N434Y; IgG1-N434A; and IgG1-T307A, E380A, N434A; wherein the numbering of the residues is that of the EU index of Kabat et al. (Kabat et al., Sequences of Proteins of Immunological Interest, 1991 Fifth edition, herein incorporated by reference).

In some embodiments, an antibody described herein comprises a variant Fc region that has been modified to reduce its effector functions. In some embodiments, the variant Fc region comprises the L234A, L235A hinge region substitutions, wherein the numbering of the residues is that of the EU index of Kabat et al.

In some embodiments, an antibody described herein comprises an Fc region having a carbohydrate structure that lacks fucose attached (directly or indirectly) to the Fc region or has a reduced level of fucosylation. In some embodiments, a fucosylation variant antibody has improved ADCC function. See, e.g., US Patent Publication Nos. US 2003/0157108; US 2004/0093621, each of which is incorporated by reference herein in its entirety. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004), each of which is incorporated by reference herein in its entirety. Examples of cell lines capable of producing defucosylated antibodies include Lee 13 CHO cells deficient in protein fucosylation (Ripka et al. Arch. Biochem. Biophys. 249:533-545 (1986); US Pat Appl No US 2003/0157108 A1; and WO 2004/056312), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94:680-688 (2006); and WO2003/085107), each of which is incorporated by reference herein in its entirety.

In some embodiments, an antibody described herein comprises bisected oligosaccharides, in which a biantennary oligosaccharide attached to the Fc region of the antibody is bisected by GlcNAc. In some embodiment, an antibody comprising bisected oligosaccharides has reduced fucosylation and/or improved ADCC function. See, e.g., WO 2003/011878; U.S. Pat. No. 6,602,684; and US 2005/0123546, each of which is incorporated by reference herein in its entirety. In some embodiment, an antibody described herein comprises at least one galactose residue in the oligosaccharide attached to the Fc region. Such antibody variants may have improved CDC function. See, e.g., in WO 1997/30087; WO 1998/58964; and WO 1999/22764, each of which is incorporated by reference herein in its entirety.

In some embodiments, an antibody described herein comprises a variant Fc region comprising a combination of substitutions with increased binding to FcRn and Fc gamma RIIIa. The combinations increase antibody half-life and ADCC. For example, such combination include antibodies with the following amino acid substitution in the Fc region: (1) S239D/I332E and T250Q/M428L; (2) S239D/I332E and M428L/N434S; (3) S239D/I332E and N434A; (4) S239D/I332E and T307A/E380A/N434A; (5) S239D/I332E and M252Y/S254T/T256E; (6) S239D/A330L/I332E and 250Q/M428L; (7) S239D/A330L/I332E and M428L/N434S; (8) S239D/A330L/I332E and N434A; (9) S239D/A330L/I332E and T307A/E380A/N434A; or (10) S239D/A330L/I332E and M252Y/S254T/T256E, wherein the numbering of the residues is that of the EU index of Kabat et al. In some embodiments, an antibody comprising the variant Fc region is directly cytotoxic to infected cells, or uses natural defenses such as complement, antibody dependent cellular cytotoxicity (ADCC), or phagocytosis by macrophages.

The present invention further embraces variants and equivalents, which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well-known in the art.

The polypeptides provided herein can be recombinant polypeptides, natural polypeptides, or synthetic polypeptides comprising an antibody, or fragment thereof. It will be recognized in the art that some amino acid sequences described herein can be varied without significant effect of the structure or function of the protein. Thus, the invention further includes variations of the polypeptides, which show substantial activity or which include regions of an antibody, or fragment thereof, against a human folate receptor protein. Such mutants include deletions, insertions, inversions, repeats, and type substitutions.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in REMINGTON'S PHARMACEUTICAL SCIENCES, 21th ed., Mack Publishing Co., Easton, PA (2005).

III. Polynucleotides

In certain aspects, provided herein are polynucleotides comprising a nucleotide sequence or nucleotide sequences encoding an antibody described herein (e.g., a variable light chain and/or variable heavy chain region) or an antigen-binding fragment thereof and vectors, e.g., vectors comprising such polynucleotides. In one embodiment, the vectors can be used for recombinant expression of an antibody described herein in host cells (e.g., E. coli and mammalian cells). In one embodiment, the vectors can be used for administration of an antibody described herein to a patient in need thereof. In one embodiment, the antibody comprises PGZL1. In one embodiment, the antibody comprises PGZL1.H4K3. In one embodiment, the antibody comprises PGZL1_gVmDmJ In one aspect, provided herein are isolated polynucleotides encoding the heavy chain variable region or heavy chain of an antibody described herein.

In one aspect, provided herein are isolated polynucleotides encoding the light chain variable region or light chain of an antibody described herein.

In one aspect, provided herein are isolated polynucleotides encoding the heavy chain variable region or heavy chain of an antibody described herein and the light chain variable region or light chain of an antibody described herein.

In one embodiment, the polynucleotide encodes PGZL1. In one embodiment, the polynucleotide encodes PGZL1.H4K3. In one embodiment, the polynucleotide encodes PGZL1_gVmDmJ In one embodiment, the polynucleotide encodes a VH or VL as shown in Table 1. In one embodiment, the polynucleotide encodes an HC or LC as shown in Table 4.

In one embodiment, the polynucleotide encodes a polypeptide comprising an amino acid sequence shown in Tables 2 and 3.

In one embodiment, the polynucleotide comprises any one of the nucleotide sequences shown in Table 5.

TABLE 5

| Nucleotide sequences. |
| --- |

PGZL1 VH

```
GAGGTGCAGCTGGTGCAGTCTGGCGGTGAGGTGAAGCGGCCTGGG
TCCTCGGTGACGGTCTCCTGCAAGGCGACTGGGGGCACATTTAGTA
CTCTTGCTTTTAACTGGGTGCGCCAGGCCCCTGGACAAGGGCCTGA
GTGGATGGGAGGAATTGTCCCTCTTTTCAGCATTGTGAATTATGGA
CAGAAATTCCAGGGCAGACTTACAATTCGGGCGGACAAATCGACG
ACCACAGTATTTTTGGATCTGAGTGGCCTCACGTCTGCGGACACGG
CCACTTATTATTGTGCGCGAGAGGGAGAGGGGTGGTTCGGGAAGCC
CCTCCGTGCTTTTGAATTTTGGGGCCAGGGGACAGTGATCACCGTCT
CCTCA (SEQ ID NO: 110)
```

PGZL1.H4K3 VH

```
AAGGTACAACTGGTGCAGTCTGGGGCTGAACTGAAGAAGCCTTGGT
CCTCGGTGAGGGTCTCCTGCAAGGCATCTGGAGGCAGCTTCAGCAG
CTATGCCTTCAACTGGGTGCGACAGGCCCCCGGACAAAGACTTGAG
TGGCTGGGAGGCATCGTCCCTCTTGTCAGCAGCACAAACTACGCAC
AGAGGTTCAGGGGCAGAGTCACAATCAGTGCGGACAGATCAACGA
GTACTGTCTACTTGGAGATGACAGGACTGACATCTGCAGACACGGC
CGTTTATTTCTGTGCGCGGGAGGGGGAGGGTTGGTTCGGGAGGCCC
CTCCGAGCGTTTGAATTCTGGGGCCAAGGAACACTCGTCACCGTTT
CTACA (SEQ ID NO: 111)
```

PGZL1_gVmDmJ VH

```
CAGGTGCAGCTGGTGCAGTCTGGGGCTGAGGTGAAGAAGCCTGGG
TCCTCGGTGAAGGTCTCCTGCAAGGCTTCTGGAGGCACCTTCAGCA
GCTATGCTATCAGCTGGGTGCGACAGGCCCCTGGACAAGGGCTTGA
GTGGATGGGAGGGATCATCCCTATCTTTGGTACAGCAAACTACGCA
CAGAAGTTCCAGGGCAGAGTCACGATTACCGCGGACAAATCCACG
AGCACAGCCTACATGGAGCTGAGCAGCCTGAGATCTGAGGACACG
GCCGTGTATTACTGTGCGAGAGAGGGAGAGGGGTGGTTCGGGAAG
CCCCTCCGTGCTTTTGAATTTTGGGGCCAGGGGACAGTGATCACCG
TCTCCTCA (SEQ ID NO: 112)
```

PGZL1 VL

```
GATGTTGTGATGACTCAGTCTCCAGGCACTTTGTCTTTGTCTCCCGG
AGAAAGGGCCACCCTCTCCTGCCGGGCCAGTCAGAGTGTCAGTGGC
GGCGCGTTAGCCTGGTACCAGCAGAAGCCTGGCCAGGCTCCCAGAC
TCCTCATCTATGACACGTCCAGCAGGCCCACTGGCGTCCCGGGCAG
GTTCAGTGGCAGTGGGTCTGGGACAGACTTCAGTCTCACCATCAGT
AGGCTGGAGCCTGAAGACTTTGCTGTGTCTATTACTGTCAGCAATATG
GAACCTCACAATCGACCTTCGGCCAGGGGACACGACTGGAGATTAA
A (SEQ ID NO: 113)
```

PGZL1.H4K3 VL

```
GAAATTGTGTTGACGCAGTCTCCAGGCACCTTTGCTTTGTCTCCCGG
AGAAAGGGCCACCCTCTCCTGCCGGGCCAGTCAGAGTGTCAGTGGC
GGCGCGTTAGCCTGGTACCAGCAGAAGGCTGGCCAGGCTCCCAGAC
TCCTCATCTATGGTACGTCCGGCAGGGCCACTGGCGTCCCGGGCAG
GTTCAGTGGCAGTGGGTCTGAGACAGACTTCAGTCTCACCATCAGC
AGGCTGGAGCCTGAAGACTTTGCAGTCTATTACTGTCAGCAATATG
GTACCTCACAATCGACCTTCGGCCAAGGGACACGACTGGAGACCAG
G (SEQ ID NO: 114)
```

PGZL1_gVmDmJ VL

```
GAAATTGTGTTGACGCAGTCTCCAGGCACCCTGTCTTTGTCTCCAGG
GGAAAGAGCCACCCTCTCCTGCAGGGCCAGTCAGAGTGTTAGCAGC
AGCTACTTAGCCTGGTACCAGCAGAAACCTGGCCAGGCTCCCAGGC
TCCTCATCTATGGTGCATCCAGCAGGGCCACTGGCATCCCAGACAG
GTTCAGTGGCAGTGGGTCTGGGACAGACTTCACTCTCACCATCAGC
AGACTGGAGCCTGAAGATTTTGCAGTGTATTACTGTCAGCAATATG
GTACCTCACAATCGACCTTCGGCCAAGGGACACGACTGGAGACCAG
G (SEQ ID NO: 115)
```

PGZL1 HC

```
ATGGAACTGGGGCTCCGCTGGGTTTTCCTTGTTGCTATTCTCGAGGG
TGTCCAGTGTGAGGTGCAGCTGGTGCAGTCTGGCGGTGAGGTGAAG
CGGCCTGGGTCCTCGGTGACGGTCTCCTGCAAGGCGACTGGGGGCA
CATTTAGTACTCTTGCTTTTAACTGGGTGCGCCAGGCCCCTGGACAA
GGGCCTGAGTGGATGGGAGGAATTGTCCCTCTTTTCAGCATTGTGA
ATTATGGACAGAAATTCCAGGGCAGACTTACAATTCGGGCGGACAA
ATCGACGACCACAGTATTTTTGGATCTGAGTGGCCTCACGTCTGCG
GACACGGCCACTTATTATTGTGCGCGAGAGGGAGAGGGGTGGTTCG
GGAAGCCCCTCCGTGCTTTTGAATTTTGGGGCCAGGGGACAGTGAT
CACCGTCTCCTCAGCTAGCACCAAGGGCCCATCGGTCTTCCCCCTG
GCACCCTCCTCCAAGAGCACCTCTGGGGGCACAGCGGCCCTGGGCT
GCCTGGTCAAGGACTACTTCCCCGAACCTGTGACGGTGTCGTGGAA
CTCAGGCGCCCTGACCAGCGGCGTGCACACCTTCCCGGCTGTCCTA
CAGTCCTCAGGACTCTACTCCCTCAGCAGCGTGGTGACCGTGCCCT
CCAGCAGCTTGGGCACCCAGACCTACATCTGCAACGTGAATCACAA
GCCCAGCAACACCAAGGTGGACAAGAGAGTTGAGCCCAAATCTTG
TGACAAAACTCACACATGCCCACCGTGCCCAGcaCCTGAACTCCTGG
GGGGACCGTCAGTCTTCCTCTTCCCCCCAAAACCCAAGGACACCCT
CATGATCTCCCGGACCCCTGAGGTCACATGCGTGGTGGTGGACGTG
AGCCACGAAGACCCTGAGGTCAAGTTCAACTGGTACGTGGACGGC
GTGGAGGTGCATAATGCCAAGACAAAGCCGCGGGAGGAGCAGTAC
```

TABLE 5-continued

| Nucleotide sequences. |
|---|

|  | AACAGCACGTACCGTGTGGTCAGCGTCCTCACCGTCCTGCACCAGG<br>ACTGGCTGAATGGCAAGGAGTACAAGTGCAAGGTCTCCAACAAAG<br>CCCTCCCAGCCCCCATCGAGAAAACCATCTCCAAAGCCAAAGggCA<br>GCCCCGAGAACCACAGGTGTACACCCTGCCCCCATCCCGGGAGGAG<br>ATGACCAAGAACCAGGTCAGCCTGACCTGCCTGGTCAAAGGCTTCT<br>ATCCCAGCGACATCGCCGTGGAGTGGGAGAGCAATGGGCAGCCGG<br>AGAACAaCTACAAGACCACGCCTCCCGTGCTGGACTCCGACGGCTC<br>CTTCTTCCTCTATAGCAAGCTCACCGTGGACAAGAGCAGGTGGCAG<br>CAGGGGAACGTCTTCTCATGCTCCGTGATGCATGAGGCTCTGCACA<br>ACCACTACACGCAGAAGAGCCTCTCCCTGTCCCCGGGTAAATGA<br>(SEQ ID NO: 116) |
| PGZL1.H4K3<br>HC | ATGGAACTGGGGCTCCGCTGGGTTTTCCTTGTTGCTATTCTCGAGGG<br>TGTCCAGTGTAAGGTACAACTGGTGCAGTCTGGGGCTGAACTGAAG<br>AAGCCTTGGTCCTCGGTGAGGGTCTCCTGCAAGGCATCTGGAGGCA<br>GCTTCAGCAGCTATGCCTTCAACTGGGTGCGACAGGCCCCCGGACA<br>AAGACTTGAGTGGCTGGGAGGCATCGTCCCTCTTGTCAGCAGCACA<br>AACTACGCACAGAGGTTCAGGGGCAGAGTCACAATCAGTGCGGAC<br>AGATCAACGAGTACTGTCTACTTGGAGATGACAGGACTGACATCTG<br>CAGACACGGCCGTTTATTTCTGTGCGCGGGAGGGGGGAGGGGTTGGTT<br>CGGGGAGGCCCCTCCGAGCGTTTGAATTCTGGGGCCAAGGAACACTC<br>GTCACCGTTTCTACAGCTAGCACCAAGGGCCCATCGGTCTTCCCCCT<br>GGCACCCTCCTCCAAGAGCACCTCTGGGGGCACAGCGGCCCTGGGC<br>TGCCTGGTCAAGGACTACTTCCCCGAACCTGTGACGGTCTCGTGGA<br>ACTCAGGCGCCCTGACCAGCGGCGTGCACACCTTCCCGGCTGTCCT<br>ACAGTCCTCAGGACTCTACTCCCTCAGCAGCGTGGTGACCGTGCCC<br>TCCAGCAGCTTGGGCACCCAGACCTACATCTGCAACGTGAATCACA<br>AGCCCAGCAACACCAAGGTGGACAAGAGAGTTGAGCCCAAATCTT<br>GTGACAAAACTCACACATGCCCACCGTGCCCAGcaCCTGAACTCCTG<br>GGGGGACCGTCAGTCTTCCTCTTCCCCCCAAAACCCAAGGACACCC<br>TCATGATCTCCCGGACCCCTGAGGTCACATGCGTGGTGGTGGATGT<br>GAGCCACGAAGACCCTGAGGTCAAGTTCAACTGGTACGTGGACGG<br>CGTGGAGGTGCATAATGCCAAGACAAAGCCGCGGGAGGAGCAGTA<br>CAACAGCACGTACCGTGTGGTCAGCGTCCTCACCGTCCTGCACCAG<br>GACTGGCTGAATGGCAAGGAGTACAAGTGCAAGGTCTCCAACAAA<br>GCCCTCCCAGCCCCCATCGAGAAAACCATCTCCAAAGCCAAAGggC<br>AGCCCCGAGAACCACAGGTGTACACCCTGCCCCCATCCCGGGAGGA<br>GATGACCAAGAACCAGGTCAGCCTGACCTGCCTGGTCAAAGGCTTC<br>TATCCCAGCGACATCGCCGTGGAGTGGGAGAGCAATGGGCAGCCG<br>GAGAACAaCTACAAGACCACGCCTCCCGTGCTGGACTCCGACGGCT<br>CCTTCTTCCTCTATAGCAAGCTCACCGTGGACAAGAGCAGGTGGCA<br>GCAGGGGAACGTCTTCTCATGCTCCGTGATGCATGAGGCTCTGCAC<br>AACCACTACACGCAGAAGAGCCTCTCCCTGTCCCCGGGTAAATGA<br>(SEQ ID NO: 117) |
| PGZL1_<br>gVmDmJ HC | ATGGAACTGGGGCTCCGCTGGGTTTTCCTTGTTGCTATTCTCGAGGG<br>TGTCCAGTGTCAGGTGCAGCTGGTGCAGTCTGGGGCTGAGGTGAAG<br>AAGCCTGGGTCCTCGGTGAAGGTCTCCTGCAAGGCTTCTGGAGGCA<br>CCTTCAGCAGCTATGCTATCAGCTGGGTGCGACAGGCCCCTGGACA<br>AGGGCTTGAGTGGATGGGAGGGATCATCCCTATCTTTGGTACAGCA<br>AACTACGCACAGAAGTTCCAGGGCAGAGTCACGATTACCGCGGAC<br>AAATCCACGAGCACAGCCTACATGGAGCTGAGCAGCCTGAGATCTG<br>AGGACACGGCCGTGTATTACTGTGCGAGAGAGGGGAGAGGGGTGGT<br>TCGGGAAGCCCCTCCGTGCTTTTGAATTTTGGGGCCAGGGGACAGT<br>GATCACCGTCTCCTCAGCTAGCACCAAGGGCCCATCGGTCTTCCCC<br>CTGGCACCCTCCTCCAAGAGCACCTCTGGGGGCACAGCGGCCCTGG<br>GCTGCCTGGTCAAGGACTACTTCCCCGAACCTGTGACGGTCTCGTG<br>GAACTCAGGCGCCCTGACCAGCGGCGTGCACACCTTCCCGGCTGTC<br>CTACAGTCCTCAGGACTCTACTCCCTCAGCAGCGTGGTGACCGTGC<br>CCTCCAGCAGCTTGGGCACCCAGACCTACATCTGCAACGTGAATCA<br>CAAGCCCAGCAACACCAAGGTGGACAAGAGAGTTGAGCCCAAATC<br>TTGTGACAAAACTCACACATGCCCACCGTGCCCAGCACCTGAACTC<br>CTGGGGGGACCGTCAGTCTTCCTCTTCCCCCCAAAACCCAAGGACA<br>CCCTCATGATCTCCCGGACCCCTGAGGTCACATGCGTGGTGGTGGA<br>CGTGAGCCACGAAGACCCTGAGGTCAAGTTCAACTGGTACGTGGAC<br>GGCGTGGAGGTGCATAATGCCAAGACAAAGCCGCGGGAGGAGCAG<br>TACAACAGCACGTACCGTGTGGTCAGCGTCCTCACCGTCCTGCACC<br>AGGACTGGCTGAATGGCAAGGAGTACAAGTGCAAGGTCTCCAACA<br>AAGCCCTCCCAGCCCCCATCGAGAAAACCATCTCCAAAGCCAAAGG<br>GCAGCCCCGAGAACCACAGGTGTACACCCTGCCCCCATCCCGGGAG<br>GAGATGACCAAGAACCAGGTCAGCCTGACCTGCCTGGTCAAAGGCT<br>TCTATCCCAGCGACATCGCCGTGGAGTGGGAGAGCAATGGGCAGCC<br>GGAGAACAACTACAAGACCACGCCTCCCGTGCTGGACTCCGACGGC<br>TCCTTCTTCCTCTATAGCAAGCTCACCGTGGACAAGAGCAGGTGGC<br>AGCAGGGGAACGTCTTCTCATGCTCCGTGATGCATGAGGCTCTGCA<br>CAACCACTACACGCAGAAGAGCCTCTCCCTGTCCCCGGGTAAATGA<br>(SEQ ID NO: 118) |

TABLE 5-continued

Nucleotide sequences.

PGZL1 LC
ATGGGATGGTCATGTATCATCCTTTTTCTAGTAGCAACTGCAACCGG
TGTACATGATGTTGTGATGACTCAGTCTCCAGGCACTTTGTCTTTGT
CTCCCGGAGAAAGGGCCACCCTCTCCTGCCGGGCCAGTCAGAGTGT
CAGTGGCGGCGCGTTAGCCTGGTACCAGCAGAAGCCTGGCCAGGCT
CCCAGACTCCTCATCTATGACACGTCCAGCAGGCCCACTGGCGTCC
CGGGCAGGTTCAGTGGCAGTGGGTCTGGGACAGACTTCAGTCTCAC
CATCAGTAGGCTGGAGCCTGAAGACTTTGCTGTCTATTACTGTCAG
CAATATGGAACCTCACAATCGACCTTCGGCCAGGGGACACGACTGG
AGATTAAACGTACGGTGGCTGCACCATCTGTCTTCATCTTCCCGCCA
TCTGATGAGCAGTTGAAATCTGGAACTGCCTCTGTTGTGTGCCTGCT
GAATAACTTCTATCCCAGAGAGGCCAAAGTACAGTGGAAGGTGGA
TAACGCCCTCCAATCGGGTAACTCCCAGGAGAGTGTCACAGAGCAG
GACAGCAAGGACAGCACCTACAGCCTCAGCAGCACCCTGACGCTG
AGCAAAGCAGACTACGAGAAACACAAAGTCTACGCCTGCGAAGTC
ACCCATCAGGGCCTGAGCTCGCCCGTCACAAAGAGCTTCAACAGGG
GAGAGTGTTAG (SEQ ID NO: 119)

PGZL1.H4K3
LC
ATGGGATGGTCATGTATCATCCTTTTTCTAGTAGCAACTGCAACCGG
TGTACATGAAATTGTGTTGACGCAGTCTCCAGGCACCTTTGCTTTGT
CTCCCGGAGAAAGGGCCACCCTCTCCTGCCGGGCCAGTCAGAGTGT
CAGTGGCGGCGCGTTAGCCTGGTACCAGCAGAAGGCTGGCCAGGCT
CCCAGACTCCTCATCTATGGTACGTCCGGCAGGGCCACTGGCGTCC
CGGGCAGGTTCAGTGGCAGTGGGTCTGAGACAGACTTCAGTCTCAC
CATCAGCAGGCTGGAGCCTGAAGACTTTGCAGTCTATTACTGTCAG
CAATATGGTACCTCACAATCGACCTTCGGCCAAGGGACACGACTGG
AGACCAGGCGTACGGTGGCTGCACCATCTGTCTTCATCTTCCCGCC
ATCTGATGAGCAGTTGAAATCTGGAACTGCCTCTGTTGTGTGCCTGC
TGAATAACTTCTATCCCAGAGAGGCCAAAGTACAGTGGAAGGTGG
ATAACGCCCTCCAATCGGGTAACTCCCAGGAGAGTGTCACAGAGCA
GGACAGCAAGGACAGCACCTACAGCCTCAGCAGCACCCTGACGCT
GAGCAAAGCAGACTACGAGAAACACAAAGTCTACGCCTGCGAAGT
CACCCATCAGGGCCTGAGCTCGCCCGTCACAAAGAGCTTCAACAGG
GGAGAGTGTTAG (SEQ ID NO: 120)

PGZL1_
gVmDmJ LC
ATGGGATGGTCATGTATCATCCTTTTTCTAGTAGCAACTGCAACCGG
TGTACATGAAATTGTGTTGACGCAGTCTCCAGGCACCCTGTCTTTGT
CTCCAGGGGAAAGAGCCACCCTCTCCTGCAGGGCCAGTCAGAGTGT
TAGCAGCAGCTACTTAGCCTGGTACCAGCAGAAACCTGGCCAGGCT
CCCAGGCTCCTCATCTATGGTGCATCCAGCAGGGCCACTGGCATCC
CAGACAGGTTCAGTGGCAGTGGGTCTGGGACAGACTTCACTCTCAC
CATCAGCAGACTGGAGCCTGAAGATTTTGCAGTGTATTACTGTCAG
CAATATGGTACCTCACAATCGACCTTCGGCCAAGGGACACGACTGG
AGACCAGGCGTACGGTGGCTGCACCATCTGTCTTCATCTTCCCGCC
ATCTGATGAGCAGTTGAAATCTGGAACTGCCTCTGTTGTGTGCCTGC
TGAATAACTTCTATCCCAGAGAGGCCAAAGTACAGTGGAAGGTGG
ATAACGCCCTCCAATCGGGTAACTCCCAGGAGAGTGTCACAGAGCA
GGACAGCAAGGACAGCACCTACAGCCTCAGCAGCACCCTGACGCT
GAGCAAAGCAGACTACGAGAAACACAAAGTCTACGCCTGCGAAGT
CACCCATCAGGGCCTGAGCTCGCCCGTCACAAAGAGCTTCAACAGG
GGAGAGTGTTAG (SEQ ID NO: 121)

In one embodiment, an isolated polynucleotide described herein encodes an antibody described herein and comprises an mRNA. In one embodiment, the mRNA comprises at least one modified nucleotide. In one embodiment, a modified mRNA encoding an antibody disclosed herein is for administering to a subject to treat or prevent HIV infection.

As used herein, an "isolated" polynucleotide or nucleic acid molecule is one, which is separated from other nucleic acid molecules, which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody or fusion polypeptide described herein is isolated or purified.

In particular aspects, provided herein are polynucleotides comprising nucleotide sequences encoding antibodies described herein, as well as antibodies that compete with such antibodies for binding to HIV, or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL of antibodies described herein (see, e.g., Table 1). The polynucleotides can comprise nucleotide sequences encoding a heavy chain comprising the VH of antibodies described herein (see, e.g., Table 1). In specific embodiments, a polynucleotide described herein encodes a VH domain shown in Table 1. In specific embodiments, a polynucleotide described herein encodes a VL domain shown in Table 1. In one embodiment, a polynucleotide described herein encodes PGZL1. In one embodiment, a polynucleotide described herein encodes PGZL1.H4K3. In one embodiment, a polynucleotide described herein encodes PGZL1_gVmDmJ. In one embodiment, the antibody is a chimeric antibody.

In particular embodiments, provided herein are poly-nucleotides comprising a nucleotide sequence encoding an antibody comprising three VL chain CDRs, e.g., containing VL CDR1, VL CDR2, and VL CDR3 of any one of antibodies described herein (e.g., see Table 2). In specific embodiments, provided herein are polynucleotides compris-ing three VH chain CDRs, e.g., containing VH CDR1, VH CDR2, and VH CDR3 of any one of antibodies described herein (e.g., see Table 2). In specific embodiments, provided herein are polynucleotides comprising a nucleotide sequence encoding an anti-Env antibody comprising three VL CDRs, e.g., containing VL CDR1, VL CDR2, and VL CDR3 of any one of antibodies described herein (e.g., see Table 2) and three VH chain CDRs, e.g., containing VH CDR1, VH CDR2, and VH CDR3 of any one of antibodies described herein (e.g., see Table 2).

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an anti-body, which immunospecifically binds to Env, wherein the antibody comprises a light chain, and wherein the amino acid sequence of the VL domain can comprise the amino acid sequence set forth in Table 1, and wherein the constant region of the light chain comprises the amino acid sequence of a human kappa light chain constant region. In another particular embodiment, a polynucleotide provided herein comprises a nucleotide sequence encoding an antibody, which immunospecifically binds to Env, and comprises a light chain, wherein the amino acid sequence of the VL domain can comprise the amino acid sequence set forth in Table 1, and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an anti-body described herein, which immunospecifically binds to Env, wherein the antibody comprises a heavy chain, wherein the amino acid sequence of the VH domain can comprise the amino acid sequence set forth in Table 1, and wherein the constant region of the heavy chain comprises the amino acid sequence of a human alpha or gamma heavy chain constant region.

In yet another specific embodiment, a polynucleotide provided herein comprises a nucleotide sequence encoding an antibody described herein, which immunospecifically binds Env, wherein the antibody comprises a VL domain and a VH domain comprising any amino acid sequences described herein, and wherein the constant regions comprise the amino acid sequences of the constant regions of a human IgA$_1$, human IgA$_2$, human IgG$_1$ (e.g., allotype 1, 17, or 3), human IgG$_2$, or human IgG$_4$.

In yet another specific embodiment, a polynucleotide provided herein comprises a nucleotide sequences encoding an anti-Env antibody or a fragment thereof that are opti-mized, e.g., by codon/RNA optimization, replacement with heterologous signal sequences, and elimination of mRNA instability elements. Methods to generate optimized nucleic acids encoding an anti-Env antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, poten-tial splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding an anti-Env antibody described herein or a fragment thereof (e.g., VL domain or VH domain) can hybridize to an antisense (e.g., complementary) polynucle-otide of an unoptimized polynucleotide sequence encoding an anti-Env antibody described herein or a fragment thereof (e.g., VL domain or VH domain). In specific embodiments, an optimized nucleotide sequence encoding an anti-Env antibody described herein or a fragment hybridizes under high stringency conditions to antisense polynucleotide of an unoptimized polynucleotide sequence encoding an anti-Env antibody described herein or a fragment thereof. In a specific embodiment, an optimized nucleotide sequence encoding an anti-Env antibody described herein or a fragment thereof hybridizes under high stringency, intermediate or lower stringency hybridization conditions to an antisense poly-nucleotide of an unoptimized nucleotide sequence encoding an anti-Env antibody described herein or a fragment thereof. Information regarding hybridization conditions has been described, see, e.g., U.S. Patent Application Publication No. US 2005/0048549 (e.g., paragraphs 72-73), which is incor-porated herein by reference.

The polynucleotides can be obtained, and the nucleotide sequence of the polynucleotides determined, by any method known in the art. Nucleotide sequences encoding antibodies described herein, and modified versions of these antibodies can be determined using methods well-known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-246), which, briefly, involves the synthesis of overlapping oligonucleotides con-taining portions of the sequence encoding the antibody, annealing and ligating of those oligonucleotides, and then amplification of the ligated oligonucleotides by PCR.

Alternatively, a polynucleotide encoding an antibody or fragment thereof described herein can be generated from nucleic acid from a suitable source (e.g., PBMCs) using methods well-known in the art (e.g., PCR and other molecu-lar cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody or fragment thereof is not available, but the sequence of the antibody molecule or fragment thereof is known, a nucleic acid encoding the immunoglobulin or fragment can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well-known in the art.

DNA encoding anti-Env antibodies described herein can be readily isolated and sequenced using conventional procedures (e.g., by using oligonucleotide probes that are capable of binding specifically to genes encoding the heavy and light chains of the anti-Env antibodies). PBMCs can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-Env antibodies in the recombinant host cells.

The DNA also can be modified, for example, by substituting the coding sequence for human heavy and light chain constant domains with a coding sequence for a non-immunoglobulin polypeptide, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3.

IV. Vectors, Cells, and Methods of Producing a Broadly Neutralizing Agent

In certain aspects, provided herein are cells (e.g., host cells) expressing (e.g., recombinantly) antibodies described herein, which specifically bind to Env and related polynucleotides and expression vectors. Provided herein are vectors (e.g., expression vectors) comprising polynucleotides comprising nucleotide sequences encoding anti-Env antibodies or a fragment thereof described herein. In one embodiment, the vectors can be used for recombinant expression of an antibody described herein in host cells (e.g., mammalian cells). In one embodiment, the vectors can be used for administration of an antibody described herein to a patient in need thereof. Also provided herein are host cells comprising such vectors for recombinantly expressing anti-Env antibodies described herein. In a particular aspect, provided herein are methods for producing an antibody described herein, comprising expressing such antibody in a host cell. In one embodiment, the antibody comprises the PGZL1 VH and VL. In one embodiment, the antibody comprises the PGZL1.H4K3 VH and VL. In one embodiment, the antibody comprises the PGZL1_gVmDmJ VH and VL.

In certain aspects, provided herein is an isolated vector comprising a polynucleotide described herein. In one embodiment, the vector is a viral vector.

In certain aspects, provided herein is a recombinant virus comprising a polynucleotide described herein. In one embodiment, the recombinant virus encodes an antibody described herein. In one embodiment, the recombinant virus encodes a bispecific antibody described herein. In one embodiment, the recombinant virus is a replication defective virus. Suitable replication defective viral vectors are known to those skilled in the art, for example, as disclosed in U.S. Pat. Nos. 7,198,784, 9,408,905, 9,862,931, 8,067,156, U.S. Pat. Appl. Pub. Nos. 20150291935, 20120220492, 20180291351, and 20170175137, each of which is incorporated herein by reference in its entirety. In one embodiment, the recombinant virus is a retrovirus or retroviral vector, for example, a lentivirus or lentiviral vector. In one embodiment, the recombinant virus is an adenovirus or adenoviral vector, HSV or HSV vector, or influenza virus or viral vector. In one embodiment, the recombinant virus is an adeno-associated virus (AAV). In one embodiment, the recombinant virus is for administration to a subject to prevent or treat HIV infection. In one embodiment, the recombinant virus is an adeno-associated virus (AAV) for administration to a subject to prevent or treat HIV infection. Recombinant AAV particles encoding an antibody that binds to HIV Env and methods for producing thereof are known to one skilled in the art, for example, as disclosed in U.S. Pat. No. 8,865,881 and US20190031740, each of which is incorporated by reference herein in its entirety for all purposes. See also, Lin and Balazs, Retrovirology 15:66 (2018) and van den Berg et al., Molecular Therapy: Methods & Clinical Development 14:100-112 (2019), each of which is incorporated by reference herein in its entirety for all purposes. In one embodiment, the antibody comprises the PGZL1 VH and VL. In one embodiment, the antibody comprises the PGZL1.H4K3 VH and VL. In one embodiment, the antibody comprises the PGZL1_gVmDmJ VH and VL.

In certain aspects, provided herein is a host cell comprising a polynucleotide described herein, or a vector described herein. In one embodiment, the vector encodes an antibody described herein. In one embodiment, a vector described herein comprises a first vector encoding a VH described herein and a second vector encoding a VL described herein. In one embodiment, a vector described herein comprises a first nucleotide sequence encoding a VH described herein and a second nucleotide sequence encoding a VL described herein. In one embodiment, the antibody comprises the PGZL1 VH and VL. In one embodiment, the antibody comprises the PGZL1.H4K3 VH and VL. In one embodiment, the antibody comprises the PGZL1_gVmDmJ VH and VL.

In one embodiment, the host cell is selected from the group consisting of *E. coli, Pseudomonas, Bacillus, Streptomyces*, yeast, CHO, YB/20, NS0, PER-C6, HEK-293T, NIH-3T3, Helga, BHK, Hep G2, SP2/0, R1.1, B-W, L-M, COS 1, COS 7, BSC1, BSC40, BMT10 cell, plant cell, insect cell, and human cell in tissue culture. In one embodiment, the host cell is CHO.

In certain aspects, provided herein is a method of producing an antibody that binds to HIV comprising culturing a host cell described herein so that the polynucleotide is expressed and the antibody is produced. In one embodiment, the method further comprises recovering the antibody.

The isolated polypeptides, i.e., anti-HIV Env antibodies described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies or fragments thereof. Recombinant expression vectors are replicable DNA constructs, which have synthetic or cDNA-derived DNA fragments encoding a polypeptide chain of an antibody or fragment thereof operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor, which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, Helga, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as E. coli, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking M K & Hofstetter H (1986) Gene 45: 101-105; and Cockett M I et al., (1990) Biotechnology 8: 662-667). In certain embodiments, antibodies described herein are produced by CHO cells or NS0 cells. In a specific embodiment, the expression of nucleotide sequences encoding antibodies described herein which immunospecifically bind Env is regulated by a constitutive promoter, inducible promoter or tissue specific promoter.

For applications where it is desired that the antibodies described herein be expressed in vivo, for example in a subject in need of treatment with an antibody described herein, any vector that allows for the expression of the antibodies and is safe for use in vivo may be used. In one embodiment, the vector is a viral vector. Viral vectors can include poxvirus (vaccinia), including vaccinia Ankara and canarypox; adenoviruses, including adenovirus type 5 (Ad5); rubella; sendai virus; rhabdovirus; alphaviruses; and adeno-associated viruses. In one embodiment, the viral vector is an adeno-associated virus. Alternatively, a polynucleotide encoding the antibody could be delivered as DNA or RNA to the subject for in vivo expression of the antibody.

Suitable host cells for expression of a polypeptide of interest such as an antibody described herein include prokaryotes, yeast, insect or higher eukaryotic cells under the control of appropriate promoters. Prokaryotes include gram negative or gram-positive organisms, for example E. coli or bacilli. Higher eukaryotic cells include established cell lines of mammalian origin. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express a recombinant protein such as an antibody described herein. Expression of recombinant proteins in mammalian cells can be performed because such proteins are generally correctly folded, appropriately modified and completely functional. Examples of suitable mammalian host cell lines include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza HA peptide sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems, which secrete recombinant protein, e.g., an antibody, into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further an agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

In specific embodiments, an antibody described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody. When the polypeptide (e.g., antibody described herein) is recombinantly produced, it is also generally substantially free of culture medium, i.e., culture medium represents less than about 20%, 10%, 2%, 1%, 0.5%, or 0.1% of the volume of the protein preparation. When the polypeptide (e.g., antibody described herein) is produced by chemical synthesis, it is generally substantially free of chemical precursors or other chemicals, i.e., it is separated from chemical precursors or other chemicals, which are involved in the synthesis of the protein. Accordingly, such preparations of the polypeptide (e.g., antibody described herein) have less than about 30%, 20%, 10%, or 5% (by dry weight) of chemical precursors or compounds other than the polypeptide of interest. In one embodiment, antibodies described herein are isolated or purified.

V. Pharmaceutical Compositions

Compositions comprising the antibodies or antigen-binding fragments described herein (e.g., PGZL1, PGZL1.H4K3, and PGZL1_gVmDmJ) are also provided. Further provided herein are compositions comprising a polynucleotide or polynucleotides encoding the antibodies or antigen-binding fragments described herein. In one embodiment, the polynucleotide comprises mRNA. In one embodiment, the composition is a pharmaceutical composition. In one embodiment, the antibody comprises PGZL1. In one embodiment, the antibody comprises PGZL1.H4K3.

In one embodiment, the composition is a lyophilized composition. In one embodiment, the composition is formulated for topical administration, and in certain embodiments the composition is formulated for vaginal or rectal administration.

In certain aspects, provided herein is a pharmaceutical composition comprising an antibody described herein (e.g., PGZL1, PGZL1.H4K3, and PGZL1_gVmDmJ) and a pharmaceutically acceptable excipient. In one embodiment, the antibody is an intact antibody. In one embodiment, the antibody is an antigen-binding antibody fragment. In one embodiment, the composition is formulated for topical administration, and in certain embodiments the composition is formulated for vaginal or rectal administration. In one embodiment, the antibody comprises PGZL1. In one embodiment, the antibody comprises PGZL1.H4K3.

In another embodiment, the disclosure provides a pharmaceutical composition comprising an antibody described herein (e.g., PGZL1, PGZL1.H4K3, and PGZL1_gVmDmJ). Such compositions are intended for prevention and treatment of HIV infection. In one embodiment, the antibody comprises PGZL1. In one embodiment, the antibody comprises PGZL1.H4K3.

In further embodiments of the present disclosure, a composition comprising the antibody described herein can additionally be combined with other compositions for the treatment of HIV infection or the prevention of HIV transmission.

In some embodiments, an antibody described herein may be administered within a pharmaceutically acceptable diluent, carrier, or excipient, in unit dose form. Conventional pharmaceutical practice may be employed to provide suitable formulations or compositions to administer to individuals being treated for HIV infection. In one embodiment, the administration is prophylactic. Any appropriate route of administration may be employed, for example, administration may be parenteral, intravenous, intra-arterial, subcutaneous, intramuscular, intraperitoneal, intranasal, aerosol, suppository, oral administration, vaginal, or anal.

The pharmaceutical compositions described herein are prepared in a manner known per se, for example, by means of conventional dissolving, lyophilizing, mixing, granulating or confectioning processes. The pharmaceutical compositions may be formulated according to conventional pharmaceutical practice (see for example, in Remington: The Science and Practice of Pharmacy (21st ed.), ed. A. R. Gennaro, 2005, Lippincott Williams & Wilkins, Philadelphia, PA, and Encyclopedia of Pharmaceutical Technology, eds. J. Swarbrick and J. C. Boylan, 2013, Marcel Dekker, New York, NY).

The injection compositions are prepared in customary manner under sterile conditions; the same applies also to introducing the compositions into ampoules or vials and sealing the containers.

Pharmaceutical compositions according to the invention may be, for example, in unit dose form, such as in the form of ampoules, vials, suppositories, tablets, pills, or capsules. The formulations can be administered to human individuals in therapeutically or prophylactic effective amounts (e.g., amounts which prevent, eliminate, or reduce a pathological condition) to provide therapy for a disease or condition. The preferred dosage of therapeutic agent to be administered is likely to depend on such variables as the type and extent of the disorder, the overall health status of the particular patient, the formulation of the compound excipients, and its route of administration.

In certain embodiments, the compositions described herein can be formulated for topical administration, and in certain embodiments the composition is formulated for vaginal or rectal administration. The composition may be formulated as a gel, or formulated as a topical cream, ointment, lotion or foam formulation. Useful formulations are known in the art, for example, as disclosed in U.S. Patent Appl. Pub. No. 20130022619, which is incorporated by reference herein in its entirety for all purposes.

In certain embodiments, the composition may further comprise a pharmaceutically acceptable excipient, a lubricant, or an antiviral agent.

The topical formulations of the present invention can be used to prevent HIV infection in a human, or to inhibit transmission of the HIV virus from an infected human to another human. The topical formulations of the present invention can inhibit the growth or replication of HIV. The topical formulations are useful in the prophylactic treatment of humans who are at risk for HIV infection. The topical formulations also can be used to treat objects or materials, such as contraceptive devices (for example condoms or intrauterine devices), medical equipment, supplies, or fluids, including biological fluids, such as blood, blood products, and tissues, to prevent or inhibit viral infection of a human. Such topical formulations also are useful to prevent transmission, such as sexual transmission of viral infections, e.g., HIV, which is the primary way in which HIV is transmitted globally. The methods of prevention or inhibition or retardation of transmission of viral infection, e.g., HIV infection, in accordance with the present invention, comprise vaginal, rectal, penile or other topical treatment with an antiviral effective amount of a topical preparation of the present invention, alone or in combination with another antiviral compound as described herein.

In one embodiment, the composition is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) containing in addition to the active ingredient, such carriers as are known in the art to be appropriate. These formulations are useful to protect not only against sexual transmission of HIV, but also to prevent infection of a baby during passage through the birth canal. Thus the vaginal administration can take place prior to sexual intercourse, during sexual intercourse, and immediately prior to childbirth.

As a vaginal formulation, the active ingredient may be used in conjunction with a spermicide and may be employed with a condom, diaphragm, sponge or other contraceptive device. Examples of suitable spermicides include nonylphenoxypolyoxyethylene glycol (nonoxynol 9), benzethonium chloride, and chlorindanol. Suitably, the pH of the composition is 4.5 to 8.5. Vaginal compositions preferably have a pH of 4.5 to 6, most preferably about 5.

Vaginal formulations include suppositories (for example, gel-covered creams), tablets and films. The suppositories can be administered by insertion with an applicator using methods well-known in the art.

Vaginal formulations further include vaginal ring devices formulated for sustained release. See, e.g., Morrow et al., Eur J Pharm Biopharm. 77:3-10 (2011), Zhao et al., Antimicrob Agents Chemother. 61:pii: e02465-16 (2017).

Buccal formulations include creams, ointments, gels, tablets or films that comprise ingredients that are safe when administered via the mouth cavity. Buccal formulations can also comprise a taste-masking or flavoring agent.

The present compositions may be associated with a contraceptive device or article, such as a vaginal ring device, an intrauterine device (IUD), vaginal diaphragm, vaginal sponge, pessary, condom, etc.

In one embodiment, the compositions described herein are used in conjunction with condoms, to enhance the risk-reducing effectiveness of condoms and provide maximum protection for users. The composition can either be coated onto condoms during manufacture, and enclosed within conventional watertight plastic or foil packages that contain one condom per package, or it can be manually applied by a user to either the inside or the outside of a condom, immediately before use. As used herein, "condom" refers to a barrier device, which is used to provide a watertight physical barrier between male and female genitalia during sexual intercourse, and which is removed after intercourse. This term includes conventional condoms that cover the penis; it also includes so-called "female condoms", which are inserted into the vaginal cavity prior to intercourse.

In another embodiment, a composition described herein is in the form of an intra-vaginal pill, an intra-rectal pill, or a suppository. The suppository or pill should be inserted into the vaginal or rectal cavity in a manner that permits the suppository or pill, as it dissolves or erodes, to coat the vaginal or rectal walls with a prophylactic layer of an antibody described herein.

In certain embodiments, the composition may further comprise a pharmaceutically acceptable excipient, a lubricant, or an antiviral agent.

Compositions used in the methods of this invention may also comprise other active agents, such as another agent to prevent HIV infection, and agents that protect individuals from conception and other sexually transmitted diseases. Thus, in another embodiment the compositions used in this invention further comprise a second anti-HIV agent, a virucide effective against viral infections other than HIV, and/or a spermicide.

The compositions used in this invention may also contain a lubricant that facilitates application of the composition to the desired areas of skin and epithelial tissue, and reduces friction during sexual intercourse. In the case of a pill or suppository, the lubricant can be applied to the exterior of the dosage form to facilitate insertion.

In the cream or ointment embodiments of the present invention, the topical formulation comprises one or more lubricants. The gels and foams of the present invention optionally can include one or more lubricants.

Non-limiting examples of useful lubricants include cetyl esters wax, hydrogenated vegetable oil, magnesium stearate, methyl stearate, mineral oil, polyoxyethylene-polyoxypropylene copolymer, polyethylene glycol, polyvinyl alcohol, sodium lauryl sulfate, white wax, or mixtures of two or more of the above.

The gel formulations of the present invention comprise one or more gelling agents. Non-limiting examples of useful gelling agents include carboxylic acid polymers including acrylic acid polymers crosslinked with cross links such as allyl ethers of sucrose (e.g. carbomer brand thickeners), cetostearyl alcohol, hydroxymethyl cellulose, polyoxyethylene-polyoxypropylene copolymer, sodium carboxymethylcellulose, polyvinyl pyrrolidone, or mixtures of two or more thereof.

VI. Uses and Methods

Therapeutic Uses and Methods:

In one aspect, provided herein is a method of treating HIV or inhibiting transmission of HIV. In one embodiment, the method of inhibiting transmission of HIV comprises administering to a subject in need thereof an effective amount of an antibody described herein (e.g., PGZL1, PGZL1.H4K3, and PGZL1_gVmDmJ), a pharmaceutical composition described herein, an isolated polynucleotide described herein, or a recombinant virus (e.g., recombinant AAV) described herein. In one embodiment, the method of inhibiting transmission of HIV comprises administering to a subject in need thereof an effective amount of an antibody (e.g., a bispecific antibody) described herein. In one embodiment, the method of inhibiting transmission of HIV comprises administering to a subject in need thereof an effective amount of a recombinant AAV encoding an antibody (e.g., a bispecific antibody) described herein. In one embodiment, the method of inhibiting transmission of HIV comprises administering to a subject in need thereof an effective amount of an antibody described herein (e.g., PGZL1, PGZL1.H4K3, and PGZL1_gVmDmJ). In one embodiment, the subject has been exposed to HIV. In one embodiment, the subject is at risk of being exposed to HIV. In one embodiment, the subject at risk of being exposed to HIV is a health care worker, a sexual partner of an HIV infected individual, or a sex worker. In one embodiment, the subject that has been exposed to HIV or is at risk of being exposed to HIV is a newborn. In one embodiment, the antibody is PGZL1. In one embodiment, the antibody is PGZL1.H4K3.

In one aspect, provided herein is a method of reducing the risk of a subject becoming infected with HIV comprising administering to the subject in need thereof an effective amount of an antibody (e.g., bispecific antibody) described herein (e.g., PGZL1, PGZL1.H4K3, and PGZL1_gVmDmJ), a pharmaceutical composition described herein, an isolated polynucleotide described herein, or a recombinant virus described herein. In one embodiment, the method comprises administering to a subject in need thereof an effective amount of an antibody (e.g., a bispecific antibody) described herein. In one embodiment, the method comprises administering to a subject in need thereof an effective amount of a recombinant AAV encoding an antibody (e.g., a bispecific antibody) described herein. In one embodiment, the subject has been exposed to HIV. In one embodiment, the subject is at risk of being exposed to HIV. In one embodiment, the subject at risk of being exposed to HIV is a health care worker, a sexual partner of an HIV infected individual, or a sex worker. In one embodiment, the subject that has been exposed to HIV or is at risk of being exposed to HIV is a newborn. In one aspect, provided herein is an antibody (e.g., PGZL1, PGZL1.H4K3, and PGZL1_gVmDmJ), a pharmaceutical composition, an isolated polynucleotide, or a recombinant virus for reducing the risk of a subject becoming infected with HIV. In one embodiment, the antibody is PGZL1. In one embodiment, the antibody is PGZL1.H4K3.

In one aspect, provided herein is a method for passively immunizing a subject comprising administering to the subject in need thereof an effective amount of an antibody described herein (e.g., PGZL1, PGZL1.H4K3, and PGZL1_gVmDmJ), a pharmaceutical composition described herein, an isolated polynucleotide described herein, or a recombinant virus described herein. In one embodiment, the method comprises administering to a subject in need thereof an effective amount of an antibody (e.g., a bispecific antibody) described herein. In one embodiment, the method comprises administering to a subject in need thereof an effective amount of a recombinant AAV encoding an antibody (e.g., a bispecific antibody) described herein. In one embodiment, the subject has been exposed to HIV. In one embodiment, the subject is at risk of being exposed to HIV. In one embodiment, the subject at risk of being exposed to HIV is a health care worker, a sexual partner of an HIV infected individual, or a sex worker. In one embodiment, the subject that has been exposed to HIV or is at risk of being exposed to HIV is a newborn. In one aspect, provided herein is an antibody (e.g., PGZL1, PGZL1.H4K3, and PGZL1_gVmDmJ), a pharmaceutical composition, an isolated polynucleotide, or a recombinant virus for passively immunizing a subject. In one embodiment, the antibody is PGZL1. In one embodiment, the antibody is PGZL1.H4K3.

Further provided herein is a method of neutralizing an HIV virus comprising contacting the virus with an effective amount of an antibody described herein (e.g., PGZL1, PGZL1.H4K3, and PGZL1_gVmDmJ). In one embodiment, the virus is comprised by a composition, for example, a fluid, including a biological fluid, such as blood or blood product. In certain embodiments, the method comprises adding an antibody described herein to a composition comprising HIV in a sufficient amount or concentration to neutralize the HIV. In one embodiment, the antibody is PGZL1. In one embodiment, the antibody is PGZL1.H4K3.

Further provided herein is a method of reducing viral load comprising administering to a subject in need thereof an effective amount of an antibody (e.g., bispecific antibody) described herein (e.g., PGZL1, PGZL1.H4K3, and PGZL1_gVmDmJ), a pharmaceutical composition described herein, an isolated polynucleotide described herein, or a recombinant virus described herein. In one embodiment, the method comprises administering to a subject in need thereof an effective amount of an antibody (e.g., a bispecific antibody) described herein. In one embodiment, the method comprises administering to a subject in need thereof an effective amount of a recombinant AAV encoding an antibody (e.g., a bispecific antibody) described herein. In one embodiment, the antibody is PGZL1. In one embodiment, the antibody is PGZL1.H4K3.

In one embodiment of a method described herein, the antibody can be a chimeric antibody, engineered antibody, recombinant antibody, or a monoclonal antibody described herein. In one embodiment, the antibody is a full antibody, an Fab fragment, or an $F(ab')_2$ fragment described herein. In a specific embodiment, the antibody is an engineered monoclonal antibody described herein. In a specific embodiment, the antibody is a recombinant monoclonal antibody described herein. In a specific embodiment, the antibody is a chimeric monoclonal antibody described herein. In a specific embodiment, the antibody is an Fab described herein. In a specific embodiment, the antibody is a $F(ab')_2$ fragment described herein.

In one embodiment, a method of preventing HIV infection provided herein comprises administering to a subject in need thereof a therapeutically sufficient amount of an antibody described herein (e.g., PGZL1, PGZL1.H4K3, and PGZL1_gVmDmJ), a pharmaceutical composition described herein, an isolated polynucleotide described herein, or a recombinant virus described herein. In one embodiment, the antibody is PGZL1. In one embodiment, the antibody is PGZL1.H4K3.

In one embodiment, a method of treating HIV/AIDS provided herein comprises administering to a subject in need thereof a therapeutically sufficient amount of an antibody described herein (e.g., PGZL1, PGZL1.H4K3, and PGZL1_gVmDmJ), a pharmaceutical composition described herein, an isolated polynucleotide described herein, or a recombinant virus described herein. In one embodiment, a method of treating HIV/AIDS comprises administering an antibody described herein. In one embodiment, a method of treating HIV/AIDS comprises administering a pharmaceutical composition described herein. In one embodiment, a method of treating HIV/AIDS comprises administering an isolated polynucleotide described herein. In one embodiment, a method of treating HIV/AIDS comprises administering a recombinant virus described herein. In one aspect, provided herein is an antibody, a pharmaceutical composition, an isolated polynucleotide, or a recombinant virus for treating HIV/AIDS. In one embodiment, the antibody is PGZL1. In one embodiment, the antibody is PGZL1.H4K3.

In one embodiment, the administering to the subject is by at least one mode selected from oral, parenteral, subcutaneous, intramuscular, intravenous, vaginal, rectal, buccal, sublingual, and transdermal In one embodiment, a method of treatment described herein further comprises administering at least one additional therapeutic agent. In one embodiment, the additional therapeutic agent comprises an antiretroviral therapy (ART) agent, a reservoir activator, an immunomodulator, a second antibody, or a second and third antibody. In one embodiment, the additional therapeutic agent comprises a second antibody. In one embodiment, the additional therapeutic agent comprises a second and third antibody. In one embodiment, the additional therapeutic agent comprises a second and optionally third antibody, which is an anti-HIV antibody. In one embodiment, the additional therapeutic agent comprises a second and optionally third antibody, which is an anti-HIV Env antibody. In one embodiment, the additional therapeutic agent comprises a second and optionally third anti-HIV Env antibody, which binds to an HIV Env epitope region different from the HIV Env epitope region bound by an antibody disclosed herein. In one embodiment, the additional therapeutic agent comprises a second and optionally third anti-HIV Env antibody, which binds to the CD4 binding site (CD4bs), V2 apex, N332/V3 base supersite, silent face, or gp120-gp41 interface. In one embodiment, the additional therapeutic agent comprises a second anti-HIV Env antibody, which binds to the CD4 binding site (CD4bs) epitope region. In one embodiment, the additional therapeutic agent comprises a second anti-HIV Env antibody, which binds to the V2 apex epitope region. In one embodiment, the additional therapeutic agent comprises a second anti-HIV Env antibody, which binds to the N332/V3 base supersite epitope region. In one embodiment, the additional therapeutic agent comprises a second anti-HIV Env antibody, which binds to the gp120-gp41 interface epitope region. In one embodiment, the additional therapeutic agent comprises a second anti-HIV Env antibody, which binds to the silent face epitope region.

In certain embodiments, the subject is at risk for exposure to HIV. In some embodiments, the subject is infected with HIV. In some embodiments, the subject is diagnosed with AIDS. In certain embodiments, the subject at risk for exposure to HIV is a health care worker. In certain embodiments, the subject at risk for exposure to HIV is a sex worker. In certain embodiments, the subject at risk for exposure to HIV is a sexual partner of an HIV infected individual. In certain embodiments, the subject at risk for exposure to HIV is a newborn.

The invention also features methods of blocking HIV infection in a subject (e.g., a human) at risk of HIV transmission. For example, in one aspect, the subject may be a fetus of an HIV-infected pregnant female and the method includes administering to the HIV-infected pregnant female an antibody described herein (e.g., PGZL1, PGZL1.H4K3, and PGZL1_gVmDmJ), thereby blocking the HIV infection in the fetus. In other instances, the subject is a newborn having an HIV-infected mother, a subject at risk of HIV transmission following a needle stick injury, or a subject at risk of HIV transmission following a sexual exposure to an HIV-infected individual. In one embodiment, the antibody is PGZL1. In one embodiment, the antibody is PGZL1.H4K3.

In instances when the subject is a newborn having an HIV-infected mother, the newborn can be administered an antibody described herein (e.g., PGZL1, PGZL1.H4K3, and PGZL1_gVmDmJ) peripartum and/or postpartum, for example, prior to, during, and/or following breastfeeding from the HIV-infected mother, in order to block an HIV infection in the newborn. In one embodiment, the antibody is PGZL1. In one embodiment, the antibody is PGZL1.H4K3.

In instances when the subject is at risk of HIV transmission following a sexual exposure to an HIV-infected individual, the subject can be administered an antibody described herein (e.g., PGZL1, PGZL1.H4K3, and PGZL1_gVmDmJ) following the sexual exposure in order to block an HIV infection in the subject. In one embodiment, the antibody is PGZL1. In one embodiment, the antibody is PGZL1.H4K3.

In some embodiments, an antibody described herein can be used as a microbicides to prevent mucosal HIV acquisition. In some embodiments, an antibody described herein is used to prevent vaginal or rectal acquisition of HIV. In some embodiments, an antibody described herein can be used as a microbicides to reduce the likelihood of mucosal HIV acquisition. In some embodiments, an antibody described herein is used to reduce the likelihood of vaginal or rectal acquisition of HIV.

In any of the methods described above, further administration of ART and/or an immunomodulator and/or a second antibody is contemplated. For example, the ART and/or immunomodulator and/or a second antibody can be administered in conjunction with, prior to, concurrently with, subsequent to, or within the context of a treatment regimen that includes administration of an antibody described herein.

An antibody described herein, or a pharmaceutical composition described herein can be delivered to a subject by a variety of routes, such as oral, parenteral, subcutaneous, intravenous, intradermal, transdermal, intranasal, vaginal, or anal. In one embodiment, the antibody or pharmaceutical composition is administered intravenously, vaginally, or anally.

The amount of an antibody described herein, or a pharmaceutical composition described herein, which will be effective in the treatment and/or prevention of a condition will depend on the nature of the disease, and can be determined by standard clinical techniques.

The precise dose to be employed in a pharmaceutical composition will also depend on the route of administration, and the seriousness of the disease, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Detection & Diagnostic Uses

An antibody described herein can be used to detect HIV and/or assay HIV levels in a biological sample using classical immunohistological methods known to those of skill in the art, including immunoassays, such as the enzyme linked immunosorbent assay (ELISA), immunoprecipitation, or Western blotting. An antibody described herein can also be used as an imaging agent, for example, a tissue-penetrating imaging agent. In one embodiment, an antibody described herein is conjugated with a detectable label. Suitable assay labels are known in the art and include enzyme labels, such as, glucose oxidase; radioisotopes, such as iodine ($^{125}I$, $^{121}I$) carbon ($^{14}C$), sulfur ($^{35}S$), tritium ($^{3}H$), indium ($^{121}In$), and technetium ($^{99}Tc$); luminescent labels, such as luminol; and fluorescent labels, such as fluorescein and rhodamine, and biotin. Such labels can be used to label an antibody or fusion polypeptide described herein. Alternatively, a second antibody that recognizes an antibody described herein can be labeled and used in combination with the antibody described herein to detect HIV levels.

As used herein, the term "biological sample" refers to any biological sample obtained from a subject, cell line, tissue, or other source potentially comprising HIV. Methods for obtaining tissue biopsies and body fluids from animals (e.g., humans) are well-known in the art.

In another embodiment, an antibody described herein can be used to detect levels of HIV, which levels can then be linked to certain disease symptoms. An antibody described herein may carry a detectable or functional label. An antibody described herein can carry a fluorescence label. Exemplary fluorescence labels include, for example, reactive and conjugated probes, e.g., Aminocoumarin, Fluorescein and Texas red, Alexa Fluor® dyes, Cy dyes and DyLight™ dyes. An antibody described herein can carry a radioactive label, such as the isotopes $^3$H, $^{14}$C, $^{32}$P $^{35}$S $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of an antibody described herein to HIV. In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an antibody described herein under conditions that allow for the formation of a complex between the antibody and HIV. Any complexes formed between the antibody and HIV are detected and compared in the sample and the control. An antibody described herein can also be used to purify HIV via immunoaffinity purification.

In some aspects, provided herein are methods for in vitro detecting HIV in a sample, comprising contacting said sample with an antibody described herein. In some aspects, provided herein is the use of an antibody described herein, for in vitro detecting HIV in a sample. In one aspect, provided herein is an antibody or pharmaceutical composition described herein for use in the detection of HIV in a subject. In one aspect, provided herein is an antibody or pharmaceutical composition described herein for use as a diagnostic. In one preferred embodiment, the antibody comprises a detectable label. In one embodiment, the subject is a human. In one embodiment, the method of detecting HIV in a sample comprises contacting the sample with an antibody described herein.

In some embodiments, the present disclosure provides methods of purifying HIV from a sample. In some embodiments, the method of purifying HIV from a sample comprises contacting the sample with an antibody described herein under conditions that allow the antibody to bind to HIV. In some embodiments, the antibody comprises a tag, for example, hexa-histidine tag or FLAG-tag to facilitate the purification of HIV.

Vaccine Design

Provided herein are methods for identifying vaccines capable of eliciting a broadly neutralizing antibody (bnAb) response in a human subject.

A key goal in HIV vaccine design is to elicit bnAbs. Recently, vaccine design has focused on targeting elements in common between similar bnAb precursors from different individuals. Notably, PGZL1 and 4E10 were elicited independently in two different individuals, and both bnAbs recognize highly conserved elements at the base of the membrane-embedded HIV spike using shared germline alleles and similar structural interactions. This presents an opportunity to develop vaccine leads that show specific high affinity binding to PGZL1-like antibodies, and may include: Env trimers, MPER peptides and/or MPER scaffolds. Screens for such germline targeted or lineage based vaccine leads have been described for other HIV-1 bnAbs, such as VRC01 Jardine J G et al., Science 351: 1458-1463 (2016); Kwong and Mascola, Immunity 48: 855-871 (2018).

Antibodies disclosed herein are particularly well suited for use in identifying vaccine candidates considering that the germline revertant antibody, PGZL1_gVmDmJ: (i) stained cells that express functional, well-ordered HIV-1 membrane Env trimers, as well as stained cells that display MPER-TM peptide in a flow cytometry assay, (ii) bound tightly to MPER peptide as assessed using biolayer interferometry (BLI) and ELISA, (iii) bound to Env trimers from detergent-solubilized HIV-1 virions in an ELISA and BN-PAGE gel mobility-shift assays, and (iv) neutralized 12% of isolates of a multiclade virus panel. That PGZL1_gVmDmJ can bind directly to HIV-1 Env and MPER peptide on membranes makes it, and the Envs it recognizes the best, an important tools for HIV vaccine design.

Antibodies disclosed have additional advantageous properties for use in vaccine design. No somatic hypermutation (SHM) in VH1-69/VK3-20 germlines were required with PGZL1 gVmDmJ and gVgDgJ in order to bind to HIV Env, which can facilitate the design of vaccines that bind to and activate germline B cells with the potential to mature into PGZL1-like bnAbs, i.e., PGZL1 germline or lineage-based approach to HIV vaccine design. In contrast, other MPER bnAb precursors, including revertants of 4E10 and 10E8 or UCA of DH511, bind more weakly or not at all to MPER peptide and HIV-1 Env, and/or require SHM in order to bind to the MPER or neutralize HIV-1.

Provided herein are methods for identifying HIV vaccine candidates. In some embodiments, a method of identifying an agent as an HIV vaccine candidate disclosed herein comprises contacting the agent with an antibody or antigen-binding fragment thereof disclosed herein under conditions sufficient to form an immune complex, and detecting the presence of the immune complex, wherein the presence of the immune complex indicates that the agent is a vaccine candidate. In some embodiments, the vaccine candidate is a priming vaccine candidate. In some embodiments, the antibody is PGZL1, PGZL1.H4K3, PGZL1_gVmDmJ, or PGZL1_gVgDgJ. In some embodiments, the antibody is PGZL1_gVmDmJ. In some embodiments, the antibody is PGZL1_gVgDgJ. In some embodiment, the agent is an Env trimer, MPER peptide and/or MPER scaffold. In some embodiments, the agent is an HIV-1 Env trimer, MPER peptide, peptidomimetic, antiidiotypic antibody or MPER peptide conjugated with a scaffold. In some embodiment, the agent is a full-length Env trimer, Env trimer with truncations to the C-terminal tail and/or transmembrane domain, or Env trimer stabilized with trimerization domains, disulfides, or chemical fixatives. In some embodiment, the agent is an Env peptide (e.g., MPER) containing natural amino acids, or an Env peptide (e.g., MPER) containing chemical modifications including unnatural amino acids or domains (e.g. transmembrane and/or trimerization domains). In some embodiment, the agent is a scaffold comprising one or more Env peptide (e.g., MPER) containing natural amino acids, or one or more Env peptide (e.g., MPER) containing chemical modifications including unnatural amino acids or domains (e.g. transmembrane and/or trimerization domains). In some embodiment, the agent is an anti-idiotypic antibody. In some embodiments, the agent is an HIV-1 Env trimer. In some embodiments, the agent is an MPER peptide. Any method known to one skilled in the art for forming an immune complex between a vaccine candidate agent and an antibody disclosed herein, e.g., ELISA, biolayer interferometry (BLI), flow cytometry, can be used in a method disclosed herein.

Provided herein are methods for selecting or identifying HIV vaccine candidates. In some embodiments, a method for selecting or identifying an agent as an HIV vaccine candidate disclosed herein comprises contacting an antibody or antigen-binding fragment thereof disclosed herein with a library of agents under conditions sufficient to form an immune complex, removing the agents in the library that do not form an immune complex with the antibody or antigen-binding fragment thereof, and isolating an agent that forms an immune complex with the antibody or antigen-binding fragment thereof. In some embodiments, the vaccine candidate is a priming vaccine candidate. In some embodiments, the antibody is PGZL1, PGZL1.H4K3, PGZL1_gVmDmJ, or PGZL1_gVgDgJ. In some embodiments, the antibody is PGZL1_gVmDmJ. In some embodiments, the antibody is PGZL1_gVgDgJ. In some embodiment, the library of agents is a library of Env trimers or MPER peptides. In some embodiment, the library of agents is a library of HIV-1 Env trimers, MPER peptides, peptidomimetics, or antiidiotypic antibodies. In some embodiment, the library of agents is a library of full-length Env trimers, Env trimers with truncations to the C-terminal tail and/or transmembrane domain, or Env trimers stabilized with trimerization domains, disulfides, or chemical fixatives. In some embodiment, the library of agents is a library of Env peptides (e.g., MPER) containing natural amino acids, or Env peptides (e.g., MPER) containing chemical modifications including unnatural amino acids or domains (e.g. transmembrane and/or trimerization domains). In some embodiment, the library of agents is a library of Env peptides (e.g., MPER) conjugated with scaffold. In some embodiment, the library of agents is a library of anti-idiotypic antibodies. In some embodiment, the library of agents is a library of HIV-1 Env trimers. In some embodiment, the library of agents is a library of MPER peptides.

VII. Kits

Provided herein are kits comprising one or more antibodies described herein (e.g., PGZL1 or PGZL1.H4K3). In some embodiments, a pharmaceutical pack or kit described herein comprises one or more containers filled with one or more of the ingredients of the pharmaceutical compositions described herein, such as one or more antibodies described herein. In some embodiments, a kit contains an antibody described herein or a pharmaceutical composition described herein, and a second prophylactic or therapeutic agent used in the treatment or prevention of HIV. In one embodiment, the second agent is an antiretroviral agent. In one embodiment, the second agent is a reservoir activator. In one embodiment, the second agent is an immunomodulator. In one embodiment, the second agent is one or more anti-HIV antibody. In one embodiment, the second agent is one or more anti-HIV Env antibody that binds to an HIV Env epitope region different from the HIV Env epitope region bound by an antibody disclosed herein. In one embodiment, the second agent is one or more anti-HIV Env antibody that binds to the CD4 binding site (CD4bs), V2 apex, N332/V3 base supersite, silent face, or gp120-gp41 interface. In some embodiments, a kit contains an antibody described herein or a pharmaceutical composition described herein, and a reagent used in the detection of HIV. In one embodiment, the detection reagent comprises DNA primers for the detection of HIV. Optionally associated with such container(s) can be a notice in the form prescribed by a governmental agency regulating the manufacture, use or sale of pharmaceuticals or biological products, which notice reflects approval by the agency of manufacture, use or sale for human administration. In one embodiment, the antibody comprises PGZL1. In one embodiment, the antibody comprises PGZL1.H4K3.

In one embodiment, a kit described herein comprises an antibody described herein or a pharmaceutical composition described herein and a) a detection reagent, b) an HIV antigen, c) a notice that reflects approval for use or sale for human administration, or d) any combination thereof.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

All documents, patent, and patent applications cited herein are hereby incorporated by reference, and may be employed in the practice described herein.

EXAMPLES

Example 1. Identification of a 4E10-Like Antibody from an African Donor

Plasma from visit 2 (out of a total of six visits) of an HIV-1 infected South African donor, PG13, in the IAVI Protocol G cohort (Simek, et al., J. Virol. 83: 7337-7348 (2009)) was tested for neutralization against HIV-2 (HIV-1 MPER) chimeric viruses. The titer was 1:6400 ($ID_{50}$) against 4E10-sensitive chimeras C1 and C4, but the 2F5-sensitive C3 chimera was not neutralized, suggesting a 4E10-like antibody (FIG. 1A; Table 6). The plasma also neutralized 5 of a 6-virus panel (FIG. 1A). MPER peptide partially blocked plasma neutralization of primary isolate Du156.12 and the C1 chimera (Table 6).

TABLE 6

Neutralization of HIV-2 (HIV-1 MPER) chimera viruses and HIV-1 virus by PG13 donor serum and monoclonal antibodies.

| Virus | MPER | PG13 Plasma (±competitor)* | | Monoclonal Ab ($IC_{50}$ µg/ml) | | |
|-------|------|------|------|------|------|------|
| | | − | + | PGZL1 | H4K3 | 4E10 |
| HIV-2 C1 | ELLALDKWASLWNWFDITKWLWYIK (SEQ ID NO: 3) | 6400 | 940 | 0.98 | n.d. | 0.8 |
| HIV-2 C3 | ELLALDKWASLWNWFDLASWVKYIQ (SEQ ID NO: 122) | <80 | n.d. | >10 | >10 | >10 |
| HIV-2 C4 | ELQKLNSWDVFGNWFDITKWLWYIK (SEQ ID NO: 4) | 6400 | n.d. | 2.38 | 1.17 | 1.41 |

TABLE 6-continued

Neutralization of HIV-2 (HIV-1 MPER) chimera viruses and HIV-1 virus by PG13 donor serum and monoclonal antibodies.

| Virus | MPER | PG13 Plasma (±competitor)[a] | | Monoclonal Ab (IC$_{50}$ µg/ml) | | |
|---|---|---|---|---|---|---|
| | | − | + | PGZL1 | H4K3 | 4E10 |
| HIV-2 | ELQKLNSWDVFGNWFDLASWVKYIQ (SEQ ID NO: 123) | <80 | n.d. | >10 | >10 | >10 |
| Du156.12 | DLLALDRWQNLWNWFDITNWLWYIK (SEQ ID NO: 2) | 1140 | 280 | 0.623 | 0.27 | 0.101 |
| Du156.12[b] | DLLALDRWQNLWNWFDITNWLWYIK (SEQ ID NO: 124) | 1140 | 1911 | 0.623 | 0.27 | 0.101 |

[a]ID$_{50}$ in reciprocal plasma dilution against each virus in the presence (+) or absence (−) of 10 µg/ml MPER peptide (residues 654-683). n.d., not determined.
[b]The fusion peptide (residues 512-534) was used as competitor.

MPER positive B cells from PG13 visit 5 were then sorted by fluorescence activated cell sorting (FACS), and the resulting heavy-chain (HC) and light-chain (LC) variable regions were cloned into IgG vectors. Antibody PGZL1 bound to full-length MPER and a 4E10-specific peptide, but not to a 2F5-specific peptide (FIG. 1B).

DNA sequencing revealed PGZL1 was from subclass IgG1, while most MPER bnAbs are IgG3s (Table 7). Phylogenetic analysis showed sequence homology between PGZL1, VRC42.01 and 4E10, due to shared germline genes VH1-69, VK3-20 and DH3-10*01 (FIG. 1C; Table 7).

PGZL1 has a high degree of SHM (20.9% nucleotides for HC and 12.6% for LC; FIG. 1E) and 5 HC and 2 LC mutations match those in 4E10 (FIG. 7). PGZL1, VRC42.01 and 4E10 use different J genes. The PGZL1 CDRH3 contains 15 residues, three residues shorter than that of 4E10, and equal in length to that of VRC42.01. The three CDRH3s share some amino acids not only from the same D-gene, e.g. W99, G100a, but also at positions E95, G96, G98, K100b, P100c and A100f, which may have arisen from N-additions or SHM (FIG. 7).

TABLE 7

Germline gene usage and characteristics of HIV-1 MPER bnAbs

| Abs | Putative heavy chain gene alleles | | | V (nt%) mutation frequency | HCDR3 aa sequence | HCDR3 Length (aa) | Isotype |
|---|---|---|---|---|---|---|---|
| PGZL1 | IGHV1-69*06 | IGHD3-10*01 | IGHJ3*01 | 20.9 | EGEGWFGKPLRAFEF (SEQ ID: 63) | 15 | IgG1 |
| 4E10 | IGHV1-69*10 | IGHD3-10*01 | IGHJ4*03 | 6.8 | EGTTGWGWLGKPIGA FAH (SEQ ID NO: 125) | 18 | IgG3 |
| VRC42.01 | IGHV1-69*10 | IGHD3-10*01 | IGHJ4*03 | 10.8 | EGAGWFGKPVGAMG Y (SEQ ID: 126) | 15 | IgG1 |
| 10E8 | IGHV3-15*05 | IGHD3-3*01 | IGHJ1*01 | 21.5 | TGKYYDFWSGYPPGE EYFQD (SEQ ID NO: 127) | 20 | IgG3 |
| DH511.2 | IGHV3-15*01 | IGHD3-3*01 | IGHJ6*03 | 17.6 | TMDEGTPVTRFLEWG YFYYYMAV (SEQ ID NO: 128) | 23 | IgG3 |
| DH517 | IGHV4-34*01 | IGHD3-16*01 | IGHJ6*01 | 18.1 | ARGTGVVVGGSWTVP PGMAYYLDV (SEQ ID NO: 129) | 24 | IgG3 |
| Z13 | IGHV4-59*03 | IGHD2-15*01 | IGHJ6*03 | 17.7 | VAIGVSGFLNYYYYM DV (SEQ ID NO: 139) | 17 | N.D. |
| 2F5 | IGHV2-5*02 | IGHD3-3*01 | IGHJ6*02 | 12.1 | RRGPTTSSGVPIARGP VNAMDV (SEQ ID NO: 130) | 22 | IgG3 |

TABLE 7-continued

Germline gene usage and characteristics of HIV-1 MPER bnAbs

| Abs | Putative heavy chain gene alleles | | V (nt%) mutation frequency | HCDR3 aa sequence | HCDR3 Length (aa) |
|---|---|---|---|---|---|
| PGZL1 | IGKV3-20*01 | IGKJ5*01 | 12.6 | QQYGTSQST (SEQ ID NO: 131) | 9 |
| 4E10 | IGKV3-20*01 | IGKJ2*01 | 4.7 | QQYGQSLST (SEQ ID NO: 132) | 9 |
| VRC42.01 | IGKV3-20*01 | IGKJ1*01 | 5.7 | QQYGGSFGT (SEQ ID NO: 133) | 9 |
| 10E8 | IGLV3-19*01 | IGLJ3*02 | 15.2 | SSRDKSGSRLSV (SEQ ID NO: 134) | 12 |
| DH511.2 | IGLK1-39*01 | IGKJ2*03 | 15.7 | QENYNTIPSLS (SEQ ID NO: 135) | 11 |
| DH517 | IGLV3-19*01 | IGLJ2*01 | 13.4 | ASRDRSGDRLGV (SEQ ID NO: 136) | 12 |
| Z13 | IGKV3-11*01 | IGKJ1*01 | 6 | QQRSDWPRT (SEQ ID NO: 137) | 9 |
| 2F5 | IGKV1D-13*02 | IGKJ4*01 | 11.8 | QQLHFYPHT (SEQ ID NO: 138) | 9 |

Example 2. Broad HIV Neutralization by PGZL1 Lineage Antibodies

PGZL1 was tested against a 6-virus panel and found that it neutralized 5 viruses with an $IC_{50}$ of 5.8 µg/ml, which was 6-fold less potent than 4E10 (FIG. 1A). To identify more potent PGZL1 variants, BCR transcripts of donor PG13 B cells taken from three visits (visits 2, 4 and 6) in a short 9-month span using a next-generation sequencing (NGS) pipeline were analyzed (Table 8). He et al., Front. Immunol. 8, 1025 (2017). The PG13 repertoire profiles were similar among visits, with PGZL1 germline gene, VH1-69, accounting for 3.9-7.2% of the repertoire, whereas VH4-34 and VH4-59 composed up to 13% (FIG. 8). Two-dimensional identity/divergence analysis (FIG. 1D) and CDRH3-based lineage tracing showed two groups of PGZL1-related HCs: one group forming an island with full-length identity of 85-100% and the other creating a long stretch of up to 80% identity, suggesting a sub-lineage related to PGZL1. As earlier PG13 PBMCs and plasma samples were depleted or unavailable, the time of lineage division could not be determined. Overall, the PGZL1 lineage appears to be highly evolved, showing similar patterns to the VRC01-class bnAbs that often diverge into many sub-lineages. Kong et al., Immunity 44, 939-950 (2016).

For functional studies, a clustering analysis of CDRH3s with at least 80% identity allowed a broad selection of 27 HCs from the PGZL1 sub-lineages (FIG. 9A, Table 9). CDRH3 remained conserved in length and sequence, perhaps due to affinity maturation against the conserved MPER. The HCs were paired with the PGZL1 LC and tested these antibodies against Du156.12. The best neutralizers, H4 and H8 from Visit 2 (Table 9), had 2-4 fold lower $IC_{50}$s than PGZL1 (FIG. 9B). Of note, H4 and H8 seemed to come from a distinct sub-lineage having low sequence identity (≤83%) with respect to PGZL1 HC (FIG. 1D). H4 and H8 HCs were then paired with 10 similarly chosen NGS variant LCs (Table 9), and LC K3, also from Visit 2, to yield H4K3 and H8K3, which neutralized Du156.12 and 92TH021 with potency further increased by 2-4 fold (FIG. 9C). PGZL1.H4K3 (hereafter H4K3) was chosen for more detailed characterization. H4K3 has less SHM than PGZL1, i.e., 17.4%/11.7% versus 20.9%/12.6% at the nucleotide level for HC/LC, respectively, consistent with H4K3 being sampled 5 months prior to PGZL1.

TABLE 8

Unbiased antibody repertoire analysis of an HIV-1-infected patient from Protocol G cohort, PG13[a].

| Visit | N read | N assign | Chain | N chain | \<length\>(nt) | % usable (%) |
|---|---|---|---|---|---|---|
| #2 | 5,692,576 | 4,161,595 | H | 2,026,540 | 554.2 | 58.2% |
| (18-18- | | | κ | 1,095,554 | 563.4 | 53.9% |
| 2008) | | | λ | 1,039,501 | 581.8 | 56.7% |
| #4 | 4,412,667 | 3,486,756 | H | 1,793,460 | 583.4 | 63.9% |
| (Mar. 12, | | | κ | 882,793 | 570.1 | 58.5% |
| 2009) | | | λ | 810,503 | 588.9 | 62.2% |
| #6 | 5,040,531 | 3,934,837 | H | 1,715,839 | 583.8 | 66.6% |

TABLE 8-continued

Unbiased antibody repertoire analysis of an HIV-
1-infected patient from Protocol G cohort, PG13[a].

| Visit | N read | N assign | Chain | N chain | <length>(nt) | % usable (%) |
|---|---|---|---|---|---|---|
| (May 18, | | | κ | 1,178,148 | 568.1 | 59.4% |
| 2009) | | | λ | 1,040,850 | 589 | 60.4% |

[a]The unbiased antibody repertoire analysis was performed using a human 5'-RACE PCR procedure for library preparation on the Ion Chef instrument and long-read sequencing on the Ion GeneStudio S5 NGS platform. Listed items include the time point of the patient visit, total number of raw reads, number of remaining reads after germline gene assignment with a cutoff E-value of 10-3, antibody chain type (H, κ, and λ), number of antibody chains, average read length, and total number of usable sequences after Antibodyomics 1.0 pipeline processing and bioinformatics filtering with a V-gene alignment cutoff of 250 bp. Nine antibody chain libraries were barcoded according to three time points and pooled on one Ion 530 chip for the NGS experiment.

TABLE 9

PGZL1-like heavy chain and light chain sequences selected from NGS lineage analysis.

| Type | Name | NGS Idx | SHM (nt %) | Sequence identity (nt %) | Amino acid sequence of variable domain |
|---|---|---|---|---|---|
| HC | V2H1 | 4140766 | 6.8 | 80.6 | QVQLVQSGAEVKKPGSSVKVSCKASG GTFSNDVISWVRQAPGQGLEWMGRVI PILDITNYAQKFQGRVTITADKSTSTVY MDLSSLRSEDTAVYFCAREGEGWFGK PLRAFEVWGQGTQITVSS (SEQ ID NO: 11) |
| HC | V2H2 | 3634260 | 13.5 | 79.3 | QVQLVQSGAEVKKPGSSVKVSCKASG STFSSYAISWVRQAPGQGLEWVGGIVP LVSSTNYAQRFRGRVTISADRSTSTVY LEMTGLTSADTAVYFCAREGEGWFGR PLRAFEFWGQGTLVTVST (SEQ ID NO: 12) |
| HC | V2H3 | 1505330 | 19.3 | 76.1 | KVQLVQSGAELKKPWSSVRVSCKASG GSFSSYAFNWVRQAPGQKLEWLGGIA SLLVSRPSYAQRFRGRITISADRSATTV YLEMTGLTSADTAVYFCAREGEGWFG KPLRAFEFWGQGTLVTVST (SEQ ID NO: 13) |
| HC | V2H4 | 1592240 | 17.6 | 77.2 | KVQLVQSGAELKKPWSSVRVSCKASG GSFSSYAFNWVRQAPGQRLEWLGGIV PLVSSTNYAQRFRGRVTISADRSTSTV YLEMTGLTSADTAVYFCAREGEGWFG RPLRAFEFWGQGTLVTVST (SEQ ID NO: 14) |
| HC | V2H5 | 2499141 | 18.5 | 92.2 | GVQLVQSGAEVKKPGSSMTVSCKATG GTFSSLAFNWVRQAPGQGPEWMGGIC PVFSALVNYGQRFQGRLTIRADKSTTT VYLDLIRLTSDDTATYYCAREGEGRFG KPLRAFEVWGQGTQITVSS (SEQ ID NO: 15) |
| HC | V2H6 | 2684075 | 20.6 | 75.0? | KVQLVQSGAEVKRPGSSVTISCKDRGG SFSSYAFNWVRQAPGQGLEWMGGIIPL ISIANYASRRFRGRVTITADRSTSSIFLD LTRLTSVDTALYFCAREGEGWFGKPL GAFEFWGQGTAVTVTS (SEQ ID NO: 16) |
| HC | V2H7 | 133943 | 21.6 | 95.2 | GVQLVQSGAEVKRPGSSVTVSCKATG GTFSTLAFSWVRQAPGQGPEWMGGIV PLFTIVNYGQRFQGRLTIRADKSTTTVF LDLSGLTSADTATYYCAREGEGWFGK PLRALEIWGQGTVITVSS (SEQ ID NO: 17) |
| HC | V2H8 | 1537468 | 18.9 | 76.9 | RVQLVQSGAELKKPWSSVRVSCKASG GSFSSYAFSWVRQAPGQGLEWLGGIVP LVSSTNYAPKFRGRITISADRSANTVYL EMTRLTSADTAVYFCAREGEGWFGRP LRAFEFWGQGTLVTVST (SEQ ID NO: 18) |

TABLE 9-continued

PGZL1-like heavy chain and light chain sequences selected from NGS lineage analysis.

| Type | Name | NGS Idx | SHM (nt %) | Sequence identity (nt %) | Amino acid sequence of variable domain |
|------|------|---------|-----------|--------------------------|----------------------------------------|
| HC | V2H9 | 891566 | 24.0 | 74.5 | KVQLVQSGAEVMRPGSSGYLSCKASG GSFSSYAFNWVRQAPGQGLEWMGGII PLISIANYAEEFRGRVTITADRSTSSIFL DLTRLTSVDTALYFCAREGEGWFGKP LGAFEFWGQGTAVTVTS (SEQ ID NO: 19) |
| HC | V2H10 | 2745751 | 25.7 | 73.1 | RVQLVQSGAEVKRPGSSVTIACKASGG SCSSYALHWERQARGQGLEWMGGIM PPYRVANYAEELRGRVTMTGDRSTSSI FLDLTRLTSVDTALYFCAREGEGWFG KPLGAFEFWGQGTAVTVTS (SEQ ID NO: 20) |
| HC | V4H1 | 4221067 | 14.5 | 79.3 | QVQLAQSGTEVKKPGSSVKVSCKSSG GTSSNYAITWVRQAPGQGLEWMGGIV PLVSSTNYAQRFKGRVTISADRSTSTVF MEVIRLTSEDTGVYFCAREGEGWFGK PLRAFEFWGHGTAVTVSS (SEQ ID NO: 21) |
| HC | V4H2 | 2042752 | 20.6 | 95.2 | GVQLVQSGAEVNEGPGSSVEVSCKAT GGTFSTLAFNWVRQAPGQGPEWMGGI VPLFSIVNYGQRFQGRVTIRADKSTTT VFLDLSRLTSADTATYYCAREGEGWF GKPLRALEIWGQGTVITVSS (SEQ ID NO: 22) |
| HC | V4H3 | 3465249 | 19.6 | 94.6 | GVQLVQSGAEVKRPGSSMTVSCRATG GTFSSLAFNWVRQAPGQGPEWMGREI VPLFRIANYGQKFQGRLTIRADKSTTTI YLDLSSLTSADTATYYCAREGEGWFG KPLRAFEFWGQGTVITVSS (SEQ ID NO: 23) |
| HC | V4H4 | 176346 | 18.2 | 78 | KVQLVQSGAELKKPWSSVNEVSCKVS GGSFSSYAFNWVRQAPGQRLEWLGGI VPLVSSTNYAQRFRGRITISADRSTSTV YLEMTGLTSADTAVYFCAREGEGWFG KPLRAFEFWGQGTLVTVST (SEQ ID NO: 24) |
| HC | V4H5 | 1254417 | 20.9 | 75.5 | KVQLVQSGAEVKRPGSSVTISCKGTRG GSFSSYAFNWVRQAPGLGLEWMGGIIP LISIANYAERFRGRVTITADRSTSSIFLD LTRLTSVDTALYFCAREGEGWFGKPL GAFEFWGQGTAVTVTS (SEQ ID NO: 25) |
| HC | V4H6 | 1122859 | 20.6 | 94.9 | RVQLVQSGAEVKRPGSSVTVSCKATG GTFSTLAFSWVRQAPGQGPEWMGGIV PLFTIVNYGQRFQGRLTIRADKSTTTVF LDLSGLTSADTATYYCAREGEGWFGK PLRAPEIWGQGTVITVSS (SEQ ID NO: 126 |
| HC | V4H7 | 1501103 | 20.3 | 89 | GVQLVASGAEVKKPGSSVEVSCKATG GTFNSLAFNWVRQAPGQGPEYMGGIV PLFSIVNYGQRFQGRLTIRADKSTTTVY MDLNRLTSDDTATYYCAREGEGWFG KPLRAFQLWGQGTVITVSS (SEQ ID NO: 27) |
| HC | V4H8 | 3307001 | 23.6 | 75.8 | KVQLVQSGAEVKRPGSSVTISCKDSGG SFSSYAFNWVRQAPGQGLEWMGGIIPL ISSTNYAEKFRGRVTITADRSTSSIFLDL TRLTSADTALYFCAREGEGWFGKPLG AFEFWGQGTAVTVTS (SEQ ID NO: 28) |

TABLE 9-continued

PGZL1-like heavy chain and light chain sequences selected from NGS lineage analysis.

| Type | Name | NGS Idx | SHM (nt %) | Sequence identity (nt %) | Amino acid sequence of variable domain |
|------|------|---------|------------|--------------------------|----------------------------------------|
| HC | V6H1 | 1008039 | 20.9 | 77.2 | KVQLVQSGDVKLKTPWSSVRVSCKAS GGSFSSYAFNWVRQAPGQRLEWLGGI VPLVSSTNYAQRFRGRVTISADRSANT VYLEMTGLTSADTAIYFCAREGEGWF GKPLRAFEFWGQGTLVSVST (SEQ ID NO: 29) |
| HC | V6H2 | 1199275 | 19.9 | 76.9 | KVQLVQSGAELKKPWSSVRVSCKASG GSFSSYAFNWVRQAPGQRLECMGGIV PLVSSTNYAQRFRGRITISADRSASTVY LEMTGLTSADTAVYFCAREGEGWFGK PLRAFEFWGQGTLVAVST (SEQ ID NO: 30) |
| HC | V6H3 | 1330540 | 21.3 | 76.9 | KVQLVQSGAELKKPWSSVRVSCKATG GSFSSYAFNWVRPAPGQRLEWLGGIVP LVSSTNYAQRFRGRITISADRSASTVYL EMTGLTSADTAVYFCAREGEGWFGRP LRAFEFWGQGTLVTVST (SEQ ID NO: 31) |
| HC | V6H4 | 1944093 | 21.3 | 76.6 | KVQLVQSGAEVKRPGSSVTISCKASGG SFSSYAFNWVRQAPGLGLEWMGGIIPL ISIANYAQRRFRGRVTITADRSTSSIFLD LTRLTSVDTALYFCAREGEGWFGKPL GAFEFWGQGTAVTVTS (SEQ ID NO: 32) |
| HC | V6H5 | 1151354 | 19.6 | 76.6 | KVQLVQSGAELKKPWSSMRVSCKASG GSFSSYAFNWVRQAPGQRLEWLGGIV PLVSSTNYAQRFRGRITISADRSASTVY LEMTGLTSADTAVYFCAREGEGWFGK PLRAFEFWGQGTLVTVSA (SEQ ID NO: 33) |
| HC | V6H6 | 774842 | 19.9 | 93 | GVQLVQSGAEVKPGSSVTVSCKATG GTFSSLAFNWVRPMAPGQGPEWMGGI VPLFSIVNYGQRFQGRLTIRADKSTTTV YLDLIRLTSDDTATYYCAREGEGWFG KPLRAFEFWGQGTLITVSS (SEQ ID NO: 34) |
| HC | V6H7 | 1093434 | 20.3 | 89.8 | GVQLVQSGAEVKKPGVSVTVSCKATG GTFSSLAFNWVRQAPGQGPEYMGGIV PLFSIVNYAQRFQGRLTIRADKSTTTVY MDLNRLTSDDTATYYCAREGEGWFG KPLRAFQLWGQGTVITVSS (SEQ ID NO: 35) |
| HC | V6H8 | 2421650 | 22.3 | 95.2 | GVQLVQSGAEVKRPGSSVEVSCKATG GTFSTLAFSWVRQAPGQGPEWMGGIV PLFTIVNYGQRFQGRLTIRADKSTTTVF LDLSGLTSADTATYYCAREGEGWFGK PLRALEIWGQGTVITVSS (SEQ ID NO: 36) |
| HC | V6H9 | 3522135 | 24.7 | 73.4 | KVQLVQSGAEMKRPGSSVHAACKDR GGSFSSYAIIWVRQARELGFEWMGGII IP LLSRANYAQRWFRGRVTITAHESTSSIF LDLTRLTSVDTALYFCAREGEGWFGK PLGAFEFWGQGTAVTVTS (SEQ ID NO: 37 |
| KC | V2K1 | 2224128 | 8.3 | 85.2 | EIVLTQSPGTLSLSPGERATLSCRASQS VNSNYLAWYQQKPGQAPRLLIYRALG RATGIPDRFSGSGSGTDFTLTISRLEPED FAVYYCQQYGTSESTFGQGTRLEIR (SEQ ID NO: 38) |

TABLE 9-continued

PGZL1-like heavy chain and light chain sequences selected from NGS lineage analysis.

| Type | Name | NGS Idx | SHM (nt %) | Sequence identity (nt %) | Amino acid sequence of variable domain |
|------|------|---------|------------|--------------------------|-----------------------------------------|
| KC | V2K2 | 5128161 | 11.0 | 92.6 | EIVLTQSPGTLSLSPGERATLSCRASQS VSGGALAWYQQKAGQAPRLLIYDTSG RATGVPGRFSGSGSETDFSLTISRLEPE DFAVYYCQQYGTSQSTFGQGTRLETR (SEQ ID NO: 39) |
| KC | V2K3 | 5476422 | 11.4 | 93.5 | EIVLTQSPGTFALSPGERATLSCRASQS VSGGALAWYQQKAGQAPRLLIYGTSG RATGVPGRFSGSGSETDFSLTISRLEPE DFAVYYCQQYGTSQSTFGQGTRLETR (SEQ ID NO: 40) |
| KC | V2K4 | 1507161 | 19.3 | 88 | RIVLTQSPGTLSLSPGARATLSCRASQS VSGGSLAWYQQKAGRAPRSVIYDAVR RATAIPGRFSGSGSETDFSLTISRLEPED LAVYYCQQYGTSQSTFGQGTRLEIR (SEQ ID NO: 41) |
| KC | V4K1 | 1064505 | 12.4 | 92 | EIVLTQPPGNFWSLSPGQRATLSCRAG QSVSGGSLAWYQQKAGQAPRLLIYDT SSRATGVRDRFSGSGSETDFSLTISRLE PEDFAVYYCQQYGTSQSTFGQGTRLE MR (SEQ ID NO: 42) |
| KC | V4K2 | 2329152 | 12.4 | 92 | EIVLTQSPVTLSLSPGRKGTLSCRASQS VSGGSLAWYQQKPGQAPRLLIYDSSTR ATGVPGRFSGSGSETDFSLTISRLEAED FAVYYCQQYGTSQSTFGQGTRLEIR (SEQ ID NO: 43) |
| KC | V4K3 | 1219291 | 20.3 | 89.5 | DIVLTQSPGRFSLSPEERATLSCRASQS VSGGYVAWYQQKAGQAPRLPIYDYVS RATGVPGRFSGSGSETDFSLTISRLEPE DFAVYYCQQYGTSQSTFGQGTRLEIR (SEQ ID NO: 44) |
| KC | V6K1 | 1899647 | 9.7 | 82.1 | EMVLTQSPGTLSLSPGEGATLSCRASQ SVVYNSLAWYQQRPGQAPRLAILAAS RRATGIPDRFSGSGSGTDFTLTISRLEPE DFAVYYCQQYGTSQGTFGQGTKVEIK (SEQ ID NO: 45) |
| KC | V6K2 | 132411 | 3.1 | 85.5 | EIVLTQSPGTLSLSPGERATLSCRASQS VSSSYLAWYQQKPGQAPRLLIYGAYIR ATGIPDRFSGSGSGTDFTLTISRLEPEDF AVYYCQQYGTSQGTFGQGTKVEIK (SEQ ID NO: 46) |
| KC | V6K3 | 2357651 | 10.3 | 81.5 | RMVLTQSPGTLSLSPGEGATLSCGASQ SVVYNSLAWYQQRPGQAPRLVILAAS RRAAGIPDRFSGSGSGTDFTLTISRLEP EDFAVYYCQQYGTSQGTFGQGTKVEI K (SEQ ID NO: 47) |

A larger panel of HIV-1 primary isolates was used to examine breadth and potency of PGZL1 and H4K3. Notably, H4K3 neutralized 1000 viruses at ≤50 μg/ml (n=130), with an $IC_{50}$ of 1.43 μg/ml (FIGS. 1E-F, Table 10). 4E10 gave similar results, neutralizing 99% isolates with an $IC_{50}$ of 0.92 μg/ml. PGZL1 neutralized 84% viruses, with an $IC_{50}$ of 6.11 μg/ml. The $IC_{50}$s of PGZL1 and H4K3 are tightly correlated (r=0.82, p<0.0001) suggesting similar neutralization mechanisms (FIG. 9D). VRC01 neutralized 91% viruses with an $IC_{50}$ of 0.161 μg/ml. Overall, H4K3 is exceptionally broad and equipotent with 4E10, which can protect against SHIV challenge in monkeys. Hessell et al., J. Virol. 84, 1302-1313 (2010).

TABLE 10

Evaluation of neutralization breadth and potency of PGZL1 antibodies, 4E10 and VRC01 against a 130-member cross-clade pseudovirus panel using the TZM-bl cell neutralization assay.

| | | $IC_{50}$ (μg/ml) | | | | |
|---|---|---|---|---|---|---|
| Clade | Virus | PGZL1_gVmDmJ | PGZL1 | H4K3 | 4E10 | VRC01 |
| A | NIH-065__191955 A11 | 33.5 | 1.89 | 0.476 | 0.011 | 0.091 |
| A | NIH-063__0330.v4.c3 | >200 | 22.1 | 2.63 | 0.963 | 0.033 |
| A | NIH-066__191084 B7.19 | >200 | 30.9 | 1.17 | 1.23 | 0.049 |
| A | NAC__BG505 | >200 | 16.7 | 2.4 | 1.15 | 0.056 |
| A | NIH-057__MS208.A1 | >200 | 10.1 | 0.726 | 0.678 | 0.063 |
| A | NIH-064__0260.v5.c1 | >200 | >50 | 7.75 | 0.227 | 0.124 |
| A | NAC__KNH1144 | >200 | >50 | 18 | 11.5 | 0.134 |
| A | NAC__94UG103 | >200 | 24.1 | 9.37 | 1.77 | 0.187 |
| A | NAC__92RW020 | >200 | 20.8 | 3.86 | 2.14 | 0.206 |
| A1 | NIH-060__Q769ENVd22 | >200 | 20.2 | 3.19 | 1.61 | 0.025 |
| A1 | NIH-058__Q23ENV17 | >200 | 16.5 | 3.13 | 1.29 | 0.038 |
| A1 | NIH-056__Q168ENVa2 | >200 | 21.7 | 2.69 | 3.78 | 0.056 |
| A1 | NIH-061__Q259ENVd2.17 | >200 | >50 | 9.87 | 7.12 | 0.114 |
| A1 | NIH-059__Q461ENVe2 | >200 | 20.2 | 3.59 | 2.33 | 0.195 |
| A1U | NIH-117__T278.5 | >200 | 23.5 | 3.49 | 1.48 | >50 |
| AC | NIH-100__6041.v3.c23 | >200 | >50 | 2.66 | 5.48 | 0.023 |
| AC | NIH-099__3301.v1.c24 | >200 | >50 | 19.8 | 20.3 | 0.112 |
| AC | NIH-102__6545.v4.c1 | >200 | >50 | 7.56 | 2.35 | >50 |
| AC | NIH-101__6540.v4.c1 | >200 | >50 | 5.5 | 5.63 | >50 |
| ACD | NIH-103__0815.v3.c3 | >200 | 18.7 | 5.17 | 1.2 | 0.019 |
| ACD | NIH-104__3103.v3.c10 | >200 | >50 | 18 | 8.11 | 1.53 |
| AE | NIH-073__C3347.c11 | 10.2 | 0.055 | 0.036 | 0.034 | 0.063 |
| AE | NIH-080__BJOX025000.01.1 | 14.6 | 7.13 | 0.379 | 0.377 | 6.04 |
| AE | NIH-075__CNE8 | 18.2 | 0.247 | 0.041 | 0.087 | 0.126 |
| AE | NAC__92TH021 | 20.9 | 2.12 | 0.235 | 0.348 | 0.324 |
| AE | NIH-081__BJOX028000.10.3 | 49.4 | 5.16 | 0.583 | 0.45 | 0.141 |
| AE | NIH-078__BJOX015000.11.5 | 79.3 | 2.59 | 0.079 | 0.165 | 0.06 |
| AE | NIH-079__BJOX010000.06.2 | 89.1 | 1.66 | 0.199 | 0.438 | 1.77 |
| AE | NIH-074__C4118.c09 | 106 | 8.37 | 0.424 | 0.322 | 0.05 |
| AE | NIH-069__C1080.c03 | 118 | 1.73 | 0.171 | 0.328 | 1.4 |
| AE | NIH-077__BJOX009000.02.4 | 161 | 3.97 | 0.522 | 0.389 | 0.565 |
| AE | NIH-068__620345.c01 | 170 | 12.6 | 1.18 | 0.663 | >50 |
| AE | NIH-076__CNE5 | >200 | 24.6 | 1.37 | 1.34 | 0.059 |
| AE | NIH-070__R2184.c04 | >200 | 12.9 | 0.976 | 0.223 | 0.103 |
| AE | NIH-072__R3265.c06 | >200 | 28 | 1.68 | 0.491 | 0.126 |
| AE | NIH-071__R1166.c01 | >200 | 4.87 | 0.623 | 0.383 | 0.488 |
| AG | NIH-115__928.28 | 32.4 | 1.38 | 0.252 | 0.112 | 0.249 |
| AG | NIH-118__T255.34 | 38.7 | 3.35 | 0.453 | 0.326 | 0.229 |
| AG | NIH-116__T263.8 | 107 | 2.02 | 0.166 | 0.206 | 0.124 |
| AG | NIH-108__T235.47 | 139 | 1.54 | 0.538 | 0.248 | 0.021 |
| AG | NIH-114__T257.31 | >200 | 29.6 | 2.65 | 1.03 | 1.61 |
| AG | NIH-107__T251.18 | >200 | 43 | 4.52 | 0.905 | 2.02 |
| AG | NIH-106__T250.4 | >200 | 13.9 | 2.53 | 0.756 | >50 |
| AG | NIH-119__T211.9 | >200 | 13.2 | 2.66 | 1.2 | 12.8 |
| B | NAC__MN | 1.21 | 0.023 | 0.005 | 0.005 | 0.01 |
| B | NAC__HxB2 | 5.64 | 0.121 | 0.026 | 0.021 | 0.022 |
| B | NIH-012__1012.11.TC21.3257 | 77.3 | 13.3 | 2.51 | 2.06 | 0.081 |
| B | NAC__ADA | 88.5 | 5.36 | 0.932 | 0.836 | 0.314 |
| B | NAC__WITO.33 | 112 | 3.56 | 2.59 | 0.435 | 0.055 |
| B | NIH-006__AC10.0.29 | 116 | 4.64 | 0.872 | 0.666 | 0.867 |
| B | NIH-003__SC422661.8 | 145 | 16.8 | 3.66 | 2.78 | 0.124 |
| B | NAC__89.6 | 162 | 25.3 | 5.02 | 2.77 | 0.807 |
| B | NAC__BaL.26 | >200 | >50 | 6.16 | 4.2 | 0.01 |
| B | NAC__RHPA4.7 | >200 | >50 | 7.93 | 4.66 | 0.035 |
| B | NIH-014__6244.13.B5.4567 | >200 | 1.31 | 0.353 | 0.077 | 0.045 |
| B | NAC__TRJO.58 | >200 | >50 | 4.88 | 2.97 | 0.057 |
| B | NAC__92BR020 | >200 | >50 | 10.3 | 2.57 | 0.059 |
| B | NIH-008__WEAU.d15.410.787 | >200 | 10 | 1.52 | 0.621 | 0.076 |
| B | NAC__REJO.67 | >200 | 10.7 | 3.39 | 1.87 | 0.106 |
| B | NIH-009__1006.11.C3.1601 | >200 | 24.6 | 5.69 | 5.66 | 0.145 |
| B | NAC__SS1196.1 | >200 | 5.4 | 0.64 | 0.99 | 0.166 |
| B | NAC__YU2 | >200 | >50 | 1.68 | 15.9 | 0.123 |

TABLE 10-continued

Evaluation of neutralization breadth and potency of PGZL1 antibodies, 4E10 and VRC01 against
a 130-member cross-clade pseudovirus panel using the TZM-bl cell neutralization assay.

| | | IC$_{50}$ (µg/ml) | | | | |
|---|---|---|---|---|---|---|
| Clade | Virus | PGZL1_gVmDmJ | PGZL1 | H4K3 | 4E10 | VRC01 |
| B | NAC__JRCSF | >200 | 13.4 | 1.69 | 0.823 | 0.172 |
| B | NAC__JRFL | >200 | >50 | 12.6 | 17.8 | 0.141 |
| B | NIH-004__PVO.4 | >200 | 49 | 7.05 | 9.59 | 0.192 |
| B | NAC__DH12 | >200 | 4.71 | 1.54 | 1.17 | 0.227 |
| B | NIH-005__TRO.11 | >200 | 2.88 | 0.669 | 0.769 | 0.231 |
| B | NAC__SF162 | >200 | 12.8 | 2.43 | 1.97 | 0.262 |
| B | NIH-011__1056.10.TA11.1826 | >200 | 3.72 | 0.595 | 0.688 | 0.372 |
| B | NIH-016__SC05.8C11.2344 | >200 | 5.77 | 1.43 | 0.828 | 0.508 |
| B | NIH-013__6240.08.TA5.4622 | >200 | 35.8 | 6.49 | 9.78 | 0.604 |
| B | NIH-007__CAAN5342.A2 | >200 | 34 | 7.61 | 2.84 | 0.691 |
| B | NIH-010__1054.07.TC4.1499 | >200 | 5.15 | 1.23 | 1.35 | 0.909 |
| B | NIH-001__6535.3 | >200 | 1.42 | 0.652 | 0.519 | 0.946 |
| B | NIH-015__62357.14.D3.4589 | >200 | 27.2 | 4.53 | 2.87 | 1.74 |
| B | NIH-002__QHO692 .42 | >200 | 42 | 4.54 | 6.19 | 1.96 |
| BC | NIH-050__CNE21 | 97.8 | 4.23 | 1.02 | 0.513 | 0.212 |
| BC | NIH-054__CNE53 | >200 | 6 | 0.842 | 0.38 | 0.042 |
| BC | NIH-055__CNE58 | >200 | 3.55 | 0.975 | 0.563 | 0.083 |
| BC | NIH-048__CNE19 | >200 | 3.12 | 1.07 | 0.31 | 0.127 |
| BC | NIH-053__CNE52 | >200 | 24.3 | 4.16 | 0.954 | 0.142 |
| BC | NIH-051__CNE17 | >200 | 12.4 | 1.87 | 0.526 | 0.219 |
| BC | NIH-052__CNE30 | >200 | 40.5 | 3.49 | 4.17 | 0.593 |
| BC | NIH-049__CNE20 | >200 | 2.42 | 0.799 | 0.383 | 4.85 |
| C | NIH-030__HIV-0013095.2.11 | 0.552 | 0.008 | 0.07 | 0.001 | 0.0002 |
| C | NIH-026__ZM135M.PL10a | 0.879 | 0.296 | 0.026 | 0.133 | 0.102 |
| C | NIH-017__Du156.12 | 6.97 | 0.623 | 0.27 | 0.101 | 0.059 |
| C | NIH-019__Du422.1 | 56.8 | 7.51 | 1.41 | 1.42 | >50 |
| C | NIH-018__Du172.17 | 75.2 | 0.424 | 0.106 | 0.102 | >50 |
| C | NIH-032__HIV-16845.2.22 | 93.2 | 0.4244 | 0.1047 | 0.097 | 0.9682 |
| C | NIH-039__Ce2060 G9 | 140 | 15 | 0.541 | 1.24 | 0.109 |
| C | NAC__93IN905 | 159 | 0.404 | 0.361 | 0.11 | 0.07 |
| C | NIH-029__HIV-001428.2.42 | >200 | >50 | 9.12 | 5.54 | 0.019 |
| C | NIH-041__BF1266.431a | >200 | 48.8 | 5.59 | 2.47 | 0.028 |
| C | NIH-023__ZM249M.PL1 | >200 | 12.7 | 2.27 | 1.44 | 0.05 |
| C | NIH-031__HIV-16055.2.3 | >200 | 10.9 | 1.38 | 1.59 | 0.053 |
| C | NIH-043__ZM249M.B10 | >200 | 6.26 | 1.47 | 1.11 | 0.071 |
| C | NIH-025__ZM109F.PB4 | >200 | 7.36 | 1.54 | 0.703 | 0.074 |
| C | NIH-040__Ce703010054 2A2 | >200 | 48.9 | 7.78 | 2.05 | 0.139 |
| C | NIH-036__Ce2010 F5 | >200 | >50 | 5.2 | 14.4 | 0.153 |
| C | NIH-020__ZM197M.PB7 | >200 | 1.91 | 0.805 | 0.226 | 0.17 |
| C | NIH-044__ZM247F.F7 | >200 | 12 | 3.49 | 1.85 | 0.236 |
| C | NIH-046__1394C9G1(Rev.) | >200 | 7.87 | 2.67 | 2.58 | 0.28 |
| C | NIH-047__Ce704809221 1B3 | >200 | 0.738 | 0.44 | 0.134 | 0.32 |
| C | NAC__IAVIC22 | >200 | 15.2 | 2.2 | 1.21 | 0.348 |
| C | NIH-034__Ce0393 C3 | >200 | 13.5 | 1.73 | 0.606 | 0.37 |
| C | NIH- | >200 | 49.6 | 4.63 | 3.41 | 0.38 |
| C | NIH-021__ZM214M.PL15 | >200 | 28.7 | 6.52 | 5.31 | 0.612 |
| C | NIH-024__ZM53M.PB12 | >200 | >50 | 12.7 | 10.4 | 0.917 |
| C | NIH-035__Ce1176 A3 | >200 | 31.7 | 11.3 | 1.74 | 1.25 |
| C | NIH-022__ZM233M.PB6 | >200 | 5.9 | 1.75 | 1.05 | 1.41 |
| C | NIH-027__CAP45.G3 | >200 | 18.3 | 1.95 | 0.886 | 1.92 |
| C | NIH-042__ZM246F.D5 | >200 | 19.9 | 3.13 | 1.68 | 10.7 |
| C | NHI-028__CAP210.E8 | >200 | 16.7 | 1.82 | 0.847 | >50 |
| C | NIH-038__Ce1172 H1 | >200 | 0.948 | 0.351 | 8.81 | >50 |
| CD | NIH-095__6480.v4.c25 | >200 | 15 | 0.335 | 0.561 | 0.014 |
| CD | NIH-096__6952.v1.c20 | >200 | 0.89 | 0.195 | 0.721 | 0.025 |
| CD | NIH-097__6811.v7.c18 | >200 | >50 | 9.54 | 2.74 | 0.14 |
| CD | NIH-094__3817.v2.c59 | >200 | 20.1 | 0.597 | 0.417 | >50 |
| CD | NIH-098__89.F1 2 25 | >200 | >50 | 8.6 | 5.11 | >50 |
| D | NIH-089__3016.v5.c45 | 74.8 | 2.4 | 0.375 | 0.915 | 0.058 |
| D | NIH-090__A07412M1.vrc12 | >200 | 13.9 | 1.01 | 2.58 | 0.051 |
| D | NIH-091__231965.c01 | >200 | >50 | 6.7 | 13.8 | 0.183 |
| G | NIH-086__X2131 C1 B5 | 14.3 | 0.885 | 0.148 | 0.194 | 0.073 |
| G | NIH-082__X1193 c1 | 29.7 | 5.31 | 0.632 | 0.359 | 0.098 |
| G | NIH-084__X1254 c3 | >200 | 45.5 | 6.06 | 2.88 | 0.039 |
| G | NIH-083__P0402 c2 11 | >200 | 8.29 | 0.382 | 0.084 | 0.04 |
| G | NIH-087__P1981 C5 3 | >200 | 1.39 | 0.147 | 0.099 | 0.203 |
| G | NIH-088__X1632 S2 B10 | >200 | 15.5 | 3.02 | 2.57 | 0.338 |
| G | NIH-085__X2088 c9 | >200 | >50 | 19.3 | >50 | >50 |
| — | NAC__AMLV | >200 | >50 | >50 | >50 | >50 |
| — | NAC__VSV | >200 | >50 | >50 | >50 | >50 |

|  | PGZL1_gVmDmJ | PGZL1 | H4K3 | 4E10 | VRC01 |
|---|---|---|---|---|---|
| # Viruses | 130 | 130 | 130 | 130 | 130 |
| | | Total Viruses Neutralized | | | |
| $IC_{50}$ < 200 µg/ml | 36 | ND | ND | ND | ND |
| $IC_{50}$ < 50 µg/ml | 15 | 109 | 130 | 129 | 118 |
| $IC_{50}$ < 10 µg/ml | 5 | 54 | 122 | 122 | 116 |
| $IC_{50}$ < 1 µg/ml | 2 | 13 | 48 | 64 | 104 |
| $IC_{50}$ < 0.1 µg/ml | 0 | 3 | 7 | 10 | 44 |
| | | Percent of Viruses Neutralized | | | |
| $IC_{50}$ < 200 µg/ml | 28 | ND | ND | ND | ND |
| $IC_{50}$ < 50 µg/ml | 12 | 84 | 100 | 99 | 91 |
| $IC_{50}$ < 10 µg/ml | 4 | 42 | 94 | 94 | 89 |
| $IC_{50}$ < 1 µg/ml | 2 | 10 | 37 | 49 | 80 |
| $IC_{50}$ < 0.1 µg/ml | 0 | 2 | 5 | 8 | 34 |
| Median $IC_{50}$ | 76.3 | 9.2 | 1.69 | 1.01 | 0.139 |
| $IC_{50}$ (Geometric Mean) | 40.2 | 6.06 | 1.39 | 0.911 | 0.16 |

| | | $IC_{80}$ (µg/ml) | | | | |
|---|---|---|---|---|---|---|
| Clade | Virus | PGZL1_gVmDmJ | PGZL1 | H4K3 | 4E10 | VRC01 |
| A | NIH-065__191955 A11 | 119 | 8.56 | 2.23 | 0.157 | 0.467 |
| A | NIH-063__0330.v4.c3 | >200 | >50 | 10.5 | 4.17 | 0.13 |
| A | NIH-066__191084 B7.19 | >200 | >50 | 5.94 | 9.04 | 0.188 |
| A | NAC__BG505 | >200 | >50 | 9.75 | 4.88 | 0.213 |
| A | NIH-057__MS208.A1 | >200 | 45.6 | 2.84 | 2.86 | 0.252 |
| A | NIH-064__0260.v5.c1 | >200 | >50 | 35.3 | 6.08 | 0.516 |
| A | NAC__KNH1144 | >200 | >50 | >50 | 47.9 | 0.535 |
| A | NAC__94UG103 | >200 | >50 | 36.6 | 7.48 | 0.752 |
| A | NAC__92RW020 | >200 | >50 | 15.5 | 9.61 | 0.811 |
| A1 | NIH-060__Q769ENVd22 | >200 | >50 | 12.9 | 6.57 | 0.092 |
| A1 | NIH-058__Q23ENV17 | >200 | >50 | 12.7 | 5.37 | 0.148 |
| A1 | NIH-056__Q168ENVa2 | >200 | >50 | 10.9 | 15.1 | 0.218 |
| A1 | NIH-061__Q259ENVd2.17 | >200 | >50 | 38.1 | 28.9 | 0.449 |
| A1 | NIH-059__Q461ENVe2 | >200 | >50 | 14.3 | 9.31 | 0.776 |
| A1U | NIH-117__T278.5 | >200 | >50 | 14 | 6.03 | >50 |
| AC | NIH-100__6041.v3.c23 | >200 | >50 | 10.9 | 22.2 | 0.087 |
| AC | NIH-099__3301.v1.c24 | >200 | >50 | >50 | >50 | 0.463 |
| AC | NIH-102__6545.v4.c1 | >200 | >50 | 29.6 | 13.3 | >50 |
| AC | NIH-101__6540.v4.c1 | >200 | >50 | 22.7 | 36.1 | >50 |
| ACD | NIH-103__0815.v3.c3 | >200 | >50 | 20.5 | 6.31 | 0.07 |
| ACD | NIH-104__3103.v3.c10 | >200 | >50 | >50 | 32.4 | 6.21 |
| AE | NIH-073__C3347.c11 | 41.3 | 0.263 | 0.165 | 0.137 | 0.254 |
| AE | NIH-080__BJOX025000.01.1 | 59.9 | 29.3 | 1.53 | 1.59 | 24.8 |
| AE | NIH-075__CNE8 | 72.2 | 0.945 | 0.21 | 0.27 | 0.514 |
| AE | NAC__92TH021 | 79.9 | 8.27 | 0.926 | 1.38 | 1.31 |
| AE | NIH-081__BJOX028000.10.3 | 199 | 20.9 | 2.38 | 1.88 | 0.573 |
| AE | NIH-078__BJOX015000.11.5 | >200 | 10.5 | 0.296 | 0.647 | 0.242 |
| AE | NIH-079__BJOX010000.06.2 | >200 | 6.6 | 0.794 | 1.73 | 7.79 |
| AE | NIH-074__C4118.c09 | >200 | 33.3 | 1.76 | 1.17 | 0.202 |
| AE | NIH-069__C1080.c03 | >200 | 6.93 | 0.69 | 1.36 | 5.7 |
| AE | NIH-077__BJOX009000.02.4 | >200 | 15.8 | 2.12 | 1.62 | 2.34 |
| AE | NIH-068__620345.c01 | >200 | >50 | 4.95 | 3.06 | >50 |
| AE | NIH-076__CNE5 | >200 | >50 | 6.58 | 5.9 | 0.238 |
| AE | NIH-070__R2184.c04 | >200 | >50 | 5.15 | 0.762 | 0.413 |
| AE | NIH-072__R3265.c06 | >200 | >50 | 8.33 | 2 | 0.502 |
| AE | NIH-071__R1166.c01 | >200 | 19.5 | 2.52 | 1.77 | 1.95 |
| AG | NIH-115__928.28 | 125 | 5.45 | 1.01 | 0.438 | 0.99 |
| AG | NIH-118__T255.34 | 148 | 13.2 | 1.78 | 1.38 | 0.925 |
| AG | NIH-116__T263.8 | >200 | 8.18 | 0.719 | 0.927 | 0.505 |
| AG | NIH-108__T235.47 | >200 | 6.62 | 2.21 | 1.07 | 0.084 |
| AG | NIH-114__T257.31 | >200 | >50 | 11 | 4.71 | 6.57 |
| AG | NIH-107__T251.18 | >200 | >50 | 17.9 | 3.97 | 8.63 |
| AG | NIH-106__T250.4 | >200 | >50 | 10.4 | 3.42 | >50 |
| AG | NIH-119__T211.9 | >200 | >50 | 10.5 | 5.08 | >50 |
| B | NAC__MN | 19.3 | 0.564 | 0.135 | 0.135 | 0.196 |
| B | NAC__HxB2 | 22.1 | 0.485 | 0.113 | 0.089 | 0.081 |
| B | NIH- | >200 | >50 | 10 | 8.25 | 0.318 |
| B | NAC__ADA | >200 | 21.8 | 3.71 | 3.34 | 1.31 |
| B | NAC__WITO.33 | >200 | 15.1 | 10.4 | 1.82 | 0.228 |
| B | NIH-006__AC10.0.29 | >200 | 18.8 | 3.5 | 2.73 | 3.52 |
| B | NIH-003__SC422661.8 | >200 | >50 | 14.5 | 11.1 | 0.481 |
| B | NAC__89.6 | >200 | >50 | 19.9 | 10.9 | 3.3 |
| B | NAC__BaL.26 | >200 | >50 | 25.2 | 17.1 | 0.037 |

-continued

| | | IC$_{80}$ (µg/ml) | | | | |
|---|---|---|---|---|---|---|
| Clade | Virus | PGZL1_gVmDmJ | PGZL1 | H4K3 | 4E10 | VRC01 |
| B | NAC__RHPA4.7 | >200 | >50 | 31.7 | 19.3 | 0.137 |
| B | NIH-014__6244.13.B5.4567 | >200 | 5.19 | 1.51 | 0.373 | 0.193 |
| B | NAC__TRJO.58 | >200 | >50 | 19.9 | 11.6 | 0.223 |
| B | NAC__92BR020 | >200 | >50 | 39.7 | 13.5 | 0.23 |
| B | NIH- | >200 | 39.6 | 6.3 | 2.59 | 0.306 |
| B | NAC__REJO.67 | >200 | 40.2 | 13.8 | 8.62 | 0.414 |
| B | NIH-009__1006.11.C3.1601 | >200 | >50 | 23 | 22.7 | 0.571 |
| B | NAC__SS1196.1 | >200 | 22.2 | 2.76 | 3.96 | 0.659 |
| B | NAC__YU2 | >200 | >50 | 20.8 | >50 | 0.69 |
| B | NAC__JRCSF | >200 | >50 | 7.58 | 3.92 | 0.69 |
| B | NAC__JRFL | >200 | >50 | >50 | >50 | 0.741 |
| B | NIH-004__PVO.4 | >200 | >50 | 27.5 | 38.7 | 0.79 |
| B | NAC__DH12 | >200 | 19 | 6.35 | 4.89 | 0.898 |
| B | NIH-005__TRO.11 | >200 | 11.8 | 2.68 | 3.08 | 0.912 |
| B | NAC__SF162 | >200 | 48.6 | 10.3 | 8.26 | 1.03 |
| B | NIH- | >200 | 14.9 | 2.38 | 2.81 | 1.48 |
| B | NIH-016__SC05.8C11.2344 | >200 | 24.6 | 5.71 | 3.44 | 1.98 |
| B | NIH-013__6240.08.TA5.4622 | >200 | >50 | 26.4 | 40.3 | 2.62 |
| B | NIH-007__CAAN5342.A2 | >200 | >50 | 30.6 | 12.1 | 2.79 |
| B | NIH-010__1054.07.TC4.1499 | >200 | 20.2 | 4.93 | 5.43 | 3.62 |
| B | NIH-001__6535.3 | >200 | 4.69 | 1.88 | 3.29 | 3.7 |
| B | NIH-015__62357.14.D3.4589 | >200 | >50 | 18.1 | 11.6 | 6.95 |
| B | NIH-002__QHO692 .42 | >200 | >50 | 18.1 | 25 | 7.93 |
| BC | NIH-050__CNE21 | >200 | 17.8 | 4.36 | 2.15 | 0.848 |
| BC | NIH-054__CNE53 | >200 | 23.9 | 3.4 | 1.52 | 0.166 |
| BC | NIH-055__CNE58 | >200 | 14.5 | 4.1 | 2.24 | 0.331 |
| BC | NIH-048__CNE19 | >200 | 12.1 | 4.3 | 1.43 | 0.512 |
| BC | NIH-053__CNE52 | >200 | >50 | 16.7 | 3.85 | 0.565 |
| BC | NIH-051__CNE17 | >200 | 48.6 | 7.46 | 2.23 | 0.904 |
| BC | NIH-052__CNE30 | >200 | >50 | 14.1 | 16.6 | 2.38 |
| BC | NIH-049__CNE20 | >200 | 9.5 | 3.26 | 1.58 | 20.2 |
| C | NIH-030__HIV-0013095.2.11 | 4.6 | 0.113 | 0.305 | 0.258 | 0.058 |
| C | NIH-026__ZM135M.PL10a | 3.13 | 2.08 | 0.195 | 0.936 | 0.379 |
| C | NIH-017__Du156.12 | 27.7 | 2.5 | 1.08 | 0.447 | 0.23 |
| C | NIH-019__Du422.1 | >200 | 30.5 | 5.65 | 5.66 | >50 |
| C | NIH-018__Du172.17 | 151 | 1.6 | 0.422 | 0.474 | >50 |
| C | NIH-032__HIV-16845.2.22 | >200 | 2.468 | 0.718 | 0.653 | 4.252 |
| C | NIH-039__Ce2060 G9 | >200 | >50 | 2.48 | 5.1 | 0.45 |
| C | NAC__93IN905 | >200 | 2.2 | 1.51 | 0.472 | 0.28 |
| C | NIH-029__HIV-001428.2.42 | >200 | >50 | 35.9 | 24.7 | 0.068 |
| C | NIH-041__BF1266.431a | >200 | >50 | 22.3 | 10 | 0.11 |
| C | NIH-023__ZM249M.PL1 | >200 | >50 | 8.97 | 5.77 | 0.197 |
| C | NIH-031__HIV-16055.2.3 | >200 | 42.6 | 5.68 | 6.57 | 0.206 |
| C | NIH-043__ZM249M.B10 | >200 | 25.6 | 5.88 | 4.55 | 0.275 |
| C | NIH-025__ZM109F.PB4 | >200 | 29.7 | 6.5 | 3.17 | 0.296 |
| C | NIH-040__Ce703010054 2A2 | >200 | >50 | 30.1 | 12.5 | 0.595 |
| C | NIH-036__Ce2010 F5 | >200 | >50 | 20.9 | >50 | 0.625 |
| C | NIH-020__ZM197M.PB7 | >200 | 7.66 | 3.27 | 1.08 | 0.682 |
| C | NIH-044__ZM247F.F7 | >200 | 48.2 | 14 | 7.5 | 0.945 |
| C | NIH-046__1394C9G1(Rev.) | >200 | 34.3 | 10.8 | 10.4 | 1.12 |
| C | NIH-047__Ce704809221 1B3 | >200 | 3.1 | 1.81 | 0.557 | 1.28 |
| C | NAC__IAVIC22 | >200 | >50 | 9 | 6.11 | 1.37 |
| C | NIH-034__Ce0393 C3 | >200 | >50 | 7.68 | 2.56 | 1.46 |
| C | NIH-045__7030102001E5(Rev.) | >200 | >50 | 18.4 | 15.7 | 1.49 |
| C | NIH-021__ZM214M.PL15 | >200 | >50 | 26.3 | 21.2 | 2.42 |
| C | NIH-024__ZM53M.PB12 | >200 | >50 | >50 | 42.6 | 3.63 |
| C | NIH-035__Ce1176 A3 | >200 | >50 | 44.2 | 7.36 | 4.99 |
| C | NIH-022__ZM233M.PB6 | >200 | 23.6 | 7.36 | 4.99 | 5.69 |
| C | NIH-027__CAP45.G3 | >200 | >50 | 8.34 | 4.19 | 10.1 |
| C | NIH-042__ZM246F.D5 | >200 | >50 | 12.7 | 6.7 | 43.7 |
| C | NHI-028__CAP210.E8 | >200 | >50 | 7.22 | 3.53 | >50 |
| C | NIH-038__Ce1172 H1 | >200 | 6.6 | 1.34 | 4.56 | >50 |
| CD | NIH-095__6480.v4.c25 | >200 | >50 | 1.61 | 3.04 | 0.054 |
| CD | NIH-096__6952.v1.c20 | >200 | 4.7 | 0.779 | 3.5 | 0.097 |
| CD | NIH-097__6811.v7.c18 | >200 | >50 | 39.2 | 17 | 0.558 |
| CD | NIH-094__3817.v2.c59 | >200 | >50 | 2.74 | 2.12 | >50 |
| CD | NIH-098__89.F1 2 25 | >200 | >50 | 33.2 | 21.7 | >50 |
| D | NIH-089__3016.v5.c45 | >200 | 10.6 | 1.59 | 3.73 | 0.223 |
| D | NIH-090__A07412M1.vrc12 | >200 | >50 | 4.05 | 10.4 | 0.216 |
| D | NIH-091__231965.c01 | >200 | >50 | 27 | >50 | 0.743 |
| G | NIH-086__X2131 C1 B5 | 57.7 | 3.5 | 0.626 | 0.765 | 0.284 |
| G | NIH-082__X1193 c1 | 121 | 21.3 | 2.62 | 1.43 | 0.408 |
| G | NIH-084__X1254 c3 | >200 | >50 | 24.2 | 11.8 | 0.149 |
| G | NIH-083__P0402 c2 11 | >200 | 32.3 | 1.82 | 0.363 | 0.164 |

-continued

| Clade | Virus | IC$_{80}$ (µg/ml) | | | | |
|---|---|---|---|---|---|---|
| | | PGZL1_gVmDmJ | PGZL1 | H4K3 | 4E10 | VRC01 |
| G | NIH-087__P1981 C5 3 | >200 | 5.55 | 0.581 | 0.406 | 0.8 |
| G | NIH-088__X1632 S2 B10 | >200 | >50 | 11.9 | 10.4 | 1.35 |
| G | NIH-085__X2088 c9 | >200 | >50 | >50 | >50 | >50 |
| — | NAC__AMLV | >200 | >50 | >50 | >50 | >50 |
| — | NAC__VSV | >200 | >50 | >50 | >50 | >50 |

IC$_{80}$ and Percent of Viruses Neutralized

| | PGZL1_gVmDmJ | PGZL1 | H4K3 | 4E10 | VRC01 |
|---|---|---|---|---|---|
| # Viruses | 130 | 130 | 130 | 130 | 130 |
| | Total Viruses Neutralized | | | | |
| IC$_{80}$ < 200 µg/ml | 16 | ND | ND | ND | ND |
| IC$_{80}$ < 50 µg/ml | 6 | 61 | 124 | 124 | 117 |
| IC$_{80}$ < 10 µg/ml | 2 | 26 | 72 | 92 | 113 |
| IC$_{80}$ < 1 µg/ml | 0 | 5 | 16 | 20 | 81 |
| IC$_{80}$ < 0.1 µg/ml | 0 | 0 | 0 | 1 | 10 |
| | Percent of Viruses Neutralized | | | | |
| IC$_{80}$ < 200 µg/ml | 12 | ND | ND | ND | ND |
| IC$_{80}$ < 50 µg/ml | 5 | 47 | 95 | 95 | 90 |
| IC$_{80}$ < 10 µg/ml | 2 | 20 | 55 | 71 | 87 |
| IC$_{80}$ < 1 µg/ml | 0 | 4 | 12 | 15 | 62 |
| IC$_{80}$ < 0.1 µg/ml | 0 | 0 | 0 | 1 | 8 |
| Median IC$_{80}$ | 66 | 13.2 | 6.58 | 4.17 | 0.561 |
| IC$_{80}$ (Geometric Mean) | 49 | 9.59 | 5.35 | 3.71 | 0.654 |

Example 3. PGZL1 Germline Revertant Binds to MPER and Neutralizes HIV

Figure 2:
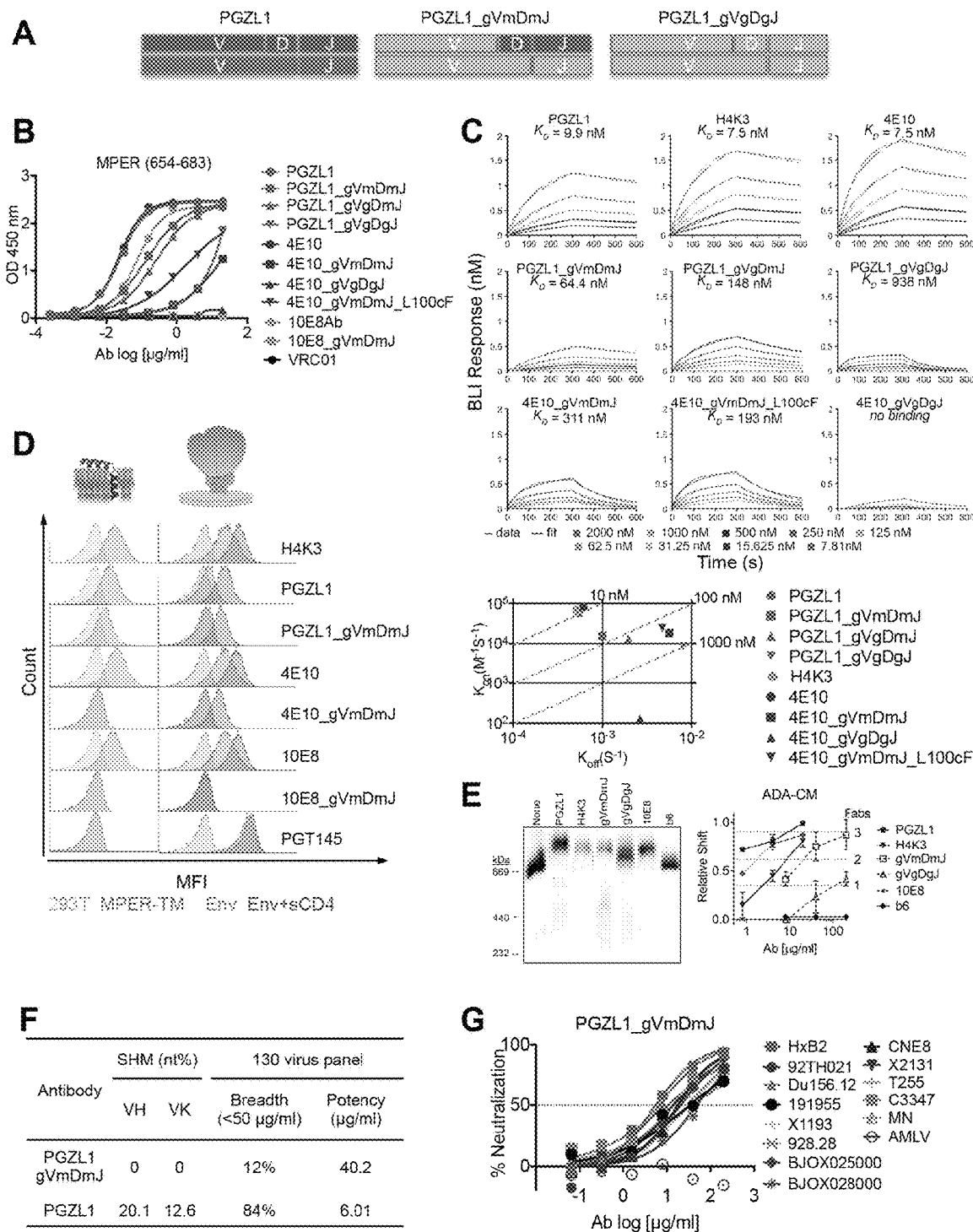
FIG. 2. Characterization of Germline-reverted Antibody PGZL1 gVmDmJ. (A) Cartoon of mature PGZL1 VH (red; top) and $V_\kappa$ (green; bottom) subdivided by V, (D) and J regions, and germline reversions (gray) to create PGZL1 gVmDmJ (middle) and PGZL1 gVgDgJ (right). (B) ELISA binding of PGZL1 germline revertants to MPER peptide, using analogous 10E8 and 4E10 controls. (C) BLI binding kinetics of PGZL1 variants to immobilized MPER peptide (top panels). 4E10 variants were also used for comparison. $k_{on}$ and $k_{off}$ of antibodies are shown on a scatter plot with affinity constant, $K_D$, as dashed lines (bottom). (D) Cells expressing MPER-TM (purple histograms, left) were stained in flow cytometry by mature and germline-reverted antibodies at 2 μg/ml. HIV Env (right) in presence and absence of soluble CD4 (sCD4; red and blue histograms, respectively) were stained by mature and germline-reverted antibodies at 2 μg/ml and 10 μg/ml, respectively. (E) BN-PAGE Env mobility shift assay. HIV-1 virions were incubated with Fab PGZL1 and H4K3 (20 μg/ml), or PGZL1 gVmDmJ and gVgDgJ (200 μg/ml). 10E8 (20 μg/ml) and non-neutralizing antibody b6 (200 μg/ml) were used as positive and negative controls, respectively. Relative shift and stoichiometry of Fab to Env was quantified. Data are the average of two experiments. (F) Neutralization potency and breadth of PGZL1 gVmDmJ against a 130-virus panel of HIV-1 in TZM-b1 assay at 200 μg/ml. (G) Neutralization of 13 isolates sensitive to PGZL1 gVmDmJ chosen from the 130-virus panel.

Germline revertants of 4E10 (Finton et al., PLoS Pathog. 10, e1004403 (2014)), and 10E8 (Soto et al., PLoS One 11, e0157409 (2016)) reportedly do not neutralize HIV-1. The V-region of PGZL1 was reverted to the most homologous germline alleles, i.e. VH1-69*06, VK3-20*01, while leaving the CDR3s unchanged, thus creating PGZL1 gVmDmJ; in a second antibody, PGZL1 gVgDgJ, putative reversions were also made to DH3-10*01 and JH3*01 (FIG. 2A, FIG. 10A). Surprisingly, PGZL1 gVmDmJ and gVgDmJ still bound the MPER peptide, but with a 6 to 12-fold increase in EC$_{50}$ (FIG. 2B); DJ-reverted PGZL1 gVgDgJ also bound, albeit with a 369-fold increase in ECSO. Analogous revertants, 4E10 gVmDmJ, 4E10 gVgDgJ and 10E8 gVmDmJ, showed little or no such binding, as previously reported (FIG. 2B). Klein et al., Cell 153, 126-138 (2013); Soto et al., PLoS One 11, e0157409 (2016).

Using biolayer interferometry (BLI), PGZL1, PGZL1_gVmDmJ, and PGZL1_gVgDgJ bound with affinities (K$_D$) ranging from 9.9 nM, to 64.4 nM and 938 nM, respectively, mostly due to different off-rates (FIG. 2C). Another mutant, PGZL1 gVgDmJ, was created to test the effect of changes in DH. PGZL1 gVgDmJ bound the MPER peptide with a K$_D$ of 148 nM, indicating that reversions in both DH and JH affect the PGZL1 off-rate. PGZL1 and H4K3 had similar K$_D$s of 9.9 nM and 7.5 nM, respectively, but on and off rates of H4K3 to MPER peptide were faster by about 24% and 8%, respectively (FIG. 2C).

To test whether the gVmDmJ germline revertants could bind to the MPER on the cell surface, a 293T cell line that displays the MPER and transmembrane domain (MPER-TM654-709) was created. The PGZL1 gVmDmJ revertant, but not 4E10 or 10E8 revertants, also stained MPER-TM cells, albeit not as well as mature PGZL1, H4K3, 4E10 and 10E8 (FIG. 2D). Antibody staining of a cell line that over-expresses Env was then assessed. Stano A, et al., J. Virol. 91, 415-417 (2017). Moderate staining of high-Env cells by PGZL1 was observed in the absence of sCD4, and strong staining by 4E10, 10E8 and H4K3 was observed (FIG. 2D). Cell surface Env was not stained by the revertants at a concentration of 10 µg/ml (FIG. 2D). Addition of sCD4 enhanced MPER bnAb staining of Env cells, as expected; notably, sCD4 also enabled staining by PGZL1 gVmDmJ and 4E10 gVmDmJ, but not by 10E8 gVmDmJ. Of note, the 4E10 revertant reportedly bound weakly to a deglycosylated MPER-containing gp140. Ma et al., PLoS Pathog. 7, e1002200 (2011).

Binding of PGZL1 variants to the detergent-extracted Env ADA-CM, which is the ADA Env containing trimer stabilizing mutations ΔN139, ΔI140, N142S, I535M, L543Q, K574R, H625N, T626M and S649A was also assessed. Leaman et al., PLoS Pathog. 9, e1003184 (2013). In the blue-native (BN) PAGE mobility shift assay, both PGZL1 and H4K3 shifted Env (FIG. 2E). Notably, PGZL1 gVmDmJ and gVgDgJ also shifted Env, but gVgDgJ required a higher concentration and did not reach 3 Fabs per trimer. BnAb 10E8 and non-nAb b6 controls showed the predicted gel shift and lack of shift, respectively (FIG. 2E). Similar results were observed using Envs HxB2 and Du156.12 (FIG. 10B). Hence, PGZL1 gVgDgJ binds to Env when detergent-extracted from membrane, but not on the cell surface, whereas PGZL1 gVmDmJ binds both solubilized and cell surface Env.

Figure 10:
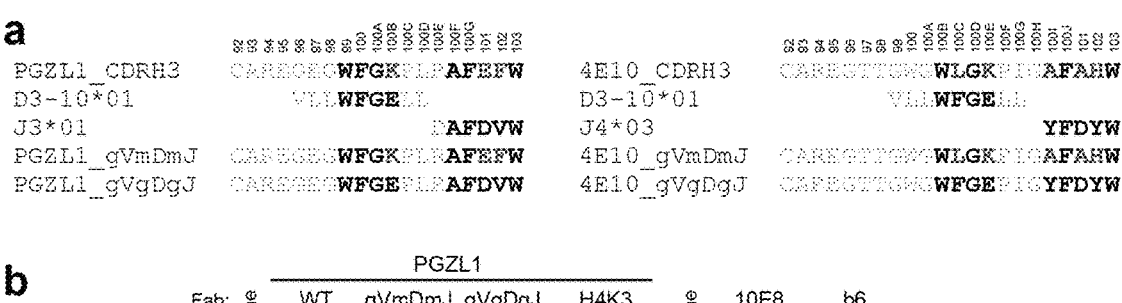
FIG. 10. CDRH3 sequences, HIV Env binding characteristics and HIV neutralization of inferred germline precursors of PGZL1 and 4E10. (A) Inferred CDRH3 germline sequences were aligned to those of PGZL1 and 4E10. Residues conserved from germline are in bold black, and SHMs are in red. Sequences shown are CAREGEGWFGKPLRAFEFW (SEQ ID NO: 149), VLLWFGELL (SEQ ID NO: 150), DAFDVW (SEQ ID NO: 151), CAREGEGWFGKPLRAFEFW (SEQ ID NO: 152), CAREGEGWFGEPLRAFDVW (SEQ ID NO: 153), CAREGTTGWGWLGKPIGAFAHW (SEQ ID NO: 154), VLLWFGELL (SEQ ID NO: 155), YFDYW (SEQ ID NO: 156), CAREGTTGWGWLGKPIGAFAHW (SEQ ID NO: 157), CAREGTTGWGWFGEPIGYFDYW (SEQ ID NO: 158). (B) BN-PAGE Env mobility shift assay. BN-PAGE Western blot analysis of HIV Env ADA-CM and relative gel mobility shift in the presence of PGZL1 variant antibodies was performed as in FIG. 2. Gel mobility shift data were also acquired for HIV-1 HxB2 and Du156.12. Relative gel mobility shifts were calculated as described in FIG. 2 for ADA-CM. (C) Neutralization of indicated PGZL1 and 4E10 inferred germline antibodies against 13 HIV pseudoviruses in the TZM-b1 assay.

Strikingly, PGZL1 gVmDmJ neutralized 12% of isolates at 50 µg/ml, and 28% of viruses at 200 µg/ml, in a dose-dependent manner (FIGS. 2F-G and Table 10). The IC$_{50}$s of PGZL1 and PGZL1 gVmDmJ correlated modestly (r=0.52, p=0.0013) (FIG. 9D). Viruses especially sensitive to PGZL1 gVmDmJ were tested against additional revertants of PGZL1 and 4E10 (FIG. 10). No virus was neutralized by PGZL1 gVgDgJ or 4E10 gVgDgJ at 200 µg/ml (FIG. 10C), despite the ability of PGZL1 gVgDgJ, but not 4E10 gVgDgJ, to bind the MPER (FIG. 2B). However, 4E10 gVmDmJ neutralized 92TH021 and CNE8, while 4E10 gVmDmJ_L100cF, which has the DH3-10*01 encoded F100c, binds the MPER ~2 fold better than 4E10 gVmDmJ (FIG. 2C) and neutralized these isolates more potently in addition to T255 and X1193 (FIG. 10C). Thus, ~1.4% isolates were neutralized by revertants of PGZL1 and 4E10 that had the D-gene encoded F100 (L100c in 4E10; FIG. 7A) in the context of mature CDR3s.

4E10 neutralizes HIV-1 by a slow and/or post-CD4-attachment mechanism as it can be washed off the virions prior to adding to target cells. Huang et al., Nature 491, 406-412 (2012). Washouts were performed with PGZL1 gVmDmJ, using VRC01 as a control that binds directly to Env and resists washout. Neutralization of Du156.12 by PGZL1 gVmDmJ was partially lost on washout, but was unchanged with VRC01 (Table 11). Notably, PGZL1 gVmDmJ neutralized 928.28, BJOX025000, HxB2 and 92TH021, albeit modestly, following the washout (Table 11. Thus, PGZL1 gVmDmJ binds weakly to and neutralizes some primary isolates prior to receptor engagement.

TABLE 11

Impact of antibody washout on neutralization
of HIV by PGZL1 gVmDmJ germline revertant

| Isolates | IC$_{50}$ (µg/ml) | | Fold change [a] |
|---|---|---|---|
| | no wash | wash | |
| T255 | 63.1 | >200 | >3.2 |
| X2131 | 85.7 | >200 | >2.3 |
| BJOX028000 | 37.1 | >200 | >5.4 |
| 928.28 | 0.5 | 36.5 | 73 |
| 1193 | 33.2 | 196 | 5.9 |
| Du156.12 | 6.47 | 103 | 16 |
| BJOX025000 | 6.99 | 63 | 9 |
| HxB2 | 2.12 | 11.9 | 5.6 |
| 92Th021 | 22.3 | 74.6 | 3.4 |
| Du156.12-(VRC01) | 0.11 | 0.16 | 1.5 |

[a] MPER accessibility was determined by washing the antibody-virion mixture prior to infecting TZM-bl cells. Pseudoviruses were incubated with antibody at 37° C. for 30 min, and antibody-virion mixture was washed or not washed prior to infecting target cells. Impact of antibody wash-out on virus neutralization is shown as the fold change in IC$_{50}$: (IC$_{50}$ wash)/(IC$_{50}$ no wash).

Figure 3:
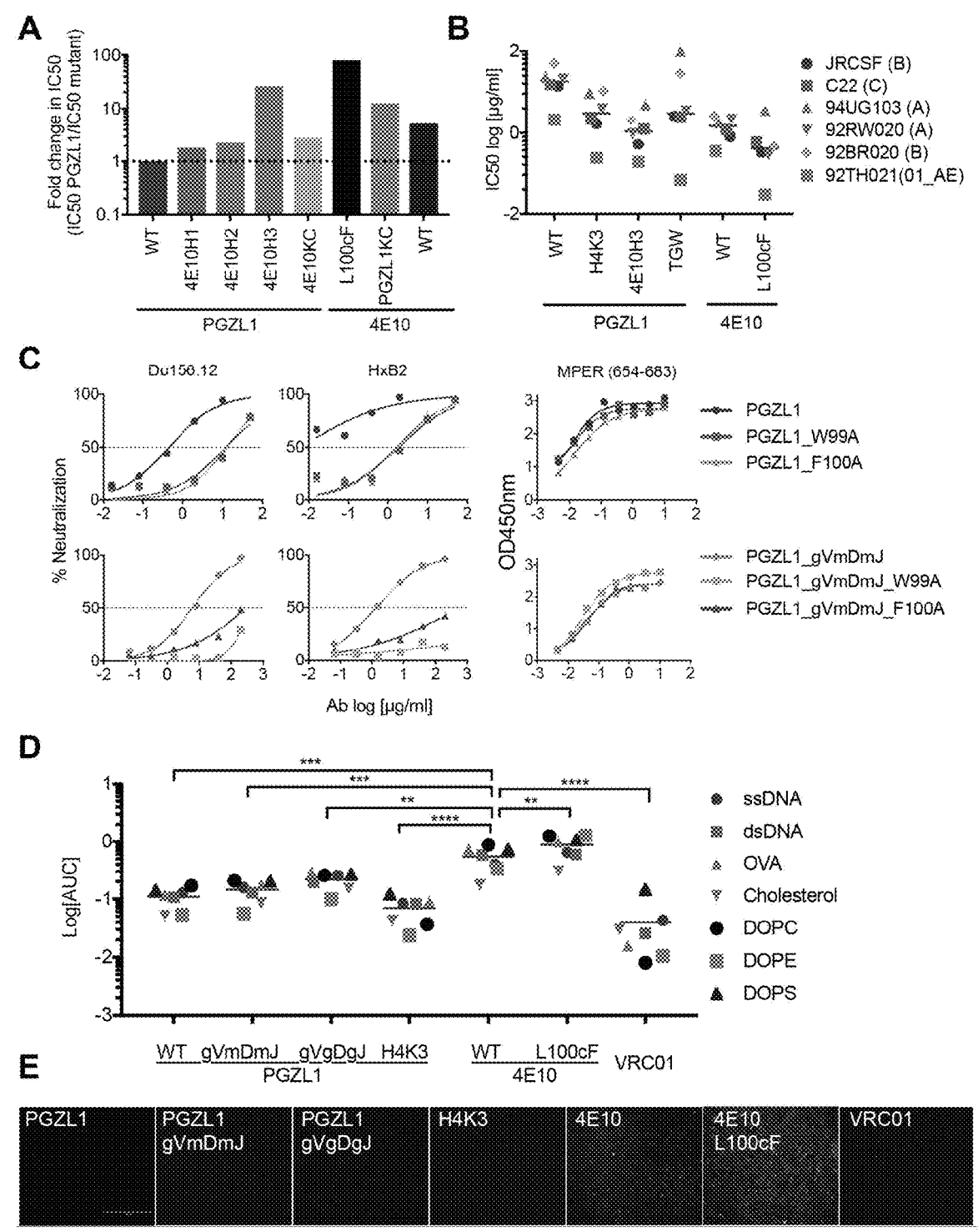
FIG. 3. Dominant Role of CDRH3 in PGZL1 HIV-1 Neutralization by D-gene Encoded Residues. (A) Fold-decrease in neutralization ($IC_{50}$) of isolate 92TH021 relative to wild-type PGZL1 by CDR grafts and LC substitution from 4E10 (left), and by 4E10 substitutions L100cF and PGZL1 LC (right). (B) Neutralization (log $IC_{50}$) of a 6-virus panel by PGZL1 and 4E10 variant antibodies. (C) Effect of Ala substitutions in DH-encoded residues W99 and F100 on the ability of PGZL1 mature (top panels) and inferred germline antibodies (bottom panels) to neutralize 92TH021 and HxB2 (left panels), as well as to bind MPER peptide in an ELISA (right panels). (D) Antibody polyreactivity in an ELISA as a function of area under the curve (AUC) of PGZL1 and 4E10 variant antibodies against non-specific antigens. VRC01 is a negative control. (E) Immunofluores-cence staining of HEp-2 cells. Antibodies were tested at 50 μg/ml using 4E10 and VRC01 as positive and negative controls, respectively; images are at 200× magnification.

Example 5 PGZL1 Uses 4E10-Like Paratope Features to Neutralize HIV with Limited Polyreactivity To dissect PGZL1 activity, chimeras of PGZL1 and 4E10 were created and tested for their ability to neutralize 92TH021. Engraftment of 4E10 CDRs H1 and H2 onto PGZL1 produced a modest ~2-fold increase in potency (FIG. 3A). Engrafting CDRH3 of 4E10 onto PGZL1 caused a 20-fold increase in neutralization. Substituting the LC or HC of PGZL1 with that of 4E10 produced 3-fold and 10-fold increases in potency, respectively. Thus, PGZL1 becomes more potent using 4E10 LC or HC CDRs, and in particular its CDRH3.

The most prominent difference in CDRH3s of PGZL1 and 4E10 is the additional 'TGW' motif in 4E10 (FIG. 7A). This motif increases CDRH3 hydrophobicity (FIG. 7B), so might enhance neutralization via membrane interaction. Of note, a putative variant of VRC42.01, termed, VRC42.N1, identified using plasma proteomics, was described that contains an "EGW" insertion at the analogous position in VRC42. Krebs et al., Immunity 50, 677-691 e613 (2019). Indeed, insertion of 'TGW' improved PGZL1 neutralization roughly 3-fold, but the fold-change varied among isolates in the 6-virus panel, indicating paratope context also affected neutralization. CDRH3s of PGZL1 and 4E10 differ at position 100, which is the DH3-10*01 encoded F100 in PGZL1, but somatically mutated to L100c in 4E10. The hydrophobic mutant 4E10 L100cF neutralized 3-fold more potently than wild-type 4E10 (FIG. 3B), and was the most potent 4E10 mutant of those tested or found in the literature.

Since PGZL1 and 4E10 share the DH3-10*01 germline gene (FIG. 10A), Ala mutants of DH3-10*01 encoded W99 and F100 were tested whether they affect the activity of PGZL1 and PGZL1 gVmDmJ. Mutations W99A and F100A decreased neutralization of Du156.12 and HxB2 by these antibodies more than ten-fold (FIG. 3C). Notably, W99A and F100A did not affect binding of either antibody to MPER peptide in ELISA (FIG. 3C), suggesting their activity may relate more to MPER recognition on virions. Hence, DH3-10*01 encoded W99 and F100 are crucial for neutralization by PGZL1.

BnAb 4E10 exhibits polyreactivity (Haynes et al., Science 308, 1906-1908 (2005)), which is of interest since 4E10 knock-in mice show B cell tolerance control Doyle-Cooper et al., J Immunol 191, 3186-3191 (2013); Finton et al., PLoS Pathog 10, e1004403 (2014). By ELISA, 4E10 was verified to be polyreactive towards ssDNA, dsDNA, ovalbumin (Ova), and lipids, cholesterol, DOPC, DOPE and DOPS; a negative control bnAb VRC01 showed no such binding (FIG. 3D). Of note, 4E10 L100cF showed higher binding than 4E10 to the above panel. PGZL1, gVmDmJ, gVgDgJ and H4K3 all showed less non-specific binding than 4E10 to the same antigens. Similarly, HEp-2 cells were stained by 4E10, whereas PGZL1, gVmDmJ, gVgDgJ and H4K3 all showed less staining (FIG. 3E).

Example 6. PGZL1 Structure Closely Resembles 4E10

Figure 4:
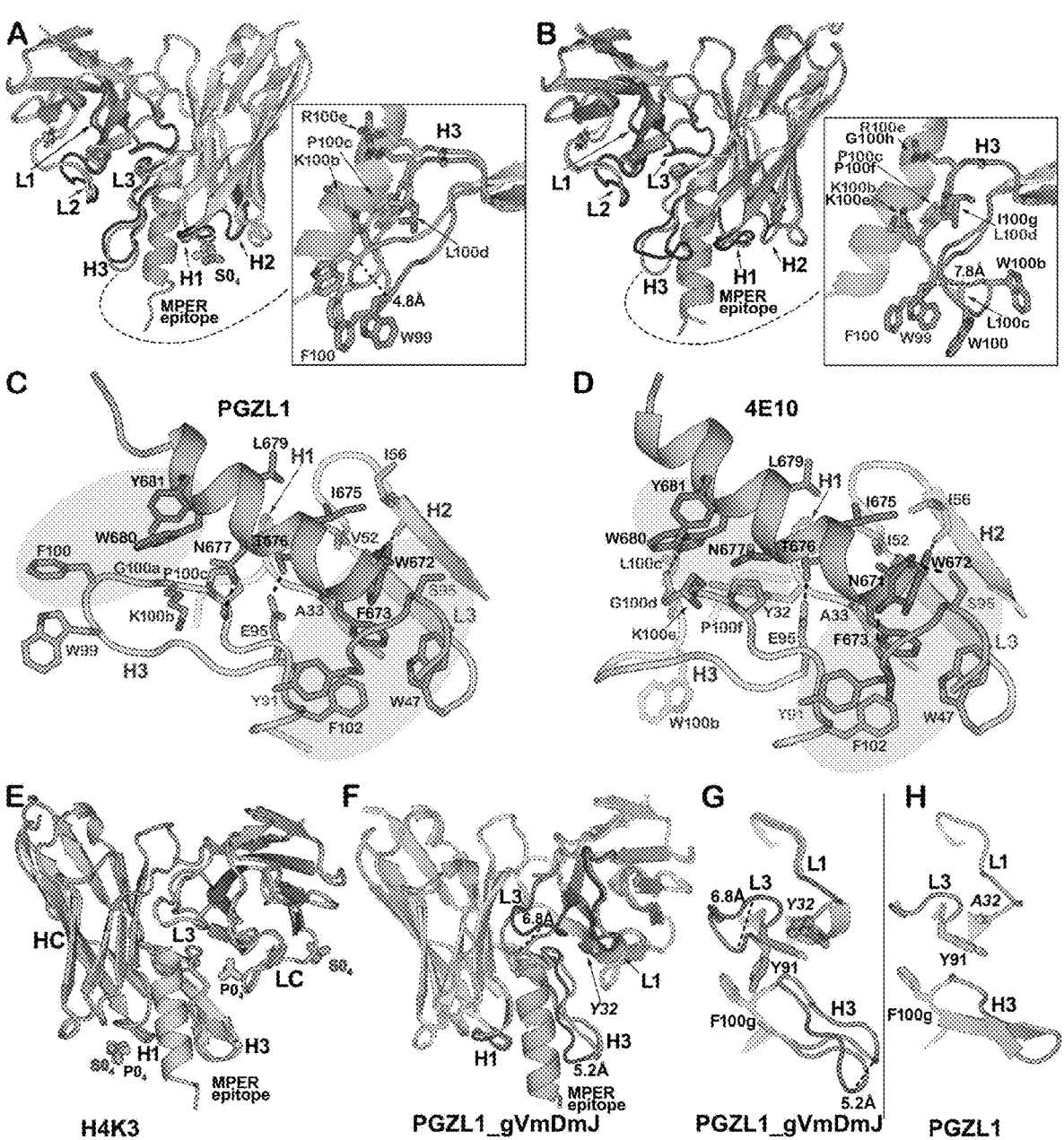
FIG. 4. PGZL1 Variant Crystal Structures and Compari-son with 4E10. (A) Superposition of the crystal structures of the mature PGZL1 variable domain (from the Fab) bound to $MPER_{671-683}$ (wheat—LC; green—HC; pink—MPER) and unbound PGZL1 (gray). CDRs of the bound structure are shown in red (LC) and green (HC) and CDRs of the unbound structure in black. Inset: superposition of free and bound CDRH3 with residues near the MPER shown as sticks. (B) Superposition of $PGZL1$-$MPER_{671-683}$ and 4E10-$MPER_{671-683}$ (gray; PDB 2FX7 13). Coloring and inset as in panel A. (C) $PGZL1$-$MPER_{671-683}$ combining site (wheat—LC; green—HC; pink—MPER; interacting residues—sticks). Shaded regions highlight aromatic clusters. (D) 4E10-$MPER_{671-683}$ combining site, colored as in panel C. (E) Superposition of unbound (blue) and $MPER_{671-683}$-bound (gray) H4K3. Ions are shown as sticks. (F) Superposition of unbound (yellow, CDR loops—brown) and $MPER_{671-683}$ bound (gray) PGZL1 gVmDmJ. (G) CDR loops in bound (gray) and unbound (brown) PGZL1 gVmDmJ with residues that influence loop conformations shown as sticks. (H) Same region as in panel G for the mature PGZL1 structure.

To gain insight into PGZL1 3-D structure and mode of binding, crystal structures of unbound (1.4 Å resolution) and MPER$_{671-683}$ bound PGZL1 (3.65 Å) Fabs were determined (FIG. 4A-B). The superposition of Cα atoms of the two PGZL1 variable domains yielded a root means square deviation (r.m.s.d.) of 0.6 A (FIG. 4A). Except for CDRH3 where residues are displaced by up to ~4.8 Å (i.e. W99), bound and unbound Fabs show only minor differences in CDR loops. PGZL1 resembles the 4E10 structure (PDB 2FX7; (Cardoso et al., Immunity 22, 163-173 (2005))) (Cα r.m.s.d. of ~0.4 Å; FIG. 4B). PGZL1 CDRH3 has well-defined density, even in the absence of peptide, compared to 4E10's 3-residue longer CDRH3, where the residues G99WGW100b at its tip were less defined. W99 in PGZL1 is ~7.8 Å apart from the equivalent W100b in 4E10 (FIG. 7A), neither of which contact MPER$_{671-683}$ (FIG. 4B-D; PDB 2FX7). 4E10 W100b may contact the TM region of gp41 (Rujas et al., J Mol Biol 429, 1213-1226 (2017)), but the shorter CDRH3 makes TM contact unlikely with PGZL1. However, F100 of PGZL1 CDRH3 (FIG. 4C), which corresponds to L100c in 4E10, may reorient to make aromatic interactions with MPER W680 and Y681 in the viral membrane.

PGZL1 binds to MPER$_{671-683}$ using similar contact residues as 4E10 in CDRs H1, H2, H3 and L3 (FIG. 4C-D). In both complex structures, MPER$_{671-683}$ is helical with W672-D674 in a capping 3$_{10}$ helix, and germline-encoded Y91 (LC) and F102, W47 (HC) form an aromatic patch with peptide F673 and W672. Another aromatic patch is seen near MPER W680 and Y681, but the paratope residues differ between PGZL1 and 4E10. In the PGZL1 structure, F100 (L100 in 4E10) is close to these MPER aromatics. In the 4E10 structure, germline-encoded Y32 of CDRH1 (L32 in PGZL1) is also involved in this patch (FIGS. 4C and 4D). The greater potency observed with 4E10 L100cF may be due to improved interaction of its CDRH3 with MPER and membrane by adding F100c to this hydrophobic patch. Some hydrogen bonds between 4E10 and MPER residues are also observed in PGZL1, but the lower resolution of the PGZL1-MPER$_{671-683}$ structure (3.65 Å) precludes a precise count.

Example 7. Unbound H4K3 is Precisely Preconfigured to Bind MPER

Crystal structures of H4K3 unliganded and with MPER$_{671-683}$ bound were determined at 1.45 Å and 1.98 Å resolution, respectively. Strikingly, their variable regions, including CDR loops, are in nearly identical conformations (Cα r.m.s.d. ~0.2 Å), which are both similar to the MPER bound PGZL1 (Cα rmsd. ~0.4 Å), suggesting H4K3 is already preconfigured for MPER binding (FIG. 4E). The shorter and more rigid CDRH3 of H4K3 may explain its lower polyreactivity compared to 4E10 whose CDRH3 is more flexible and hydrophobic.

Figure 11:
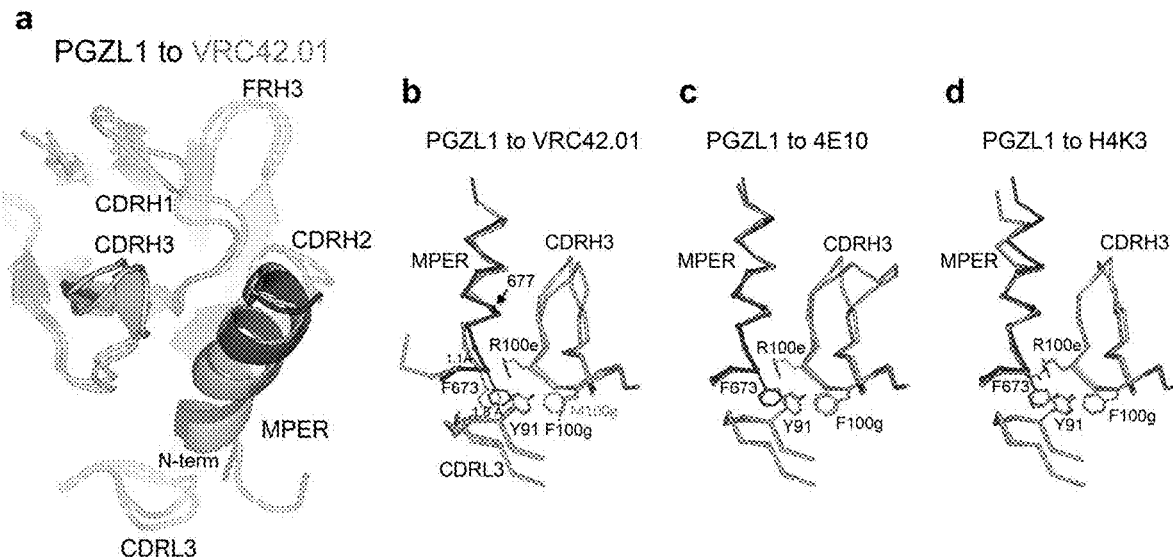
FIG. 11. PGZL1 and VRC42.01 structural comparison. (A) Superposition of variable domain of PGZL1 (green-HC; yellow-LC; red-MPER) to VRC42.01 (blue) reveals slight differences in the position of the MPER N-term region. (B) Zoom into the superposition of PGZL1 (green-HC; yellow-LC; red-MPER) to VRC42.01 (blue) showing aromatic residues (sticks) of the combining site in the N-term region of the epitope. Ca atoms of F673 in the two structures are 1.1 Å apart, and equivalent atoms of its aromatic ring are as much as 1.8 Å apart. Position of F100g in PGZL1 corresponds to M100g in VRC42.01. The position of residue 677 that is an asparagine in our MPER peptide and a lysine in the MPER used in VRC42.01 structure is indicated with an arrow. (C) Zoom into the superposition of PGZL1 (green-HC; yellow-LC; red-MPER) to 4E10 (blue) shows similar position of the MPER epitope and Fabs residues (sticks) in the two structures. (D) Zoom into the superposition of PGZL1 (green-HC; yellow-LC; red-MPER) to H4K3 (blue) shows similar position of the MPER epitope and Fabs residues (sticks) in the two structures. Ca atoms of the MPER epitope residues interacting with each antibody are shown as small spheres in panels (B), (C) and (D).

PGZL1 and H4K3 structures closely resemble VRC42.01 structure (Cα r.m.s.d. of the variable domains ~0.6 Å). However, a slight difference in MPER binding is observed at the N-terminal region of the epitope (residues 671-675; FIG. 11A). All MPER epitope residues are in nearly identical positions when bound to PGZL1, H4K3 and 4E10 (FIGS. 11C and 11D). In contrast, the N-term region is shifted slightly away from the combining site in VRC42.01 (1.1 Å difference between the Ca of MPER F673 in PGZL1 and VRC42.01 and as much as 1.8 Å in the aromatic ring position; FIG. 11B). Note that the MPER peptide used in our crystal structures differs at position 677 from that used in the VRC42.01 complex, asparagine versus lysine, respectively (FIG. 11B). This residue is located at the periphery of the combining site where the MPER position is similar in both structures. Thus, the different positioning of the N-terminal region of the MPER might be due to difference in residues of the J gene region between PGZL1 and VRC42.01 (FIG. 7A; Table 12). Phenylalanine at the position 100g in the CDRH3 loops of PGZL1, H4K3 and 4E10 form an aromatic cluster with CDRL3 Y91 and MPER F673. In VRC42.01, this aromatic cluster is less tightly packed due to a methionine at CDRH3 position 100 g (FIG. 11B-D).

TABLE 12

| Germline gene usage and characteristics of HIV-1 MPER bnAbs. | | | | | | |
|---|---|---|---|---|---|---|
| Abs | Putative heavy chain gene alleles | | | V (nt%) mutation frequency | HCDR3 aa sequence | HCDR3 Length (aa) | Isotype |
| PGZL1 | IGHV1-69*06 | IGHD3-10*01 | IGHJ3*01 | 20.9 | EGEGWF GKPLRAF EF (SEQ ID NO: 63) | 15 | IgG1 |
| 4E10 | IGHV1-69*10 | IGHD3-10*01 | IGHJ4*03 | 6.8 | EGTTGW GWLGKPI GAFAH (SEQ ID: 125) | 18 | IgG3 |
| VRC42.01 | IGHV1-69*10 | IGHD3-10*01 | IGHJ4*03 | 10.8 | EGAGWF GKPVGA MGY (SEQ ID: 126) | 15 | IgG1 |
| 10E8 | IGHV3-15*05 | IGHD3-3*01 | IGHJ1*01 | 21.5 | TGKYYDF WSGYPPG EEYFQD (SEQ ID NO: 127) | 20 | IgG3 |
| DH511.2 | IGHV3-15*01 | IGHD3-3*01 | IGHJ6*03 | 17.6 | TMDEGTP VTRFLEW GYFYYY MAV (SEQ ID NO: 128) | 23 | IgG3 |
| DH517 | IGHV4-34*01 | IGHD3-16*01 | IGHJ6*01 | 18.1 | ARGTGV VVGGSW TVPPGMA YYLDV (SEQ ID NO: 129) | 24 | IgG3 |
| Z13 | IGHV4-59*03 | IGHD2-15*01 | IGHJ6*03 | 17.7 | VAIGVSG FLNYYYY MDV (SEQ ID NO: 139) | 17 | N.D. |

TABLE 12-continued

| Germline gene usage and characteristics of HIV-1 MPER bnAbs. | | | | | | | |
|---|---|---|---|---|---|---|---|
| 2F5 | IGHV2-5*02 | IGHD3-3*01 | IGHJ6*02 | 12.1 | RRGPTTS SGVPIAR GPVNAM DV (SEQ ID NO: 130) | 22 | IgG3 |

| Abs | Putative light chain gene alleles | | V (nt%) mutation frequency | LCDR3 aa sequence | HCDR3 Length (aa) |
|---|---|---|---|---|---|
| PGZL1 | IGKV3-20*01 | IGKJ5*01 | 12.6 | QQYGTSQ ST (SEQ ID NO: 131) | 9 |
| 4E10 | IGKV3-20*01 | IGKJ2*01 | 4.7 | QQYGQSL ST (SEQ ID NO: 132) | 9 |
| VRC42.01 | IGKV3-20*01 | IGKJ1*01 | 5.7 | QQYGGSF GT (SEQ ID NO: 133) | 9 |
| 10E8 | IGLV3-19*01 | IGLJ3*02 | 15.2 | SSRDKSG SRLSV (SEQ ID NO: 134) | 12 |
| DH511.2 | IGLK1-39*01 | IGKJ2*03 | 15.7 | QENYNTI PSLS (SEQ ID NO: 135) | 11 |
| DH517 | IGLV3-19*01 | IGLJ2*01 | 13.4 | ASRDRSG DRLGV (SEQ ID NO: 136) | 12 |
| Z13 | IGKV3-11*01 | IGKJ1*01 | 6 | QQRSDW PRT (SEQ ID NO: 137) | 9 |
| 2F5 | IGKV1D-13*02 | IGKJ4*01 | 11.8 | QQLHFYP HT (SEQ ID NO: 138) | 9 |

Example 8. PGZL1 Neutralization Resistance Mutations from PG13 Donor Envs and MPER Ala Scan To identify resistance mutations to PGZL1, long-read NGS analyses was first performed on env rescued from contemporaneous PG13 donor plasma. Sequences were determined for 58 clade B Envs. One small sublineage, and a larger more diverse clade, was predicted to be CXCR4 tropic, and CCR5 tropic, respectively (FIG. 12A). Notably, MPER polymorphisms D674S, D674T and D674E are predicted to contact PGZL1, and are distinct from other reported 4E10 resistance mutations, F673L or W680G/R (FIG. 12A). Nakamura et al., PLoS One 5, e9786 (2010). Viruses pseudotyped with PG13 Envs lacked infectivity (data not shown), so the MPER polymorphisms was tested in the context of primary isolate COT6, while also testing PGZL1 and 4E10 against a COT6 MPER Ala mutant virus panel. Indeed, D674S, D674E and D674T all made COT6 more resistant to neutralization by PGZL1, H4K3 and 10E8 (Table 13). Mutant D674A was resistant to PGZL1 and H4K3, but less so with 4E10. Some PG13 Envs have Gly at MPER position 662, which is present in 1.2% (vs Glu in 71.7%) of Envs in the LANL database (FIG. 12C). However, A662G resulted in COT6 being 10-fold more sensitive to PGZL1 and 4E10 (FIG. 12B). All COT6 mutants were similarly sensitive to control antibody VRC01 (data not shown). Overall, it can be inferred that some viruses in the PG13 donor developed polymorphisms in D674 to resist PGZL1 antibodies.

TABLE 13

Impact of MPER sequence changes on neutralization of HIV COT6 by PGZL1 and control antibodies.

| Virus | MPER Epitope | COT6 mutants | Fold increase in $IC_{50}$ | | | | |
|---|---|---|---|---|---|---|---|
| | | | PGZL1 | H4K3 | 4E10 | 10E8 | VRC01 |
| COT6 | SWFDITKWLW (SEQ ID NO: 140) | WT | 1 | 1 | 1 | 1 | 1 |
| PG13 Cons | NWFDITNWLW (SEQ ID NO: 141) | | na* | na | na | na | na |
| PG13 isolate 1 | NWFSITNWLW (SEQ ID NO: 142) | D674S | 7.7 | 6.29 | 1.65 | na | na |
| PG13 isolate 2 | NWFEITNWLW (SEQ ID NO: 143) | D674E | 26 | 12 | 10 | 17.5 | 1.2 |
| PG13 isolate 3 | NWFTITNWLW (SEQ ID NO: 144) | D674T | 120 | 38 | 25 | 36 | 1 |

*na: not attempted

COT6 Ala mutants W672A, F673A and W680A were resistant to PGZL1, HK43 and 4E10 (FIG. 12C) as well as 10E8. Kim et al., PLoS Pathog. 10, e1004271 (2014); Zwick et al., J. Virol. 79, 1252-1261 (2005). However, MPER Ala mutations rarely occur naturally (FIG. 12C). Fold-changes in $IC_{50}$ differed between the 4E10-like bnAbs and mutants S671A, D674A, I675A and L679A (FIG. 12B). Thus, S671A and L679A differentially impacted the $IC_{50}$s of H4K3 and 4E10 by up to 100-fold, despite a cross-clade correlation in their $IC_{50}$s (FIG. 9D). In H4K3 and 4E10-bound forms, S671A has a similar structural environment, so this mutation might impact MPER folding or accessibility. However, neutralization differences with COT6 L679A seem more likely to be due to HC position 54, which is occupied by a valine, phenylalanine and leucine in H4K3, PGZL1 and 4E10, respectively; structural analysis of this region reveals more tightly packed interactions between the MPER and 4E10 versus PGZL1 or H4K3. Of note, MPER mutations L663A, D664A, S665A, W666A, K667A, L669A, W670A, K677A and W678A enhanced HIV neutralization by the three MPER bnAbs, as also reported previously for 4E10. Zwick et al., J. Virol. 79, 1252-1261 (2005). The neutralization enhancement effect with these mutants is not fully understood but might be explained by changes in Env conformation that increase accessibility and/or susceptibility to functional inactivation by the MPER bnAbs. Kim et al., PLoS Pathog. 10, e1004271 (2014).

PGZL1 inferred germline structure gives insight into an evolving MPER binding site. The $MPER_{671-683}$ bound (2.47 Å) and unbound (2.6 Å) structures of inferred germline PGZL1 gVmDmJ notably differ in the conformation of their CDRs L1, L3 and H3 (FIG. 4F). When superimposed, residues in CDRL3 in the unbound structure are shifted up to 6.8 Å from that in the bound complex. This shift of CDRL3 in the bound structure may arise from MPER binding, which cause a rearrangement in the aromatic interaction between Y32 (CDRL1) and Y91 (CDRL3) (FIG. 4G). Y32 has affinity matured in PGZL1 to alanine, which does not affect Y91's orientation; thus, CDR L3 and L1 conformations are similar in both unbound and bound PGZL1 and resemble the bound inferred germline PGZL1 (FIG. 4H).

Example 8. Structural and Functional Evidence for Membrane Binding by PGZL1

Figure 5:
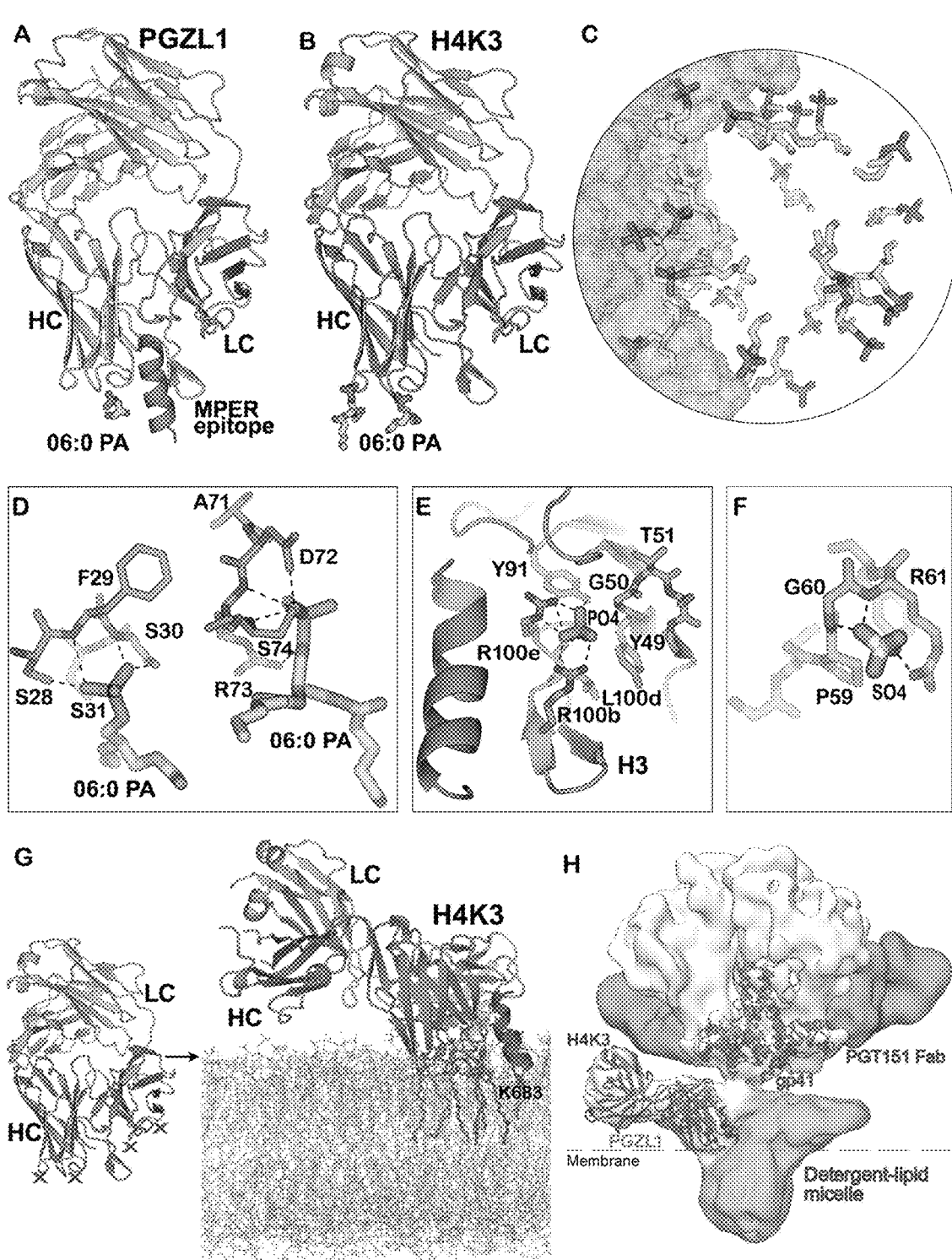
FIG. 5. Lipid Binding and Angle of Approach of PGZL1 Variants to the Viral Membrane. (A) Cartoon of the $PGZL1$-$MPER_{671-683}$ complex structure (wheat—LC; green—HC; pink—MPER) crystallized with 06:0 PA (sticks). (B) Car-toon of H4K3 (brown—LC; blue—HC) crystallized with 06:0 PA (sticks). (C) Stick rendering of 06:0 PA fragments forming a lipid vesicle at the interface of 12 crystallographic and non-crystallographic related H4K3 Fabs. The four Fabs in the asymmetric unit are shown as gray, green, yellow and blue color surfaces. (D) Stick rendering of observed lipid-binding sites in H4K3. (E) Phosphate binding site near to H4K3 CDRH3 when $MPER_{671-683}$ (pink) is bound. Colors as in panel B. (F) Sulfate binding site in FRL3 of H4K3. (G) Model of H4K3 binding to the MPER (red)—viral mem-brane (green) epitope. The model at the right side of the arrow was built based on the regions where experimental lipids and anions (red X) bind on H4K3 (left side of the arrow); cognate lipids are shown as sticks inside the mod-eled membrane. The position of the MPER K683 residue is indicated with a yellow dot. (H) Cryo-EM reconstruction of full-length AMC011-PGT151-PGZL1 complex at 8.9 Å with H4K3 (blue/brown ribbons) fitted into the Env density at the base of the gp41 stem. The MPER is shown as a red ribbon and lipid head-groups as sticks. The detergent-lipid micelle is shown in olive and PGT151 density in blue. Dashed lines show the approximate location where the outer surface of the membrane would be on the virus or infected cells.

To elucidate potential membrane interactions of PGZL1, crystal structures of $PGZL1-MPER_{671-683}$ and unliganded H4K3 were solved in the presence of a short acyl tail phosphatidic acid (06:0 PA) at 3.42 Å and 3.11 Å resolution, respectively. Lipid-binding sites in both antibody structures were observed (FIGS. 5A and 5B). The first lipid site in PGZL1 and H4K3 is in a similar position in 4E10 (Irimia et al., Immunity 44, 21-31 (2016)), proximal to CDRH1 S28, F29 and S30 (FIG. 5D). Next to this site in H4K3, a second PA lipid interacts with D72, R73, and S74 in the HC framework region, FRH3. Of note, in H4K3, these two lipids are part of a ~33 Å lipid vesicle formed at the interface of 12 symmetry-related Fabs that each contain the two lipid sites (FIG. 5C), as also observed in the 4E10 structure. Irimia et al., Immunity 44, 21-31 (2016).

PO4 and SO4 ions were both bound at the CDRH1 site of the H4K3 structures obtained in lipid-free buffer (FIG. 4E). Another PO4 ion interacts with R100b and R100e of CDRH3 and Y91 of CDRL3 in the $H4K3-MPER_{671-683}$ structure (FIGS. 4E and 5E). As this anion-binding site is absent in peptide-free H4K3, despite the crystallization buffer containing SO4, this site may be induced by MPER binding. This site is also H4K3 specific, as it is absent in peptide-bound PGZL1, where LC SHM-residue D50 replaces G50 (FIGS. 6A and 6B) and residue 100b is lysine. Another SO4 ion was observed in unbound H4K3 proximal to FRL3, and interacts with P59, G60 and R61 (FIG. 5F). Thus, these two anion-binding sites may also represent phospholipid-binding sites.

To determine if the lipid-binding sites observed in our structures are biologically relevant, the H4K3 lipid binding sites were mutated. Both CDRH1 and FRH3 regions form plateau-like structures with main-chain nitrogens making contacts with the lipid head groups (FIGS. 5A, 5B, 5D, and 5F). Thus, the lipid binding regions S28F29S30 of CDRH1 and D72R73S74 of FRH3 were mutated to E28P29E30 and D72P73E74, respectively, with the proline mutation chosen to perturb the lipid interaction with the main chain and the glutamate mutation to introduce negative charges that are repulsive to the viral membrane. Residue G50 of the H4K3 light chain was mutated to D50 to disrupt the CDRH3 R100b-R100e site. To summarize, the following three mutants were created: 1) H4K3_SFS28EPE that includes E28P29E30 in the heavy chain and D50 in the light chain; 2) H4K3_RS73PE that includes P73E74 in the heavy chain and D50 in the light chain; 3) H4K3_5M that includes all five mutations in the heavy chain combined with D50 in the light chain. ELISA and BLI experiments show that the three mutants retain similar nM binding affinity to the MPER peptide as H4K3 suggesting that the mutations do not interfere with the MPER binding (FIGS. 6C and 6E). However, the neutralization potency ($IC_{50}$) against HxB2 and Du156.12 is reduced with all three mutants by 7-84 fold, with the H4K3_SFS28EPE and H4K3_5M suffering higher losses in potency (FIGS. 6D and 6E). Hence, mutation of the lipid binding sites influences binding to membrane-embedded Env on the virus, but not binding to MPER out of the membrane context.

Analysis of the surface potential of PGZL1 variants and 4E10 show that the lipid head groups and anions bind to electropositive clefts on the antibody surface (FIGS. 6F to 6I). Germline PGZL1 gVmDmJ and mature PGZL1 have less basic patches compared to H4K3 and 4E10. Thus, their lower neutralization potency may correlate with reduced electrostatic interaction with specific lipids in the viral membrane.

Considering the position and orientation of lipids, anion binding sites (FIGS. 5B to 5G), and MPER orientation (FIG. 4E), a molecular model of H4K3 binding to the MPER-viral membrane was generated using CHARMM force field and molecular dynamics (MD) simulation, in a similar way to the published 4E10 and 10E8 models Irimia et al., Immunity 44, 21-31 (2016); Irimia A et al., PLoS Pathog. 13, e1006212 (2017); Brooks et al., J. Compu. Chem. 30, 1545-1614 (2009). The lipid head groups of the membrane outer leaflet were placed in a plane that roughly includes K683 of gp41 as well as the two lipid head groups and anion sites observed in our crystal structures (FIG. 5G). Our model suggests that H4K3 contacts the membrane-MPER epitope in a similar manner to 4E10 (Irimia et al., Immunity 44, 21-31 (2016)) with the MPER helix tilted 67°-73° from the bilayer surface. CDRH1, CDRH3 tip, FRH3 (residues 73-76), N-terminal HC residue K1, and CDRL2 and FRL3 (residues 56-61 and R77) are proximal to and interact with the lipid heads. A hydrophobicity plot showed similar membrane-transfer propensity between PGZL1, H4K3, VRC42.01 and 4E10 in both HCs and LCs, except that VRC42.01 and 4E10 CDRH3 showed higher hydrophobicity (FIG. 7B).

Figure 12:
FIG. 12. Isolation and phylogenetic analysis of PG13 donor Envs and sensitivity of HIV COT6 MPER mutants to neutralization by PGZL1 antibodies. (A) Alignment of MPER sequences obtained from Envs rescued from plasma derived viral RNA of donor PG13 using long-read NGS. The X in the MPER sequence is a stop codon. The adjacent phylogeny is annotated with circles whose size corresponds to the number of variant frequency and whose color indicates whether the Env is predicted to be CXCR4-tropic (red) or CCR5-tropic (blue). The units of the scale bar are "nucleotide substitutions per site". Sequence shown is ELDKWASLWNWFDITNWLW (SEQ ID NO: 148). (B) Relative neutralization sensitivity of HIV COT6.15 wild-type vs COT6.15 MPER mutants to PGZL1, H4K3 and 4E10 antibodies. Results are reported as fold-increase in $IC_{50}$ relative to wild-type COT6.15. (C) Logoplot of MPER sequence for all Envs in the LANL database.

Example 9. Cryo-EM Structure of Env-PGT151-PGZL1 Complex Confirms PGZL1 Angle of Approach To explore the topology of the PGZL1-Env interaction, a cryo-EM reconstruction at 8.9 Å resolution of a full-length Env of isolate AMC011 was obtained (van Gils et al., Nat. Microbiol. 2, 16199 (2016)) in complex with PGZL1 and PGT151. Despite notable structural heterogeneity between the well-resolved ectodomain versus detergent-lipid micelle containing the TM and cytoplasmic tail (CT), a subset of particles were classified and a 3D map with one PGZL1 Fab bound to one MPER of the AMC011 trimer was reconstructed (FIGS. 5H and 12). Two PGT151 Fabs were also observed, whereas the gp41 TM region cannot be distinguished from the detergent-lipid micelle. Fitting of the PGZL1 lipid-bound Fab crystal structure (FIG. 5G) into the cryo-EM map confirms the antibody orientation relative to the bilayer, and suggests both HC and LC contact the membrane (FIG. 5H). The angle of approach revealed in the MD simulation (FIG. 5G) agrees with the cryo-EM docking model.

DISCUSSION

HIV bnAbs that share epitope and paratope features have been of increasing interest for vaccine design. Kwong &

Mascola, Immunity 48, 855-871 (2018). The bnAbs 4E10, 10E8 and DH511 show near pan-neutralization of HIV-1 by targeting nearly identical α-helical epitopes in the MPER, but these antibodies have uncommon features. Described herein is PGZL1 as well as its lineage variant H4K3 and germline revertants that have some common features that may aid vaccine design, especially given the homology to 4E10 and the recently described VRC42 antibody. PGZL1 antibodies have a 15-residue CDRH3 that is close to the average in humans of ~13.2 7. Like all MPER bnAbs, CDRH3 aromatics were crucial for HIV neutralization, but the observed pre-configuration of H4K3 to bind the MPER and lipid heads on the membrane may explain its faster on-rate compared to PGZL1, where reorientation of the CDRH3 is needed. An induced lipid site at residues R100e/R100b of H4K3 may also have improved its potency while reducing polyreactivity. By comparison, longer CDRH3s on 4E10 and VRC42 variant VRC42.N1 may interact more with the TM domain in the upper membrane core. Nakamura et al., PLoS One 5, e9786 (2010). Using x-ray crystallography and cryo-EM, the orientation, angle of approach, and composition of the PGZL1-Env interaction were determined. These valuable data can inform the design of HIV vaccines and therapies, involving a vulnerable site that has long precluded description due to ambiguity of the membrane interaction.

PGZL1, 4E10 and VRC42 are derived from similar V/D genes but different J genes. Whether other shared CDRH3 residues arose from SHM or N1/N2 additions is unknown but should be considered as they may affect antibody activity. Vaccine design must also consider how to elicit bnAbs with few SHM. Fortunately, the SHM-reverted PGZL1 gVmDmJ antibody neutralized up to 28% of viruses tested, albeit mostly with limited potency; many somatic mutations in 4E10 and 10E8 are also non-essential. Klein et al., Cell 153, 126-138 (2013); Soto et al., PLoS One 11, e0157409 (2016). VH1-69 is also highly mutable due to several SHM hotspots. Yuan et al., PLoS One 12, e0167602 (2017). VH1-69 has been associated with autoantibodies of leukemia (Yuan et al., PLoS One 12, e0167602 (2017)), HCV-associated mixed cryoglubulinemia (Charles et al., Arthritis Rheum. 65, 2430-2440 (2013)), as well as bnAbs highly specific to the influenza hemagglutinin stem (Lang et al., Cell Rep. 20, 2935-2943 (2017)) and HCV E2 (Kong et al., Science 342, 1090-1094 (2013)). Thus, any vaccine strategy to elicit VH1-69 MPER bnAbs must be MPER specific and contend with off-target B cells.

A few Envs were found that were recognized and neutralized by germline revertants of PGZL1 and 4E10. Such Envs, or perhaps the T/F Env of the VRC42 donor (Krebs et al., Immunity 50, 677-691 e613 (2019)), might be useful for activating 4E10-like B cell precursors whose CDRH3s can engage membrane bound Env. These B cells could be boosted with a heterologous Env to drive the maturation process required for achieving neutralization breadth and potency (Pathway 1). Alternatively, VH1-69 restricted B cells that lack crucial lipid-interacting residues might be activated, perhaps using specific Envs, scaffolds, peptides or anti-idiotype antibodies. Molinos-Albert et al., Front. Immunol. 8, 1154 (2017); Correia et al., Structure 18, 1116-1126 (2010); Avnir et al., Cell Rep. 21, 3243-3255 (2017). Lipid-interacting residues would have to be provided by the maturation process and the B cells boosted perhaps by a membrane-anchored MPER (Pathway 2). Contrarily, 10E8 and DH511 do not bind Env as germline revertants, so specific strategies may be needed to activate such lineages. Because soluble Env differs somewhat from its membrane counterpart in glycosylation and conformation (Cao et al., Nat. Commun. 9, 3693 (2018); Sarkar et al., Nat. Commun. 9, 1956 (2018)), development of membrane-embedded Env vaccines or suitable soluble alternatives seems justified. Stano A, et al., J. Virol. 91, 415-417 (2017). H4K3 currently lacks the potency of bnAbs being developed for therapy, such as 10E8. Huang et al., Nature 491, 406-412 (2012). However, its exceptional breadth warrants efforts to engineer H4K3 to be more potent without enhancing polyreactivity, as was done recently with 10E8. Rujas et al., J. Virol. 92, e02249-02217 (2018); Kwon et al., Cell Rep. 22, 1798-1809 (2018).

MPER bnAbs have been associated with IgG3-prone B cell subsets. Haynes et al., Hum. Antibodies 14, 59-67 (2005). PGZL1 shows that IgG1 MPER B cells can also be elicited in humans, which may arose from a precursor of minimal polyreactivity that bound directly to Env. Non-IgG3 MPER nAbs have notably also been observed in donor plasma (Gray et al., J. Virol. 83, 11265-11274 (2009)), and variants of VRC42 are both IgG1s and IgG3s. Whether differences in isotype, polyreactivity or autoreactivity of 4E10-like bnAbs are useful correlates for eliciting MPER bnAbs requires immunization studies.

MPER bnAbs have been associated with IgG3-prone B cell subsets 4. PGZL1 shows that IgG1 MPER B cells can also be elicited in humans, which likely arose from a precursor of minimal polyreactivity that bound directly to Env. Non-IgG3 MPER nAbs have notably also been observed in donor plasma (Gray et al., J. Virol. 83, 11265-11274 (2009)), and variants of VRC42 are both IgG1s and IgG3s. The observed differences in isotype, polyreactivity or autoreactivity of 4E10-like bnAbs can be exploited to develop an immunization protocol to elicit MPER bnAbs in humans.

Methods

Isolation of PGZL1 monoclonal antibodies. Fluorescent-labeled antibodies, which target cell surface markers were purchased from BD Biosciences. Biotin-labeled MPER peptide PDT-081 (E[654]KNEQELLELDKWASLWNWFDITNWLWYIK[683]-biotin (SEQ ID NO: 145)) was purchased from GenScript and coupled separately to streptavidin-PE and streptavidin-APC (Life Technologies). PBMCs were stained using the LIVE/DEAD Fixable Near-IR Dead Cell Kit (Life Technologies) for 30 min on ice. Cells were then labeled with antibodies cocktail along with MPER probes for 1 h in Brilliant Staining buffer (BD Biosciences) on ice. Cell population CD19+/CD20+, CD3–/CD8–, CD14–/CD16–, IgG+, IgD–/IgM–; MPER double positive were sorted using BD FACSAria III sorter into individual wells of a 96-well plate containing lysis buffer, and plates were immediately sealed and stored at –80° C.

Antibody sequence amplification, analysis and cloning. The first-strand cDNA from B cells was synthesized using Superscript III Reverse Transcriptase (Life Technologies) and random hexamers (Gene Link). Nested PCR amplification of HC and LC variable regions was performed using Multiplex PCR Kit (Qiagen). Amplified HC and LC variable regions were sequenced and then analyzed using IMGT online tools. Antibodies of interest were cloned into expression vectors by re-amplification of the variable regions using the same primers but modified to introduce homology to the vector. Landais et al., Immunity 47, 990-1003 e1009 (2017).

PG13 antibody repertoire sequencing and bioinformatics analysis. The 5'-RACE PCR protocol used for unbiased human B cell repertoire analysis has been previously described. Kong et al., Immunity 44, 939-950 (2016); He et al., Sci Rep. 4, 6778 (2014). Briefly, total RNA was extracted from 5 million PBMCs into 30 µl of water with RNeasy™ Mini Kit (Qiagen). 5'-RACE was performed with SMARTer RACE cDNA Amplification Kit (Clontech). The immunoglobulin PCRs were set up with Platinum Taq High-Fidelity DNA Polymerase (Life Technologies) in a total volume of 50 µl, with 5 µl of cDNA as template, 1 µl of 5'-RACE primer, and 1 µl of 10 µM reverse primer. The 5'-RACE primer contained a PGM/S5 P1 adaptor, while the reverse primer contained a PGM/S5 A adaptor. A total of 25 PCR cycles were performed and the expected PCR products (~600 bp) were gel purified (Qiagen). Next-generation sequencing (NGS) was performed on the Ion S5 system as previously described. He et al., Front. Immunol. 8, 1025 (2017). Briefly, heavy (H), kappa (κ), and lambda (λ) chain libraries were quantitated using Qubit® 2.0 Fluorometer with Qubit® dsDNA HS Assay Kit, and mixed at a ratio of 2:1:1 before antibody libraries from three time points were further mixed at a ratio of 1:1:1. Ion Xpress™ barcodes (Life Technologies), #1-#3, were used to tag antibody libraries in order to differentiate three time points. Template preparation and (Ion 520) chip loading were performed on Ion Chef™ using the Ion 520/530 Ext Kit, followed by sequencing on the Ion GeneStudio™ S5 platform with default settings. Raw data were processed without the 3'-end trimming in base calling to extend the read length. An improved version of the Antibodyomics pipeline (He et al., Front. Immunol. 8, 1025 (2017)) was used to process, annotate, and analyze the sequencing data of PG13 antibody repertoires. After pipeline processing, a bioinformatics filter was applied to remove erroneous sequences that may contain swapped gene segments due to PCR errors. Specifically, a full-length variable region sequence would be removed if the V-gene alignment was less than 250 bp. The results for pipeline processing are summarized in Table 8. The pipeline-processed antibody chain sequences were subjected to two-dimensional (2D) divergence/identity analysis and CDR3-based lineage analysis, with putative somatic variants determined at CDR3 identity cutoffs of 80% and 95% (FIG. 1D).

Expression and purification of the PGZL1 IgG and Fab variants. PGZL1 heavy and light chains were cloned using Gibson Assembly™ Enzyme mix (NEB) into expression vectors with the appropriate IgG1, Ig kappa or Ig lambda constant domains. Landais et al., Immunity 47, 990-1003 e1009 (2017). Antibodies were expressed in Expi 293F cells (Life Technologies A14527). Briefly, ~750 µg DNA (500 µg heavy chain and 250 µg light chain plasmid) were added to 25 ml Opti-MEM™ (Life Technologies—31985-070), which was mixed with Opti-MEM™ containing 2,250 µg polyethylene imine MAX (MW 40,000; Polyscience—24765-1). After incubation for 20 min at RT, the transfection mix was added to 1 L cells at a density of ~1.2×106 cells/ml in Expi293 Expression Medium (Life Technologies—A1435101). The cells were incubated at 37° C. and 8% CO2 for 6 days. After harvesting the cells, the supernatant, containing IgG or Fab, was filtered and loaded into a protein A beads column (Thermo Scientific) or HiTrap™ KappaSelect column (GE Healthcare Life Sciences—17545812). The column was washed with phosphate buffered saline and eluted with 0.2 M citric acid pH 3.0 or 0.1 M glycine pH 2.7. The fractions were concentrated and the buffer was changed to 20 mM sodium acetate pH 5.5. The Fab was loaded into a Mono S column and was eluted with a 0 to 60% linear gradient of 1M sodium chloride, 20 mM sodium acetate pH 5.5 buffer. The Fabs were concentrated and stored in 20 mM sodium acetate pH 5.5 at 4° C.

Crystallization of the PGZL1 Fab variants. All crystal trials were performed with our Scripps/IAVI/JCSG high-throughput CrystalMation robot (Rigaku) using protein sample (unbound or peptide bound Fab) at ~7 mg/ml. Crystals were obtained using sitting drop vapor diffusion by mixing 1:1 protein:reservoir solutions in 200 nl drops. The MPER$_{671-683}$ peptide used for complexes has the sequence N671WFDITNWLWYIK683-KKK (SEQ ID NO: 146). Fab-MPER$_{671-683}$ complexes were prepared by mixing Fab with peptide in 1:5 protein:peptide molar ratio. PGZL1-MPER$_{671-683}$ and H4K3 were co-crystallized with 06:0 PA by mixing highly concentrated protein sample with 06:0 PA (stock solution of 15 mM in 20 mM sodium acetate, pH 5.5) such that the final concentrations of the protein and lipid in the mixture were ~7 mg/ml and ~8 mM, respectively.

Data collection, structure determination and refinement. X-ray diffraction data sets were collected at SSRL on the 9-2 or 12-2 beamlines. The data sets were processed using HKL2000 (Otwinowski et al., Meth. Enzymol. 276, 307-326 (1997)) or XDS (Kabsch W. Acta Crystallogr. D66, 125-132 (2010)). Phaser was used to find molecular replacement solutions employing the 4E10 Fab variable and constant domains (PDB 2FX7) as the search model. McCoy et al., J. Appl. Crystallogr. 40, 658-674 (2007). After an initial round of rigid body refinement, model rebuilding was carried out with Coot 51 and refinement with Phenix (Adams et al., Acta Crystallogr. Biol. Crystallogr. D66, 213-221 (2010)) using different refinement strategies as appropriate for the resolution of each structure. Structural images were generated using PyMOL (The PyMOL molecular graphics system).

MD simulation model of the PGZL1.H4K3 interaction with HIV MPER epitope on membrane. A trimeric model of MPER epitope-gp41 transmembrane region was constructed as previously described (Irimia et al., Immunity 44, 21-31 (2016)) using PDB 2MOM as a template. The orientation of the MPER in this model is based on the MPER$_{671-683}$ and lipid orientation observed in our crystal structures. The H4K3 Fabs and the 06:0 PA lipids fragments were added to the model by superposing the MPER$_{671-683}$ to the same region of the model. The acyl tails of the crystallographic lipids were extended to the size of a 1,2-dipalmitoyl-sn-glycero-3-phosphate (DPPA) molecule and the SO4 and PO4 ions bound to CDRH3 and FRL3 regions were replaced with DPPAs with the lipid tails pointing in the same direction as those of the lipids observed in the structures. Thus, the lipids tails are oriented ~perpendicular to the plane that roughly includes the observed lipid head groups, two anions and Lys683 of the MPER. The lipid bilayer was placed with CHARMM (Brooks et al., J. Compu. Chem. 30, 1545-1614 (2009)) on the putative transmembrane region built to anchor in the membrane. The replacement method was used to place 424 and 455 lipids in the upper and lower leaflet, respectively, of a heterogenous lipid bilayer in a rectangular box of x=y=161.2 Å. The membrane composition of the heterogenous bilayer was chosen based on the HIV-1 membrane lipid composition as described in Irimia et al., 2016. Potassium counter ions were placed with the Monte-Carlo method. In the final model, the head group of the lipids corresponding to the sites observed in the crystal structure and the Lys683 of MPER are located within the head group region of the membrane outer leaflet.

Full-length Env sample preparation for cryo-EM. Recombinant full-length AMC011 Env was expressed in HEK293F cells and purified as described previously. Rantalainen et al., Cell Rep. 23, 3249-3261 (2018); Torrents de la Pena et al., bioRxiv 500975 (2018). Purified protein was concentrated to 5.6 mg/ml prior to cryo-EM grid preparation. 3 μl of PGZL1 Fab at 4.5 mg/ml and 1 μl of 1 mM lipid mix (DOPC:DOPS: CHS:PIP2 at 40:40:16:4 molar ratio, Avanti Polar Lipids) was added to 10 μl of purified and concentrated AMC011 Env. Detergent removal was initiated by three additions of ~3-5 SM-2 bio beads (Bio-Rad) with one hour incubation between each addition. After the last incubation, 3 μl of sample was applied to either plasma cleaned 1.2/1.3 C-Flat Holey Carbon grid (Protochips) with 0.5 μl of 0.01% amphiphol A8-35 or to 2/2 Quantifoil Holey Carbon Grid with 0.5 μl of 35 μM LMNG. Amphiphol or LMNG was added directly on grid to improve orientation distribution of particles. Grids were plunge-frozen in liquid ethane using Vitrobot mark IV (Thermo Fisher Scientific) without wait time, blot force of 0 and 7 see blot time.

Figure 13:
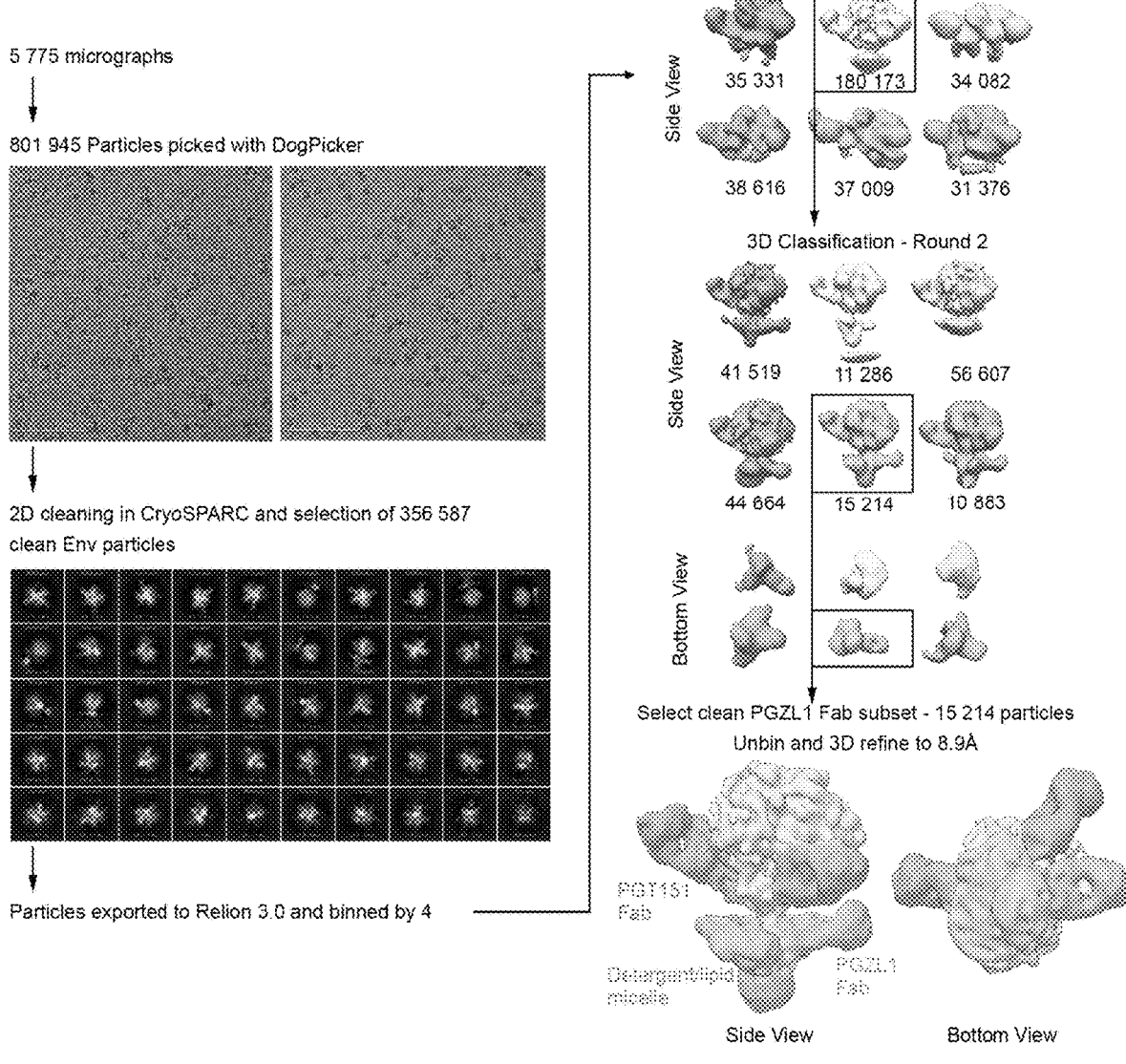
FIG. 13. Cryo-EM data processing workflow for full-length AMC011 Env in complex with PGT151 and PGZL1 Fabs. Particles were picked with DoGPicker and after 2D classification in cryoSPARC, clean particle stack was further curated with two rounds of 3D classification, yielding a final class of 15214 particles with one PGZL1 Fab per trimer and refined to 8.9 Å resolution.

Cryo-EM data collection and processing. 5775 micrographs were collected using our Titan Krios (Thermo Fisher Scientific) operating at 300 keV and K2 Summit direct electron detector (Gatan). Data were collected with Leginon automated image acquisition software (Potter et al., Ultra-microscopy 77, 153-161 (1999)) at 29,000× magnification resulting in pixel size of 1.03 Å in the specimen plane. 46 frames were collected for each micrograph with 250 ms exposure time per frame at dose rate of 4.7 e$^-$/pix/sec and with defocus values ranging from −1.0 to −2.5. Frames were aligned and dose weighted with MotionCor2 (Zheng et al., Nat. Methods 14, 331-332 (2017)) and CTF models for each micrograph were calculated using GCTF (Zhang et al., J. Struct. Biol. 193, 1-12 (2016)). Workflow for subsequent data processing is presented in FIG. 13. Particles were picked using DoGPicker 58 and after initial round of 2D classification in CryoSPARC 59, 356 587 Env particles were moved to Relion (Zivanov et al., eLife 7, e42166 (2018)) for 3D processing. After two rounds of 3D classification, a class of 15 214 particles with one PGZL1 Fab bound showed the best Fab definition and was refined to 8.9 Å resolution according to the FSC 0.143 gold-standard criterion.

HIV-1 neutralization assays. Neutralization activity of PG13 donor plasma and monoclonal antibodies was assessed using pseudovirus and a single round of replication in TZM-b1 target cells. Pseudoviruses were generated by co-transfection of HEK 293T cells with an Env-expressing plasmid and an Env-deficient genomic backbone plasmid (pSG3ΔEnv). Pseudoviruses were harvested 48-72 h post transfection and stored at −80° C. Serial dilutions of plasma/antibody were incubated with virus in presence of DEAE-dextran and the neutralizing activity was assessed by measuring luciferase activity after 48-72 h. Dose-response curves were fitted using nonlinear regression to determine IC$_{50}$ values. For competition assays, plasma/antibody dilutions were pre-incubated 30 min at RT in the presence or absence of 10 μg/mL of MPER peptide.

ELISA. Half-area 96-well ELISA plates were coated overnight at 4° C. with 50 μL PBS containing 250 ng of antigens per well. The wells were washed four times with PBS containing 0.05% Tween® 20 and blocked with 4% non-fat milk (NFM) for 1 h at 37° C. Serial dilutions of sera/antibodies were then added to the wells, and the plates were incubated for 1 h at 37° C. After washing four times, the wells were treated with goat anti-human IgG Fc conjugated to HRP, diluted 1:1000 in PBS containing 0.4% NFM and 0.05% Tween® 20. The plates were incubated for 1 h at 37° C., washed four times, and developed by adding HRP substrate diluted in alkaline phosphatase staining buffer (pH 9.8), according to the manufacturer's instructions. The optical density at 405 nm was read on a microplate reader (Biotek Synergy). EC50 values were calculated using Prism6 (GraphPad).

HEp-2 assay. Antibodies were assayed for autoreactivity using a HEp-2 indirect immunofluorescence kit (Bio-Rad) according to the manufacturer's instructions.

Antibody binding by bio-layer interferometry (BLI). An Octet® RED96 system (ForteBio) with BLI was used to assess the binding of PGZL1 and its variants Fab to MPER peptide PDT-081. Biotinylated peptide at 7.5 µg/ml in PBS/ 0.002% Tween® 20/0.01% BSA was captured on the surface of Streptavidin biosensors (ForteBio) for 8 min. The biosensor was exposed to a serial dilution of Fabs for 5 min, and then to buffer for 5 min, to acquire association and dissociation sensograms, respectively. $K_D$ values were calculated as $k_{off}/k_{on}$ based on 5 sensograms from the dilution series with a minimum R2 value of 0.99. The sensograms were corrected using the blank reference and fitting was accomplished using the ForteBio Data Analysis 7 software package.

Flow cytometry. Comb-mut V4 cell line was generated and characterized as described. Ma et al., PLoS Pathog 7, e1002200 (2011). Following a similar protocol, the MPER-TM654-709 cell line was developed. Briefly, a PCR amplicon encoding a TPA leader sequence, codon optimized MPER-TM (654-709) of BG505, followed by a stop codon was cloned into NotI and XhoI sites of pLenti-III-HA (Applied Biological Materials). The resulting MPER-TM lentiviral vector was used to generate lentiviral particles, which were then used to transduce 293T cells following the manufacturer's instructions. The transduced cells were cultured in medium containing 10 µg/ml puromycin to select for stable integrants, and sorted on a BD Aria flow cytometer to select the 10E8 (high) stable cell line, MPER-TM654-709.

For flow cytometry experiments, a total of 107 cells of stable cell lines HIV-1 MPER-TM654-709 or Comb-mut Env (V4) were washed in PBS and labeled with Fixable Aqua Dead Cell Stain (Life Technologies). Cells were washed in FACS buffer (PBS supplemented with 2% heat-inactivated FBS) and stained with monoclonal antibody. After another wash, cells were stained using APC-conjugated goat anti-human Fc. Soluble CD4 was incubated with cells for 30 min prior to staining cells with antibody. Cells were acquired and analyzed by using NovoCyte® (ACEA Biosciences). Data were analyzed using FlowJo software (Tree Star).

BN-PAGE mobility shift assay. Virus samples were preincubated with Fab fragments of antibodies for 30 min at RT. Samples were then solubilized with 1% DDM for 20 min on ice. Env was separated using Blue Native (BN)-PAGE and detected by Western blot using a cocktail of gp120 and gp41 antibody probes. Western blots were imaged using a Chemidoc XRS (Bio-Rad) and analyzed using Image Lab software (Bio-Rad). The center of intensity for each Env trimer band and the distance that it had migrated along the gel was calculated. The relative shift of each band was calculated by setting the maximum shifted band in each experiment to 1, which corresponds to 3-fold occupancy of Fab per trimer, and the antibody-free control to 0. The trimer occupancy at each Fab concentration was determined by calculating the relative shift for control Fabs PGT126 (3 Fabs/trimer), PGT151 (2 Fabs/trimer), and PG9 (1 Fab/trimer).

Site-directed mutagenesis. Mutagenesis was performed using a Quikchange® site-directed mutagenesis kit (Agilent Technologies).

Lipid insertion propensity. Lipid insertion propensity scores were calculated using the MPEx (Membrane Protein Explorer) software as the sum of ΔGwif, the free energy of transfer of an amino acid from water to POPC interface, over all amino acids of the antibody variable heavy and light domains.

Statistical analysis. For all mAb/serum pseudovirus neutralization and ELISA assays, the $IC_{50}$, or concentration of mAb/dilution of serum needed to obtain 50% neutralization against a given pseudovirus, was calculated from the linear regression of the linear part of the neutralization curve. For neutralization assays in which a fold-change in $IC_{50}$ imparted by a particular virus mutant or virus treatment was reported, the $IC_{50}$ obtained for one virus/assay condition was divided by the $IC_{50}$ obtained for the other virus/assay condition, as indicated in the figure legends. Two-way ANOVA was used for multiple group comparison.

Full-length Env amplification sequencing and computational analysis. HIV-1 Env was sequenced as described. Landais et al., Immunity 47, 990-1003 e1009 (2017). Briefly, virions were purified from plasma through a sucrose cushion and ultracentrifugation. RNA was extracted (Viral RNA Mini Kit, Qiagen) and reverse transcribed (SuperScript III, Thermo Fisher). PCR was performed with subtype B primers using 45 PCR cycles. Four replicate PCR reactions were pooled, purified (QIAquick®, Qiagen), visualized and quantitated (2100 Bioanalyzer System, Agilent Biosciences). Preparation and sequencing of SMRTbell template libraries of ~2.6-kb insert size were performed according to the manufacturer's instructions (Pacific Biosciences) using P6/C4 chemistry on the RS-II. CCS sequences were constructed using the PacBio SMRTportal software (version 2.3). The Robust Amplicon Denoising algorithm (Kumar et al., bioRxiv 383794 (2018)) was used for error correction and MAFFT (Katoh & Standley Mol. Biol. Evol. 30, 772-780 (2013)), with manual curation, was used to construct a multiple sequence alignment. Phylogenies were reconstructed using FastTree v2.1, and visualized with FigTree. Geno2Pheno 2.5 was used to predict co-receptor tropism. Lengauer et al., Nat. Biotechnol. 25, 1407-1410 (2007). Env sequences, and browser-based visualizations, are available at HyperText Transfer Protocol://flea.murrell.group/view/PG13/sequences.

Data availability. The PGZL1 HC and LC variable region sequences have been deposited into Genbank™, accession MK497833-MK497838. The atomic coordinates and structure factors of PGZL1 variants have been deposited in the Protein Data Bank, with accession codes: 603D (PGZL1); 603G (PGZL1-$MPER_{671-683}$); 603J (PGZL1-$MPER_{671-683}$-06:0 PA); 603K (H4K3); 603L (H4K3-$MPER_{671-683}$); 603U (H4K3-06:0 PA); 6041 (PGZL1 gVmDmJ-Protein G); 6042 (PGZL1 gVmDmJ-$MPER_{671-683}$-06:0 PA). The Cryo-EM reconstruction of full-length AMC011-PGT151-PGZL1 complex has been deposited to Electron Microscopy Data Bank with accession code EMD-0620.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence were specifically and individually indicated to be so incorporated by reference.

What is claimed is:

1. An isolated monoclonal antibody or antigen-binding fragment thereof that binds Human Immunodeficiency Virus (HIV) envelope glycoprotein (Env) membrane-proximal external region (MPER) and comprises a heavy chain variable region (VH) comprising a VH CDR1, VH CDR2, and VH CDR3 and a light chain variable region (VL) comprising a VL CDR1, VL CDR2, and VL CDR3, wherein the VH CDR1, VH CDR2, VH CDR3, VL CDR1, VL CDR2, and VL CDR3 comprise the amino acid sequence of (a) SEQ ID NO: 61, 62, 63, 70, 71, and 72, respectively, or (b) SEQ ID NO: 64, 65, 66, 73, 74, and 75, respectively, wherein the HIV Env MPER comprises the amino acid sequence of DLLA-LDRWQNLWNWFDITNWLWYIK (SEQ ID NO: 2).

2. The isolated monoclonal antibody or antigen-binding fragment thereof of claim 1, wherein the VH and VL comprise the amino acid sequence of SEQ ID NO: 5 and 8, respectively, or SEQ ID NO: 6 and 9, respectively.

3. The isolated monoclonal antibody or antigen-binding fragment thereof of claim 1, wherein the antibody is not PGZL1, or PGZL1.H4K3.

4. The isolated monoclonal antibody or antigen-binding fragment thereof of claim 1 characterized by one or more of:

(a) the isolated monoclonal antibody or antigen-binding fragment thereof is a recombinant antibody, a chimeric antibody, a bispecific antibody, or a trispecific antibody; and (b) the isolated monoclonal antibody or antigen-binding fragment thereof comprises a single-chain Fv (scFv), Fab fragment, or F(ab')2 fragment.

5. A pharmaceutical composition comprising the isolated monoclonal antibody or antigen-binding fragment thereof of claim 1 and a pharmaceutically acceptable excipient.

6. An isolated polynucleotide encoding the isolated monoclonal antibody or antigen-binding fragment thereof of claim 1.

7. The isolated polynucleotide of claim 6, wherein the polynucleotide comprises an mRNA.

8. A host cell comprising the polynucleotide of claim 6.

9. A method of producing the isolated monoclonal antibody or antigen-binding fragment thereof of claim 1 comprising culturing a host cell comprising an expression vector comprising a polynucleotide encoding the isolated monoclonal antibody or antigen-binding fragment thereof so that the isolated monoclonal antibody or antigen-binding fragment thereof is expressed and the isolated monoclonal antibody or antigen-binding fragment thereof is produced.

10. A method of neutralizing an HIV virus comprising contacting the virus with a sufficient amount of the isolated monoclonal antibody or antigen-binding fragment thereof of claim 2, wherein the VH and VL comprise the amino acid sequence of SEQ ID NO: 6 and 9, respectively.

11. A method of reducing the likelihood of becoming infected by a subject exposed to HIV comprising administering to the subject a therapeutically sufficient amount of the isolated monoclonal antibody or antigen-binding fragment thereof of claim 2, wherein the VH and VL comprise the amino acid sequence of SEQ ID NO: 6 and 9, respectively.

12. A method of treating HIV/AIDS comprising administering to a subject in need thereof a therapeutically sufficient amount of the isolated monoclonal antibody or antigen-binding fragment thereof of claim 2, wherein the VH and VL comprise the amino acid sequence of SEQ ID NO: 6 and 9, respectively.

13. The method of claim 12, further comprising administering at least one additional therapeutic agent.

14. The method of claim 11 characterized by one or more of:

(a) wherein the isolated monoclonal antibody or antigen-binding fragment thereof further comprises a heavy and/or light chain constant region;

(b) wherein the isolated monoclonal antibody or antigen-binding fragment thereof further comprises a human heavy and/or light chain constant region;

(c) wherein the isolated monoclonal antibody or antigen-binding fragment thereof further comprises a heavy chain constant region selected from the group consisting of a human immunoglobulin IgG1, IgG2, IgG3, IgG4, IgA1, and IgA2 constant region;

(d) wherein the isolated monoclonal antibody or antigen-binding fragment thereof further comprises a heavy chain constant region comprising a native amino acid sequence;

(e) wherein the isolated monoclonal antibody or antigen-binding fragment thereof further comprises a heavy chain constant region comprising a non-native variant amino acid sequence;

(f) wherein the isolated monoclonal antibody or antigen-binding fragment thereof is a recombinant antibody, a chimeric antibody, a bispecific antibody, or a trispecific antibody; and (g) wherein the isolated monoclonal antibody or antigen-binding fragment thereof comprises a single-chain Fv (scFv), Fab fragment, or F(ab')2 fragment.

15. The method of claim 12 characterized by one or more of:

(a) wherein the isolated monoclonal antibody or antigen-binding fragment thereof further comprises a heavy and/or light chain constant region;

(b) wherein the isolated monoclonal antibody or antigen-binding fragment thereof further comprises a human heavy and/or light chain constant region;

(c) wherein the isolated monoclonal antibody or antigen-binding fragment thereof further comprises a heavy chain constant region selected from the group consisting of a human immunoglobulin IgG1, IgG2, IgG3, IgG4, IgA1, and IgA2 constant region;

(d) wherein the isolated monoclonal antibody or antigen-binding fragment thereof further comprises a heavy chain constant region comprising a native amino acid sequence;

(e) wherein the isolated monoclonal antibody or antigen-binding fragment thereof further comprises a heavy chain constant region comprising a non-native variant amino acid sequence;

(f) wherein the isolated monoclonal antibody or antigen-binding fragment thereof is a recombinant antibody, a chimeric antibody, a bispecific antibody, or a trispecific antibody; and (g) wherein the isolated monoclonal antibody or antigen-binding fragment thereof comprises a single-chain Fv (scFv), Fab fragment, or F(ab')2 fragment.

16. The isolated monoclonal antibody or antigen-binding fragment thereof of claim 1 characterized by one or more of:

(a) the isolated monoclonal antibody or antigen-binding fragment thereof further comprises a heavy and/or light chain constant region;

(b) the isolated monoclonal antibody or antigen-binding fragment thereof further comprises a human heavy and/or light chain constant region; and (c) the isolated monoclonal antibody or antigen-binding fragment thereof further comprises a heavy chain constant region selected from the group consisting of a human immunoglobulin IgG1, IgG2, IgG3, IgG4, IgA1, and IgA2 constant region.

17. The isolated monoclonal antibody or antigen-binding fragment thereof of claim 1 further comprising a heavy chain constant region comprising a non-native variant amino acid sequence.

\* \* \* \* \*

SEQUENCE LISTING

<160> NUMBER OF SEQ ID NOS: 174

<210> SEQ ID NO 1
<211> LENGTH: 857
<212> TYPE: PRT
<213> ORGANISM: Artificial Sequence
<220> FEATURE:
<223> OTHER INFORMATION: Recombinant polypeptide

<400> SEQUENCE: 1

```
Met Arg Val Arg Gly Ile Pro Arg Asn Trp Pro Gln Trp Trp Thr Trp
1               5                   10                  15

Gly Ile Leu Gly Phe Trp Met Ile Ile Met Cys Lys Val Ala Gly Asn
            20                  25                  30

Ser Trp Val Thr Val Tyr Tyr Gly Val Pro Val Trp Thr Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Ile Phe Leu Lys Asn Val Thr Glu Asn Phe Asn Met Trp Lys
                85                  90                  95

Asn Asp Met Val Asp Gln Met His Glu Asp Ile Ile Ser Leu Trp Asp
                100                 105                 110

Gln Ser Leu Lys Pro Cys Val Lys Leu Thr Pro Leu Cys Val Thr Leu
        115                 120                 125

Asn Cys Val Thr Tyr Asn Asn Ser Met Asn Ser Ser Ala Thr Tyr Asn
    130                 135                 140

Asn Ser Met Asn Gly Glu Ile Lys Asn Cys Ser Phe Asn Thr Thr Thr
145                 150                 155                 160

Glu Leu Arg Asp Lys Lys Gln Lys Val Tyr Ala Leu Phe Tyr Arg Thr
                165                 170                 175

Asp Val Val Pro Leu Asn Asn Asn Asn Asn Ser Glu Tyr Ile Leu
                180                 185                 190

Ile Asn Cys Asn Thr Ser Thr Ile Thr Gln Ala Cys Pro Lys Val Ser
                195                 200                 205

Phe Asp Pro Ile Pro Ile His Tyr Cys Ala Pro Ala Gly Tyr Ala Ile
    210                 215                 220

Leu Lys Cys Thr Asp Lys Lys Phe Asn Gly Thr Gly Ser Cys Asn Asn
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Glu Ile Ile Ile Lys
                260                 265                 270

Ser Glu Asn Leu Thr Asp Asn Ile Lys Thr Ile Ile Val Gln Leu Asn
        275                 280                 285

Gln Ser Ile Gly Ile Asn Cys Thr Arg Pro Asn Asn Asn Thr Arg Lys
    290                 295                 300

Ser Val Arg Ile Gly Pro Gly Gln Thr Phe Tyr Ala Thr Gly Asp Ile
305                 310                 315                 320

Ile Gly Asp Ile Arg Gln Ala His Cys Asn Ile Ser Arg Asn Gln Trp
                325                 330                 335
```

-continued

```
Asn Glu Thr Leu Glu Gln Val Lys Lys Lys Leu Gly Glu His Phe His
        340                 345                 350

Asn Gln Thr Lys Ile Lys Phe Glu Pro Pro Ser Gly Gly Asp Leu Glu
        355                 360                 365

Ile Thr Thr His Ser Phe Asn Cys Arg Gly Glu Phe Phe Tyr Cys Asn
        370                 375                 380

Thr Ala Asp Leu Phe Thr Asn Ala Thr Lys Leu Val Asn Asp Thr Glu
385                 390                 395                 400

Asn Lys Ala Val Ile Thr Ile Pro Cys Arg Ile Lys Gln Ile Ile Asn
                405                 410                 415

Met Trp Gln Gly Val Gly Arg Ala Met Tyr Ala Pro Pro Ile Glu Gly
        420                 425                 430

Asn Ile Thr Cys Asn Ser Asn Ile Thr Gly Leu Leu Leu Thr Arg Asp
        435                 440                 445

Gly Gly Gly Asn Val Thr Glu Ile Asn Arg Thr Glu Ile Phe Arg Pro
    450                 455                 460

Gly Gly Gly Asn Met Lys Asp Asn Trp Arg Asn Glu Leu Tyr Lys Tyr
465                 470                 475                 480

Lys Val Val Glu Ile Lys Pro Leu Gly Val Ala Pro Thr Gly Ala Lys
                485                 490                 495

Arg Lys Val Val Lys Arg Glu Lys Arg Ala Val Gly Leu Gly Ala Val
                500                 505                 510

Leu Phe Gly Phe Leu Gly Ala Ala Gly Ser Thr Met Gly Ala Ala Ser
        515                 520                 525

Ile Thr Leu Thr Ala Gln Ala Arg Gln Leu Leu Ser Gly Ile Val Gln
        530                 535                 540

Gln Gln Ser Asn Leu Leu Arg Ala Ile Glu Ala Gln Gln His Met Leu
545                 550                 555                 560

Gln Leu Thr Val Trp Gly Ile Lys Gln Leu Gln Ala Arg Val Leu Ala
                565                 570                 575

Ile Glu Arg Tyr Leu Lys Asp Gln Gln Leu Leu Gly Leu Trp Gly Cys
        580                 585                 590

Ser Gly Lys Leu Ile Cys Thr Thr Asn Val Pro Trp Asn Ser Ser Trp
        595                 600                 605

Ser Asn Lys Ser Gln Thr Asp Ile Trp Asn Asn Thr Thr Trp Met Gln
        610                 615                 620

Trp Glu Arg Glu Ile Ser Asn Tyr Thr Asp Thr Ile Tyr Arg Leu Leu
625                 630                 635                 640

Glu Asp Ser Gln Asn Gln Gln Glu Glu Asn Glu Lys Asp Leu Leu Ala
                645                 650                 655

Leu Asp Arg Trp Gln Asn Leu Trp Asn Trp Phe Asp Ile Thr Asn Trp
        660                 665                 670

Leu Trp Tyr Ile Lys Ile Phe Ile Met Ile Val Gly Gly Leu Ile Gly
        675                 680                 685

Leu Arg Ile Ile Phe Gly Val Leu Ser Ile Val Lys Arg Val Arg Glu
        690                 695                 700

Gly Tyr Ser Pro Leu Ser Phe Gln Thr Leu Thr Pro Thr Pro Arg Gly
705                 710                 715                 720

Leu Asp Arg Leu Gly Arg Ile Glu Glu Glu Gly Gly Glu Gln Asp Lys
                725                 730                 735

Asp Arg Ser Ile Arg Leu Val Asn Gly Phe Leu Ala Leu Ala Trp Asp
        740                 745                 750
```

-continued

```
Asp Leu Arg Ser Leu Cys Leu Phe Ser Tyr His Gln Leu Arg Asp Phe
        755                 760                 765

Ile Leu Ile Ala Ala Arg Ala Val Glu Leu Leu Gly Arg Ser Ser Leu
    770                 775                 780

Arg Gly Leu Gln Lys Gly Trp Glu Ala Leu Lys Tyr Leu Gly Asn Leu
785                 790                 795                 800

Ile Gln Tyr Trp Gly Leu Glu Leu Lys Arg Arg Ala Ile Asn Leu Leu
                805                 810                 815

Asp Ile Ser Ala Ile Ala Val Ala Glu Gly Thr Asp Arg Ile Ile Asp
            820                 825                 830

Ile Val Leu Arg Thr Gly Arg Ala Ile Arg Asn Ile Pro Arg Arg Ile
        835                 840                 845

Arg Gln Gly Phe Gly Ala Thr Leu Leu
    850                 855

<210> SEQ ID NO 2
<211> LENGTH: 25
<212> TYPE: PRT
<213> ORGANISM: Artificial Sequence
<220> FEATURE:
<223> OTHER INFORMATION: Recombinant polypeptide

<400> SEQUENCE: 2

Asp Leu Leu Ala Leu Asp Arg Trp Gln Asn Leu Trp Asn Trp Phe Asp
1               5                   10                  15

Ile Thr Asn Trp Leu Trp Tyr Ile Lys
            20                  25

<210> SEQ ID NO 3
<211> LENGTH: 25
<212> TYPE: PRT
<213> ORGANISM: Artificial Sequence
<220> FEATURE:
<223> OTHER INFORMATION: Recombinant polypeptide

<400> SEQUENCE: 3

Glu Leu Leu Ala Leu Asp Lys Trp Ala Ser Leu Trp Asn Trp Phe Asp
1               5                   10                  15

Ile Thr Lys Trp Leu Trp Tyr Ile Lys
            20                  25

<210> SEQ ID NO 4
<211> LENGTH: 25
<212> TYPE: PRT
<213> ORGANISM: Artificial Sequence
<220> FEATURE:
<223> OTHER INFORMATION: Recombinant polypeptide

<400> SEQUENCE: 4

Glu Leu Gln Lys Leu Asn Ser Trp Asp Val Phe Gly Asn Trp Phe Asp
1               5                   10                  15

Ile Thr Lys Trp Leu Trp Tyr Ile Lys
            20                  25

<210> SEQ ID NO 5
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 5
```

-continued

```
Glu Val Gln Leu Val Gln Ser Gly Gly Glu Val Lys Arg Pro Gly Ser
1               5                   10                  15

Ser Val Thr Val Ser Cys Lys Ala Thr Gly Gly Thr Phe Ser Thr Leu
            20                  25                  30

Ala Phe Asn Trp Val Arg Gln Ala Pro Gly Gln Gly Pro Glu Trp Met
        35                  40                  45

Gly Gly Ile Val Pro Leu Phe Ser Ile Val Asn Tyr Gly Gln Lys Phe
    50                  55                  60

Gln Gly Arg Leu Thr Ile Arg Ala Asp Lys Ser Thr Thr Thr Val Phe
65                  70                  75                  80

Leu Asp Leu Ser Gly Leu Thr Ser Ala Asp Thr Ala Thr Tyr Tyr Cys
                85                  90                  95

Ala Arg Glu Gly Glu Gly Trp Phe Gly Lys Pro Leu Arg Ala Phe Glu
                100                 105                 110

Phe Trp Gly Gln Gly Thr Val Ile Thr Val Ser Ser
                115                 120
```

<210> SEQ ID NO 6
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 6

```
Lys Val Gln Leu Val Gln Ser Gly Ala Glu Leu Lys Lys Pro Trp Ser
1               5                   10                  15

Ser Val Arg Val Ser Cys Lys Ala Ser Gly Gly Ser Phe Ser Ser Tyr
            20                  25                  30

Ala Phe Asn Trp Val Arg Gln Ala Pro Gly Gln Arg Leu Glu Trp Leu
        35                  40                  45

Gly Gly Ile Val Pro Leu Val Ser Ser Thr Asn Tyr Ala Gln Arg Phe
    50                  55                  60

Arg Gly Arg Val Thr Ile Ser Ala Asp Arg Ser Thr Ser Thr Val Tyr
65                  70                  75                  80

Leu Glu Met Thr Gly Leu Thr Ser Ala Asp Thr Ala Val Tyr Phe Cys
                85                  90                  95

Ala Arg Glu Gly Glu Gly Trp Phe Gly Arg Pro Leu Arg Ala Phe Glu
                100                 105                 110

Phe Trp Gly Gln Gly Thr Leu Val Thr Val Ser Thr
                115                 120
```

<210> SEQ ID NO 7
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

```
Gln Gly Arg Val Thr Ile Thr Ala Asp Lys Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Glu Gly Glu Gly Trp Phe Gly Lys Pro Leu Arg Ala Phe Glu
            100                 105                 110

Phe Trp Gly Gln Gly Thr Val Ile Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 8

Asp Val Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Gly Gly
            20                  25                  30

Ala Leu Ala Trp Tyr Gln Gln Lys Pro Gly Gln Ala Pro Arg Leu Leu
        35                  40                  45

Ile Tyr Asp Thr Ser Ser Arg Pro Thr Gly Val Pro Gly Arg Phe Ser
    50                  55                  60

Gly Ser Gly Ser Gly Thr Asp Phe Ser Leu Thr Ile Ser Arg Leu Glu
65              70                  75                  80

Pro Glu Asp Phe Ala Val Tyr Tyr Cys Gln Gln Tyr Gly Thr Ser Gln
                85                  90                  95

Ser Thr Phe Gly Gln Gly Thr Arg Leu Glu Ile Lys
            100                 105

<210> SEQ ID NO 9
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 9

Glu Ile Val Leu Thr Gln Ser Pro Gly Thr Phe Ala Leu Ser Pro Gly
1               5                   10                  15

Glu Arg Ala Thr Leu Ser Cys Arg Ala Ser Gln Ser Val Ser Gly Gly
            20                  25                  30

Ala Leu Ala Trp Tyr Gln Gln Lys Ala Gly Gln Ala Pro Arg Leu Leu
        35                  40                  45

Ile Tyr Gly Thr Ser Gly Arg Ala Thr Gly Val Pro Gly Arg Phe Ser
    50                  55                  60

Gly Ser Gly Ser Glu Thr Asp Phe Ser Leu Thr Ile Ser Arg Leu Glu
65              70                  75                  80

Pro Glu Asp Phe Ala Val Tyr Tyr Cys Gln Gln Tyr Gly Thr Ser Gln
                85                  90                  95

Ser Thr Phe Gly Gln Gly Thr Arg Leu Glu Thr Arg
            100                 105

<210> SEQ ID NO 10
<211> LENGTH: 108
<212> TYPE: PRT
```

<213> ORGANISM: Artificial Sequence
<220> FEATURE:
<223> OTHER INFORMATION: Recombinant polypeptide

<400> SEQUENCE: 10

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Gln
                85                  90                  95

Ser Thr Phe Gly Gln Gly Thr Arg Leu Glu Thr Arg
            100                 105
```

<210> SEQ ID NO 11
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 11

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Asp
            20                  25                  30

Val Ile Ser Trp Val Arg Gln Ala Pro Gly Gln Gly Leu Glu Trp Met
        35                  40                  45

Gly Arg Val Ile Pro Ile Leu Asp Ile Thr Asn Tyr Ala Gln Lys Phe
    50                  55                  60

Gln Gly Arg Val Thr Ile Thr Ala Asp Lys Ser Thr Ser Thr Val Tyr
65                  70                  75                  80

Met Asp Leu Ser Ser Leu Arg Ser Glu Asp Thr Ala Val Tyr Phe Cys
                85                  90                  95

Ala Arg Glu Gly Glu Gly Trp Phe Gly Lys Pro Leu Arg Ala Phe Glu
            100                 105                 110

Val Trp Gly Gln Gly Thr Gln Ile Thr Val Ser Ser
        115                 120
```

<210> SEQ ID NO 12
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 12

```
Gln Val Gln Leu Val Gln Ser Gly Ala Glu Val Lys Lys Pro Gly Ser
1               5                   10                  15

Ser Val Lys Val Ser Cys Lys Ala Ser Gly Ser Thr Phe Ser Ser Tyr
            20                  25                  30

Ala Ile Ser Trp Val Arg Gln Ala Pro Gly Gln Gly Leu Glu Trp Val
        35                  40                  45
```

```
Gly Gly Ile Val Pro Leu Val Ser Ser Thr Asn Tyr Ala Gln Arg Phe
    50              55              60

Arg Gly Arg Val Thr Ile Ser Ala Asp Arg Ser Thr Ser Thr Val Tyr
65              70              75              80

Leu Glu Met Thr Gly Leu Thr Ser Ala Asp Thr Ala Val Tyr Phe Cys
                85              90              95

Ala Arg Glu Gly Glu Gly Trp Phe Gly Arg Pro Leu Arg Ala Phe Glu
            100             105             110

Phe Trp Gly Gln Gly Thr Leu Val Thr Val Ser Thr
        115             120
```

```
<210> SEQ ID NO 13
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 13
```

```
Lys Val Gln Leu Val Gln Ser Gly Ala Glu Leu Lys Lys Pro Trp Ser
1               5               10              15

Ser Val Arg Val Ser Cys Lys Ala Ser Gly Gly Ser Phe Ser Ser Tyr
            20              25              30

Ala Phe Asn Trp Val Arg Gln Ala Pro Gly Gln Lys Leu Glu Trp Leu
        35              40              45

Gly Gly Ile Ala Ser Leu Leu Val Ser Arg Pro Ser Tyr Ala Gln Arg
    50              55              60

Phe Arg Gly Arg Ile Thr Ile Ser Ala Asp Arg Ser Ala Thr Thr Val
65              70              75              80

Tyr Leu Glu Met Thr Gly Leu Thr Ser Ala Asp Thr Ala Val Tyr Phe
                85              90              95

Cys Ala Arg Glu Gly Glu Gly Trp Phe Gly Lys Pro Leu Arg Ala Phe
            100             105             110

Glu Phe Trp Gly Gln Gly Thr Leu Val Thr Val Ser Thr
        115             120             125
```

```
<210> SEQ ID NO 14
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 14
```

```
Lys Val Gln Leu Val Gln Ser Gly Ala Glu Leu Lys Lys Pro Trp Ser
1               5               10              15

Ser Val Arg Val Ser Cys Lys Ala Ser Gly Gly Ser Phe Ser Ser Tyr
            20              25              30

Ala Phe Asn Trp Val Arg Gln Ala Pro Gly Gln Arg Leu Glu Trp Leu
        35              40              45

Gly Gly Ile Val Pro Leu Val Ser Ser Thr Asn Tyr Ala Gln Arg Phe
    50              55              60

Arg Gly Arg Val Thr Ile Ser Ala Asp Arg Ser Thr Ser Thr Val Tyr
65              70              75              80

Leu Glu Met Thr Gly Leu Thr Ser Ala Asp Thr Ala Val Tyr Phe Cys
                85              90              95

Ala Arg Glu Gly Glu Gly Trp Phe Gly Arg Pro Leu Arg Ala Phe Glu
```

-continued

```
              100               105               110

Phe Trp Gly Gln Gly Thr Leu Val Thr Val Ser Thr
        115               120

<210> SEQ ID NO 15
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 15

Gly Val Gln Leu Val Gln Ser Gly Ala Glu Val Lys Lys Pro Gly Ser
1               5                   10                  15

Ser Met Thr Val Ser Cys Lys Ala Thr Gly Gly Thr Phe Ser Ser Leu
            20                  25                  30

Ala Phe Asn Trp Val Arg Gln Ala Pro Gly Gln Gly Pro Glu Trp Met
        35                  40                  45

Gly Gly Ile Cys Pro Val Phe Ser Ala Leu Val Asn Tyr Gly Gln Arg
    50                  55                  60

Phe Gln Gly Arg Leu Thr Ile Arg Ala Asp Lys Ser Thr Thr Thr Val
65                  70                  75                  80

Tyr Leu Asp Leu Ile Arg Leu Thr Ser Asp Asp Thr Ala Thr Tyr Tyr
                85                  90                  95

Cys Ala Arg Glu Gly Glu Gly Arg Phe Gly Lys Pro Leu Arg Ala Phe
            100               105               110

Glu Val Trp Gly Gln Gly Thr Gln Ile Thr Val Ser Ser
        115               120               125

<210> SEQ ID NO 16
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 16

Lys Val Gln Leu Val Gln Ser Gly Ala Glu Val Lys Arg Pro Gly Ser
1               5                   10                  15

Ser Val Thr Ile Ser Cys Lys Asp Arg Gly Gly Ser Phe Ser Ser Tyr
            20                  25                  30

Ala Phe Asn Trp Val Arg Gln Ala Pro Gly Gln Gly Leu Glu Trp Met
        35                  40                  45

Gly Gly Ile Ile Pro Leu Ile Ser Ile Ala Asn Tyr Ala Ser Arg Arg
    50                  55                  60

Phe Arg Gly Arg Val Thr Ile Thr Ala Asp Arg Ser Thr Ser Ser Ile
65                  70                  75                  80

Phe Leu Asp Leu Thr Arg Leu Thr Ser Val Asp Thr Ala Leu Tyr Phe
                85                  90                  95

Cys Ala Arg Glu Gly Glu Gly Trp Phe Gly Lys Pro Leu Gly Ala Phe
            100               105               110

Glu Phe Trp Gly Gln Gly Thr Ala Val Thr Val Thr Ser
        115               120               125

<210> SEQ ID NO 17
<211> LENGTH: 124
<212> TYPE: PRT
<213> ORGANISM: Artificial Sequence
<220> FEATURE:
```

-continued

<223> OTHER INFORMATION: Recombinant polypeptide

<400> SEQUENCE: 17

Gly Val Gln Leu Val Gln Ser Gly Ala Glu Val Lys Arg Pro Gly Ser
1               5                   10                  15

Ser Val Thr Val Ser Cys Lys Ala Thr Gly Gly Thr Phe Ser Thr Leu
            20                  25                  30

Ala Phe Ser Trp Val Arg Gln Ala Pro Gly Gln Gly Pro Glu Trp Met
        35                  40                  45

Gly Gly Ile Val Pro Leu Phe Thr Ile Val Asn Tyr Gly Gln Arg Phe
    50                  55                  60

Gln Gly Arg Leu Thr Ile Arg Ala Asp Lys Ser Thr Thr Thr Val Phe
65                  70                  75                  80

Leu Asp Leu Ser Gly Leu Thr Ser Ala Asp Thr Ala Thr Tyr Tyr Cys
                85                  90                  95

Ala Arg Glu Gly Glu Gly Trp Phe Gly Lys Pro Leu Arg Ala Leu Glu
            100                 105                 110

Ile Trp Gly Gln Gly Thr Val Ile Thr Val Ser Ser
        115                 120

<210> SEQ ID NO 18
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 18

Arg Val Gln Leu Val Gln Ser Gly Ala Glu Leu Lys Lys Pro Trp Ser
1               5                   10                  15

Ser Val Arg Val Ser Cys Lys Ala Ser Gly Gly Ser Phe Ser Ser Tyr
            20                  25                  30

Ala Phe Ser Trp Val Arg Gln Ala Pro Gly Gln Gly Leu Glu Trp Leu
        35                  40                  45

Gly Gly Ile Val Pro Leu Val Ser Ser Thr Asn Tyr Ala Pro Lys Phe
    50                  55                  60

Arg Gly Arg Ile Thr Ile Ser Ala Asp Arg Ser Ala Asn Thr Val Tyr
65                  70                  75                  80

Leu Glu Met Thr Arg Leu Thr Ser Ala Asp Thr Ala Val Tyr Phe Cys
                85                  90                  95

Ala Arg Glu Gly Glu Gly Trp Phe Gly Arg Pro Leu Arg Ala Phe Glu
            100                 105                 110

Phe Trp Gly Gln Gly Thr Leu Val Thr Val Ser Thr
        115                 120

<210> SEQ ID NO 19
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 19

Lys Val Gln Leu Val Gln Ser Gly Ala Glu Val Met Arg Pro Gly Ser
1               5                   10                  15

Ser Gly Tyr Leu Ser Cys Lys Ala Ser Gly Gly Ser Phe Ser Ser Tyr
            20                  25                  30

Ala Phe Asn Trp Val Arg Gln Ala Pro Gly Gln Gly Leu Glu Trp Met

-continued

```
              35                    40                    45
Gly Gly Ile Ile Pro Leu Ile Ser Ile Ala Asn Tyr Ala Glu Glu Phe
     50                    55                    60

Arg Gly Arg Val Thr Ile Thr Ala Asp Arg Ser Thr Ser Ser Ile Phe
65                    70                    75                    80

Leu Asp Leu Thr Arg Leu Thr Ser Val Asp Thr Ala Leu Tyr Phe Cys
                    85                    90                    95

Ala Arg Glu Gly Glu Gly Trp Phe Gly Lys Pro Leu Gly Ala Phe Glu
                    100                   105                   110

Phe Trp Gly Gln Gly Thr Ala Val Thr Val Thr Ser
              115                   120
```

<210> SEQ ID NO 20
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 20

```
Arg Val Gln Leu Val Gln Ser Gly Ala Glu Val Lys Arg Pro Gly Ser
1                     5                     10                    15

Ser Val Thr Ile Ala Cys Lys Ala Ser Gly Gly Ser Cys Ser Ser Tyr
                    20                    25                    30

Ala Leu His Trp Glu Arg Gln Ala Arg Gly Gln Gly Leu Glu Trp Met
              35                    40                    45

Gly Gly Ile Met Pro Pro Tyr Arg Val Ala Asn Tyr Ala Glu Glu Leu
     50                    55                    60

Arg Gly Arg Val Thr Met Thr Gly Asp Arg Ser Thr Ser Ser Ile Phe
65                    70                    75                    80

Leu Asp Leu Thr Arg Leu Thr Ser Val Asp Thr Ala Leu Tyr Phe Cys
                    85                    90                    95

Ala Arg Glu Gly Glu Gly Trp Phe Gly Lys Pro Leu Gly Ala Phe Glu
              100                   105                   110

Phe Trp Gly Gln Gly Thr Ala Val Thr Val Thr Ser
              115                   120
```

<210> SEQ ID NO 21
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 21

```
Gln Val Gln Leu Ala Gln Ser Gly Thr Glu Val Lys Lys Pro Gly Ser
1                     5                     10                    15

Ser Val Lys Val Ser Cys Lys Ser Ser Gly Gly Thr Ser Ser Asn Tyr
                    20                    25                    30

Ala Ile Thr Trp Val Arg Gln Ala Pro Gly Gln Gly Leu Glu Trp Met
              35                    40                    45

Gly Gly Ile Val Pro Leu Val Ser Ser Thr Asn Tyr Ala Gln Arg Phe
     50                    55                    60

Lys Gly Arg Val Thr Ile Ser Ala Asp Arg Ser Thr Ser Thr Val Phe
65                    70                    75                    80

Met Glu Val Ile Arg Leu Thr Ser Glu Asp Thr Gly Val Tyr Phe Cys
                    85                    90                    95
```

-continued

Ala Arg Glu Gly Glu Gly Trp Phe Gly Lys Pro Leu Arg Ala Phe Glu
                100                     105                     110

Phe Trp Gly His Gly Thr Ala Val Thr Val Ser Ser
        115                     120

<210> SEQ ID NO 22
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 22

Gly Val Gln Leu Val Gln Ser Gly Ala Glu Val Asn Glu Gly Pro Gly
1                   5                       10                      15

Ser Ser Val Glu Val Ser Cys Lys Ala Thr Gly Gly Thr Phe Ser Thr
                20                      25                      30

Leu Ala Phe Asn Trp Val Arg Gln Ala Pro Gly Gln Gly Pro Glu Trp
        35                      40                      45

Met Gly Gly Ile Val Pro Leu Phe Ser Ile Val Asn Tyr Gly Gln Arg
    50                      55                      60

Phe Gln Gly Arg Val Thr Ile Arg Ala Asp Lys Ser Thr Thr Thr Val
65                      70                      75                      80

Phe Leu Asp Leu Ser Arg Leu Thr Ser Ala Asp Thr Ala Thr Tyr Tyr
                85                      90                      95

Cys Ala Arg Glu Gly Glu Gly Trp Phe Gly Lys Pro Leu Arg Ala Leu
                100                     105                     110

Glu Ile Trp Gly Gln Gly Thr Val Ile Thr Val Ser Ser
        115                     120                     125

<210> SEQ ID NO 23
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 23

Gly Val Gln Leu Val Gln Ser Gly Ala Glu Val Lys Arg Pro Gly Ser
1                   5                       10                      15

Ser Met Thr Val Ser Cys Arg Ala Thr Gly Gly Thr Phe Ser Ser Leu
                20                      25                      30

Ala Phe Asn Trp Val Arg Gln Ala Pro Gly Gln Gly Pro Glu Trp Met
        35                      40                      45

Gly Arg Glu Ile Val Pro Leu Phe Arg Ile Ala Asn Tyr Gly Gln Lys
    50                      55                      60

Phe Gln Gly Arg Leu Thr Ile Arg Ala Asp Lys Ser Thr Thr Thr Ile
65                      70                      75                      80

Tyr Leu Asp Leu Ser Ser Leu Thr Ser Ala Asp Thr Ala Thr Tyr Tyr
                85                      90                      95

Cys Ala Arg Glu Gly Glu Gly Trp Phe Gly Lys Pro Leu Arg Ala Phe
                100                     105                     110

Glu Phe Trp Gly Gln Gly Thr Val Ile Thr Val Ser Ser
        115                     120                     125

<210> SEQ ID NO 24
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 24

```
Lys Val Gln Leu Val Gln Ser Gly Ala Glu Leu Lys Lys Pro Trp Ser
1               5                   10                  15

Ser Val Asn Glu Val Ser Cys Lys Val Ser Gly Gly Ser Phe Ser Ser
            20                  25                  30

Tyr Ala Phe Asn Trp Val Arg Gln Ala Pro Gly Gln Arg Leu Glu Trp
        35                  40                  45

Leu Gly Gly Ile Val Pro Leu Val Ser Ser Thr Asn Tyr Ala Gln Arg
    50                  55                  60

Phe Arg Gly Arg Ile Thr Ile Ser Ala Asp Arg Ser Thr Ser Thr Val
65                  70                  75                  80

Tyr Leu Glu Met Thr Gly Leu Thr Ser Ala Asp Thr Ala Val Tyr Phe
                85                  90                  95

Cys Ala Arg Glu Gly Glu Gly Trp Phe Gly Lys Pro Leu Arg Ala Phe
            100                 105                 110

Glu Phe Trp Gly Gln Gly Thr Leu Val Thr Val Ser Thr
        115                 120                 125
```

<210> SEQ ID NO 25
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 25

```
Lys Val Gln Leu Val Gln Ser Gly Ala Glu Val Lys Arg Pro Gly Ser
1               5                   10                  15

Ser Val Thr Ile Ser Cys Lys Gly Thr Arg Gly Gly Ser Phe Ser Ser
            20                  25                  30

Tyr Ala Phe Asn Trp Val Arg Gln Ala Pro Gly Leu Gly Leu Glu Trp
        35                  40                  45

Met Gly Gly Ile Ile Pro Leu Ile Ser Ile Ala Asn Tyr Ala Glu Arg
    50                  55                  60

Phe Arg Gly Arg Val Thr Ile Thr Ala Asp Arg Ser Thr Ser Ser Ile
65                  70                  75                  80

Phe Leu Asp Leu Thr Arg Leu Thr Ser Val Asp Thr Ala Leu Tyr Phe
                85                  90                  95

Cys Ala Arg Glu Gly Glu Gly Trp Phe Gly Lys Pro Leu Gly Ala Phe
            100                 105                 110

Glu Phe Trp Gly Gln Gly Thr Ala Val Thr Val Thr Ser
        115                 120                 125
```

<210> SEQ ID NO 26
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 26

```
Arg Val Gln Leu Val Gln Ser Gly Ala Glu Val Lys Arg Pro Gly Ser
1               5                   10                  15

Ser Val Thr Val Ser Cys Lys Ala Thr Gly Gly Thr Phe Ser Thr Leu
            20                  25                  30
```

-continued

Ala Phe Ser Trp Val Arg Gln Ala Pro Gly Gln Gly Pro Glu Trp Met
        35                  40                  45

Gly Gly Ile Val Pro Leu Phe Thr Ile Val Asn Tyr Gly Gln Arg Phe
    50                  55                  60

Gln Gly Arg Leu Thr Ile Arg Ala Asp Lys Ser Thr Thr Thr Val Phe
65                  70                  75                  80

Leu Asp Leu Ser Gly Leu Thr Ser Ala Asp Thr Ala Thr Tyr Tyr Cys
                85                  90                  95

Ala Arg Glu Gly Glu Gly Trp Phe Gly Lys Pro Leu Arg Ala Pro Glu
            100                 105                 110

Ile Trp Gly Gln Gly Thr Val Ile Thr Val Ser Ser
        115                 120

<210> SEQ ID NO 27
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 27

Gly Val Gln Leu Val Ala Ser Gly Ala Glu Val Lys Lys Pro Gly Ser
1               5                   10                  15

Ser Val Glu Val Ser Cys Lys Ala Thr Gly Gly Thr Phe Asn Ser Leu
            20                  25                  30

Ala Phe Asn Trp Val Arg Gln Ala Pro Gly Gln Gly Pro Glu Tyr Met
        35                  40                  45

Gly Gly Ile Val Pro Leu Phe Ser Ile Val Asn Tyr Gly Gln Arg Phe
    50                  55                  60

Gln Gly Arg Leu Thr Ile Arg Ala Asp Lys Ser Thr Thr Thr Val Tyr
65                  70                  75                  80

Met Asp Leu Asn Arg Leu Thr Ser Asp Asp Thr Ala Thr Tyr Tyr Cys
                85                  90                  95

Ala Arg Glu Gly Glu Gly Trp Phe Gly Lys Pro Leu Arg Ala Phe Gln
            100                 105                 110

Leu Trp Gly Gln Gly Thr Val Ile Thr Val Ser Ser
        115                 120

<210> SEQ ID NO 28
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 28

Lys Val Gln Leu Val Gln Ser Gly Ala Glu Val Lys Arg Pro Gly Ser
1               5                   10                  15

Ser Val Thr Ile Ser Cys Lys Asp Ser Gly Gly Ser Phe Ser Ser Tyr
            20                  25                  30

Ala Phe Asn Trp Val Arg Gln Ala Pro Gly Gln Gly Leu Glu Trp Met
        35                  40                  45

Gly Gly Ile Ile Pro Leu Ile Ser Ser Thr Asn Tyr Ala Glu Lys Phe
    50                  55                  60

Arg Gly Arg Val Thr Ile Thr Ala Asp Arg Ser Thr Ser Ser Ile Phe
65                  70                  75                  80

Leu Asp Leu Thr Arg Leu Thr Ser Ala Asp Thr Ala Leu Tyr Phe Cys
                85                  90                  95

-continued

Ala Arg Glu Gly Glu Gly Trp Phe Gly Lys Pro Leu Gly Ala Phe Glu
                100                     105                     110

Phe Trp Gly Gln Gly Thr Ala Val Thr Val Thr Ser
        115                     120

<210> SEQ ID NO 29
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 29

Lys Val Gln Leu Val Gln Ser Gly Asp Val Lys Leu Lys Thr Pro Trp
1                   5                       10                      15

Ser Ser Val Arg Val Ser Cys Lys Ala Ser Gly Gly Ser Phe Ser Ser
                20                      25                      30

Tyr Ala Phe Asn Trp Val Arg Gln Ala Pro Gly Gln Arg Leu Glu Trp
        35                      40                      45

Leu Gly Gly Ile Val Pro Leu Val Ser Ser Thr Asn Tyr Ala Gln Arg
    50                      55                      60

Phe Arg Gly Arg Val Thr Ile Ser Ala Asp Arg Ser Ala Asn Thr Val
65                      70                      75                      80

Tyr Leu Glu Met Thr Gly Leu Thr Ser Ala Asp Thr Ala Ile Tyr Phe
                85                      90                      95

Cys Ala Arg Glu Gly Glu Gly Trp Phe Gly Lys Pro Leu Arg Ala Phe
                100                     105                     110

Glu Phe Trp Gly Gln Gly Thr Leu Val Ser Val Ser Thr
        115                     120                     125

<210> SEQ ID NO 30
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 30

Lys Val Gln Leu Val Gln Ser Gly Ala Glu Leu Lys Lys Pro Trp Ser
1                   5                       10                      15

Ser Val Arg Val Ser Cys Lys Ala Ser Gly Gly Ser Phe Ser Ser Tyr
                20                      25                      30

Ala Phe Asn Trp Val Arg Gln Ala Pro Gly Gln Arg Leu Glu Cys Met
        35                      40                      45

Gly Gly Ile Val Pro Leu Val Ser Ser Thr Asn Tyr Ala Gln Arg Phe
    50                      55                      60

Arg Gly Arg Ile Thr Ile Ser Ala Asp Arg Ser Ala Ser Thr Val Tyr
65                      70                      75                      80

Leu Glu Met Thr Gly Leu Thr Ser Ala Asp Thr Ala Val Tyr Phe Cys
                85                      90                      95

Ala Arg Glu Gly Glu Gly Trp Phe Gly Lys Pro Leu Arg Ala Phe Glu
                100                     105                     110

Phe Trp Gly Gln Gly Thr Leu Val Ala Val Ser Thr
        115                     120

<210> SEQ ID NO 31
<211> LENGTH: 124
<212> TYPE: PRT

```
<213> ORGANISM: Artificial Sequence
<220> FEATURE:
<223> OTHER INFORMATION: Recombinant polypeptide

<400> SEQUENCE: 31

Lys Val Gln Leu Val Gln Ser Gly Ala Glu Leu Lys Lys Pro Trp Ser
1               5                   10                  15

Ser Val Arg Val Ser Cys Lys Ala Thr Gly Gly Ser Phe Ser Ser Tyr
            20                  25                  30

Ala Phe Asn Trp Val Arg Pro Ala Pro Gly Gln Arg Leu Glu Trp Leu
        35                  40                  45

Gly Gly Ile Val Pro Leu Val Ser Ser Thr Asn Tyr Ala Gln Arg Phe
    50                  55                  60

Arg Gly Arg Ile Thr Ile Ser Ala Asp Arg Ser Ala Ser Thr Val Tyr
65                  70                  75                  80

Leu Glu Met Thr Gly Leu Thr Ser Ala Asp Thr Ala Val Tyr Phe Cys
                85                  90                  95

Ala Arg Glu Gly Glu Gly Trp Phe Gly Arg Pro Leu Arg Ala Phe Glu
            100                 105                 110

Phe Trp Gly Gln Gly Thr Leu Val Thr Val Ser Thr
        115                 120

<210> SEQ ID NO 32
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 32

Lys Val Gln Leu Val Gln Ser Gly Ala Glu Val Lys Arg Pro Gly Ser
1               5                   10                  15

Ser Val Thr Ile Ser Cys Lys Ala Ser Gly Gly Ser Phe Ser Ser Tyr
            20                  25                  30

Ala Phe Asn Trp Val Arg Gln Ala Pro Gly Leu Gly Leu Glu Trp Met
        35                  40                  45

Gly Gly Ile Ile Pro Leu Ile Ser Ile Ala Asn Tyr Ala Gln Arg Arg
    50                  55                  60

Phe Arg Gly Arg Val Thr Ile Thr Ala Asp Arg Ser Thr Ser Ser Ile
65                  70                  75                  80

Phe Leu Asp Leu Thr Arg Leu Thr Ser Val Asp Thr Ala Leu Tyr Phe
                85                  90                  95

Cys Ala Arg Glu Gly Glu Gly Trp Phe Gly Lys Pro Leu Gly Ala Phe
            100                 105                 110

Glu Phe Trp Gly Gln Gly Thr Ala Val Thr Val Thr Ser
        115                 120                 125

<210> SEQ ID NO 33
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 33

Lys Val Gln Leu Val Gln Ser Gly Ala Glu Leu Lys Lys Pro Trp Ser
1               5                   10                  15

Ser Met Arg Val Ser Cys Lys Ala Ser Gly Gly Ser Phe Ser Ser Tyr
            20                  25                  30
```

Ala Phe Asn Trp Val Arg Gln Ala Pro Gly Gln Arg Leu Glu Trp Leu
        35                      40                      45

Gly Gly Ile Val Pro Leu Val Ser Ser Thr Asn Tyr Ala Gln Arg Phe
    50                      55                      60

Arg Gly Arg Ile Thr Ile Ser Ala Asp Arg Ser Ala Ser Thr Val Tyr
65                      70                      75                      80

Leu Glu Met Thr Gly Leu Thr Ser Ala Asp Thr Ala Val Tyr Phe Cys
                        85                      90                      95

Ala Arg Glu Gly Glu Gly Trp Phe Gly Lys Pro Leu Arg Ala Phe Glu
                        100                     105                     110

Phe Trp Gly Gln Gly Thr Leu Val Thr Val Ser Ala
        115                     120

<210> SEQ ID NO 34
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 34

Gly Val Gln Leu Val Gln Ser Gly Ala Glu Val Lys Lys Pro Gly Ser
1                       5                       10                      15

Ser Val Thr Val Ser Cys Lys Ala Thr Gly Gly Thr Phe Ser Ser Leu
                        20                      25                      30

Ala Phe Asn Trp Val Arg Pro Met Ala Pro Gly Gln Gly Pro Glu Trp
        35                      40                      45

Met Gly Gly Ile Val Pro Leu Phe Ser Ile Val Asn Tyr Gly Gln Arg
    50                      55                      60

Phe Gln Gly Arg Leu Thr Ile Arg Ala Asp Lys Ser Thr Thr Thr Val
65                      70                      75                      80

Tyr Leu Asp Leu Ile Arg Leu Thr Ser Asp Asp Thr Ala Thr Tyr Tyr
                        85                      90                      95

Cys Ala Arg Glu Gly Glu Gly Trp Phe Gly Lys Pro Leu Arg Ala Phe
                        100                     105                     110

Glu Phe Trp Gly Gln Gly Thr Leu Ile Thr Val Ser Ser
        115                     120                     125

<210> SEQ ID NO 35
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 35

Gly Val Gln Leu Val Gln Ser Gly Ala Glu Val Lys Lys Pro Gly Val
1                       5                       10                      15

Ser Val Thr Val Ser Cys Lys Ala Thr Gly Gly Thr Phe Ser Ser Leu
                        20                      25                      30

Ala Phe Asn Trp Val Arg Gln Ala Pro Gly Gln Gly Pro Glu Tyr Met
        35                      40                      45

Gly Gly Ile Val Pro Leu Phe Ser Ile Val Asn Tyr Ala Gln Arg Phe
    50                      55                      60

Gln Gly Arg Leu Thr Ile Arg Ala Asp Lys Ser Thr Thr Thr Val Tyr
65                      70                      75                      80

Met Asp Leu Asn Arg Leu Thr Ser Asp Asp Thr Ala Thr Tyr Tyr Cys

-continued

```
              85              90              95

Ala Arg Glu Gly Glu Gly Trp Phe Gly Lys Pro Leu Arg Ala Phe Gln
              100             105             110

Leu Trp Gly Gln Gly Thr Val Ile Thr Val Ser Ser
              115             120

<210> SEQ ID NO 36
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 36

Gly Val Gln Leu Val Gln Ser Gly Ala Glu Val Lys Arg Pro Gly Ser
1               5               10              15

Ser Val Glu Val Ser Cys Lys Ala Thr Gly Gly Thr Phe Ser Thr Leu
              20              25              30

Ala Phe Ser Trp Val Arg Gln Ala Pro Gly Gln Gly Pro Glu Trp Met
              35              40              45

Gly Gly Ile Val Pro Leu Phe Thr Ile Val Asn Tyr Gly Gln Arg Phe
        50              55              60

Gln Gly Arg Leu Thr Ile Arg Ala Asp Lys Ser Thr Thr Thr Val Phe
65              70              75              80

Leu Asp Leu Ser Gly Leu Thr Ser Ala Asp Thr Ala Thr Tyr Tyr Cys
              85              90              95

Ala Arg Glu Gly Glu Gly Trp Phe Gly Lys Pro Leu Arg Ala Leu Glu
              100             105             110

Ile Trp Gly Gln Gly Thr Val Ile Thr Val Ser Ser
        115             120

<210> SEQ ID NO 37
<211> LENGTH: 125
<212> TYPE: PRT
<213> ORGANISM: Artificial Sequence
<220> FEATURE:
<223> OTHER INFORMATION: Recombinant polypeptide

<400> SEQUENCE: 37

Lys Val Gln Leu Val Gln Ser Gly Ala Glu Met Lys Arg Pro Gly Ser
1               5               10              15

Ser Val His Ala Ala Cys Lys Asp Arg Gly Gly Ser Phe Ser Ser Tyr
              20              25              30

Ala Ile Ile Trp Val Arg Gln Ala Arg Glu Leu Gly Phe Glu Trp Met
        35              40              45

Gly Gly Ile Ile Pro Leu Leu Ser Arg Ala Asn Tyr Ala Gln Arg Trp
        50              55              60

Phe Arg Gly Arg Val Thr Ile Thr Ala His Glu Ser Thr Ser Ser Ile
65              70              75              80

Phe Leu Asp Leu Thr Arg Leu Thr Ser Val Asp Thr Ala Leu Tyr Phe
              85              90              95

Cys Ala Arg Glu Gly Glu Gly Trp Phe Gly Lys Pro Leu Gly Ala Phe
              100             105             110

Glu Phe Trp Gly Gln Gly Thr Ala Val Thr Val Thr Ser
        115             120             125

<210> SEQ ID NO 38
<211> LENGTH: 108
```

<212> TYPE: PRT
<213> ORGANISM: Artificial Sequence
<220> FEATURE:
<223> OTHER INFORMATION: Recombinant polypeptide

<400> SEQUENCE: 38

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Ser Asn
            20                  25                  30

Tyr Leu Ala Trp Tyr Gln Gln Lys Pro Gly Gln Ala Pro Arg Leu Leu
        35                  40                  45

Ile Tyr Arg Ala Leu Gly Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Glu
                85                  90                  95

Ser Thr Phe Gly Gln Gly Thr Arg Leu Glu Ile Arg
            100                 105
```

<210> SEQ ID NO 39
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 39

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Gly Gly
            20                  25                  30

Ala Leu Ala Trp Tyr Gln Gln Lys Ala Gly Gln Ala Pro Arg Leu Leu
        35                  40                  45

Ile Tyr Asp Thr Ser Gly Arg Ala Thr Gly Val Pro Gly Arg Phe Ser
    50                  55                  60

Gly Ser Gly Ser Glu Thr Asp Phe Ser Leu Thr Ile Ser Arg Leu Glu
65                  70                  75                  80

Pro Glu Asp Phe Ala Val Tyr Tyr Cys Gln Gln Tyr Gly Thr Ser Gln
                85                  90                  95

Ser Thr Phe Gly Gln Gly Thr Arg Leu Glu Thr Arg
            100                 105
```

<210> SEQ ID NO 40
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 40

```
Glu Ile Val Leu Thr Gln Ser Pro Gly Thr Phe Ala Leu Ser Pro Gly
1               5                   10                  15

Glu Arg Ala Thr Leu Ser Cys Arg Ala Ser Gln Ser Val Ser Gly Gly
            20                  25                  30

Ala Leu Ala Trp Tyr Gln Gln Lys Ala Gly Gln Ala Pro Arg Leu Leu
        35                  40                  45

Ile Tyr Gly Thr Ser Gly Arg Ala Thr Gly Val Pro Gly Arg Phe Ser
```

```
        50              55              60

Gly Ser Gly Ser Glu Thr Asp Phe Ser Leu Thr Ile Ser Arg Leu Glu
65              70              75              80

Pro Glu Asp Phe Ala Val Tyr Tyr Cys Gln Gln Tyr Gly Thr Ser Gln
                85              90              95

Ser Thr Phe Gly Gln Gly Thr Arg Leu Glu Thr Arg
            100             105

<210> SEQ ID NO 41
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 41

Arg Ile Val Leu Thr Gln Ser Pro Gly Thr Leu Ser Leu Ser Pro Gly
1               5               10              15

Ala Arg Ala Thr Leu Ser Cys Arg Ala Ser Gln Ser Val Ser Gly Gly
                20              25              30

Ser Leu Ala Trp Tyr Gln Gln Lys Ala Gly Arg Ala Pro Arg Ser Val
            35              40              45

Ile Tyr Asp Ala Val Arg Arg Ala Thr Ala Ile Pro Gly Arg Phe Ser
        50              55              60

Gly Ser Gly Ser Glu Thr Asp Phe Ser Leu Thr Ile Ser Arg Leu Glu
65              70              75              80

Pro Glu Asp Leu Ala Val Tyr Tyr Cys Gln Gln Tyr Gly Thr Ser Gln
                85              90              95

Ser Thr Phe Gly Gln Gly Thr Arg Leu Glu Ile Arg
            100             105

<210> SEQ ID NO 42
<211> LENGTH: 109
<212> TYPE: PRT
<213> ORGANISM: Artificial Sequence
<220> FEATURE:
<223> OTHER INFORMATION: Recombinant polypeptide

<400> SEQUENCE: 42

Glu Ile Val Leu Thr Gln Pro Pro Gly Asn Phe Trp Ser Leu Ser Pro
1               5               10              15

Gly Gln Arg Ala Thr Leu Ser Cys Arg Ala Gly Gln Ser Val Ser Gly
                20              25              30

Gly Ser Leu Ala Trp Tyr Gln Gln Lys Ala Gly Gln Ala Pro Arg Leu
            35              40              45

Leu Ile Tyr Asp Thr Ser Ser Arg Ala Thr Gly Val Arg Asp Arg Phe
        50              55              60

Ser Gly Ser Gly Ser Glu Thr Asp Phe Ser Leu Thr Ile Ser Arg Leu
65              70              75              80

Glu Pro Glu Asp Phe Ala Val Tyr Tyr Cys Gln Gln Tyr Gly Thr Ser
                85              90              95

Gln Ser Thr Phe Gly Gln Gly Thr Arg Leu Glu Met Arg
            100             105

<210> SEQ ID NO 43
<211> LENGTH: 108
<212> TYPE: PRT
<213> ORGANISM: Artificial Sequence
<220> FEATURE:
```

-continued

```
<223> OTHER INFORMATION: Recombinant polypeptide

<400> SEQUENCE: 43

Glu Ile Val Leu Thr Gln Ser Pro Val Thr Leu Ser Leu Ser Pro Gly
1               5                   10                  15

Arg Lys Gly Thr Leu Ser Cys Arg Ala Ser Gln Ser Val Ser Gly Gly
            20                  25                  30

Ser Leu Ala Trp Tyr Gln Gln Lys Pro Gly Gln Ala Pro Arg Leu Leu
        35                  40                  45

Ile Tyr Asp Ser Ser Thr Arg Ala Thr Gly Val Pro Gly Arg Phe Ser
    50                  55                  60

Gly Ser Gly Ser Glu Thr Asp Phe Ser Leu Thr Ile Ser Arg Leu Glu
65                  70                  75                  80

Ala Glu Asp Phe Ala Val Tyr Tyr Cys Gln Gln Tyr Gly Thr Ser Gln
                85                  90                  95

Ser Thr Phe Gly Gln Gly Thr Arg Leu Glu Ile Arg
            100                 105

<210> SEQ ID NO 44
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 44

Asp Ile Val Leu Thr Gln Ser Pro Gly Arg Phe Ser Leu Ser Pro Glu
1               5                   10                  15

Glu Arg Ala Thr Leu Ser Cys Arg Ala Ser Gln Ser Val Ser Gly Gly
            20                  25                  30

Tyr Val Ala Trp Tyr Gln Gln Lys Ala Gly Gln Ala Pro Arg Leu Pro
        35                  40                  45

Ile Tyr Asp Tyr Val Ser Arg Ala Thr Gly Val Pro Gly Arg Phe Ser
    50                  55                  60

Gly Ser Gly Ser Glu Thr Asp Phe Ser Leu Thr Ile Ser Arg Leu Glu
65                  70                  75                  80

Pro Glu Asp Phe Ala Val Tyr Tyr Cys Gln Gln Tyr Gly Thr Ser Gln
                85                  90                  95

Ser Thr Phe Gly Gln Gly Thr Arg Leu Glu Ile Arg
            100                 105

<210> SEQ ID NO 45
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 45

Glu Met Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Val Tyr Asn
            20                  25                  30

Ser Leu Ala Trp Tyr Gln Gln Arg Pro Gly Gln Ala Pro Arg Leu Ala
        35                  40                  45

Ile Leu Ala Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
```

```
65              70              75              80

Pro Glu Asp Phe Ala Val Tyr Tyr Cys Gln Gln Tyr Gly Thr Ser Gln
                85              90              95

Gly Thr Phe Gly Gln Gly Thr Lys Val Glu Ile Lys
            100             105
```

<210> SEQ ID NO 46
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 46

```
Glu Ile Val Leu Thr Gln Ser Pro Gly Thr Leu Ser Leu Ser Pro Gly
1               5               10              15

Glu Arg Ala Thr Leu Ser Cys Arg Ala Ser Gln Ser Val Ser Ser Ser
                20              25              30

Tyr Leu Ala Trp Tyr Gln Gln Lys Pro Gly Gln Ala Pro Arg Leu Leu
            35              40              45

Ile Tyr Gly Ala Tyr Ile Arg Ala Thr Gly Ile Pro Asp Arg Phe Ser
        50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys Gln Gln Tyr Gly Thr Ser Gln
                85              90              95

Gly Thr Phe Gly Gln Gly Thr Lys Val Glu Ile Lys
            100             105
```

<210> SEQ ID NO 47
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 47

```
Arg Met Val Leu Thr Gln Ser Pro Gly Thr Leu Ser Leu Ser Pro Gly
1               5               10              15

Glu Gly Ala Thr Leu Ser Cys Gly Ala Ser Gln Ser Val Val Tyr Asn
                20              25              30

Ser Leu Ala Trp Tyr Gln Gln Arg Pro Gly Gln Ala Pro Arg Leu Val
            35              40              45

Ile Leu Ala Ala Ser Arg Arg Ala Ala Gly Ile Pro Asp Arg Phe Ser
        50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys Gln Gln Tyr Gly Thr Ser Gln
                85              90              95

Gly Thr Phe Gly Gln Gly Thr Lys Val Glu Ile Lys
            100             105
```

<210> SEQ ID NO 48
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 48

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Gly Trp Phe Gly Glu Pro Leu Arg Ala Phe Asp
            100                 105                 110

Val Trp Gly Gln Gly Thr Val Ile Thr Val Ser Ser
        115                 120
```

```
<210> SEQ ID NO 49
<211> LENGTH: 109
<212> TYPE: PRT
<213> ORGANISM: Artificial Sequence
<220> FEATURE:
<223> OTHER INFORMATION: Recombinant polypeptide

<400> SEQUENCE: 49
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Gln
                85                  90                  95

Ser Thr Phe Gly Gln Gly Thr Arg Leu Glu Ile Lys Arg
            100                 105
```

```
<210> SEQ ID NO 50
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 50
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
```

-continued

```
65              70              75              80

Met Glu Leu Ser Ser Leu Arg Ser Glu Asp Thr Ala Val Tyr Tyr Cys
                85              90              95

Ala Arg Glu Gly Glu Gly Trp Phe Gly Glu Pro Leu Arg Ala Phe Glu
            100             105             110

Phe Trp Gly Gln Gly Thr Val Ile Thr Val Ser Ser
        115             120
```

<210> SEQ ID NO 51
<211> LENGTH: 109
<212> TYPE: PRT
<213> ORGANISM: Artificial Sequence
<220> FEATURE:
<223> OTHER INFORMATION: Recombinant polypeptide

<400> SEQUENCE: 51

```
Glu Ile Val Leu Thr Gln Ser Pro Gly Thr Leu Ser Leu Ser Pro Gly
1               5               10              15

Glu Arg Ala Thr Leu Ser Cys Arg Ala Ser Gln Ser Val Ser Ser Ser
            20              25              30

Tyr Leu Ala Trp Tyr Gln Gln Lys Pro Gly Gln Ala Pro Arg Leu Leu
        35              40              45

Ile Tyr Gly Ala Ser Ser Arg Ala Thr Gly Ile Pro Asp Arg Phe Ser
    50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys Gln Gln Tyr Gly Thr Ser Gln
                85              90              95

Ser Thr Phe Gly Gln Gly Thr Arg Leu Glu Ile Lys Arg
            100             105
```

<210> SEQ ID NO 52
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 52

```
Gln Val Gln Leu Val Gln Ser Gly Gly Glu Val Lys Arg Pro Gly Ser
1               5               10              15

Ser Val Thr Val Ser Cys Lys Ala Thr Gly Gly Thr Phe Ser Thr Leu
            20              25              30

Ala Phe Asn Trp Val Arg Gln Ala Pro Gly Gln Gly Pro Glu Trp Met
        35              40              45

Gly Gly Ile Val Pro Leu Phe Ser Ile Val Asn Tyr Gly Gln Lys Phe
    50              55              60

Gln Gly Arg Leu Thr Ile Arg Ala Asp Lys Ser Thr Thr Thr Val Phe
65              70              75              80

Leu Asp Leu Ser Gly Leu Thr Ser Ala Asp Thr Ala Thr Tyr Tyr Cys
                85              90              95

Ala Arg Glu Gly Glu Gly Ala Phe Gly Lys Pro Leu Arg Ala Phe Glu
            100             105             110

Phe Trp Gly Gln Gly Thr Val Ile Thr Val Ser Ser
        115             120
```

<210> SEQ ID NO 53
<211> LENGTH: 124

```
<212> TYPE: PRT
<213> ORGANISM: Artificial Sequence
<220> FEATURE:
<223> OTHER INFORMATION: Recombinant polypeptide

<400> SEQUENCE: 53

Gln Val Gln Leu Val Gln Ser Gly Gly Glu Val Lys Arg Pro Gly Ser
1               5                   10                  15

Ser Val Thr Val Ser Cys Lys Ala Thr Gly Gly Thr Phe Ser Thr Leu
                20                  25                  30

Ala Phe Asn Trp Val Arg Gln Ala Pro Gly Gln Gly Pro Glu Trp Met
            35                  40                  45

Gly Gly Ile Val Pro Leu Phe Ser Ile Val Asn Tyr Gly Gln Lys Phe
        50                  55                  60

Gln Gly Arg Leu Thr Ile Arg Ala Asp Lys Ser Thr Thr Thr Val Phe
65                  70                  75                  80

Leu Asp Leu Ser Gly Leu Thr Ser Ala Asp Thr Ala Thr Tyr Tyr Cys
                85                  90                  95

Ala Arg Glu Gly Glu Gly Trp Ala Gly Lys Pro Leu Arg Ala Phe Glu
            100                 105                 110

Phe Trp Gly Gln Gly Thr Val Ile Thr Val Ser Ser
        115                 120

<210> SEQ ID NO 54
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Glu Gly Ala Phe Gly Lys Pro Leu Arg Ala Phe Glu
            100                 105                 110

Phe Trp Gly Gln Gly Thr Val Ile Thr Val Ser Ser
        115                 120

<210> SEQ ID NO 55
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

-continued

```
                20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Gly Glu Gly Trp Ala Gly Lys Pro Leu Arg Ala Phe Glu
                100                 105                 110
Phe Trp Gly Gln Gly Thr Val Ile Thr Val Ser Ser
        115                 120
```

<210> SEQ ID NO 56
<211> LENGTH: 127
<212> TYPE: PRT
<213> ORGANISM: Artificial Sequence
<220> FEATURE:
<223> OTHER INFORMATION: Recombinant polypeptide

<400> SEQUENCE: 56

```
Gln Val Gln Leu Val Gln Ser Gly Gly Glu Val Lys Arg Pro Gly Ser
1               5                   10                  15
Ser Val Thr Val Ser Cys Lys Ala Thr Gly Gly Thr Phe Ser Thr Leu
                20                  25                  30
Ala Phe Asn Trp Val Arg Gln Ala Pro Gly Gln Gly Pro Glu Trp Met
        35                  40                  45
Gly Gly Ile Val Pro Leu Phe Ser Ile Val Asn Tyr Gly Gln Lys Phe
    50                  55                  60
Gln Gly Arg Leu Thr Ile Arg Ala Asp Lys Ser Thr Thr Thr Val Phe
65                  70                  75                  80
Leu Asp Leu Ser Gly Leu Thr Ser Ala Asp Thr Ala Thr Tyr Tyr Cys
                85                  90                  95
Ala Arg Glu Gly Glu Thr Gly Trp Gly Trp Phe Gly Lys Pro Leu Arg
                100                 105                 110
Ala Phe Glu Phe Trp Gly Gln Gly Thr Val Ile Thr Val Ser Ser
        115                 120                 125
```

<210> SEQ ID NO 57
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 57

```
Lys Val Gln Leu Val Gln Ser Gly Ala Glu Leu Lys Lys Pro Trp Ser
1               5                   10                  15
Ser Val Arg Val Ser Cys Lys Ala Ser Gly Gly Ser Phe Ser Ser Tyr
                20                  25                  30
Ala Phe Asn Trp Val Arg Gln Ala Pro Gly Gln Arg Leu Glu Trp Leu
        35                  40                  45
Gly Gly Ile Val Pro Leu Val Ser Ser Thr Asn Tyr Ala Gln Arg Phe
    50                  55                  60
Arg Gly Arg Val Thr Ile Ser Ala Asp Pro Glu Thr Ser Thr Val Tyr
65                  70                  75                  80
```

```
Leu Glu Met Thr Gly Leu Thr Ser Ala Asp Thr Ala Val Tyr Phe Cys
                85                  90                  95

Ala Arg Glu Gly Glu Gly Trp Phe Gly Arg Pro Leu Arg Ala Phe Glu
            100                 105                 110

Phe Trp Gly Gln Gly Thr Leu Val Thr Val Ser Thr
        115                 120
```

<210> SEQ ID NO 58
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 58

```
Lys Val Gln Leu Val Gln Ser Gly Ala Glu Leu Lys Lys Pro Trp Ser
1               5                   10                  15

Ser Val Arg Val Ser Cys Lys Ala Ser Gly Gly Glu Pro Glu Ser Tyr
            20                  25                  30

Ala Phe Asn Trp Val Arg Gln Ala Pro Gly Gln Arg Leu Glu Trp Leu
        35                  40                  45

Gly Gly Ile Val Pro Leu Val Ser Ser Thr Asn Tyr Ala Gln Arg Phe
    50                  55                  60

Arg Gly Arg Val Thr Ile Ser Ala Asp Arg Ser Thr Ser Thr Val Tyr
65                  70                  75                  80

Leu Glu Met Thr Gly Leu Thr Ser Ala Asp Thr Ala Val Tyr Phe Cys
                85                  90                  95

Ala Arg Glu Gly Glu Gly Trp Phe Gly Arg Pro Leu Arg Ala Phe Glu
            100                 105                 110

Phe Trp Gly Gln Gly Thr Leu Val Thr Val Ser Thr
        115                 120
```

<210> SEQ ID NO 59
<211> LENGTH: 124
<212> TYPE: PRT
<213> ORGANISM: Artificial Sequence
<220> FEATURE:
<223> OTHER INFORMATION: Recombinant polypeptide

<400> SEQUENCE: 59

```
Lys Val Gln Leu Val Gln Ser Gly Ala Glu Leu Lys Lys Pro Trp Ser
1               5                   10                  15

Ser Val Arg Val Ser Cys Lys Ala Ser Gly Gly Glu Pro Glu Ser Tyr
            20                  25                  30

Ala Phe Asn Trp Val Arg Gln Ala Pro Gly Gln Arg Leu Glu Trp Leu
        35                  40                  45

Gly Gly Ile Val Pro Leu Val Ser Ser Thr Asn Tyr Ala Gln Arg Phe
    50                  55                  60

Arg Gly Arg Val Thr Ile Ser Ala Asp Pro Glu Thr Ser Thr Val Tyr
65                  70                  75                  80

Leu Glu Met Thr Gly Leu Thr Ser Ala Asp Thr Ala Val Tyr Phe Cys
                85                  90                  95

Ala Arg Glu Gly Glu Gly Trp Phe Gly Arg Pro Leu Arg Ala Phe Glu
            100                 105                 110

Phe Trp Gly Gln Gly Thr Leu Val Thr Val Ser Thr
        115                 120
```

<210> SEQ ID NO 60

```
<211> LENGTH: 108
<212> TYPE: PRT
<213> ORGANISM: Artificial Sequence
<220> FEATURE:
<223> OTHER INFORMATION: Recombinant polypeptide

<400> SEQUENCE: 60

Glu Ile Val Leu Thr Gln Ser Pro Gly Thr Phe Ala Leu Ser Pro Gly
1               5                   10                  15

Glu Arg Ala Thr Leu Ser Cys Arg Ala Ser Gln Ser Val Ser Gly Gly
            20                  25                  30

Ala Leu Ala Trp Tyr Gln Gln Lys Ala Gly Gln Ala Pro Arg Leu Leu
        35                  40                  45

Ile Tyr Asp Thr Ser Gly Arg Ala Thr Gly Val Pro Gly Arg Phe Ser
    50                  55                  60

Gly Ser Gly Ser Glu Thr Asp Phe Ser Leu Thr Ile Ser Arg Leu Glu
65                  70                  75                  80

Pro Glu Asp Phe Ala Val Tyr Tyr Cys Gln Gln Tyr Gly Thr Ser Gln
                85                  90                  95

Ser Thr Phe Gly Gln Gly Thr Arg Leu Glu Thr Arg
            100                 105

<210> SEQ ID NO 61
<211> LENGTH: 8
<212> TYPE: PRT
<213> ORGANISM: Artificial Sequence
<220> FEATURE:
<223> OTHER INFORMATION: Recombinant polypeptide

<400> SEQUENCE: 61

Gly Gly Thr Phe Ser Thr Leu Ala
1               5

<210> SEQ ID NO 62
<211> LENGTH: 8
<212> TYPE: PRT
<213> ORGANISM: Artificial Sequence
<220> FEATURE:
<223> OTHER INFORMATION: Recombinant polypeptide

<400> SEQUENCE: 62

Ile Val Pro Leu Phe Ser Ile Val
1               5

<210> SEQ ID NO 63
<211> LENGTH: 15
<212> TYPE: PRT
<213> ORGANISM: Artificial Sequence
<220> FEATURE:
<223> OTHER INFORMATION: Recombinant polypeptide

<400> SEQUENCE: 63

Glu Gly Glu Gly Trp Phe Gly Lys Pro Leu Arg Ala Phe Glu Phe
1               5                   10                  15

<210> SEQ ID NO 64
<211> LENGTH: 8
<212> TYPE: PRT
<213> ORGANISM: Artificial Sequence
<220> FEATURE:
<223> OTHER INFORMATION: Recombinant polypeptide

<400> SEQUENCE: 64

Gly Gly Ser Phe Ser Ser Tyr Ala
```

-continued

```
1               5
```

<210> SEQ ID NO 65
<211> LENGTH: 8
<212> TYPE: PRT
<213> ORGANISM: Artificial Sequence
<220> FEATURE:
<223> OTHER INFORMATION: Recombinant polypeptide

<400> SEQUENCE: 65

```
Ile Val Pro Leu Val Ser Ser Thr
1               5
```

<210> SEQ ID NO 66
<211> LENGTH: 15
<212> TYPE: PRT
<213> ORGANISM: Artificial Sequence
<220> FEATURE:
<223> OTHER INFORMATION: Recombinant polypeptide

<400> SEQUENCE: 66

```
Glu Gly Glu Gly Trp Phe Gly Arg Pro Leu Arg Ala Phe Glu Phe
1               5                   10                  15
```

<210> SEQ ID NO 67
<211> LENGTH: 8
<212> TYPE: PRT
<213> ORGANISM: Artificial Sequence
<220> FEATURE:
<223> OTHER INFORMATION: Recombinant polypeptide

<400> SEQUENCE: 67

```
Gly Gly Thr Phe Ser Ser Tyr Ala
1               5
```

<210> SEQ ID NO 68
<211> LENGTH: 8
<212> TYPE: PRT
<213> ORGANISM: Artificial Sequence
<220> FEATURE:
<223> OTHER INFORMATION: Recombinant polypeptide

<400> SEQUENCE: 68

```
Ile Ile Pro Ile Phe Gly Thr Ala
1               5
```

<210> SEQ ID NO 69
<211> LENGTH: 15
<212> TYPE: PRT
<213> ORGANISM: Artificial Sequence
<220> FEATURE:
<223> OTHER INFORMATION: Recombinant polypeptide

<400> SEQUENCE: 69

```
Glu Gly Glu Gly Trp Phe Gly Lys Pro Leu Arg Ala Phe Glu Phe
1               5                   10                  15
```

<210> SEQ ID NO 70
<211> LENGTH: 7
<212> TYPE: PRT
<213> ORGANISM: Artificial Sequence
<220> FEATURE:
<223> OTHER INFORMATION: Recombinant polypeptide

<400> SEQUENCE: 70

```
Gln Ser Val Ser Gly Gly Ala
1               5
```

```
<210> SEQ ID NO 71
<211> LENGTH: 3
<212> TYPE: PRT
<213> ORGANISM: Artificial Sequence
<220> FEATURE:
<223> OTHER INFORMATION: Recombinant polypeptide

<400> SEQUENCE: 71

Asp Thr Ser
1

<210> SEQ ID NO 72
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 72

Gln Gln Tyr Gly Thr Ser Gln Ser Thr Phe
1               5                   10

<210> SEQ ID NO 73
<211> LENGTH: 7
<212> TYPE: PRT
<213> ORGANISM: Artificial Sequence
<220> FEATURE:
<223> OTHER INFORMATION: Recombinant polypeptide

<400> SEQUENCE: 73

Gln Ser Val Ser Gly Gly Ala
1               5

<210> SEQ ID NO 74
<211> LENGTH: 3
<212> TYPE: PRT
<213> ORGANISM: Artificial Sequence
<220> FEATURE:
<223> OTHER INFORMATION: Recombinant polypeptide

<400> SEQUENCE: 74

Gly Thr Ser
1

<210> SEQ ID NO 75
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 75

Gln Gln Tyr Gly Thr Ser Gln Ser Thr Phe
1               5                   10

<210> SEQ ID NO 76
<211> LENGTH: 7
<212> TYPE: PRT
<213> ORGANISM: Artificial Sequence
<220> FEATURE:
<223> OTHER INFORMATION: Recombinant polypeptide

<400> SEQUENCE: 76

Gln Ser Val Ser Ser Ser Tyr
1               5
```

-continued

<210> SEQ ID NO 77
<211> LENGTH: 3
<212> TYPE: PRT
<213> ORGANISM: Artificial Sequence
<220> FEATURE:
<223> OTHER INFORMATION: Recombinant polypeptide

<400> SEQUENCE: 77

Gly Ala Ser
1

<210> SEQ ID NO 78
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 78

Gln Gln Tyr Gly Thr Ser Gln Ser Thr Phe
1               5                   10

<210> SEQ ID NO 79
<211> LENGTH: 25
<212> TYPE: PRT
<213> ORGANISM: Artificial Sequence
<220> FEATURE:
<223> OTHER INFORMATION: Recombinant polypeptide

<400> SEQUENCE: 79

Glu Val Gln Leu Val Gln Ser Gly Gly Glu Val Lys Arg Pro Gly Ser
1               5                   10                  15

Ser Val Thr Val Ser Cys Lys Ala Thr
            20                  25

<210> SEQ ID NO 80
<211> LENGTH: 17
<212> TYPE: PRT
<213> ORGANISM: Artificial Sequence
<220> FEATURE:
<223> OTHER INFORMATION: Recombinant polypeptide

<400> SEQUENCE: 80

Phe Asn Trp Val Arg Gln Ala Pro Gly Gln Gly Pro Glu Trp Met Gly
1               5                   10                  15

Gly

<210> SEQ ID NO 81
<211> LENGTH: 40
<212> TYPE: PRT
<213> ORGANISM: Artificial Sequence
<220> FEATURE:
<223> OTHER INFORMATION: Recombinant polypeptide

<400> SEQUENCE: 81

Asn Tyr Gly Gln Lys Phe Gln Gly Arg Leu Thr Ile Arg Ala Asp Lys
1               5                   10                  15

Ser Thr Thr Thr Val Phe Leu Asp Leu Ser Gly Leu Thr Ser Ala Asp
            20                  25                  30

Thr Ala Thr Tyr Tyr Cys Ala Arg
            35                  40

<210> SEQ ID NO 82
<211> LENGTH: 11

<212> TYPE: PRT
<213> ORGANISM: Artificial Sequence
<220> FEATURE:
<223> OTHER INFORMATION: Recombinant polypeptide

<400> SEQUENCE: 82

Trp Gly Gln Gly Thr Val Ile Thr Val Ser Ser
1               5                   10

<210> SEQ ID NO 83
<211> LENGTH: 25
<212> TYPE: PRT
<213> ORGANISM: Artificial Sequence
<220> FEATURE:
<223> OTHER INFORMATION: Recombinant polypeptide

<400> SEQUENCE: 83

Lys Val Gln Leu Val Gln Ser Gly Ala Glu Leu Lys Lys Pro Trp Ser
1               5                   10                  15

Ser Val Arg Val Ser Cys Lys Ala Ser
            20                  25

<210> SEQ ID NO 84
<211> LENGTH: 17
<212> TYPE: PRT
<213> ORGANISM: Artificial Sequence
<220> FEATURE:
<223> OTHER INFORMATION: Recombinant polypeptide

<400> SEQUENCE: 84

Phe Asn Trp Val Arg Gln Ala Pro Gly Gln Arg Leu Glu Trp Leu Gly
1               5                   10                  15

Gly

<210> SEQ ID NO 85
<211> LENGTH: 40
<212> TYPE: PRT
<213> ORGANISM: Artificial Sequence
<220> FEATURE:
<223> OTHER INFORMATION: Recombinant polypeptide

<400> SEQUENCE: 85

Asn Tyr Ala Gln Arg Phe Arg Gly Arg Val Thr Ile Ser Ala Asp Arg
1               5                   10                  15

Ser Thr Ser Thr Val Tyr Leu Glu Met Thr Gly Leu Thr Ser Ala Asp
            20                  25                  30

Thr Ala Val Tyr Phe Cys Ala Arg
        35                  40

<210> SEQ ID NO 86
<211> LENGTH: 11
<212> TYPE: PRT
<213> ORGANISM: Artificial Sequence
<220> FEATURE:
<223> OTHER INFORMATION: Recombinant polypeptide

<400> SEQUENCE: 86

Trp Gly Gln Gly Thr Leu Val Thr Val Ser Thr
1               5                   10

<210> SEQ ID NO 87
<211> LENGTH: 25
<212> TYPE: PRT
<213> ORGANISM: Artificial Sequence
<220> FEATURE:

<223> OTHER INFORMATION: Recombinant polypeptide

<400> SEQUENCE: 87

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 88
<211> LENGTH: 17
<212> TYPE: PRT
<213> ORGANISM: Artificial Sequence
<220> FEATURE:
<223> OTHER INFORMATION: Recombinant polypeptide

<400> SEQUENCE: 88

Ile Ser Trp Val Arg Gln Ala Pro Gly Gln Gly Leu Glu Trp Met Gly
1               5                   10                  15

Gly

<210> SEQ ID NO 89
<211> LENGTH: 40
<212> TYPE: PRT
<213> ORGANISM: Artificial Sequence
<220> FEATURE:
<223> OTHER INFORMATION: Recombinant polypeptide

<400> SEQUENCE: 89

Asn Tyr Ala Gln Lys Phe Gln Gly Arg Val Thr Ile Thr Ala Asp Lys
1               5                   10                  15

Ser Thr Ser Thr Ala Tyr Met Glu Leu Ser Ser Leu Arg Ser Glu Asp
            20                  25                  30

Thr Ala Val Tyr Tyr Cys Ala Arg
        35                  40

<210> SEQ ID NO 90
<211> LENGTH: 11
<212> TYPE: PRT
<213> ORGANISM: Artificial Sequence
<220> FEATURE:
<223> OTHER INFORMATION: Recombinant polypeptide

<400> SEQUENCE: 90

Trp Gly Gln Gly Thr Val Ile Thr Val Ser Ser
1               5                   10

<210> SEQ ID NO 91
<211> LENGTH: 26
<212> TYPE: PRT
<213> ORGANISM: Artificial Sequence
<220> FEATURE:
<223> OTHER INFORMATION: Recombinant polypeptide

<400> SEQUENCE: 91

Asp Val Val Met Thr Gln Ser Pro Gly Thr Leu Ser Leu Ser Pro Gly
1               5                   10                  15

Glu Arg Ala Thr Leu Ser Cys Arg Ala Ser
            20                  25

<210> SEQ ID NO 92
<211> LENGTH: 17
<212> TYPE: PRT
<213> ORGANISM: Artificial Sequence
<220> FEATURE:

-continued

<223> OTHER INFORMATION: Recombinant polypeptide

<400> SEQUENCE: 92

Leu Ala Trp Tyr Gln Gln Lys Pro Gly Gln Ala Pro Arg Leu Leu Ile
1               5                   10                  15

Tyr

<210> SEQ ID NO 93
<211> LENGTH: 36
<212> TYPE: PRT
<213> ORGANISM: Artificial Sequence
<220> FEATURE:
<223> OTHER INFORMATION: Recombinant polypeptide

<400> SEQUENCE: 93

Ser Arg Pro Thr Gly Val Pro Gly Arg Phe Ser Gly Ser Gly Ser Gly
1               5                   10                  15

Thr Asp Phe Ser Leu Thr Ile Ser Arg Leu Glu Pro Glu Asp Phe Ala
                20                  25                  30

Val Tyr Tyr Cys
        35

<210> SEQ ID NO 94
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 94

Gly Gln Gly Thr Arg Leu Glu Ile Lys
1               5

<210> SEQ ID NO 95
<211> LENGTH: 26
<212> TYPE: PRT
<213> ORGANISM: Artificial Sequence
<220> FEATURE:
<223> OTHER INFORMATION: Recombinant polypeptide

<400> SEQUENCE: 95

Glu Ile Val Leu Thr Gln Ser Pro Gly Thr Phe Ala Leu Ser Pro Gly
1               5                   10                  15

Glu Arg Ala Thr Leu Ser Cys Arg Ala Ser
                20                  25

<210> SEQ ID NO 96
<211> LENGTH: 17
<212> TYPE: PRT
<213> ORGANISM: Artificial Sequence
<220> FEATURE:
<223> OTHER INFORMATION: Recombinant polypeptide

<400> SEQUENCE: 96

Leu Ala Trp Tyr Gln Gln Lys Ala Gly Gln Ala Pro Arg Leu Leu Ile
1               5                   10                  15

Tyr

<210> SEQ ID NO 97
<211> LENGTH: 36
<212> TYPE: PRT
<213> ORGANISM: Artificial Sequence
<220> FEATURE:
<223> OTHER INFORMATION: Recombinant polypeptide -continued

<400> SEQUENCE: 97

Gly Arg Ala Thr Gly Val Pro Gly Arg Phe Ser Gly Ser Gly Ser Glu
1               5                   10                  15

Thr Asp Phe Ser Leu Thr Ile Ser Arg Leu Glu Pro Glu Asp Phe Ala
                20                  25                  30

Val Tyr Tyr Cys
        35

<210> SEQ ID NO 98
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 98

Gly Gln Gly Thr Arg Leu Glu Thr Arg
1               5

<210> SEQ ID NO 99
<211> LENGTH: 26
<212> TYPE: PRT
<213> ORGANISM: Artificial Sequence
<220> FEATURE:
<223> OTHER INFORMATION: Recombinant polypeptide

<400> SEQUENCE: 99

Glu Ile Val Leu Thr Gln Ser Pro Gly Thr Leu Ser Leu Ser Pro Gly
1               5                   10                  15

Glu Arg Ala Thr Leu Ser Cys Arg Ala Ser
                20                  25

<210> SEQ ID NO 100
<211> LENGTH: 17
<212> TYPE: PRT
<213> ORGANISM: Artificial Sequence
<220> FEATURE:
<223> OTHER INFORMATION: Recombinant polypeptide

<400> SEQUENCE: 100

Leu Ala Trp Tyr Gln Gln Lys Pro Gly Gln Ala Pro Arg Leu Leu Ile
1               5                   10                  15

Tyr

<210> SEQ ID NO 101
<211> LENGTH: 36
<212> TYPE: PRT
<213> ORGANISM: Artificial Sequence
<220> FEATURE:
<223> OTHER INFORMATION: Recombinant polypeptide

<400> SEQUENCE: 101

Ser Arg Ala Thr Gly Ile Pro Asp Arg Phe Ser Gly Ser Gly Ser Gly
1               5                   10                  15

Thr Asp Phe Thr Leu Thr Ile Ser Arg Leu Glu Pro Glu Asp Phe Ala
                20                  25                  30

Val Tyr Tyr Cys
        35

<210> SEQ ID NO 102
<211> LENGTH: 9
<212> TYPE: PRT

-continued

<210> ORGANISM: Artificial Sequence
<220> FEATURE:
<223> OTHER INFORMATION: Recombinant polypeptide

<400> SEQUENCE: 102

Gly Gln Gly Thr Arg Leu Glu Thr Arg
1               5

<210> SEQ ID NO 103
<211> LENGTH: 473
<212> TYPE: PRT
<213> ORGANISM: Artificial Sequence
<220> FEATURE:
<223> OTHER INFORMATION: Recombinant polypeptide

<400> SEQUENCE: 103

Met Glu Leu Gly Leu Arg Trp Val Phe Leu Val Ala Ile Leu Glu Gly
1               5                   10                  15

Val Gln Cys Glu Val Gln Leu Val Gln Ser Gly Gly Glu Val Lys Arg
                20                  25                  30

Pro Gly Ser Ser Val Thr Val Ser Cys Lys Ala Thr Gly Gly Thr Phe
            35                  40                  45

Ser Thr Leu Ala Phe Asn Trp Val Arg Gln Ala Pro Gly Gln Gly Pro
        50                  55                  60

Glu Trp Met Gly Gly Ile Val Pro Leu Phe Ser Ile Val Asn Tyr Gly
65                  70                  75                  80

Gln Lys Phe Gln Gly Arg Leu Thr Ile Arg Ala Asp Lys Ser Thr Thr
                85                  90                  95

Thr Val Phe Leu Asp Leu Ser Gly Leu Thr Ser Ala Asp Thr Ala Thr
                100                 105                 110

Tyr Tyr Cys Ala Arg Glu Gly Glu Gly Trp Phe Gly Lys Pro Leu Arg
            115                 120                 125

Ala Phe Glu Phe Trp Gly Gln Gly Thr Val Ile Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
                180                 185                 190

Val His Thr Phe Pro Ala Val Leu Gln Ser Ser Gly Leu Tyr Ser Leu
                195                 200                 205

Ser Ser Val Val Thr Val Pro Ser Ser Ser Leu Gly Thr Gln Thr Tyr
            210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
        290                 295                 300

Val Asp Gly Val Glu Val His Asn Ala Lys Thr Lys Pro Arg Glu Glu
305                 310                 315                 320

```
Gln Tyr Asn Ser Thr Tyr Arg Val Val Ser Val Leu Thr Val Leu His
            325             330             335

Gln Asp Trp Leu Asn Gly Lys Glu Tyr Lys Cys Lys Val Ser Asn Lys
        340             345             350

Ala Leu Pro Ala Pro Ile Glu Lys Thr Ile Ser Lys Ala Lys Gly Gln
        355             360             365

Pro Arg Glu Pro Gln Val Tyr Thr Leu Pro Pro Ser Arg Glu Glu Met
    370             375             380

Thr Lys Asn Gln Val Ser Leu Thr Cys Leu Val Lys Gly Phe Tyr Pro
385             390             395             400

Ser Asp Ile Ala Val Glu Trp Glu Ser Asn Gly Gln Pro Glu Asn Asn
            405             410             415

Tyr Lys Thr Thr Pro Pro Val Leu Asp Ser Asp Gly Ser Phe Phe Leu
            420             425             430

Tyr Ser Lys Leu Thr Val Asp Lys Ser Arg Trp Gln Gln Gly Asn Val
        435             440             445

Phe Ser Cys Ser Val Met His Glu Ala Leu His Asn His Tyr Thr Gln
    450             455             460

Lys Ser Leu Ser Leu Ser Pro Gly Lys
465             470
```

```
<210> SEQ ID NO 104
<211> LENGTH: 473
<212> TYPE: PRT
<213> ORGANISM: Artificial Sequence
<220> FEATURE:
<223> OTHER INFORMATION: Recombinant polypeptide

<400> SEQUENCE: 104

Met Glu Leu Gly Leu Arg Trp Val Phe Leu Val Ala Ile Leu Glu Gly
1               5               10              15

Val Gln Cys Lys Val Gln Leu Val Gln Ser Gly Ala Glu Leu Lys Lys
            20              25              30

Pro Trp Ser Ser Val Arg Val Ser Cys Lys Ala Ser Gly Gly Ser Phe
        35              40              45

Ser Ser Tyr Ala Phe Asn Trp Val Arg Gln Ala Pro Gly Gln Arg Leu
    50              55              60

Glu Trp Leu Gly Gly Ile Val Pro Leu Val Ser Ser Thr Asn Tyr Ala
65              70              75              80

Gln Arg Phe Arg Gly Arg Val Thr Ile Ser Ala Asp Arg Ser Thr Ser
            85              90              95

Thr Val Tyr Leu Glu Met Thr Gly Leu Thr Ser Ala Asp Thr Ala Val
        100             105             110

Tyr Phe Cys Ala Arg Glu Gly Glu Gly Trp Phe Gly Arg Pro Leu Arg
        115             120             125

Ala Phe Glu Phe Trp Gly Gln Gly Thr Leu Val Thr Val Ser Thr Ala
    130             135             140

Ser Thr Lys Gly Pro Ser Val Phe Pro Leu Ala Pro Ser Ser Lys Ser
145             150             155             160

Thr Ser Gly Gly Thr Ala Ala Leu Gly Cys Leu Val Lys Asp Tyr Phe
            165             170             175

Pro Glu Pro Val Thr Val Ser Trp Asn Ser Gly Ala Leu Thr Ser Gly
        180             185             190

Val His Thr Phe Pro Ala Val Leu Gln Ser Ser Gly Leu Tyr Ser Leu
        195             200             205
```

Ser Ser Val Val Thr Val Pro Ser Ser Ser Leu Gly Thr Gln Thr Tyr
    210             215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
            245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 105
<211> LENGTH: 473
<212> TYPE: PRT
<213> ORGANISM: Artificial Sequence
<220> FEATURE:
<223> OTHER INFORMATION: Recombinant polypeptide

<400> SEQUENCE: 105

Met Glu Leu Gly Leu Arg Trp Val Phe Leu Val Ala Ile Leu Glu Gly
1               5                   10                  15

Val Gln Cys Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
            35                  40                  45

Ser Ser Tyr Ala Ile Ser Trp Val Arg Gln Ala Pro Gly Gln Gly Leu
    50                  55                  60

Glu Trp Met Gly Gly Ile Ile Pro Ile Phe Gly Thr Ala Asn Tyr Ala
65                  70                  75                  80

Gln Lys Phe Gln Gly Arg Val Thr Ile Thr Ala Asp Lys Ser Thr Ser
            85                  90                  95

```
Thr Ala Tyr Met Glu Leu Ser Ser Leu Arg Ser Glu Asp Thr Ala Val
            100                 105                 110

Tyr Tyr Cys Ala Arg Glu Gly Glu Gly Trp Phe Gly Lys Pro Leu Arg
        115                 120                 125

Ala Phe Glu Phe Trp Gly Gln Gly Thr Val Ile Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Arg
225                 230                 235                 240

Val Glu Pro Lys Ser Cys Asp Lys Thr His Thr Cys Pro Pro Cys Pro
            245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

<210> SEQ ID NO 106
<211> LENGTH: 233
<212> TYPE: PRT
<213> ORGANISM: Artificial Sequence
<220> FEATURE:
<223> OTHER INFORMATION: Recombinant polypeptide -continued

<400> SEQUENCE: 106

```
Met Gly Trp Ser Cys Ile Ile Leu Phe Leu Val Ala Thr Ala Thr Gly
1               5                   10                  15

Val His Asp Val Val Met Thr Gln Ser Pro Gly Thr Leu Ser Leu Ser
            20                  25                  30

Pro Gly Glu Arg Ala Thr Leu Ser Cys Arg Ala Ser Gln Ser Val Ser
            35                  40                  45

Gly Gly Ala Leu Ala Trp Tyr Gln Gln Lys Pro Gly Gln Ala Pro Arg
        50                  55                  60

Leu Leu Ile Tyr Asp Thr Ser Ser Arg Pro Thr Gly Val Pro Gly Arg
65                  70                  75                  80

Phe Ser Gly Ser Gly Ser Gly Thr Asp Phe Ser Leu Thr Ile Ser Arg
                85                  90                  95

Leu Glu Pro Glu Asp Phe Ala Val Tyr Tyr Cys Gln Gln Tyr Gly Thr
            100                 105                 110

Ser Gln Ser Thr Phe Gly Gln Gly Thr Arg Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
225                 230
```

<210> SEQ ID NO 107
<211> LENGTH: 233
<212> TYPE: PRT
<213> ORGANISM: Artificial Sequence
<220> FEATURE:
<223> OTHER INFORMATION: Recombinant polypeptide

<400> SEQUENCE: 107

```
Met Gly Trp Ser Cys Ile Ile Leu Phe Leu Val Ala Thr Ala Thr Gly
1               5                   10                  15

Val His Glu Ile Val Leu Thr Gln Ser Pro Gly Thr Phe Ala Leu Ser
            20                  25                  30

Pro Gly Glu Arg Ala Thr Leu Ser Cys Arg Ala Ser Gln Ser Val Ser
            35                  40                  45

Gly Gly Ala Leu Ala Trp Tyr Gln Gln Lys Ala Gly Gln Ala Pro Arg
        50                  55                  60

Leu Leu Ile Tyr Gly Thr Ser Gly Arg Ala Thr Gly Val Pro Gly Arg
65                  70                  75                  80

Phe Ser Gly Ser Gly Ser Glu Thr Asp Phe Ser Leu Thr Ile Ser Arg
                85                  90                  95

Leu Glu Pro Glu Asp Phe Ala Val Tyr Tyr Cys Gln Gln Tyr Gly Thr
            100                 105                 110
```

```
Ser Gln Ser Thr Phe Gly Gln Gly Thr Arg Leu Glu Thr Arg Arg Thr
    115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 108
<211> LENGTH: 233
<212> TYPE: PRT
<213> ORGANISM: Artificial Sequence
<220> FEATURE:
<223> OTHER INFORMATION: Recombinant polypeptide

<400> SEQUENCE: 108

Met Gly Trp Ser Cys Ile Ile Leu Phe Leu Val Ala Thr Ala Thr Gly
1               5                   10                  15

Val His Glu Ile Val Leu Thr Gln Ser Pro Gly Thr Leu Ser Leu Ser
                20                  25                  30

Pro Gly Glu Arg Ala Thr Leu Ser Cys Arg Ala Ser Gln Ser Val Ser
        35                  40                  45

Ser Ser Tyr Leu Ala Trp Tyr Gln Gln Lys Pro Gly Gln Ala Pro Arg
    50                  55                  60

Leu Leu Ile Tyr Gly Ala Ser Ser Arg Ala Thr Gly Ile Pro Asp Arg
65                  70                  75                  80

Phe Ser Gly Ser Gly Ser Gly Thr Asp Phe Thr Leu Thr Ile Ser Arg
                85                  90                  95

Leu Glu Pro Glu Asp Phe Ala Val Tyr Tyr Cys Gln Gln Tyr Gly Thr
                100                 105                 110

Ser Gln Ser Thr Phe Gly Gln Gly Thr Arg Leu Glu Thr Arg Arg Thr
    115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 109
<211> LENGTH: 330
<212> TYPE: PRT
<213> ORGANISM: Artificial Sequence
<220> FEATURE:
<223> OTHER INFORMATION: Recombinant polypeptide

<400> SEQUENCE: 109

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ser His Tyr Thr
305                 310                 315                 320

Gln Lys Ser Leu Ser Leu Ser Pro Gly Lys
                325                 330

<210> SEQ ID NO 110
<211> LENGTH: 372
<212> TYPE: DNA
<213> ORGANISM: Artificial Sequence
<220> FEATURE:

```
<223> OTHER INFORMATION: Recombinant polynucleotide

<400> SEQUENCE: 110
gaggtgcagc tggtgcagtc tggcggtgag gtgaagcggc ctgggtcctc ggtgacggtc      60
tcctgcaagg cgactggggg cacatttagt actcttgctt ttaactgggt gcgccaggcc     120
cctggacaag ggcctgagtg gatgggagga attgtccctc ttttcagcat tgtgaattat     180
ggacagaaat tccagggcag acttacaatt cgggcggaca aatcgacgac cacagtattt     240
ttggatctga gtggcctcac gtctgcggac acggccactt attattgtgc gcgagaggga     300
gaggggtggt tcgggaagcc cctccgtgct tttgaatttt ggggccaggg gacagtgatc     360
accgtctcct ca                                                          372

<210> SEQ ID NO 111
<211> LENGTH: 372
<212> TYPE: DNA
<213> ORGANISM: Artificial Sequence
<220> FEATURE:
<223> OTHER INFORMATION: Recombinant polynucleotide

<400> SEQUENCE: 111
aaggtacaac tggtgcagtc tggggctgaa ctgaagaagc cttggtcctc ggtgagggtc      60
tcctgcaagg catctggagg cagcttcagc agctatgcct tcaactgggt gcgacaggcc     120 cccgacaaa gacttgagtg gctgggaggc atcgtccctc ttgtcagcag cacaaactac     180
gcacagaggt tcaggggcag agtcacaatc agtgcggaca atcaacgag tactgtctac      240 ttggagatga caggactgac atctgcagac acggccgttt atttctgtgc gcgggagggg     300
gagggttggt tcgggaggcc cctccgagcg tttgaattct ggggccaagg aacactcgtc     360
accgtttcta ca                                                          372

<210> SEQ ID NO 112
<211> LENGTH: 372
<212> TYPE: DNA
<213> ORGANISM: Artificial Sequence
<220> FEATURE:
<223> OTHER INFORMATION: Recombinant polynucleotide

<400> SEQUENCE: 112
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggaca atccacgag cacagcctac      240 atggagctga gcagcctgag atctgaggac acggccgtgt attactgtgc gagagaggga     300
gaggggtggt tcgggaagcc cctccgtgct tttgaatttt ggggccaggg gacagtgatc     360
accgtctcct ca                                                          372

<210> SEQ ID NO 113
<211> LENGTH: 324
<212> TYPE: DNA
<213> ORGANISM: Artificial Sequence
<220> FEATURE:
<223> OTHER INFORMATION: Recombinant polynucleotide

<400> SEQUENCE: 113
gatgttgtga tgactcagtc tccaggcact ttgtctttgt ctcccggaga aagggccacc      60
ctctcctgcc gggccagtca gagtgtcagt ggcggcgcgt tagcctggta ccagcagaag     120
```

-continued

```
cctggccagg ctcccagact cctcatctat gacacgtcca gcaggcccac tggcgtcccg      180
ggcaggttca gtggcagtgg gtctgggaca gacttcagtc tcaccatcag taggctggag      240
cctgaagact ttgctgtcta ttactgtcag caatatggaa cctcacaatc gaccttcggc      300 cagggacac gactggagat taaa                                              324

<210> SEQ ID NO 114
<211> LENGTH: 324
<212> TYPE: DNA
<213> ORGANISM: Artificial Sequence
<220> FEATURE:
<223> OTHER INFORMATION: Recombinant polynucleotide

<400> SEQUENCE: 114
gaaattgtgt tgacgcagtc tccaggcacc tttgctttgt ctcccggaga aagggccacc       60
ctctcctgcc gggccagtca gagtgtcagt ggcggcgcgt tagcctggta ccagcagaag      120
gctggccagg ctcccagact cctcatctat ggtacgtccg gcagggccac tggcgtcccg      180
ggcaggttca gtggcagtgg gtctgagaca gacttcagtc tcaccatcag caggctggag      240
cctgaagact ttgcagtcta ttactgtcag caatatggta cctcacaatc gaccttcggc      300
caagggacac gactggagac cagg                                             324

<210> SEQ ID NO 115
<211> LENGTH: 324
<212> TYPE: DNA
<213> ORGANISM: Artificial Sequence
<220> FEATURE:
<223> OTHER INFORMATION: Recombinant polynucleotide

<400> SEQUENCE: 115
gaaattgtgt tgacgcagtc tccaggcacc ctgtctttgt ctccagggga aagagccacc       60
ctctcctgca gggccagtca gagtgttagc agcagctact tagcctggta ccagcagaaa      120
cctggccagg ctcccaggct cctcatctat ggtgcatcca gcaggccac tggcatccca       180 gacaggttca gtggcagtgg gtctgggaca gacttcactc tcaccatcag cagactggag      240
cctgaagatt ttgcagtgta ttactgtcag caatatggta cctcacaatc gaccttcggc      300
caagggacac gactggagac cagg                                             324

<210> SEQ ID NO 116
<211> LENGTH: 1422
<212> TYPE: DNA
<213> ORGANISM: Artificial Sequence
<220> FEATURE:
<223> OTHER INFORMATION: Recombinant polynucleotide

<400> SEQUENCE: 116
atggaactgg ggctccgctg ggttttcctt gttgctattc tcgagggtgt ccagtgtgag       60
gtgcagctgg tgcagtctgg cggtgaggtg aagcggcctg gtcctcggt gacggtctcc       120 tgcaaggcga ctgggggcac atttagtact cttgctttta actgggtgcg ccaggcccct      180
ggacaagggc ctgagtggat gggaggaatt gtccctcttt tcagcattgt gaattatgga      240
cagaaattcc agggcagact acaattcggc gcggacaaat cgacgaccac agtattttg      300 gatctgagtg gcctcacgtc tgcggacacg gccacttatt attgtgcgcg agagggagag      360
gggtggttcg ggaagcccct ccgtgctttt gaattttggg gccagggac agtgatcacc      420 gtctcctcag ctagcaccaa gggcccatcg gtcttccccc tggcacccctc ctccaagagc      480
```

-continued

```
acctctgggg gcacagcggc cctgggctgc ctggtcaagg actacttccc cgaacctgtg      540
acggtctcgt ggaactcagg cgccctgacc agcggcgtgc acaccttccc ggctgtccta      600
cagtcctcag gactctactc cctcagcagc gtggtgaccg tgccctccag cagcttgggc      660
acccagacct acatctgcaa cgtgaatcac aagcccagca acaccaaggt ggacaagaga      720
gttgagccca aatcttgtga caaaactcac acatgcccac cgtgcccagc acctgaactc      780 ctgggggggac cgtcagtctt cctcttcccc ccaaaaccca aggacaccct catgatctcc      840
cggacccctg aggtcacatg cgtggtggtg gacgtgagcc acgaagaccc tgaggtcaag      900
ttcaactggt acgtggacgg cgtggaggtg cataatgcca agacaaagcc gcgggaggag      960
cagtacaaca gcacgtaccg tgtggtcagc gtcctcaccg tcctgcacca ggactggctg     1020
aatggcaagg agtacaagtg caaggtctcc aacaaagccc tcccagcccc catcgagaaa     1080
accatctcca aagccaaagg gcagccccga gaaccacagg tgtacaccct gccccccatcc    1140 cgggaggaga tgaccaagaa ccaggtcagc ctgacctgcc tggtcaaagg cttctatccc     1200
agcgacatcg ccgtggagtg ggagagcaat gggcagccgg agaacaacta caagaccacg     1260
cctcccgtgc tggactccga cggctccttc ttcctctata gcaagctcac cgtggacaag     1320
agcaggtggc agcaggggaa cgtcttctca tgctccgtga tgcatgaggc tctgcacaac     1380
cactacacgc agaagagcct ctccctgtcc ccgggtaaat ga                        1422
```

```
<210> SEQ ID NO 117
<211> LENGTH: 1422
<212> TYPE: DNA
<213> ORGANISM: Artificial Sequence
<220> FEATURE:
<223> OTHER INFORMATION: Recombinant polynucleotide

<400> SEQUENCE: 117
```

```
atggaactgg ggctccgctg ggttttcctt gttgctattc tcgagggtgt ccagtgtaag       60
gtacaactgg tgcagtctgg ggctgaactg aagaagcctt ggtcctcggt gagggtctcc      120
tgcaaggcat ctggaggcag cttcagcagc tatgccttca ctgggtgcg acaggccccc       180 ggacaaagac ttgagtggct gggaggcatc gtccctcttg tcagcagcac aaactacgca      240
cagaggttca ggggcagagt cacaatcagt gcggacagat caacgagtac tgtctacttg      300
gagatgacag gactgacatc tgcagacacg gccgtttatt tctgtgcgcg ggagggggag      360
ggttggttcg ggaggcccct ccgagcgttt gaattctggg gccaaggaac actcgtcacc      420
gtttctacag ctagcaccaa gggcccatcg gtcttccccc tggcaccctc tccaagagc      480 acctctgggg gcacagcggc cctgggctgc ctggtcaagg actacttccc cgaacctgtg      540
acggtctcgt ggaactcagg cgccctgacc agcggcgtgc acaccttccc ggctgtccta      600
cagtcctcag gactctactc cctcagcagc gtggtgaccg tgccctccag cagcttgggc      660
acccagacct acatctgcaa cgtgaatcac aagcccagca acaccaaggt ggacaagaga      720
gttgagccca aatcttgtga caaaactcac acatgcccac cgtgcccagc acctgaactc      780 ctgggggggac cgtcagtctt cctcttcccc ccaaaaccca aggacaccct catgatctcc      840
cggacccctg aggtcacatg cgtggtggtg gacgtgagcc acgaagaccc tgaggtcaag      900
ttcaactggt acgtggacgg cgtggaggtg cataatgcca agacaaagcc gcgggaggag      960
cagtacaaca gcacgtaccg tgtggtcagc gtcctcaccg tcctgcacca ggactggctg     1020
aatggcaagg agtacaagtg caaggtctcc aacaaagccc tcccagcccc catcgagaaa     1080
accatctcca aagccaaagg gcagccccga gaaccacagg tgtacaccct gccccccatcc    1140
```

-continued

```
cgggaggaga tgaccaagaa ccaggtcagc ctgacctgcc tggtcaaagg cttctatccc      1200
agcgacatcg ccgtggagtg ggagagcaat gggcagccgg agaacaacta caagaccacg      1260
cctcccgtgc tggactccga cggctccttc ttcctctata gcaagctcac cgtggacaag      1320
agcaggtggc agcaggggaa cgtcttctca tgctccgtga tgcatgaggc tctgcacaac      1380
cactacacgc agaagagcct ctccctgtcc ccgggtaaat ga                        1422
```

```
<210> SEQ ID NO 118
<211> LENGTH: 1422
<212> TYPE: DNA
<213> ORGANISM: Artificial Sequence
<220> FEATURE:
<223> OTHER INFORMATION: Recombinant polynucleotide

<400> SEQUENCE: 118
```

```
atggaactgg ggctccgctg ggttttcctt gttgctattc tcgagggtgt ccagtgtcag       60
gtgcagctgg tgcagtctgg ggctgaggtg aagaagcctg gtcctcggt gaaggtctcc      120 tgcaaggctt ctggaggcac cttcagcagc tatgctatca gctgggtgcg acaggcccct      180
ggacaagggc ttgagtggat gggagggatc atccctatct ttggtacagc aaactacgca      240
cagaagttcc agggcagagt cacgattacc gcggacaaat ccacgagcac agcctacatg      300
gagctgagca gcctgagatc tgaggacacg gccgtgtatt actgtgcgag agagggagag      360
gggtggttcg ggaagcccct ccgtgctttt gaattttggg gccaggggac agtgatcacc      420
gtctcctcag ctagcaccaa gggcccatcg gtcttccccc tggcaccctc ctccaagagc      480
acctctgggg gcacagcggc cctgggctgc ctggtcaagg actacttccc cgaacctgtg      540
acggtctcgt ggaactcagg cgccctgacc agcggcgtgc acaccttccc ggctgtccta      600
cagtcctcag gactctactc cctcagcagc gtggtgaccg tgccctccag cagcttgggc      660
acccagacct acatctgcaa cgtgaatcac aagcccagca acaccaaggt ggacaagaga      720
gttgagccca aatcttgtga caaaactcac acatgcccac cgtgcccagc acctgaactc      780
ctggggggac cgtcagtctt cctcttcccc ccaaaaccca aggacaccct catgatctcc      840
cggacccctg aggtcacatg cgtggtggtg gacgtgagcc acgaagaccc tgaggtcaag      900
ttcaactggt acgtggacgg cgtggaggtg cataatgcca agacaaagcc gcgggaggag      960
cagtacaaca gcacgtaccg tgtggtcagc gtcctcaccg tcctgcacca ggactggctg     1020
aatggcaagg agtacaagtg caaggtctcc aacaaagccc tcccagcccc catcgagaaa     1080
accatctcca aagccaaagg gcagccccga gaaccacagg tgtacaccct gcccccatcc     1140
cgggaggaga tgaccaagaa ccaggtcagc ctgacctgcc tggtcaaagg cttctatccc     1200
agcgacatcg ccgtggagtg ggagagcaat gggcagccgg agaacaacta caagaccacg     1260
cctcccgtgc tggactccga cggctccttc ttcctctata gcaagctcac cgtggacaag     1320
agcaggtggc agcaggggaa cgtcttctca tgctccgtga tgcatgaggc tctgcacaac     1380
cactacacgc agaagagcct ctccctgtcc ccgggtaaat ga                       1422
```

```
<210> SEQ ID NO 119
<211> LENGTH: 702
<212> TYPE: DNA
<213> ORGANISM: Artificial Sequence
<220> FEATURE:
<223> OTHER INFORMATION: Recombinant polynucleotide

<400> SEQUENCE: 119
```

-continued

```
atgggatggt catgtatcat ccttttttcta gtagcaactg caaccggtgt acatgatgtt      60
gtgatgactc agtctccagg cactttgtct ttgtctcccg gagaaagggc caccctctcc     120
tgccgggcca gtcagagtgt cagtggcggc gcgttagcct ggtaccagca gaagcctggc     180
caggctccca gactcctcat ctatgacacg tccagcaggc ccactggcgt cccgggcagg     240
ttcagtggca gtgggtctgg gacagacttc agtctcacca tcagtaggct ggagcctgaa     300
gactttgctg tctattactg tcagcaatat ggaacctcac aatcgacctt cggccagggg     360
acacgactgg agattaaacg tacggtggct gcaccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ag                        702
```

<210> SEQ ID NO 120
<211> LENGTH: 702
<212> TYPE: DNA
<213> ORGANISM: Artificial Sequence
<220> FEATURE:
<223> OTHER INFORMATION: Recombinant polynucleotide

<400> SEQUENCE: 120

```
atgggatggt catgtatcat ccttttttcta gtagcaactg caaccggtgt acatgaaatt      60
gtgttgacgc agtctccagg cacctttgct ttgtctcccg gagaaagggc caccctctcc     120
tgccgggcca gtcagagtgt cagtggcggc gcgttagcct ggtaccagca gaaggctggc     180
caggctccca gactcctcat ctatggtacg tccggcaggg ccactggcgt cccgggcagg     240
ttcagtggca gtgggtctga gacagacttc agtctcacca tcagcaggct ggagcctgaa     300
gactttgcag tctattactg tcagcaatat ggtacctcac aatcgacctt cggccaaggg     360
acacgactgg agaccaggcg tacggtggct gcaccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgtt ag                        702
```

<210> SEQ ID NO 121
<211> LENGTH: 702
<212> TYPE: DNA
<213> ORGANISM: Artificial Sequence
<220> FEATURE:
<223> OTHER INFORMATION: Recombinant polynucleotide

<400> SEQUENCE: 121

```
atgggatggt catgtatcat ccttttttcta gtagcaactg caaccggtgt acatgaaatt      60
gtgttgacgc agtctccagg caccctgtct ttgtctccag gggaaagagc caccctctcc     120
tgcagggcca gtcagagtgt tagcagcagc tacttagcct ggtaccagca gaaacctggc     180
caggctccca ggctcctcat ctatggtgca tccagcaggg ccactggcat cccagacagg     240
ttcagtggca gtgggtctgg gacagacttc actctcacca tcagcagact ggagcctgaa     300
gattttgcag tgtattactg tcagcaatat ggtacctcac aatcgacctt cggccaaggg     360
```

```
acacgactgg agaccaggcg tacggtggct gcaccatctg tcttcatctt cccgccatct       420
gatgagcagt tgaaatctgg aactgcctct gttgtgtgcc tgctgaataa cttctatccc       480
agagaggcca aagtacagtg gaaggtggat aacgccctcc aatcgggtaa ctcccaggag       540
agtgtcacag agcaggacag caaggacagc acctacagcc tcagcagcac cctgacgctg       600
agcaaagcag actacgagaa acacaaagtc tacgcctgcg aagtcaccca tcagggcctg       660
agctcgcccg tcacaaagag cttcaacagg ggagagtgtt ag                          702
```

```
<210> SEQ ID NO 122
<211> LENGTH: 25
<212> TYPE: PRT
<213> ORGANISM: Artificial Sequence
<220> FEATURE:
<223> OTHER INFORMATION: Recombinant polypeptide

<400> SEQUENCE: 122

Glu Leu Leu Ala Leu Asp Lys Trp Ala Ser Leu Trp Asn Trp Phe Asp
1               5                   10                  15

Leu Ala Ser Trp Val Lys Tyr Ile Gln
            20                  25
```

```
<210> SEQ ID NO 123
<211> LENGTH: 25
<212> TYPE: PRT
<213> ORGANISM: Artificial Sequence
<220> FEATURE:
<223> OTHER INFORMATION: Recombinant polypeptide

<400> SEQUENCE: 123

Glu Leu Gln Lys Leu Asn Ser Trp Asp Val Phe Gly Asn Trp Phe Asp
1               5                   10                  15

Leu Ala Ser Trp Val Lys Tyr Ile Gln
            20                  25
```

```
<210> SEQ ID NO 124
<211> LENGTH: 25
<212> TYPE: PRT
<213> ORGANISM: Artificial Sequence
<220> FEATURE:
<223> OTHER INFORMATION: Recombinant polypeptide

<400> SEQUENCE: 124

Asp Leu Leu Ala Leu Asp Arg Trp Gln Asn Leu Trp Asn Trp Phe Asp
1               5                   10                  15

Ile Thr Asn Trp Leu Trp Tyr Ile Lys
            20                  25
```

```
<210> SEQ ID NO 125
<211> LENGTH: 18
<212> TYPE: PRT
<213> ORGANISM: Artificial Sequence
<220> FEATURE:
<223> OTHER INFORMATION: Recombinant polypeptide

<400> SEQUENCE: 125

Glu Gly Thr Thr Gly Trp Gly Trp Leu Gly Lys Pro Ile Gly Ala Phe
1               5                   10                  15

Ala His
```

```
<210> SEQ ID NO 126
<211> LENGTH: 15
```

-continued

```
<212> TYPE: PRT
<213> ORGANISM: Artificial Sequence
<220> FEATURE:
<223> OTHER INFORMATION: Recombinant polypeptide

<400> SEQUENCE: 126

Glu Gly Ala Gly Trp Phe Gly Lys Pro Val Gly Ala Met Gly Tyr
1               5                   10                  15

<210> SEQ ID NO 127
<211> LENGTH: 20
<212> TYPE: PRT
<213> ORGANISM: Artificial Sequence
<220> FEATURE:
<223> OTHER INFORMATION: Recombinant polypeptide

<400> SEQUENCE: 127

Thr Gly Lys Tyr Tyr Asp Phe Trp Ser Gly Tyr Pro Pro Gly Glu Glu
1               5                   10                  15

Tyr Phe Gln Asp
            20

<210> SEQ ID NO 128
<211> LENGTH: 23
<212> TYPE: PRT
<213> ORGANISM: Artificial Sequence
<220> FEATURE:
<223> OTHER INFORMATION: Recombinant polypeptide

<400> SEQUENCE: 128

Thr Met Asp Glu Gly Thr Pro Val Thr Arg Phe Leu Glu Trp Gly Tyr
1               5                   10                  15

Phe Tyr Tyr Tyr Met Ala Val
            20

<210> SEQ ID NO 129
<211> LENGTH: 24
<212> TYPE: PRT
<213> ORGANISM: Artificial Sequence
<220> FEATURE:
<223> OTHER INFORMATION: Recombinant polypeptide

<400> SEQUENCE: 129

Ala Arg Gly Thr Gly Val Val Val Gly Gly Ser Trp Thr Val Pro Pro
1               5                   10                  15

Gly Met Ala Tyr Tyr Leu Asp Val
            20

<210> SEQ ID NO 130
<211> LENGTH: 22
<212> TYPE: PRT
<213> ORGANISM: Artificial Sequence
<220> FEATURE:
<223> OTHER INFORMATION: Recombinant polypeptide

<400> SEQUENCE: 130

Arg Arg Gly Pro Thr Thr Ser Ser Gly Val Pro Ile Ala Arg Gly Pro
1               5                   10                  15

Val Asn Ala Met Asp Val
            20

<210> SEQ ID NO 131
<211> LENGTH: 9
<212> TYPE: PRT
<213> ORGANISM: Artificial Sequence
```

<220> FEATURE:
<223> OTHER INFORMATION: Recombinant polypeptide

<400> SEQUENCE: 131

Gln Gln Tyr Gly Thr Ser Gln Ser Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 132

Gln Gln Tyr Gly Gln Ser Leu Ser Thr
1               5

<210> SEQ ID NO 133
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 133

Gln Gln Tyr Gly Gly Ser Phe Gly Thr
1               5

<210> SEQ ID NO 134
<211> LENGTH: 12
<212> TYPE: PRT
<213> ORGANISM: Artificial Sequence
<220> FEATURE:
<223> OTHER INFORMATION: Recombinant polypeptide

<400> SEQUENCE: 134

Ser Ser Arg Asp Lys Ser Gly Ser Arg Leu Ser Val
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Recombinant polypeptide

<400> SEQUENCE: 135

Gln Glu Asn Tyr Asn Thr Ile Pro Ser Leu Ser
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Recombinant polypeptide

<400> SEQUENCE: 136

Ala Ser Arg Asp Arg Ser Gly Asp Arg Leu Gly Val
1               5                   10

<210> SEQ ID NO 137
<211> LENGTH: 9
<212> TYPE: PRT
<213> ORGANISM: Artificial Sequence
<220> FEATURE:

<223> OTHER INFORMATION: Recombinant polypeptide

<400> SEQUENCE: 137

Gln Gln Arg Ser Asp Trp Pro Arg Thr
1               5

<210> SEQ ID NO 138
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 138

Gln Gln Leu His Phe Tyr Pro His Thr
1               5

<210> SEQ ID NO 139
<211> LENGTH: 17
<212> TYPE: PRT
<213> ORGANISM: Artificial Sequence
<220> FEATURE:
<223> OTHER INFORMATION: Recombinant polypeptide

<400> SEQUENCE: 139

Val Ala Ile Gly Val Ser Gly Phe Leu Asn Tyr Tyr Tyr Tyr Met Asp
1               5                   10                  15

Val

<210> SEQ ID NO 140
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 140

Ser Trp Phe Asp Ile Thr Lys Trp Leu Trp
1               5                   10

<210> SEQ ID NO 141
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 141

Asn Trp Phe Asp Ile Thr Asn Trp Leu Trp
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 142

Asn Trp Phe Ser Ile Thr Asn Trp Leu Trp
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 143

Asn Trp Phe Glu Ile Thr Asn Trp Leu Trp
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 144

Asn Trp Phe Thr Ile Thr Asn Trp Leu Trp
1               5                   10

<210> SEQ ID NO 145
<211> LENGTH: 30
<212> TYPE: PRT
<213> ORGANISM: Artificial Sequence
<220> FEATURE:
<223> OTHER INFORMATION: Recombinant polypeptide

<400> SEQUENCE: 145

Glu Lys Asn Glu Gln Glu Leu Leu Glu Leu Asp Lys Trp Ala Ser Leu
1               5                   10                  15

Trp Asn Trp Phe Asp Ile Thr Asn Trp Leu Trp Tyr Ile Lys
            20                  25                  30

<210> SEQ ID NO 146
<211> LENGTH: 16
<212> TYPE: PRT
<213> ORGANISM: Artificial Sequence
<220> FEATURE:
<223> OTHER INFORMATION: Recombinant polypeptide

<400> SEQUENCE: 146

Asn Trp Phe Asp Ile Thr Asn Trp Leu Trp Tyr Ile Lys Lys Lys Lys
1               5                   10                  15

<210> SEQ ID NO 147
<211> LENGTH: 12
<212> TYPE: PRT
<213> ORGANISM: Artificial Sequence
<220> FEATURE:
<223> OTHER INFORMATION: Recombinant polypeptide

<400> SEQUENCE: 147

Gly Lys Asn Cys Asp Tyr Asn Trp Asp Phe Glu His
1               5                   10

<210> SEQ ID NO 148
<211> LENGTH: 19
<212> TYPE: PRT
<213> ORGANISM: Artificial Sequence
<220> FEATURE:
<223> OTHER INFORMATION: Recombinant polypeptide

<400> SEQUENCE: 148

Glu Leu Asp Lys Trp Ala Ser Leu Trp Asn Trp Phe Asp Ile Thr Asn
1               5                   10                  15

Trp Leu Trp

<210> SEQ ID NO 149
<211> LENGTH: 19
<212> TYPE: PRT
<213> ORGANISM: Artificial Sequence
<220> FEATURE:
<223> OTHER INFORMATION: Recombinant polypeptide

<400> SEQUENCE: 149

Cys Ala Arg Glu Gly Glu Gly Trp Phe Gly Lys Pro Leu Arg Ala Phe
1               5                   10                  15

Glu Phe Trp

<210> SEQ ID NO 150
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 150

Val Leu Leu Trp Phe Gly Glu Leu Leu
1               5

<210> SEQ ID NO 151
<211> LENGTH: 6
<212> TYPE: PRT
<213> ORGANISM: Artificial Sequence
<220> FEATURE:
<223> OTHER INFORMATION: Recombinant polypeptide

<400> SEQUENCE: 151

Asp Ala Phe Asp Val Trp
1               5

<210> SEQ ID NO 152
<211> LENGTH: 19
<212> TYPE: PRT
<213> ORGANISM: Artificial Sequence
<220> FEATURE:
<223> OTHER INFORMATION: Recombinant polypeptide

<400> SEQUENCE: 152

Cys Ala Arg Glu Gly Glu Gly Trp Phe Gly Lys Pro Leu Arg Ala Phe
1               5                   10                  15

Glu Phe Trp

<210> SEQ ID NO 153
<211> LENGTH: 19
<212> TYPE: PRT
<213> ORGANISM: Artificial Sequence
<220> FEATURE:
<223> OTHER INFORMATION: Recombinant polypeptide

<400> SEQUENCE: 153

Cys Ala Arg Glu Gly Glu Gly Trp Phe Gly Glu Pro Leu Arg Ala Phe
1               5                   10                  15

Asp Val Trp

<210> SEQ ID NO 154
<211> LENGTH: 22
<212> TYPE: PRT
<213> ORGANISM: Artificial Sequence
<220> FEATURE:
<223> OTHER INFORMATION: Recombinant polypeptide

<400> SEQUENCE: 154

```
Cys Ala Arg Glu Gly Thr Thr Gly Trp Gly Trp Leu Gly Lys Pro Ile
1               5                   10                  15

Gly Ala Phe Ala His Trp
            20

<210> SEQ ID NO 155
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 155

Val Leu Leu Trp Phe Gly Glu Leu Leu
1               5

<210> SEQ ID NO 156
<211> LENGTH: 5
<212> TYPE: PRT
<213> ORGANISM: Artificial Sequence
<220> FEATURE:
<223> OTHER INFORMATION: Recombinant polypeptide

<400> SEQUENCE: 156

Tyr Phe Asp Tyr Trp
1               5

<210> SEQ ID NO 157
<211> LENGTH: 22
<212> TYPE: PRT
<213> ORGANISM: Artificial Sequence
<220> FEATURE:
<223> OTHER INFORMATION: Recombinant polypeptide

<400> SEQUENCE: 157

Cys Ala Arg Glu Gly Thr Thr Gly Trp Gly Trp Leu Gly Lys Pro Ile
1               5                   10                  15

Gly Ala Phe Ala His Trp
            20

<210> SEQ ID NO 158
<211> LENGTH: 22
<212> TYPE: PRT
<213> ORGANISM: Artificial Sequence
<220> FEATURE:
<223> OTHER INFORMATION: Recombinant polypeptide

<400> SEQUENCE: 158

Cys Ala Arg Glu Gly Thr Thr Gly Trp Gly Trp Phe Gly Glu Pro Ile
1               5                   10                  15

Gly Tyr Phe Asp Tyr Trp
            20

<210> SEQ ID NO 159
<211> LENGTH: 98
<212> TYPE: PRT
<213> ORGANISM: Artificial Sequence
<220> FEATURE:
<223> OTHER INFORMATION: Recombinant polypeptide

<400> SEQUENCE: 159

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

-continued

```
              20              25              30
Ala Ile Ser Trp Val Arg Gln Ala Pro Gly Gln Gly Leu Glu Trp Met
        35              40              45

Gly Gly Ile Ile Pro Ile Phe Gly Thr Ala Asn Tyr Ala Gln Lys Phe
    50              55              60

Gln Gly Arg Val Thr Ile Thr Ala Asp Lys Ser Thr Ser Thr Ala Tyr
65              70              75              80

Met Glu Leu Ser Ser Leu Arg Ser Glu Asp Thr Ala Val Tyr Tyr Cys
                85              90              95

Ala Arg

<210> SEQ ID NO 160
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 160

Val Leu Leu Trp Phe Gly Glu Leu Leu
1               5

<210> SEQ ID NO 161
<211> LENGTH: 6
<212> TYPE: PRT
<213> ORGANISM: Artificial Sequence
<220> FEATURE:
<223> OTHER INFORMATION: Recombinant polypeptide

<400> SEQUENCE: 161

Asp Ala Phe Asp Val Trp
1               5

<210> SEQ ID NO 162
<211> LENGTH: 89
<212> TYPE: PRT
<213> ORGANISM: Artificial Sequence
<220> FEATURE:
<223> OTHER INFORMATION: Recombinant polypeptide

<400> SEQUENCE: 162

Glu Ile Val Leu Thr Gln Ser Pro Gly Thr Leu Ser Leu Ser Pro Gly
1               5              10              15

Glu Arg Ala Thr Leu Ser Cys Arg Ala Ser Gln Ser Val Ser Ser Ser
                20              25              30

Tyr Leu Ala Trp Tyr Gln Gln Lys Pro Gly Gln Ala Pro Arg Leu Leu
        35              40              45

Ile Tyr Gly Ala Ser Ser Arg Ala Thr Gly Ile Pro Asp Arg Phe Ser
    50              55              60

Gly Ser Gly Ser Gly Thr Asp Phe Thr Leu Thr Ile Ser Arg Leu Glu
65              70              75              80

Pro Glu Asp Phe Ala Val Tyr Tyr Cys
                85

<210> SEQ ID NO 163
<211> LENGTH: 12
<212> TYPE: PRT
<213> ORGANISM: Artificial Sequence
<220> FEATURE:
<223> OTHER INFORMATION: Recombinant polypeptide

<400> SEQUENCE: 163
```

Gly Trp Phe Gly Lys Pro Leu Arg Ala Phe Glu Phe
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Recombinant polypeptide

<400> SEQUENCE: 164

Gly Gln Gly Thr Val Ile Thr Val Ser Ser
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Recombinant polypeptide

<400> SEQUENCE: 165

Gly Trp Phe Gly Arg Pro Leu Arg Ala Phe Glu Phe
1               5                   10

<210> SEQ ID NO 166
<211> LENGTH: 18
<212> TYPE: PRT
<213> ORGANISM: Artificial Sequence
<220> FEATURE:
<223> OTHER INFORMATION: Recombinant polypeptide

<400> SEQUENCE: 166

Glu Gly Thr Thr Gly Trp Gly Trp Leu Gly Lys Pro Ile Gly Ala Phe
1               5                   10                  15

Ala His

<210> SEQ ID NO 167
<211> LENGTH: 12
<212> TYPE: PRT
<213> ORGANISM: Artificial Sequence
<220> FEATURE:
<223> OTHER INFORMATION: Recombinant polypeptide

<400> SEQUENCE: 167

Gly Trp Phe Gly Lys Pro Val Gly Ala Met Gly Tyr
1               5                   10

<210> SEQ ID NO 168
<211> LENGTH: 5
<212> TYPE: PRT
<213> ORGANISM: Artificial Sequence
<220> FEATURE:
<223> OTHER INFORMATION: Recombinant polypeptide

<400> SEQUENCE: 168

Leu Val Ser Ser Thr
1               5

<210> SEQ ID NO 169
<211> LENGTH: 5
<212> TYPE: PRT
<213> ORGANISM: Artificial Sequence
<220> FEATURE:
<223> OTHER INFORMATION: Recombinant polypeptide

```
<400> SEQUENCE: 169

Leu Leu Thr Ile Thr
1               5

<210> SEQ ID NO 170
<211> LENGTH: 20
<212> TYPE: PRT
<213> ORGANISM: Artificial Sequence
<220> FEATURE:
<223> OTHER INFORMATION: Recombinant polypeptide

<400> SEQUENCE: 170

Gln Gln Tyr Gly Thr Ser Gln Ser Thr Phe Gly Gln Gly Thr Arg Leu
1               5                   10                  15

Glu Ile Lys Arg
            20

<210> SEQ ID NO 171
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 171

Gln Gln Tyr Gly Thr Ser Gln Ser Thr
1               5

<210> SEQ ID NO 172
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 172

Gln Gln Tyr Gly Gln Ser Leu Ser Thr
1               5

<210> SEQ ID NO 173
<211> LENGTH: 9
<212> TYPE: PRT
<213> ORGANISM: Artificial Sequence
<220> FEATURE:
<223> OTHER INFORMATION: Recombinant polypeptide

<400> SEQUENCE: 173

Gln Gln Tyr Gly Gly Ser Phe Gly Thr
1               5

<210> SEQ ID NO 174
<211> LENGTH: 4
<212> TYPE: PRT
<213> ORGANISM: Artificial Sequence
<220> FEATURE:
<223> OTHER INFORMATION: Recombinant polypeptide

<400> SEQUENCE: 174

Gly Asn Asn Lys
1
```